US012448646B2

(12) United States Patent
White et al.

(10) Patent No.: US 12,448,646 B2
(45) Date of Patent: Oct. 21, 2025

(54) SSB METHOD

(71) Applicant: Oxford Nanopore Technologies PLC, Oxford (GB)

(72) Inventors: James White, Oxford (GB); Ruth Moysey, Oxford (GB); Mihaela Misca, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 210 days.

(21) Appl. No.: 17/481,374

(22) Filed: Sep. 22, 2021

(65) Prior Publication Data

US 2022/0145383 A1 May 12, 2022

Related U.S. Application Data

(63) Continuation of application No. 14/415,459, filed as application No. PCT/GB2013/051924 on Jul. 18, 2013, now Pat. No. 11,155,860.

(60) Provisional application No. 61/774,688, filed on Mar. 8, 2013, provisional application No. 61/673,457, filed on Jul. 19, 2012.

(51) Int. Cl.
*C12Q 1/6869* (2018.01)

(52) U.S. Cl.
CPC .................................. *C12Q 1/6869* (2013.01)

(58) Field of Classification Search
None
See application file for complete search history.

(56) References Cited

U.S. PATENT DOCUMENTS 5,215,899 A 6/1993 Dattagupta
5,424,413 A 6/1995 Hogan et al.
5,561,043 A 10/1996 Cantor et al.
5,714,320 A 2/1998 Kool
5,777,078 A 7/1998 Bayley et al.
5,795,782 A 8/1998 Church et al.
5,817,771 A 10/1998 Bayley et al.
5,866,328 A 2/1999 Bensimon et al.
5,866,336 A 2/1999 Nazarenko et al.
5,985,834 A 11/1999 Engel et al.
6,015,714 A 1/2000 Baldarelli et al.
6,087,099 A 7/2000 Gupte et al.
6,123,819 A 9/2000 Peeters
6,127,166 A 10/2000 Bayley et al.
6,251,610 B1 6/2001 Gupte et al.
6,274,320 B1 8/2001 Rothberg et al.
6,362,002 B1 3/2002 Denison et al.
6,403,319 B1 6/2002 Lizardi et al.
6,426,231 B1 7/2002 Bayley et al.
6,451,563 B1 9/2002 Wittig et al.
6,451,593 B1 9/2002 Wittig et al.
6,465,193 B2 10/2002 Akeson et al.
6,498,023 B1 12/2002 Abarzua
6,627,067 B1 9/2003 Branton et al.
6,709,861 B2 3/2004 Mead et al.
6,787,308 B2 9/2004 Balasubramanian et al.
6,824,659 B2 11/2004 Bayley et al.
6,863,833 B1 3/2005 Bloom et al.
6,916,665 B2 7/2005 Bayley et al.
6,927,070 B1 8/2005 Bayley et al.
7,087,729 B1 8/2006 Prive
7,189,503 B2 3/2007 Akeson et al.
7,238,485 B2 7/2007 Akeson et al.
7,361,466 B2 4/2008 Korlach et al.
7,507,575 B2 3/2009 Bedingham et al.
7,700,281 B2 * 4/2010 Kubu .................... C12Q 1/686 435/6.1
7,745,116 B2 6/2010 Williams
8,105,846 B2 1/2012 Bayley et al.
8,143,030 B2 3/2012 Maxham et al.
8,153,375 B2 4/2012 Travers et al.
8,343,746 B2 1/2013 Rank et al.
8,383,369 B2 2/2013 Maxham et al.
8,628,940 B2 1/2014 Sorenson et al.
8,652,779 B2 2/2014 Turner et al.
8,785,211 B2 7/2014 Bayley et al.
8,822,160 B2 9/2014 Bayley et al.
8,889,348 B2 11/2014 Ju
9,057,102 B2 6/2015 Turner et al.
9,116,118 B2 8/2015 Turner et al.
9,145,623 B2 9/2015 Kavanagh et al.
(Continued)

FOREIGN PATENT DOCUMENTS

CN 101495656 A 7/2009
CN 102245760 A 11/2011
(Continued)

OTHER PUBLICATIONS

Cui et al., Maize Mu transposon and its application in reverse genetic research. Bulletin of Agricultural Science and Technology. Dec. 31, 2010;1:35-38.
Manosas et al., Magnetic tweezers for the study of DNA tracking motors. Methods Enzymol. 2010;475:297-320. doi: 10.1016/S0076-6879(10)75013-8.
Matson et al., The gene 4 protein of bacteriophage T7. Characterization of helicase activity. J Biol Chem. Nov. 25, 1983;258(22):14017-24.
Mitchel et al., Heteroduplex DNA position defines the roles of the Sgs1, Srs2, and Mph1 helicases in promoting distinct recombination outcomes. PLOS Genet. 2013;9(3):e1003340. doi: 10.1371/journal.pgen.1003340. Epub Mar. 14, 2013.
Nakai et al., Handoff from recombinase to replisome: insights from transposition. Proc Natl Acad Sci U S A. Jul. 17, 2001;98(15):8247-54. doi: 10.1073/pnas.111007898.
(Continued)

*Primary Examiner* — Katherine D Salmon
(74) *Attorney, Agent, or Firm* — Wolf, Greenfield & Sacks, P.C.

(57) ABSTRACT

The invention relates to a method of characterising a target polynucleotide using a single-stranded binding protein (SSB). The SSB is either an SSB comprising a carboxy-terminal (C-terminal) region which does not have a net negative charge or a modified SSB comprising one or more modifications in its C-terminal region which decreases the net negative charge of the C-terminal region.

13 Claims, 15 Drawing Sheets

Specification includes a Sequence Listing.

(56) References Cited

U.S. PATENT DOCUMENTS

| | | | |
|---|---|---|---|
| 9,150,918 | B2 | 10/2015 | Turner et al. |
| 9,542,527 | B2 | 1/2017 | Travers et al. |
| 9,546,400 | B2 | 1/2017 | Turner et al. |
| 9,551,023 | B2 | 1/2017 | Turner et al. |
| 9,556,480 | B2 | 1/2017 | Turner et al. |
| 9,670,526 | B2 | 6/2017 | Kokoris et al. |
| 9,678,056 | B2 | 6/2017 | Turner et al. |
| 9,738,929 | B2 | 8/2017 | Turner et al. |
| 9,957,560 | B2 | 5/2018 | Brown et al. |
| 10,131,944 | B2 | 11/2018 | Bernick et al. |
| 10,221,450 | B2 | 3/2019 | Heron et al. |
| 10,227,632 | B2 | 3/2019 | Jarvius |
| 10,501,767 | B2 | 12/2019 | Stoddart et al. |
| 10,570,440 | B2 | 2/2020 | White et al. |
| 10,597,713 | B2 | 3/2020 | Brown et al. |
| 10,669,578 | B2 | 6/2020 | Clarke et al. |
| 10,851,409 | B2 | 12/2020 | Brown et al. |
| 11,155,860 | B2 | 10/2021 | White et al. |
| 11,168,363 | B2 | 11/2021 | Brown et al. |
| 11,186,857 | B2 | 11/2021 | Stoddart et al. |
| 11,261,487 | B2 | 3/2022 | Brown et al. |
| 11,268,139 | B2 | 3/2022 | Lu |
| 11,352,664 | B2 | 6/2022 | Mckeown |
| 11,390,904 | B2 | 7/2022 | White |
| 11,459,606 | B2 | 10/2022 | Mckeown |
| 11,542,551 | B2 | 1/2023 | Clarke et al. |
| 11,560,589 | B2 | 1/2023 | Heron et al. |
| 11,649,480 | B2 | 5/2023 | Stoddart et al. |
| 11,725,205 | B2 | 8/2023 | White |
| 2001/0039039 | A1 | 11/2001 | Weissman et al. |
| 2002/0028458 | A1 | 3/2002 | Lexow |
| 2002/0094526 | A1 | 7/2002 | Bayley et al. |
| 2002/0098530 | A1 | 7/2002 | Pfeifer et al. |
| 2002/0132350 | A1 | 9/2002 | Suzuki et al. |
| 2002/0142331 | A1 | 10/2002 | Fu et al. |
| 2002/0177701 | A1 | 11/2002 | Weissman et al. |
| 2002/0197618 | A1 | 12/2002 | Sampson |
| 2003/0044816 | A1 | 3/2003 | Denison et al. |
| 2003/0059778 | A1 | 3/2003 | Berlin et al. |
| 2003/0087232 | A1 | 5/2003 | Christians et al. |
| 2003/0099951 | A1 | 5/2003 | Akeson et al. |
| 2003/0108902 | A1 | 6/2003 | Abarzua |
| 2003/0118595 | A1 | 6/2003 | Niemeyer et al. |
| 2003/0165936 | A1 | 9/2003 | Rabbani et al. |
| 2003/0166137 | A1 | 9/2003 | Zuker et al. |
| 2003/0211502 | A1 | 11/2003 | Sauer et al. |
| 2003/0215881 | A1 | 11/2003 | Bayley et al. |
| 2004/0055901 | A1 | 3/2004 | Petersen et al. |
| 2004/0214177 | A1 | 10/2004 | Bension |
| 2004/0229315 | A1 | 11/2004 | Lee et al. |
| 2005/0053961 | A1 | 3/2005 | Akeson et al. |
| 2005/0142559 | A1 | 6/2005 | Makrigiorgos |
| 2005/0221316 | A1 | 10/2005 | Pedersen et al. |
| 2005/0227239 | A1 | 10/2005 | Joyce |
| 2005/0260655 | A1 | 11/2005 | Liu et al. |
| 2006/0063171 | A1 | 3/2006 | Akeson et al. |
| 2006/0086626 | A1 | 4/2006 | Joyce |
| 2006/0141516 | A1 | 6/2006 | Kobold et al. |
| 2006/0147935 | A1 | 7/2006 | Linnarsson |
| 2006/0292611 | A1 | 12/2006 | Berka et al. |
| 2007/0015182 | A1 | 1/2007 | Abarzua |
| 2007/0020640 | A1 | 1/2007 | McCloskey |
| 2007/0031857 | A1 | 2/2007 | Makarov et al. |
| 2007/0122885 | A1 | 5/2007 | Reeves et al. |
| 2007/0224613 | A1 | 9/2007 | Strathmann |
| 2008/0108082 | A1 | 5/2008 | Rank et al. |
| 2008/0166724 | A1 | 7/2008 | Gerber et al. |
| 2008/0206252 | A1 | 8/2008 | Pennica et al. |
| 2008/0311582 | A1 | 12/2008 | Bayley et al. |
| 2009/0098612 | A1 | 4/2009 | Rhee et al. |
| 2009/0191598 | A1 | 7/2009 | Ruan et al. |
| 2009/0256116 | A1 | 10/2009 | Shumaker-Parry et al. |
| 2009/0269771 | A1 | 10/2009 | Schroeder |
| 2009/0280538 | A1 | 11/2009 | Patel et al. |
| 2009/0298075 | A1 | 12/2009 | Travers et al. |
| 2010/0003560 | A1 | 1/2010 | Shibata |
| 2010/0035254 | A1 | 2/2010 | Williams |
| 2010/0035260 | A1 | 2/2010 | Olasagasti et al. |
| 2010/0075309 | A1 | 3/2010 | Maxham et al. |
| 2010/0075327 | A1 | 3/2010 | Maxham et al. |
| 2010/0075328 | A1 | 3/2010 | Bjornson et al. |
| 2010/0092960 | A1 | 4/2010 | Fehr |
| 2010/0120098 | A1 | 5/2010 | Grunenwald et al. |
| 2010/0121582 | A1 | 5/2010 | Pan et al. |
| 2010/0221212 | A1 | 9/2010 | Stagliano et al. |
| 2010/0221716 | A1 | 9/2010 | Flusberg et al. |
| 2010/0276588 | A1 | 11/2010 | Syms |
| 2010/0331194 | A1* | 12/2010 | Turner ................. G01N 27/447 438/49 |
| 2011/0019186 | A1 | 1/2011 | Himmelhaus et al. |
| 2011/0136676 | A1 | 6/2011 | Greene |
| 2011/0214991 | A1 | 9/2011 | Kim et al. |
| 2011/0224106 | A1 | 9/2011 | Eshoo et al. |
| 2011/0281768 | A1 | 11/2011 | Travers et al. |
| 2011/0287435 | A1 | 11/2011 | Grunenwald et al. |
| 2011/0311965 | A1 | 12/2011 | Maglia et al. |
| 2012/0010085 | A1 | 1/2012 | Rava et al. |
| 2012/0015821 | A1 | 1/2012 | Raymond |
| 2012/0058468 | A1 | 3/2012 | Mckeown |
| 2012/0100530 | A1 | 4/2012 | Moysey et al. |
| 2012/0107802 | A1 | 5/2012 | Stoddart et al. |
| 2012/0196279 | A1 | 8/2012 | Underwood et al. |
| 2012/0244525 | A1 | 9/2012 | Hendrickson |
| 2013/0017978 | A1 | 1/2013 | Kavanagh et al. |
| 2013/0048499 | A1 | 2/2013 | Mayer et al. |
| 2013/0078624 | A1 | 3/2013 | Holmes et al. |
| 2013/0143802 | A1 | 6/2013 | Chilkoti |
| 2013/0195908 | A1 | 8/2013 | Leonetti et al. |
| 2013/0203123 | A1 | 8/2013 | Nelson et al. |
| 2013/0327644 | A1 | 12/2013 | Turner et al. |
| 2014/0134618 | A1 | 5/2014 | Kokoris et al. |
| 2014/0134629 | A1 | 5/2014 | Turner et al. |
| 2014/0186823 | A1 | 7/2014 | Clarke et al. |
| 2014/0206842 | A1 | 7/2014 | Majeed et al. |
| 2014/0262784 | A1 | 9/2014 | Clarke et al. |
| 2014/0296089 | A1 | 10/2014 | Holmes et al. |
| 2014/0308661 | A1 | 10/2014 | Holmes et al. |
| 2015/0008126 | A1 | 1/2015 | Maglia et al. |
| 2015/0045257 | A1 | 2/2015 | Kavanagh et al. |
| 2015/0152492 | A1 | 6/2015 | Brown et al. |
| 2015/0167075 | A1 | 6/2015 | Turner et al. |
| 2015/0175663 | A1 | 6/2015 | Yokoi et al. |
| 2015/0197796 | A1 | 7/2015 | White et al. |
| 2015/0218629 | A1 | 8/2015 | Heron et al. |
| 2015/0265994 | A1 | 9/2015 | Hyde et al. |
| 2015/0285781 | A1 | 10/2015 | Heron et al. |
| 2015/0307934 | A1 | 10/2015 | Turner et al. |
| 2016/0010147 | A1 | 1/2016 | Heron et al. |
| 2016/0010148 | A1 | 1/2016 | Turner et al. |
| 2016/0011169 | A1 | 1/2016 | Turner et al. |
| 2016/0194677 | A1 | 7/2016 | Stoddart et al. |
| 2016/0257942 | A1 | 9/2016 | Bruce et al. |
| 2016/0281159 | A1 | 9/2016 | Brown et al. |
| 2016/0362739 | A1 | 12/2016 | Brown et al. |
| 2017/0002406 | A1 | 1/2017 | Bowen et al. |
| 2017/0067101 | A1 | 3/2017 | Clarke et al. |
| 2017/0226503 | A1 | 8/2017 | Strachan et al. |
| 2017/0240955 | A1 | 8/2017 | White |
| 2017/0314062 | A1 | 11/2017 | Kokoris et al. |
| 2017/0321266 | A1 | 11/2017 | Mckeown |
| 2018/0051277 | A1 | 2/2018 | Godfrey et al. |
| 2018/0291440 | A1 | 10/2018 | Mckeown |
| 2018/0291441 | A1 | 10/2018 | Brown et al. |
| 2019/0194722 | A1 | 6/2019 | Stoddart et al. |
| 2019/0211390 | A1 | 7/2019 | Heron et al. |
| 2019/0376132 | A1 | 12/2019 | Mckeown |
| 2020/0002761 | A1 | 1/2020 | Mckeown |
| 2020/0024655 | A1 | 1/2020 | Brown et al. |
| 2020/0032248 | A1 | 1/2020 | White et al. |
| 2020/0109396 | A1 | 4/2020 | Tsai et al. |
| 2020/0131549 | A1 | 4/2020 | Stoddart et al. |
| 2020/0239950 | A1 | 7/2020 | Brown et al. |
| 2020/0291452 | A1 | 9/2020 | White |
| 2020/0318179 | A1 | 10/2020 | Clarke et al. |

(56) References Cited

U.S. PATENT DOCUMENTS

| | | | |
|---|---|---|---|
| 2022/0127669 A1 | 4/2022 | Brown et al. |
| 2022/0186274 A1 | 6/2022 | Stoddart et al. |
| 2023/0046363 A1 | 2/2023 | White |
| 2023/0065890 A1 | 3/2023 | Mckeown |
| 2023/0212665 A1 | 7/2023 | Heron et al. |
| 2023/0250474 A1 | 8/2023 | Clarke et al. |
| 2023/0374567 A1 | 11/2023 | Stoddart et al. |

FOREIGN PATENT DOCUMENTS

| | | | |
|---|---|---|---|
| CN | 105209634 | A | 12/2015 |
| CN | 105705656 | A | 6/2016 |
| EP | 2682460 | A1 | 1/2014 |
| GB | 2130219 | A | 5/1984 |
| GB | 2237390 | A | 5/1991 |
| GB | 2453377 | A | 4/2009 |
| JP | H11-137260 | A | 5/1999 |
| JP | 2012-506704 | A | 3/2012 |
| WO | WO 1994/23065 | | 10/1994 |
| WO | WO 1999/05167 | | 2/1999 |
| WO | WO 2000/28312 | A1 | 5/2000 |
| WO | WO 2001/40516 | A2 | 6/2001 |
| WO | WO 2001/42782 | A1 | 6/2001 |
| WO | WO 2001/59453 | A2 | 8/2001 |
| WO | WO 2002/42496 | A2 | 5/2002 |
| WO | WO 2003/095669 | A1 | 11/2003 |
| WO | WO 2005/056750 | A2 | 6/2005 |
| WO | WO 2005/068656 | A1 | 7/2005 |
| WO | WO 2005/118877 | A2 | 12/2005 |
| WO | WO 2005/124888 | A1 | 12/2005 |
| WO | WO 2006/020775 | A2 | 2/2006 |
| WO | WO 2006/028508 | A2 | 3/2006 |
| WO | WO 2006/100484 | A2 | 9/2006 |
| WO | WO 2007/057668 | A1 | 5/2007 |
| WO | WO 2007/075987 | A2 | 7/2007 |
| WO | WO 2007/084103 | A2 | 7/2007 |
| WO | WO 2007/146158 | A1 | 12/2007 |
| WO | WO 2008/045575 | A2 | 4/2008 |
| WO | WO 2008/083554 | A1 | 7/2008 |
| WO | WO 2008/102120 | A1 | 8/2008 |
| WO | WO 2008/102121 | A1 | 8/2008 |
| WO | WO 2008/124107 | A1 | 10/2008 |
| WO | WO 2009/035647 | A1 | 3/2009 |
| WO | WO 2009/044170 | A1 | 4/2009 |
| WO | WO 2009/077734 | A2 | 6/2009 |
| WO | WO 2009/120374 | A2 | 10/2009 |
| WO | WO 2010/004265 | A1 | 1/2010 |
| WO | WO 2010/004273 | A1 | 1/2010 |
| WO | WO 2010/030683 | A1 | 3/2010 |
| WO | WO 2010/034018 | A2 | 3/2010 |
| WO | WO 2010/048605 | A1 | 4/2010 |
| WO | WO 2010/051773 | A1 | 5/2010 |
| WO | WO 2010/086602 | A1 | 8/2010 |
| WO | WO 2010/086603 | A1 | 8/2010 |
| WO | WO 2010/086622 | A1 | 8/2010 |
| WO | WO 2010/094040 | A1 | 8/2010 |
| WO | WO 2010/109107 | A1 | 9/2010 |
| WO | WO 2010/109197 | A2 | 9/2010 |
| WO | WO 2010/122293 | A1 | 10/2010 |
| WO | WO 2010/146349 | A1 | 12/2010 |
| WO | WO 2011/067559 | A1 | 6/2011 |
| WO | WO 2012/033524 | A2 | 3/2012 |
| WO | WO 2012/061832 | A1 | 5/2012 |
| WO | WO 2012/083249 | A2 | 6/2012 |
| WO | WO 2012/098561 | A2 | 7/2012 |
| WO | WO 2012/098562 | A2 | 7/2012 |
| WO | WO 2012/103545 | A1 | 8/2012 |
| WO | WO 2012/107778 | A2 | 8/2012 |
| WO | WO 2012/164270 | A1 | 12/2012 |
| WO | WO 2013/014451 | A1 | 1/2013 |
| WO | WO 2013/041878 | A1 | 3/2013 |
| WO | WO 2013/057495 | A2 | 4/2013 |
| WO | WO 2013/098561 | A1 | 7/2013 |
| WO | WO 2013/098562 | A2 | 7/2013 |
| WO | WO 2013/131962 | A1 | 9/2013 |
| WO | WO 2013/153359 | A1 | 10/2013 |
| WO | WO 2013/185137 | A1 | 12/2013 |
| WO | WO 2014/013259 | A1 | 1/2014 |
| WO | WO 2014/013260 | A1 | 1/2014 |
| WO | WO 2014/013262 | A1 | 1/2014 |
| WO | WO 2014/064443 | A2 | 5/2014 |
| WO | WO 2014/064444 | A1 | 5/2014 |
| WO | WO 2014/108810 | A2 | 7/2014 |
| WO | WO 2014/135838 | A1 | 9/2014 |
| WO | WO 2014/153408 | A1 | 9/2014 |
| WO | WO 2015/022544 | A1 | 2/2015 |
| WO | WO 2015/031909 | A1 | 3/2015 |
| WO | WO 2015/055981 | A2 | 4/2015 |
| WO | WO 2015/056028 | A1 | 4/2015 |
| WO | WO 2015/110777 | A1 | 7/2015 |
| WO | WO 2015/110813 | A1 | 7/2015 |
| WO | WO 2015/189636 | A1 | 12/2015 |
| WO | WO 2015/200609 | A1 | 12/2015 |
| WO | WO 2016/003814 | A1 | 1/2016 |
| WO | WO 2016/028887 | A1 | 2/2016 |
| WO | WO 2016/034591 | A2 | 3/2016 |
| WO | WO 2016/055777 | A2 | 4/2016 |
| WO | WO 2016/059363 | A1 | 4/2016 |

OTHER PUBLICATIONS

Notomi et al., Loop-mediated isothermal amplification of DNA. Nucleic Acids Res. Jun. 15, 2000;28(12):E63. doi: 10.1093/nar/28.12.e63.

Singleton et al., Structure and mechanism of helicases and nucleic acid translocases. Annu Rev Biochem. 2007;76:23-50. doi: 10.1146/annurev.biochem.76.052305.115300.

Skipper et al., DNA transposon-based gene vehicles—scenes from an evolutionary drive. J Biomed Sci. Dec. 9, 2013;20(1):92. doi: 10.1186/1423-0127-20-92.

U.S. Appl. No. 18/340,824, filed Jun. 23, 2023, White.

International Search Report and Written Opinion for Application No. PCT/GB2013/051924, mailed Oct. 9, 2013.

International Preliminary Report on Patentability for Application No. PCT/GB2013/051924, mailed Jan. 20, 2015.

[No Author Listed], Multiplex sequencing. https://www.illumina.com/science/technology/next-generation-sequencing/multiplex-sequencing.html. Printed on Nov. 4, 2021. 1 page.

[No Author Listed], Single-molecule real-time sequencing. Wikipedia entry/ Sep. 19, 2021. Retrieved from https://en.wikipedia.org/w/index.php?title+Singlemolecule_real-time_sequencing&oldid=1045146197. Printed on Nov. 4, 2021. 10 pages.

Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Amblard et al., Cu(I)-catalyzed Huisgen azide-alkyne 1,3-dipolar cycloaddition reaction in nucleoside, nucleotide, and oligonucleotide chemistry. Chem Rev. Sep. 2009;109(9):4207-20. doi: 10.1021/cr9001462.

Ashkenasy et al., Recognizing a single base in an individual DNA strand: a step toward DNA sequencing in nanopores. Angew Chem Int Ed Engl. Feb. 18, 2005;44(9):1401-4.

Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.

Astier et al., Stochastic detection of motor protein-RNA complexes by single-channel current recording. Chemphyschem. Oct. 22, 2007;8(15):2189-94.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

(56) References Cited

OTHER PUBLICATIONS

Avrameas, Coupling of enzymes to proteins with glutaraldehyde. Use of the conjugates for the detection of antigens and antibodies. Immunochemistry. Jan. 1969;6(1):43-52.
Bayley et al., Stochastic sensors inspired by biology. Nature. Sep. 13, 2001;413(6852):226-30.
Bayley, Sequencing single molecules of DNA. Curr Opin Chem Biol. Dec. 2006;10(6):628-37. Epub Nov. 20, 2006.
Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.
Berger et al., Universal bases for hybridization, replication and chain termination. Nucleic Acids Res. Aug. 1, 2000;28(15):2911-4.
Bowie et al., Deciphering the message in protein sequences: tolerance to amino acid substitutions. Science. Mar. 16, 1990;247(4948):1306-10.
Braha et al., Carriers versus adapters in stochastic sensing. Chemphyschem. May 2005;6(5):889-92.
Braha et al., Designed protein pores as components for biosensors. Chem Biol. Jul. 1997;4(7):497-505.
Branton et al., The potential and challenges of nanopore sequencing. Nat Biotechnol. Oct. 2008;26(10):1146-53. doi:10.1038/nbt.1495.
Braslavsky et al., Sequence information can be obtained from single DNA molecules. Proc Natl Acad Sci U S A. Apr. 1, 2003;100(7):3960-4. Epub Mar. 21, 2003.
Budanova et al., Heptakis(6-amino-6-deoxy)-beta-cyclodextrin as a chiral selector for the separation of anionic analyte enantiomers by capillary electrophoresis. Electrophoresis. Aug. 2004;25(16):2795-800.
Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Busam, Structure of *Escherichia coli* exonuclease I in complex with thymidine 5'- monophosphate. Acta Crystallogr D Biol Crystallogr. Feb. 2008;64(Pt 2):206-10. doi: 10.1107/S090744490706012X. Epub Jan. 16, 2008.
Butler et al., Determination of RNA orientation during translocation through a biological nanopore. Biophys J. Jan. 1, 2006;90(1):190-9. Epub Oct. 7, 2005.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Case 1:17-cv-00275-LPS Document 18. Notice of subsequent events relating to Oxford's motion to dismiss (D.I. 9). Oct. 18, 2017.
Case 1:17-cv-00275-LPS Document 19. Oxford Nanopore Technologies, Inc.'s response to Pacific Biosciences of California, Inc.'s notice of subsequent events. Oct. 24, 2017.
Case 1:17-cv-00275-RGA Document 10. Oxford's opening brief in support of its motion to dismiss PacBio's complaint for patent infringement. May 8, 2017.
Case 1:17-cv-00275-RGA Document 14. PacBio's response to Oxford's motion to dismiss. Jun. 5, 2017.
Case 1:17-cv-00275-RGA Document 16. Oxford's reply brief in support of its motion to dismiss PacBio's complaint for patent infringement. Jun. 26, 2017.
Case 1:17-cv-01353-LPS Document 13. First Amended Complaint for Patent Infringement. Nov. 30, 2017.
Case 1:17-cv-01353-LPS Document 15. Plaintiff's response to Oxford Nanopore Techologies, Inc.'s Motion to Dismiss and Request for Scheduling Conference. Nov. 30, 2017.
Case 1:17-cv-01353-RGA Document 10. Oxford's opening brief in support of its motion to partially dismiss Pacbio's complaint for patent infringement. Nov. 16, 2017.
Chan, Advances in sequencing technology. Mutat Res. Jun. 3, 2005;573(1-2):13-40.
Cheley et al., A functional protein pore with a "retro" transmembrane domain. Protein Sci. Jun. 1999;8(6):1257-67.
Cheley et al., A genetically encoded pore for the stochastic detection of a protein kinase. Chembiochem. Dec. 2006;7(12):1923-7.
Cheley et al., Spontaneous oligomerization of a staphylococcal alpha-hemolysin conformationally constrained by removal of residues that form the transmembrane beta-barrel. Protein Eng. Dec. 1997; 10(12):1433-43.
Cheley et al., Stochastic sensing of nanomolar inositol 1,4,5-trisphosphate with an engineered pore. Chem Biol. Jul. 2002;9(7):829-38.
Chen et al., Atomic Layer Deposition to Fine-Tune the Surface Properties and Diameters of Fabricated Nanopores. Nano Lett. Jun. 25, 2004;4(7):1333-1337.
Chen et al., Outer membrane protein G: Engineering a quiet pore for biosensing. Proc Natl Acad Sci U S A. Apr. 28, 2008;105(17):6272-7. doi: 10.1073/pnas.0711561105. Epub Apr. 28, 2008.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Comai et al., Protein engineering modulates the transport properties and ion selectivity of the pores formed by staphylococcal gamma-haemolysins in lipid membranes. Mol Microbiol. Jun. 2002;44(5):1251-67.
Comer et al., Microscopic mechanics of hairpin DNA translocation through synthetic nanopores. Biophys J. Jan. 2009;96(2):593-608. doi: 10.1016/j.bpj.2008.09.023.
Cudic et al., Binding of Nucleotides in Water by Phenathridinium Bis(intercaland) Receptor Molecules. J. Chem. Soc., Chem. Commun., pp. 1073-1075 (1995).
Dapprich, Single-molecule DNA digestion by lambda-exonuclease. Cytometry. Jul. 1, 1999;36(3):163-8.
Deamer et al., Characterization of nucleic acids by nanopore analysis. Acc Chem Res. Oct. 2002;35(10):817-25.
Deamer et al., Nanopores and nucleic acids: prospects for ultrarapid sequencing. Trends Biotechnol. Apr. 2000;18(4):147-51.
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Devereux et al., A comprehensive set of sequence analysis programs for the VAX. Nucleic Acids Res. Jan. 11, 1984;12(1 Pt 1):387-95.
Dong et al., Amplified detection of nucleic acid by G-quadruplex based hybridization chain reaction. Biosens Bioelectron. Oct.-Dec. 2012;38(1):258-63. doi: 10.1016/j.bios.2012.05.042. Epub Jun. 8, 2012.
Dorre et al., Techniques for single molecule sequencing. Bioimaging, vol. 5:139-152 (1997).
Eid et al., Real-time DNA sequencing from single polymerase molecules. Science. Jan. 2, 2009;323(5910):133-8. doi:10.1126/science.1162986. Epub Nov. 20, 2008.
Eliseev et al., Aminocyclodextrins as Selective Hosts with Several Binding Sites for Nucleotides. Angew. Chem. Int. Ed. Engl., vol. 32(9):1331-1333 (1993).
Eliseev et al., Molecular Recognition of Nucleotides, Nucleosides, and Sugars by Aminocyclodextrins. J. Am. Chem. Soc., 1994;116:6081-6088.
El-Sagheer et al., Synthesis and polymerase chain reaction amplification of DNA strands containing an unnatural triazole linkage. J Am Chem Soc. Mar. 25, 2009;131(11):3958-64. doi: 10.1021/ja8065896.
Erie et al., A dumbbell-shaped, double-hairpin structure of DNA: a thermodynamic investigation. Biochemistry. Nov. 3, 1987;26(22):7150-9.
Faller et al., The structure of a mycobacterial outer-membrane channel. Science. Feb. 20, 2004;303(5661):1189-92. doi: 10.1126/science.1094114.
Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.

(56) References Cited

OTHER PUBLICATIONS

Flusberg et al., Direct detection of DNA methylation during single-molecule, real-time sequencing. Nat Methods. Jun. 2010;7(6):461-5. doi: 10.1038/nmeth.1459. Epub May 9, 2010.
Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.
Gershow et al., Recapturing and trapping single molecules with a solid-state nanopore. Nat Nanotechnol. Dec. 2007;2(12):775-9. doi:10.1038/nnano.2007.381. Epub Dec. 2, 2007.
Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.
Gill et al., Nucleic acid isothermal amplification technologies: a review. Nucleosides Nucleotides Nucleic Acids. Mar. 2008;27(3):224-43. doi: 10.1080/15257770701845204.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Grant et al., A facile method for attaching nitroxide spin labels at the 5' terminus of nucleic acids. Nucleic Acids Res. 2007;35(10):e77. Epub May 21, 2007.
Gu et al., Capture of a single molecule in a nanocavity. Science. Jan. 26, 2001;291(5504):636-40.
Gu et al., Electroosmotic enhancement of the binding of a neutral molecule to a transmembrane pore. Proc Natl Acad Sci U S A. Dec. 23, 2003;100(26):15498-503. Epub Dec. 15, 2003.
Gu et al., Prolonged residence time of a noncovalent molecular adapter, beta-cyclodextrin, within the lumen of mutant alpha-hemolysin pores. J Gen Physiol. Nov. 2001;118(5):481-94.
Gu et al., Reversal of charge selectivity in transmembrane protein pores by using noncovalent molecular adapters. Proc Natl Acad Sci U S A. Apr. 11, 2000;97(8):3959-64.
Gu et al., Single molecule sensing by nanopores and nanopore devices. Analyst. Mar. 2010;135(3):441-51. doi: 10.1039/b907735a. Epub Dec. 22, 2009.
Gu et al., Stochastic sensing of organic analytes by a pore-forming protein containing a molecular adapter. Nature. Apr. 22, 1999;398(6729):686-90.
Guan et al., Stochastic sensing of TNT with a genetically engineered pore. Chembiochem. Oct. 2005;6(10):1875-81.
Han et al., Characterization and optimization of an entropic trap for DNA separation. Anal Chem. Jan. 15, 2002;74(2):394-401.
Han et al., RecJ exonuclease: substrates, products and interaction with SSB. Nucleic Acids Res. Feb. 18, 2006;34(4):1084-91. Print 2006.
He et al., The carboxyl-terminal domain of bacteriophage T7 single-stranded DNA-binding protein modulates DNA binding and interaction with T7 DNA polymerase. J Biol Chem. Aug. 8, 2003;278(32):29538-45. doi: 10.1074/jbc.M304318200. Epub May 24, 2003.
Hein et al., Click chemistry, a powerful tool for pharmaceutical sciences. Pharm Res. Oct. 2008;25(10):2216-30. doi: 10.1007/s11095-008-9616-1. Epub May 29, 2008.
Henrickson et al., Driven DNA transport into an asymmetric nanometer-scale pore. Phys Rev Lett. Oct. 2, 2000;85(14):3057-60.
Heredia et al., In vitro double transposition for DNA identification. Anal Biochem. Apr. 1, 2010;399(1):78-83. doi:10.1016/j.ab.2009.11.030. Epub Nov. 26, 2009.
Heron et al., Simultaneous measurement of ionic current and fluorescence from single protein pores. J Am Chem Soc. Feb. 11, 2009;131(5):1652-3. doi: 10.1021/ja808128s.
Hobbs et al., SSB protein limits RecOR binding onto single-stranded DNA. J Biol Chem. Apr. 13, 20073;282(15):11058-67. Epub Feb. 1, 2007.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hollis et al., Structure of the gene 2.5 protein, a single-stranded DNA binding protein encoded by bacteriophage T7. Proc Natl Acad Sci U S A. Aug. 15, 2001;98(17):9557-62. doi: 10.1073/pnas.171317698. Epub Jul. 31, 2001.
Hornblower et al., Single-molecule analysis of DNA-protein complexes using nanopores. Nat Methods. Apr. 2007;4(4):315-7. Epub Mar. 4, 2007.
Howorka et al., DNA Duplex Formation of Individual DNA Strands within a Single Protein Pore. Biophysical Journal, vol. 82{1, pt. 2):508a, No. 2482-Plat (2002).
Howorka et al., Improved protocol for high-throughput cysteine scanning mutagenesis. Biotechniques. Nov. 1998;25(5):764-6, 768, 770 passim.
Howorka et al., Kinetics of duplex formation for individual DNA strands within a single protein nanopore. Proc Natl Acad Sci U S A. Nov. 6, 2001;98(23):12996-3001. Epub Oct. 23, 2001.
Howorka et al., Probing distance and electrical potential within a protein pore with tethered DNA. Biophys J. Dec. 2002;83(6):3202-10.
Howorka et al., Sequence-specific detection of individual DNA strands using engineered nanopores. Nat Biotechnol. Jul. 2001;19(7):636-9.
Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.
Hwang et al., Electrical behavior of droplet interface bilayer networks: experimental analysis and modeling. J Am Chem Soc. Sep. 26, 2007;129(38):11854-64. Epub Sep. 1, 2007.
Hyland et al., The DNA binding domain of the gene 2.5 single-stranded DNA-binding protein of bacteriophage T7. J Biol Chem. Feb. 28, 2003;278(9):7247-56. doi: 10.1074/jbc.M210605200. Epub Dec. 20, 2002.
Jayasinghe et al., The leukocidin pore: evidence for an octamer with four LukF subunits and four LukS subunits alternating around a central axis. Protein Sci. Oct. 2005;14(10):2550-61.
Jung et al., The internal cavity of the staphylococcal alpha-hemolysin pore accommodates approximately 175 exogenous amino acid residues. Biochemistry. Jun. 28, 2005;44(25):8919-29.
Kahvejian et al., Making single-molecule sequencing a reality. American Laboratory. Jan. 1, 2008;40(20):48-53. www.americanlaboratory.com/913-Technical-Articles/780-Making-Single- Molecule-Sequencing-a-Reality/. Last accessed Dec. 10, 2021.
Kalisch et al., Covalently linked sequencing primer linkers (splinkers) for sequence analysis of restriction fragments. Gene. 1986;44(2-3):263-70.
Kanan et al., Reaction discovery enabled by DNA-templated synthesis and in vitro selection. Nature. Sep. 30, 2004;431(7008):545-9.
Kang et al., Single protein pores containing molecular adapters at high temperatures. Angew Chem Int Ed Engl. Feb. 25, 2005;44(10):1495-9.
Kasianowicz et al., Characterization of individual polynucleotide molecules using a membrane channel. Proc Natl Acad Sci U S A. Nov. 26, 1996;93(24):13770-3.
Keyser, Controlling molecular transport through nanopores. J R Soc Interface. Oct. 7, 2011;8(63):1369-78. doi: 10.1098/rsif.2011.0222. Epub Jun. 29, 2011.
Khulbe et al., DNA translocation through a-hemolysin nanopores with potential application to macromolecular data storage. Journal Applied Physics, vol. 97(104317):1-7 (2005).
Kocalka et al., Rapid and efficient DNA strand cross-linking by click chemistry. Chembiochem. May 23, 2008;9(8):1280-5. doi: 10.1002/cbic.200800006.
Kolb et al., Click Chemistry: Diverse Chemical Function from a Few Good Reactions. Angew Chem Int Ed Engl. Jun. 1, 2001;40(11):2004-2021.
Kovall et al., Toroidal structure of lambda-exonuclease. Science. Sep. 19, 1997;277(5333):1824-7.

(56) References Cited

OTHER PUBLICATIONS

Kozlov et al., Regulation of Single-stranded DNA Binding by the C Termini of *Esherichia coli* Single-stranded DNA-binding (SBB) Protein. J. Biol. Chem. May 28, 2010;285(22):17246-52.
Kuipers, Random mutagenesis by using mixtures of dNTP and dITP in PCR. Methods Mol Biol. 1996;57:351-6. doi: 10.1385/0-89603-332-5:351.
Langecker et al., Synthetic lipid membrane channels formed by designed DNA nanostructures. Science. Nov. 16, 2012;338(6109):932-6. doi: 10.1126/science.1225624.
Lazar et al., Transforming growth factor alpha: mutation of aspartic acid 47 and leucine 48 results in different biological activities. Mol Cell Biol. Mar. 1988;8(3):1247-52.
Li et al., DNA molecules and configurations in a solid-state nanopore microscope. Nat Mater. Sep. 2003;2(9):611-5. Epub Aug. 24, 2003.
Liang, Structure of outer membrane protein G by solution NMR spectroscopy. Proc Natl Acad Sci U S A. Oct. 9, 2007;104(41):16140-5. doi: 10.1073/pnas.0705466104. Epub Oct. 2, 2007.
Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Locher et al., Transmembrane signaling across the ligand-gated FhuA receptor: crystal structures of free and ferrichrome-bound states reveal allosteric changes. Cell. Dec. 11, 1998;95(6):771-8. doi: 10.1016/s0092-8674(00)81700-6.
Lovett et al., Identification and purification of a single-stranded-DNA-specific exonuclease encoded by the recJ gene of *Escherichia coli*. Proc Natl Acad Sci U S A. Apr. 1989;86(8):2627-31.
Lovrinovic et al., Rapid synthesis of DNA-cysteine conjugates for expressed protein ligation. Biochem Biophys Res Commun. Sep. 30, 2005;335(3):943-8.
Lu et al., Peptide inhibitors identify roles for SSB C-terminal residues in SSB/Exonuclease I complex formation. Biochemistry. Jul. 28, 2009; 48(29): 6764-6771. doi: 10.1021/bi900361r. Author Manuscript.
Lu et al., Structural basis of *Escherichia coli* single-stranded DNA-binding protein stimulation of exonuclease I. Proc Natl Acad Sci U S A. Jul. 8, 2008;105(27):9169-74. doi: 10.1073/pnas.0800741105. Epub Jun. 30, 2008.
Luo et al., Influence of polymer-pore interactions on translocation. Phys Rev Lett. Oct. 5, 2007;99(14):148102. Epub Oct. 1, 2007.
Lutz et al., Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.
Maglia et al., Analysis of single nucleic acid molecules with protein nanopores. Methods Enzymol. 2010;475:591-623. doi: 10.1016/S0076-6879(10)75022-9.
Maglia et al., Enhanced translocation of single DNA molecules through alpha-hemolysin nanopores by manipulation of internal charge. Proc Natl Acad Sci U S A. Dec. 16, 2008;105(50):19720-5. doi: 10.1073/pnas.0808296105. Epub Dec. 5, 2008.
Martin et al., Nanoscale protein pores modified with PAMAM dendrimers. J Am Chem Soc. Aug. 8, 2007;129(31):9640-9. Epub Jul. 18, 2007.
Martînez et al., The mRNA cap structure stimulates rate of poly(A) removal and amplifies processivity of degradation. J Biol Chem. Jul. 27, 2001;276(30):27923-9. Epub May 18, 2001.
Marziali et al., New DNA sequencing methods. Annu Rev Biomed Eng. 2001;3:195-223.
Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.
Matsuura et al., Real-time observation of a single DNA digestion by lambda exonuclease under a fluorescence microscope field. Nucleic Acids Res. Aug. 15, 2001;29(16):E79.
Meller et al., Rapid nanopore discrimination between single polynucleotide molecules. Proc Natl Acad Sci U S A. Feb. 1, 2000;97(3):1079-84.
Meller et al., Single molecule measurements of DNA transport through a nanopore. Electrophoresis. Aug. 2002;23(16):2583-91.
Meller, Dynamics of polynucleotide transport through nanometre-scale pores. Journal Physics: Condensed Matter, vol. 15:R581-R607 (2003).
Merzlyak et al., Conductance and ion selectivity of a mesoscopic protein nanopore probed with cysteine scanning mutagenesis. Biophys J. Nov. 2005;89(5):3059-70. Epub Aug. 5, 2005.
Miles et al., Single molecule sensing with solid-state nanopores: novel materials, methods, and applications. Chem Soc Rev. Jan. 7, 2013;42(1):15-28. doi: 10.1039/c2cs35286a. Epub Sep. 19, 2012.
Miner et al., Molecular barcodes detect redundancy and contamination in hairpin-bisulfite PCR. Nucleic Acids Res. 2004; 32(17): e135. EPub Sep. 30, 2004. doi: 10.1093/nar/gnh132.
Mitchell et al., Chemical tags facilitate the sensing of individual DNA strands with nanopores. Angew Chem Int Ed Engl. 2008;47(30):5565-8. doi: 10.1002/anie.200800183.
Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.
Mol et al., Structure and function of the multifunctional DNA-repair enzyme exonuclease III. Nature. Mar. 23, 1995;374(6520):381-6.
Montal et al., Formation of bimolecular membranes from lipid monolayers and a study of their electrical properties. Proc Natl Acad Sci U S A. Dec. 1972;69(12):3561-6.
Movileanu et al., Detecting protein analytes that modulate transmembrane movement of a polymer chain within a single protein pore. Nat Biotechnol. Oct. 2000;18(10):1091-5.
Movileanu et al., Location of a constriction in the lumen of a transmembrane pore by targeted covalent attachment of polymer molecules. J Gen Physiol. Mar. 2001;117(3):239-52.
Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.
Nakane et al., A nanosensor for transmembrane capture and identification of single nucleic Acid molecules. Biophys J. Jul. 2004;87(1):615-21. Erratum in: Biophys J. Nov. 2004;87(5):3618.
Nakane et al., Nanopore sensors for nucleic acid analysis. J. Phys.: Condens. Matter, vol. 15: R 1365-R1393 (2003).
Niemeyer et al., DNA-directed assembly of bienzymic complexes from in vivo biotinylated NAD(P)H:FMN oxidoreductase and luciferase. Chembiochem. Mar. 1, 2002;3(2-3):242-5.
Nikolov et al., Behavior of giant vesicles with anchored DNA molecules. Biophys J. Jun. 15, 2007;92(12):4356-68. Epub Mar. 23, 2007.
North et al., Host factors that promote transpososome disassembly and the PriA-PriC pathway for restart primosome assembly. Mol Microbiol. Jun. 2005;56(6):1601-16.
Nwe et al., Growing applications of "click chemistry" for bioconjugation in contemporary biomedical research. Cancer Biother Radiopharm. Jun. 2009;24(3):289-302. doi: 10.1089/cbr.2008.0626.
Paner et al., Studies of DNA dumbbells. III. Theoretical analysis of optical melting curves of dumbbells with a 16 base-pair duplex stem and Tn end loops (n=2, 3, 4, 6, 8, 10, 14). Biopolymers. Jul. 1992;32(7):881-92.
Paner et al., Studies of DNA dumbbells. VI. Analysis of optical melting curves of dumbbells with a sixteen-base pair duplex stem and end-loops of variable size and sequence. Biopolymers. Dec. 1996;39(6):779-93.
Pettersson et al., Generations of sequencing technologies. Genomics. Feb. 2009;93(2):105-11. doi: 10.1016/j.ygeno.2008.10.003. Epub Nov. 21, 2008.
Phoenix et al., OmpF-Lpp signal sequence mutants with varying charge hydrophobicity ratios provide evidence for a phosphatidylglycerol-signal sequence interaction during protein translocation across the *Escherichia coli* inner membrane. J Biol Chem. Aug. 15, 1993;268(23):17069-73.
Purnell et al., Nucleotide identification and orientation discrimination of DNA homopolymers immobilized in a protein nanopore. Nano Lett. Sep. 2008;8(9):3029-34. doi: 10.1021/n1802312f. Epub Aug. 13, 2008.
Rezende et al., Essential amino acid residues in the single-stranded DNA-binding protein of bacteriophage T7. Identification of the

(56) References Cited

OTHER PUBLICATIONS dimer interface. J Biol Chem. Dec. 27, 2002;277(52):50643-53. doi: 10.1074/jbc.M207359200. Epub Oct. 12, 2002.
Sanchez-Quesada et al., Cyclic Peptides as Molecular Adapters for a Pore-Forming Protein. Journal American Chemical Society, vol. 122(48):11757-11766 (2000).
Sanchez-Quesada et al., Single DNA rotaxanes of a transmembrane pore protein. Angew Chem Int Ed Engl. Jun. 7, 2004;43(23):3063-7.
Sanderson, Personal genomes: Standard and pores. Nature. Nov. 6, 2008;456(7218):23-5. doi: 10.1038/456023a.
Satapathy et al., ATPase activity of RecD is essential for growth of the Antarctic Pseudomonas syringae Lz4W at low temperature. Febs J. Apr. 2008;275(8):1835-51. doi: 10.1111/j.1742-4658.2008.06342.x. Epub Mar. 9, 2008.
Sauer-Budge et al., Unzipping kinetics of double-stranded DNA in a nanopore. Phys Rev Lett. Jun. 13, 2003;90(23):238101. Epub Jun. 9, 2003.
Schneider et al., DNA sequencing with nanopores. Nat Biotechnol. Apr. 10, 2012;30(4):326-8. doi: 10.1038/nbt.2181.
Seeman, Nucleic acid junctions and lattices. J Theor Biol. Nov. 21, 1982;99(2):237-47.
Seo et al., Click chemistry to construct fluorescent oligonucleotides for DNA sequencing. J Org Chem. Jan. 24, 2003;68(2):609-12.
Seol et al., Stretching of homopolymeric RNA reveals single-stranded helices and base-stacking. Phys Rev Lett. Apr. 13, 2007;98(15):158103. Epub Apr. 12, 2007.
Shank et al., Redesigning channel-forming peptides: amino acid substitutions that enhance rates of supramolecular self-assembly and raise ion transport activity. Biophys J. Mar. 15, 2006;90(6):2138-50. Epub Dec. 30, 2005.
Shendure et al., Overview of DNA sequencing strategies. Curr Protoc Mol Biol. Jan. 2008;Chapter 7:Unit 7.1. doi: 10.1002/0471142727.mb0701s81.
Shin et al., Kinetics of a reversible covalent-bond-forming reaction observed at the single-molecule level. Angew Chem Int Ed Engl. Oct. 4, 2002;41(19):3707-9; 3523.
Smeets et al., Salt dependence of ion transport and DNA translocation through solid-state nanopores. Nano Lett. Jan. 2006;6(1):89-95.
Smith et al., Capture, Unfolding, and Detection of Individual tRNA Molecules Using a Nanopore Device. Front Bioeng Biotechnol. Jun. 24, 2015;3:91. doi: 10.3389/fbioe.2015.00091.
Song et al., Structure of staphylococcal alpha-hemolysin, a heptameric transmembrane pore. Science. Dec. 13, 1996;274(5294):1859-66.
Spee et al., Efficient random mutagenesis method with adjustable mutation frequency by use of PCR and dITP. Nucleic Acids Res. Feb. 11, 1993;21(3):777-8. doi: 10.1093/nar/21.3.777.
Stoddart et al., Multiple base-recognition sites in a biological nanopore: two heads are better than one. Angew Chem Int Ed Engl. 2010;49(3):556-9. doi: 10.1002/anie.200905483.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Sutherland et al., An analysis of mismatched duplex DNA unzipping through a bacterial nanopore. Biochem Cell Biol. Jun. 2004;82(3):407-12.
Tadey et al., Capillary electrophoretic separation of nucleotide isomers via complexation with cyclodextrin and borate. J Chromatogr B Biomed Appl. Jul. 15, 1994;657(2):365-72.
Thomas et al., Processivity of DNA exonucleases. J Biol Chem. Jan. 25, 1978;253(2):424-9.
Tohda et al., "Channel Mimetic Sensing Membranes for Nucleotides Based on Multitopic Hydrogen Bonding," Israel Journal of Chemistry, vol. 37:267-275 (1997).
Travers et al., A flexible and efficient template format for circular consensus sequencing and SNP detection. Nucleic Acids Res. Aug. 2010;38(15):e159. doi: 10.1093/nar/gkq543. Epub Jun. 22, 2010.
Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.
Tung et al., Preparation and applications of peptide-oligonucleotide conjugates. Bioconjug Chem. Sep.-Oct. 2000;11(5):605-18.
United States District Court for the District of Delaware Order. *Pacific Biosciences of California, Inc.* v. *Oxford Nanopore Technolgoies, Inc.* Civil Action No. 17-275-RGA. Nov. 9, 2017.
Van De Goor, Nanopore Detection: Threading DNA Through a Tiny Hole. PharmaGenomics, vol. 4 (3):28-30 (2004).
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Venkatesan et al., Nanopore sensors for nucleic acid analysis. Nat Nanotechnol. Sep. 18, 2011;6(10):615-24. doi: 10.1038/nnano.2011.129.
Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.
Wang et al., A simple and reproducible method for directed evolution: combination of random mutation with dITP and DNA fragmentation with endonuclease V. Mol Biotechnol. Jan. 2013;53(1):49-54. doi: 10.1007/s12033-012-9516-9.
Wang et al., Bioconjugation by copper(I)-catalyzed azide-alkyne [3 + 2] cycloaddition. J Am Chem Soc. Mar. 19, 2003;125(11):3192-3.
Wang et al., Nanopores with a spark for single-molecule detection. Nat Biotechnol. Jul. 2001;19(7):622-3.
Wanunu et al., Discrimination of methylcytosine from hydroxymethylcytosine in DNA molecules. J Am Chem Soc. Jan. 26, 2011;133(3):486-92. doi:10.1021/ja107836t. Epub Dec. 14, 2010.
Wanunu et al., DNA translocation governed by interactions with solid-state nanopores. Biophys J. Nov. 15, 2008;95(10):4716-25. doi: 10.1529/biophysj.108.140475. Epub Aug. 15, 2008.
Wemmer et al., Preparation and melting of single strand circular DNA loops. Nucleic Acids Res. Dec. 9, 1985;13(23):8611-21.
Winters-Hilt et al., Highly accurate classification of Watson-Crick basepairs on termini of single DNA molecules. Biophys J. Feb. 2003;84(2 Pt 1):967-76.
Wolfe et al., Catalyzing the translocation of polypeptides through attractive interactions. J Am Chem Soc. Nov. 14, 2007;129(45):14034-41. Epub Oct. 19, 2007.
Wong et al., Polymer capture by electro-osmotic flow of oppositely charged nanopores. J Chem Phys. Apr. 28, 2007;126(16):164903.
Wu et al., Protein nanopores with covalently attached molecular adapters. J Am Chem Soc. Dec. 26, 20076;129(51):16142-8. Epub Nov. 30, 2007.
Xie et al., Single-molecule observation of the catalytic subunit of cAMP-dependent protein kinase binding to an inhibitor peptide. Chem Biol. Jan. 2005;12(1):109-20.
Yamagata et al., Overexpression, purification and characterization of RecJ protein from Thermus thermophilus HB8 and its core domain. Nucleic Acids Res. Nov. 15, 2001;29(22):4617-24.
Yamashita et al., Crystal structures of the OmpF porin: function in a colicin translocon. Embo J. Aug. 6, 2008;27(15):2171-80. doi: 10.1038/emboj.2008.137. Epub Jul. 17, 2008.
U.S. Appl. No. 17/509,988, filed Oct. 25, 2021, Stoddart et al.
U.S. Appl. No. 17/496,956, filed Oct. 8, 2021, Brown et al.
PCT/GB2013/051924, Oct. 9, 2013, International Search Report and Written Opinion.
PCT/GB2013/051924, Jan. 20, 2015, International Preliminary Report on Patentability.

* cited by examiner

SEQUENCE LISTING

```
<160> NUMBER OF SEQ ID NOS: 95

<210> SEQ ID NO 1
```

-continued

<211> LENGTH: 558
<212> TYPE: DNA
<213> ORGANISM: Artificial sequence
<220> FEATURE:
<223> OTHER INFORMATION: Mycobacterium smegmatis porin A mutant
(D90N/D91N/D93N/D118R/D134R/E139K)

<400> SEQUENCE: 1

```
atgggtctgg ataatgaact gagcctggtg gacggtcaag atcgtaccct gacggtgcaa     60

caatgggata cctttctgaa tggcgttttt ccgctggatc gtaatcgcct gacccgtgaa    120

tggtttcatt ccggtcgcgc aaaatatatc gtcgcaggcc cgggtgctga cgaattcgaa    180

ggcacgctgg aactgggtta tcagattggc tttccgtggt cactgggcgt tggtatcaac    240

ttctcgtaca ccacgccgaa tattctgatc aacaatggta acattaccgc accgccgttt    300

ggcctgaaca gcgtgattac gccgaacctg tttccgggtg ttagcatctc tgcccgtctg    360

ggcaatggtc cgggcattca agaagtggca acctttagtg tgcgcgtttc cggcgctaaa    420

ggcggtgtcg cggtgtctaa cgcccacggt accgttacgg gcgcggccgg cggtgtcctg    480

ctgcgtccgt tcgcgcgcct gattgcctct accggcgaca gcgttacgac ctatggcgaa    540

ccgtggaata tgaactaa                                                  558
```

<210> SEQ ID NO 2
<211> LENGTH: 184
<212> TYPE: PRT
<213> ORGANISM: Artificial sequence
<220> FEATURE:
<223> OTHER INFORMATION: Mycobacterium smegmatis porin A mutant
(D90N/D91N/D93N/D118R/D134R/E139K)

<400> SEQUENCE: 2

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 3
<211> LENGTH: 885

<212> TYPE: DNA
<213> ORGANISM: Artificial sequence
<220> FEATURE:
<223> OTHER INFORMATION: alpha-hemolysin mutant E111N/K147N

<400> SEQUENCE: 3

```
atggcagatt ctgatattaa tattaaaacc ggtactacag atattggaag caatactaca     60

gtaaaaacag gtgatttagt cacttatgat aaagaaaatg gcatgcacaa aaaagtattt    120

tatagtttta tcgatgataa aaatcacaat aaaaaactgc tagttattag aacaaaaggt    180

accattgctg gtcaatatag agtttatagc gaagaaggtg ctaacaaaag tggtttagcc    240

tggccttcag cctttaaggt acagttgcaa ctacctgata atgaagtagc tcaaatatct    300

gattactatc caagaaattc gattgataca aaaaactata tgagtacttt aacttatgga    360

ttcaacggta atgttactgg tgatgataca ggaaaaattg gcggccttat tggtgcaaat    420

gtttcgattg gtcatacact gaactatgtt caacctgatt tcaaaacaat tttagagagc    480

ccaactgata aaaaagtagg ctggaaagtg atatttaaca atatggtgaa tcaaaattgg    540

ggaccatacg atcgagattc ttggaacccg gtatatggca atcaactttt catgaaaact    600

agaaatggtt ctatgaaagc agcagataac ttccttgatc ctaacaaagc aagttctcta    660

ttatcttcag ggttttcacc agacttcgct acagttatta ctatggatag aaaagcatcc    720

aaacaacaaa caaatataga tgtaatatac gaacgagttc gtgatgatta ccaattgcat    780

tggacttcaa caaattggaa aggtaccaat actaaagata aatggacaga tcgttcttca    840

gaaagatata aaatcgattg ggaaaaagaa gaaatgacaa attaa                    885
```

<210> SEQ ID NO 4
<211> LENGTH: 293
<212> TYPE: PRT
<213> ORGANISM: Artificial sequence
<220> FEATURE:
<223> OTHER INFORMATION: alpha-hemolysin mutant E111N/K147N

<400> SEQUENCE: 4

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175
```

```
Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290


<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180


<210> SEQ ID NO 6
<211> LENGTH: 184
<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
1               5                   10                  15
```

```
Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180


<210> SEQ ID NO 7
<211> LENGTH: 183
<212> TYPE: PRT
<213> ORGANISM: Mycobacterium smegmatis

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180
```

<210> SEQ ID NO 8
<211> LENGTH: 8
<212> TYPE: PRT
<213> ORGANISM: Artificial sequence
<220> FEATURE:
<223> OTHER INFORMATION: Amino acid sequence of the Hel308 motif
<220> FEATURE:
<221> NAME/KEY: MISC_FEATURE
<222> LOCATION: (2)..(2)
<223> OTHER INFORMATION: Xaa = C, M or L
<220> FEATURE:
<221> NAME/KEY: MISC_FEATURE
<222> LOCATION: (3)..(3)
<223> OTHER INFORMATION: Xaa = any amino acid

<400> SEQUENCE: 8

```
Gln Xaa Xaa Gly Arg Ala Gly Arg
1               5
```

<210> SEQ ID NO 9
<211> LENGTH: 9
<212> TYPE: PRT
<213> ORGANISM: Artificial sequence
<220> FEATURE:
<223> OTHER INFORMATION: Amino acid sequence of the extended Hel308 motif
<220> FEATURE:
<221> NAME/KEY: MISC_FEATURE
<222> LOCATION: (2)..(2)
<223> OTHER INFORMATION: Xaa = C, M or L
<220> FEATURE:
<221> NAME/KEY: MISC_FEATURE
<222> LOCATION: (3)..(3)
<223> OTHER INFORMATION: Xaa = any amino acid

<400> SEQUENCE: 9

```
Gln Xaa Xaa Gly Arg Ala Gly Arg Pro
1               5
```

<210> SEQ ID NO 10
<211> LENGTH: 760
<212> TYPE: PRT
<213> ORGANISM: Methanococcoides burtonii

<400> SEQUENCE: 10

```
Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
            20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
            100                 105                 110

Val Asn Asp Ile Ile Val Ala Thr Ser Glu Lys Thr Asp Ser Leu Leu
        115                 120                 125

Arg Asn Gly Thr Ser Trp Met Asp Glu Ile Thr Thr Val Val Val Asp
    130                 135                 140

Glu Ile His Leu Leu Asp Ser Lys Asn Arg Gly Pro Thr Leu Glu Val
145                 150                 155                 160
```

-continued

```
Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
        195                 200                 205

Val Leu Phe Gly Asp Ala Ile Asn Phe Pro Gly Ser Gln Lys Lys Ile
    210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser
        275                 280                 285

Thr Gly Glu Thr Asp Thr Ala Ile Val Leu Ala Asn Cys Ile Arg Lys
    290                 295                 300

Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Arg Arg Phe Asp Ser Asn Phe Gly Met Gln Pro Ile Pro
        355                 360                 365

Val Leu Glu Tyr Lys Gln Met Ala Gly Arg Ala Gly Arg Pro His Leu
    370                 375                 380

Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
                405                 410                 415

Ser Lys Leu Gly Thr Glu Asn Ala Leu Arg Thr His Val Leu Ser Thr
            420                 425                 430

Ile Val Asn Gly Phe Ala Ser Thr Arg Gln Glu Leu Phe Asp Phe Phe
        435                 440                 445

Gly Ala Thr Phe Phe Ala Tyr Gln Gln Asp Lys Trp Met Leu Glu Glu
    450                 455                 460

Val Ile Asn Asp Cys Leu Glu Phe Leu Ile Asp Lys Ala Met Val Ser
465                 470                 475                 480

Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
            500                 505                 510

Ser Lys Ile Val Asp Gly Phe Lys Asp Ile Gly Lys Ser Thr Gly Gly
        515                 520                 525

Asn Met Gly Ser Leu Glu Asp Asp Lys Gly Asp Asp Ile Thr Val Thr
    530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575
```

Ala His Ser Asp Glu Phe His Glu Ile Pro Asp Lys Leu Lys Glu Thr
580 585 590

Asp Tyr Glu Trp Phe Met Gly Glu Val Lys Thr Ala Met Leu Leu Glu
595 600 605

Glu Trp Val Thr Glu Val Ser Ala Glu Asp Ile Thr Arg His Phe Asn
610 615 620

Val Gly Glu Gly Asp Ile His Ala Leu Ala Asp Thr Ser Glu Trp Leu
625 630 635 640

Met His Ala Ala Ala Lys Leu Ala Glu Leu Leu Gly Val Glu Tyr Ser
645 650 655

Ser His Ala Tyr Ser Leu Glu Lys Arg Ile Arg Tyr Gly Ser Gly Leu
660 665 670

Asp Leu Met Glu Leu Val Gly Ile Arg Gly Val Gly Arg Val Arg Ala
675 680 685

Arg Lys Leu Tyr Asn Ala Gly Phe Val Ser Val Ala Lys Leu Lys Gly
690 695 700

Ala Asp Ile Ser Val Leu Ser Lys Leu Val Gly Pro Lys Val Ala Tyr
705 710 715 720

Asn Ile Leu Ser Gly Ile Gly Val Arg Val Asn Asp Lys His Phe Asn
725 730 735

Ser Ala Pro Ile Ser Ser Asn Thr Leu Asp Thr Leu Leu Asp Lys Asn
740 745 750

Gln Lys Thr Phe Asn Asp Phe Gln
755 760

<210> SEQ ID NO 11
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 11

Gln Met Ala Gly Arg Ala Gly Arg
1 5

<210> SEQ ID NO 12
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 12

Gln Met Ala Gly Arg Ala Gly Arg Pro
1 5

<210> SEQ ID NO 13
<211> LENGTH: 707
<212> TYPE: PRT
<213> ORGANISM: Cenarchaeum symbiosum

<400> SEQUENCE: 13

Met Arg Ile Ser Glu Leu Asp Ile Pro Arg Pro Ala Ile Glu Phe Leu
1 5 10 15

Glu Gly Glu Gly Tyr Lys Lys Leu Tyr Pro Pro Gln Ala Ala Ala Ala
20 25 30

Lys Ala Gly Leu Thr Asp Gly Lys Ser Val Leu Val Ser Ala Pro Thr
35 40 45

-continued

```
Ala Ser Gly Lys Thr Leu Ile Ala Ala Ile Ala Met Ile Ser His Leu
    50                  55                  60

Ser Arg Asn Arg Gly Lys Ala Val Tyr Leu Ser Pro Leu Arg Ala Leu
65                  70                  75                  80

Ala Ala Glu Lys Phe Ala Glu Phe Gly Lys Ile Gly Gly Ile Pro Leu
                85                  90                  95

Gly Arg Pro Val Arg Val Gly Val Ser Thr Gly Asp Phe Glu Lys Ala
            100                 105                 110

Gly Arg Ser Leu Gly Asn Asn Asp Ile Leu Val Leu Thr Asn Glu Arg
        115                 120                 125

Met Asp Ser Leu Ile Arg Arg Arg Pro Asp Trp Met Asp Glu Val Gly
    130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
            180                 185                 190

Ala Gly Trp Leu Asp Cys Thr Leu Val His Ser Thr Trp Arg Pro Val
        195                 200                 205

Pro Leu Ser Glu Gly Val Tyr Gln Asp Gly Glu Val Ala Met Gly Asp
    210                 215                 220

Gly Ser Arg His Glu Val Ala Ala Thr Gly Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
            260                 265                 270

Ile Pro Glu Ala Lys Gly Ala Asp Ala Ala Lys Leu Ala Ala Ala Ala
        275                 280                 285

Lys Lys Ile Ile Ser Ser Gly Gly Glu Thr Lys Leu Ala Lys Thr Leu
    290                 295                 300

Ala Glu Leu Val Glu Lys Gly Ala Ala Phe His His Ala Gly Leu Asn
305                 310                 315                 320

Gln Asp Cys Arg Ser Val Val Glu Glu Glu Phe Arg Ser Gly Arg Ile
                325                 330                 335

Arg Leu Leu Ala Ser Thr Pro Thr Leu Ala Ala Gly Val Asn Leu Pro
            340                 345                 350

Ala Arg Arg Val Val Ile Ser Ser Val Met Arg Tyr Asn Ser Ser Ser
        355                 360                 365

Gly Met Ser Glu Pro Ile Ser Ile Leu Glu Tyr Lys Gln Leu Cys Gly
    370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Gly Glu
                405                 410                 415

Pro Glu Pro Ile Arg Ser Ala Met Val Asp Asp Arg Ala Leu Arg Ile
            420                 425                 430

His Val Leu Ser Leu Val Thr Thr Ser Pro Gly Ile Lys Glu Asp Asp
        435                 440                 445

Val Thr Glu Phe Phe Leu Gly Thr Leu Gly Gly Gln Gln Ser Gly Glu
    450                 455                 460

Ser Thr Val Lys Phe Ser Val Ala Val Ala Leu Arg Phe Leu Gln Glu
```

465 470 475 480

Glu Gly Met Leu Gly Arg Arg Gly Gly Arg Leu Ala Ala Thr Lys Met
485 490 495

Gly Arg Leu Val Ser Arg Leu Tyr Met Asp Pro Met Thr Ala Val Thr
500 505 510

Leu Arg Asp Ala Val Gly Glu Ala Ser Pro Gly Arg Met His Thr Leu
515 520 525

Gly Phe Leu His Leu Val Ser Glu Cys Ser Glu Phe Met Pro Arg Phe
530 535 540

Ala Leu Arg Gln Lys Asp His Glu Val Ala Glu Met Met Leu Glu Ala
545 550 555 560

Gly Arg Gly Glu Leu Leu Arg Pro Val Tyr Ser Tyr Glu Cys Gly Arg
565 570 575

Gly Leu Leu Ala Leu His Arg Trp Ile Gly Glu Ser Pro Glu Ala Lys
580 585 590

Leu Ala Glu Asp Leu Lys Phe Glu Ser Gly Asp Val His Arg Met Val
595 600 605

Glu Ser Ser Gly Trp Leu Leu Arg Cys Ile Trp Glu Ile Ser Lys His
610 615 620

Gln Glu Arg Pro Asp Leu Leu Gly Glu Leu Asp Val Leu Arg Ser Arg
625 630 635 640

Val Ala Tyr Gly Ile Lys Ala Glu Leu Val Pro Leu Val Ser Ile Lys
645 650 655

Gly Ile Gly Arg Val Arg Ser Arg Arg Leu Phe Arg Gly Gly Ile Lys
660 665 670

Gly Pro Gly Asp Leu Ala Ala Val Pro Val Glu Arg Leu Ser Arg Val
675 680 685

Glu Gly Ile Gly Ala Thr Leu Ala Asn Asn Ile Lys Ser Gln Leu Arg
690 695 700

Lys Gly Gly
705

<210> SEQ ID NO 14
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 14

Gln Leu Cys Gly Arg Ala Gly Arg
1 5

<210> SEQ ID NO 15
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 15

Gln Leu Cys Gly Arg Ala Gly Arg Pro
1 5

<210> SEQ ID NO 16
<211> LENGTH: 720
<212> TYPE: PRT
<213> ORGANISM: Thermococcus gammatolerans

```
<400> SEQUENCE: 16

Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
            20                  25                  30

Lys Ser Gly Ala Leu Glu Gly Arg Asn Leu Val Leu Ala Ile Pro Thr
        35                  40                  45

Ala Ser Gly Lys Thr Leu Val Ser Glu Ile Val Met Val Asn Lys Leu
    50                  55                  60

Ile Gln Glu Gly Gly Lys Ala Val Tyr Leu Val Pro Leu Lys Ala Leu
65                  70                  75                  80

Ala Glu Glu Lys Tyr Arg Glu Phe Lys Glu Trp Glu Lys Leu Gly Leu
                85                  90                  95

Lys Val Ala Ala Thr Thr Gly Asp Tyr Asp Ser Thr Asp Asp Trp Leu
            100                 105                 110

Gly Arg Tyr Asp Ile Ile Val Ala Thr Ala Glu Lys Phe Asp Ser Leu
        115                 120                 125

Leu Arg His Gly Ala Arg Trp Ile Asn Asp Val Lys Leu Val Val Ala
    130                 135                 140

Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser
                165                 170                 175

Ala Thr Val Gly Asn Ala Glu Glu Leu Ala Glu Trp Leu Asp Ala Ser
            180                 185                 190

Leu Val Val Ser Asp Trp Arg Pro Val Gln Leu Arg Arg Gly Val Phe
        195                 200                 205

His Leu Gly Thr Leu Ile Trp Glu Asp Gly Lys Val Glu Ser Tyr Pro
    210                 215                 220

Glu Asn Trp Tyr Ser Leu Val Val Asp Ala Val Lys Arg Gly Lys Gly
225                 230                 235                 240

Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
            260                 265                 270

Ala Leu Glu Ser Leu Ala Ser Gln Leu Glu Asp Asn Pro Thr Ser Glu
        275                 280                 285

Lys Leu Lys Arg Ala Leu Arg Gly Gly Val Ala Phe His His Ala Gly
    290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                325                 330                 335

Leu Pro Ser Phe Arg Val Ile Ile Arg Asp Thr Lys Arg Tyr Ala Gly
            340                 345                 350

Phe Gly Trp Thr Asp Ile Pro Val Leu Glu Ile Gln Gln Met Met Gly
        355                 360                 365

Arg Ala Gly Arg Pro Arg Tyr Asp Lys Tyr Gly Glu Ala Ile Ile Val
    370                 375                 380

Ala Arg Thr Asp Glu Pro Gly Lys Leu Met Glu Arg Tyr Ile Arg Gly
385                 390                 395                 400

Lys Pro Glu Lys Leu Phe Ser Met Leu Ala Asn Glu Gln Ala Phe Arg
                405                 410                 415
```

Ser Gln Val Leu Ala Leu Ile Thr Asn Phe Gly Ile Arg Ser Phe Pro
420 425 430

Glu Leu Val Arg Phe Leu Glu Arg Thr Phe Tyr Ala His Gln Arg Lys
435 440 445

Asp Leu Ser Ser Leu Glu Tyr Lys Ala Lys Glu Val Val Tyr Phe Leu
450 455 460

Ile Glu Asn Glu Phe Ile Asp Leu Asp Leu Glu Asp Arg Phe Ile Pro
465 470 475 480

Leu Pro Phe Gly Lys Arg Thr Ser Gln Leu Tyr Ile Asp Pro Leu Thr
485 490 495

Ala Lys Lys Phe Lys Asp Ala Phe Pro Ala Ile Glu Arg Asn Pro Asn
500 505 510

Pro Phe Gly Ile Phe Gln Leu Ile Ala Ser Thr Pro Asp Met Ala Thr
515 520 525

Leu Thr Ala Arg Arg Arg Glu Met Glu Asp Tyr Leu Asp Leu Ala Tyr
530 535 540

Glu Leu Glu Asp Lys Leu Tyr Ala Ser Ile Pro Tyr Tyr Glu Asp Ser
545 550 555 560

Arg Phe Gln Gly Phe Leu Gly Gln Val Lys Thr Ala Lys Val Leu Leu
565 570 575

Asp Trp Ile Asn Glu Val Pro Glu Ala Arg Ile Tyr Glu Thr Tyr Ser
580 585 590

Ile Asp Pro Gly Asp Leu Tyr Arg Leu Leu Glu Leu Ala Asp Trp Leu
595 600 605

Met Tyr Ser Leu Ile Glu Leu Tyr Lys Leu Phe Glu Pro Lys Glu Glu
610 615 620

Ile Leu Asn Tyr Leu Arg Asp Leu His Leu Arg Leu Arg His Gly Val
625 630 635 640

Arg Glu Glu Leu Leu Glu Leu Val Arg Leu Pro Asn Ile Gly Arg Lys
645 650 655

Arg Ala Arg Ala Leu Tyr Asn Ala Gly Phe Arg Ser Val Glu Ala Ile
660 665 670

Ala Asn Ala Lys Pro Ala Glu Leu Leu Ala Val Glu Gly Ile Gly Ala
675 680 685

Lys Ile Leu Asp Gly Ile Tyr Arg His Leu Gly Ile Glu Lys Arg Val
690 695 700

Thr Glu Glu Lys Pro Lys Arg Lys Gly Thr Leu Glu Asp Phe Leu Arg
705 710 715 720

<210> SEQ ID NO 17
<211> LENGTH: 8
<212> TYPE: PRT
<213> ORGANISM: Artificial sequence
<220> FEATURE:
<223> OTHER INFORMATION: Exemplary extended Hel308 motif

<400> SEQUENCE: 17

Gln Met Met Gly Arg Ala Gly Arg
1 5

<210> SEQ ID NO 18
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 18

Gln Met Met Gly Arg Ala Gly Arg Pro
1 5

<210> SEQ ID NO 19
<211> LENGTH: 799
<212> TYPE: PRT
<213> ORGANISM: Methanospirillum hungatei

<400> SEQUENCE: 19

Met Glu Ile Ala Ser Leu Pro Leu Pro Asp Ser Phe Ile Arg Ala Cys
1 5 10 15

His Ala Lys Gly Ile Arg Ser Leu Tyr Pro Pro Gln Ala Glu Cys Ile
20 25 30

Glu Lys Gly Leu Leu Glu Gly Lys Asn Leu Leu Ile Ser Ile Pro Thr
35 40 45

Ala Ser Gly Lys Thr Leu Leu Ala Glu Met Ala Met Trp Ser Arg Ile
50 55 60

Ala Ala Gly Gly Lys Cys Leu Tyr Ile Val Pro Leu Arg Ala Leu Ala
65 70 75 80

Ser Glu Lys Tyr Asp Glu Phe Ser Lys Lys Gly Val Ile Arg Val Gly
85 90 95

Ile Ala Thr Gly Asp Leu Asp Arg Thr Asp Ala Tyr Leu Gly Glu Asn
100 105 110

Asp Ile Ile Val Ala Thr Ser Glu Lys Thr Asp Ser Leu Leu Arg Asn
115 120 125

Arg Thr Pro Trp Leu Ser Gln Ile Thr Cys Ile Val Leu Asp Glu Val
130 135 140

His Leu Ile Gly Ser Glu Asn Arg Gly Ala Thr Leu Glu Met Val Ile
145 150 155 160

Thr Lys Leu Arg Tyr Thr Asn Pro Val Met Gln Ile Ile Gly Leu Ser
165 170 175

Ala Thr Ile Gly Asn Pro Ala Gln Leu Ala Glu Trp Leu Asp Ala Thr
180 185 190

Leu Ile Thr Ser Thr Trp Arg Pro Val Asp Leu Arg Gln Gly Val Tyr
195 200 205

Tyr Asn Gly Lys Ile Arg Phe Ser Asp Ser Glu Arg Pro Ile Gln Gly
210 215 220

Lys Thr Lys His Asp Asp Leu Asn Leu Cys Leu Asp Thr Ile Glu Glu
225 230 235 240

Gly Gly Gln Cys Leu Val Phe Val Ser Ser Arg Arg Asn Ala Glu Gly
245 250 255

Phe Ala Lys Lys Ala Ala Gly Ala Leu Lys Ala Gly Ser Pro Asp Ser
260 265 270

Lys Ala Leu Ala Gln Glu Leu Arg Arg Leu Arg Asp Arg Asp Glu Gly
275 280 285

Asn Val Leu Ala Asp Cys Val Glu Arg Gly Ala Ala Phe His His Ala
290 295 300

Gly Leu Ile Arg Gln Glu Arg Thr Ile Ile Glu Glu Gly Phe Arg Asn
305 310 315 320

Gly Tyr Ile Glu Val Ile Ala Ala Thr Pro Thr Leu Ala Ala Gly Leu
325 330 335

Asn Leu Pro Ala Arg Arg Val Ile Ile Arg Asp Tyr Asn Arg Phe Ala
340 345 350

-continued

```
Ser Gly Leu Gly Met Val Pro Ile Pro Val Gly Glu Tyr His Gln Met
        355                 360                 365

Ala Gly Arg Ala Gly Arg Pro His Leu Asp Pro Tyr Gly Glu Ala Val
    370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
                405                 410                 415

Ser Leu Cys Ala His Ile Leu Ser Leu Ile Ala Thr Gly Phe Ala His
            420                 425                 430

Asp Gln Glu Ala Leu Ser Ser Phe Met Glu Arg Thr Phe Tyr Phe Phe
        435                 440                 445

Gln His Pro Lys Thr Arg Ser Leu Pro Arg Leu Val Ala Asp Ala Ile
    450                 455                 460

Arg Phe Leu Thr Thr Ala Gly Met Val Glu Glu Arg Glu Asn Thr Leu
465                 470                 475                 480

Ser Ala Thr Arg Leu Gly Ser Leu Val Ser Arg Leu Tyr Leu Asn Pro
                485                 490                 495

Cys Thr Ala Arg Leu Ile Leu Asp Ser Leu Lys Ser Cys Lys Thr Pro
            500                 505                 510

Thr Leu Ile Gly Leu Leu His Val Ile Cys Val Ser Pro Asp Met Gln
        515                 520                 525

Arg Leu Tyr Leu Lys Ala Ala Asp Thr Gln Leu Leu Arg Thr Phe Leu
    530                 535                 540

Phe Lys His Lys Asp Asp Leu Ile Leu Pro Leu Pro Phe Glu Gln Glu
545                 550                 555                 560

Glu Glu Glu Leu Trp Leu Ser Gly Leu Lys Thr Ala Leu Val Leu Thr
                565                 570                 575

Asp Trp Ala Asp Glu Phe Ser Glu Gly Met Ile Glu Glu Arg Tyr Gly
            580                 585                 590

Ile Gly Ala Gly Asp Leu Tyr Asn Ile Val Asp Ser Gly Lys Trp Leu
        595                 600                 605

Leu His Gly Thr Glu Arg Leu Val Ser Val Glu Met Pro Glu Met Ser
    610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                645                 650                 655

Arg Thr Leu Tyr Asn Ala Gly Tyr Pro Asp Pro Glu Ala Val Ala Arg
            660                 665                 670

Ala Gly Leu Ser Thr Ile Ala Arg Ile Ile Gly Glu Gly Ile Ala Arg
        675                 680                 685

Gln Val Ile Asp Glu Ile Thr Gly Val Lys Arg Ser Gly Ile His Ser
    690                 695                 700

Ser Asp Asp Asp Tyr Gln Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
                725                 730                 735

Ile Thr Val Ser Asp Leu Leu Thr Ala Asp Glu Val Leu Leu Ser Asp
            740                 745                 750

Val Leu Gly Ala Ala Arg Ala Arg Lys Val Leu Ala Phe Leu Ser Asn
        755                 760                 765

Ser Glu Lys Glu Asn Ser Ser Ser Asp Lys Thr Glu Glu Ile Pro Asp
```

```
    770                 775                 780

Thr Gln Lys Ile Arg Gly Gln Ser Ser Trp Glu Asp Phe Gly Cys
785                 790                 795


<210> SEQ ID NO 20
<211> LENGTH: 8
<212> TYPE: PRT
<213> ORGANISM: Artificial sequence
<220> FEATURE:
<223> OTHER INFORMATION: RecD-like motif I
<220> FEATURE:
<221> NAME/KEY: MISC_FEATURE
<222> LOCATION: (1)..(1)
<223> OTHER INFORMATION: Xaa = G, S or A
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = P, A, S or G
<220> FEATURE:
<221> NAME/KEY: MISC_FEATURE
<222> LOCATION: (5)..(5)
<223> OTHER INFORMATION: Xaa = T, A, V, S or C
<220> FEATURE:
<221> NAME/KEY: MISC_FEATURE
<222> LOCATION: (6)..(6)
<223> OTHER INFORMATION: Xaa = G or A
<220> FEATURE:
<221> NAME/KEY: MISC_FEATURE
<222> LOCATION: (7)..(7)
<223> OTHER INFORMATION: Xaa = K or R
<220> FEATURE:
<221> NAME/KEY: MISC_FEATURE
<222> LOCATION: (8)..(8)
<223> OTHER INFORMATION: Xaa = T or S

<400> SEQUENCE: 20

Xaa Xaa Xaa Gly Xaa Xaa Xaa Xaa
1               5


<210> SEQ ID NO 21
<211> LENGTH: 25
<212> TYPE: PRT
<213> ORGANISM: Artificial sequence
<220> FEATURE:
<223> OTHER INFORMATION: Extended RecD-like motif I
<220> FEATURE:
<221> NAME/KEY: MISC_FEATURE
<222> LOCATION: (2)..(17)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = G, S or A
<220> FEATURE:
<221> NAME/KEY: MISC_FEATURE
<222> LOCATION: (19)..(19)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = P, A, S or G
<220> FEATURE:
<221> NAME/KEY: MISC_FEATURE
<222> LOCATION: (22)..(22)
<223> OTHER INFORMATION: Xaa = T, A, V, S or C
<220> FEATURE:
<221> NAME/KEY: MISC_FEATURE
<222> LOCATION: (23)..(23)
<223> OTHER INFORMATION: Xaa = G or A
<220> FEATURE:
<221> NAME/KEY: MISC_FEATURE
```

<222> LOCATION: (24)..(24)
<223> OTHER INFORMATION: Xaa = K or R
<220> FEATURE:
<221> NAME/KEY: MISC_FEATURE
<222> LOCATION: (25)..(25)
<223> OTHER INFORMATION: Xaa = T or S

<400> SEQUENCE: 21

```
Gln Xaa Xaa Xaa Xaa Xaa Xaa Xaa Xaa Xaa Xaa Xaa Xaa Xaa Xaa Xaa
1               5                   10                  15

Xaa Xaa Xaa Xaa Gly Xaa Xaa Xaa Xaa
            20                  25
```

<210> SEQ ID NO 22
<211> LENGTH: 26
<212> TYPE: PRT
<213> ORGANISM: Artificial sequence
<220> FEATURE:
<223> OTHER INFORMATION: Extended RecD-like motif I
<220> FEATURE:
<221> NAME/KEY: MISC_FEATURE
<222> LOCATION: (2)..(18)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = G, S or A
<220> FEATURE:
<221> NAME/KEY: MISC_FEATURE
<222> LOCATION: (20)..(20)
<223> OTHER INFORMATION: Xaa = any amino acid
<220> FEATURE:
<221> NAME/KEY: MISC_FEATURE
<222> LOCATION: (21)..(21)
<223> OTHER INFORMATION: Xaa = P, A, S or G
<220> FEATURE:
<221> NAME/KEY: MISC_FEATURE
<222> LOCATION: (23)..(23)
<223> OTHER INFORMATION: Xaa = T, A, V, S or C
<220> FEATURE:
<221> NAME/KEY: MISC_FEATURE
<222> LOCATION: (24)..(24)
<223> OTHER INFORMATION: Xaa = G or A
<220> FEATURE:
<221> NAME/KEY: MISC_FEATURE
<222> LOCATION: (25)..(25)
<223> OTHER INFORMATION: Xaa = K or A
<220> FEATURE:
<221> NAME/KEY: MISC_FEATURE
<222> LOCATION: (26)..(26)
<223> OTHER INFORMATION: Xaa = T or S

<400> SEQUENCE: 22

```
Gln Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Gly Xaa Xaa Xaa Xaa
            20                  25
```

<210> SEQ ID NO 23
<211> LENGTH: 27
<212> TYPE: PRT
<213> ORGANISM: Artificial sequence
<220> FEATURE:
<223> OTHER INFORMATION: Extended RecD-like motif I
<220> FEATURE:
<221> NAME/KEY: MISC_FEATURE
<222> LOCATION: (2)..(19)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = G, S or A
<220> FEATURE:

<221> NAME/KEY: MISC_FEATURE
<222> LOCATION: (21)..(21)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = P, A, S or G
<220> FEATURE:
<221> NAME/KEY: MISC_FEATURE
<222> LOCATION: (24)..(24)
<223> OTHER INFORMATION: Xaa = T, A, V, S or C
<220> FEATURE:
<221> NAME/KEY: MISC_FEATURE
<222> LOCATION: (25)..(25)
<223> OTHER INFORMATION: Xaa = G or A
<220> FEATURE:
<221> NAME/KEY: MISC_FEATURE
<222> LOCATION: (26)..(26)
<223> OTHER INFORMATION: Xaa = K or R
<220> FEATURE:
<221> NAME/KEY: MISC_FEATURE
<222> LOCATION: (27)..(27)
<223> OTHER INFORMATION: Xaa = T or S

<400> SEQUENCE: 23

```
Gln Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Gly Xaa Xaa Xaa Xaa
            20                  25
```

<210> SEQ ID NO 24
<211> LENGTH: 8
<212> TYPE: PRT
<213> ORGANISM: Artificial sequence
<220> FEATURE:
<223> OTHER INFORMATION: RecD motif I
<220> FEATURE:
<221> NAME/KEY: MISC_FEATURE
<222> LOCATION: (5)..(5)
<223> OTHER INFORMATION: Xaa = T, V or C
<220> FEATURE:
<221> NAME/KEY: MISC_FEATURE
<222> LOCATION: (8)..(8)
<223> OTHER INFORMATION: Xaa = T or S

<400> SEQUENCE: 24

```
Gly Gly Pro Gly Xaa Gly Lys Xaa
1               5
```

<210> SEQ ID NO 25
<211> LENGTH: 8
<212> TYPE: PRT
<213> ORGANISM: Artificial sequence
<220> FEATURE:
<223> OTHER INFORMATION: Preferred RecD motif I

<400> SEQUENCE: 25

```
Gly Gly Pro Gly Thr Gly Lys Thr
1               5
```

<210> SEQ ID NO 26
<211> LENGTH: 25
<212> TYPE: PRT
<213> ORGANISM: Artificial sequence
<220> FEATURE:
<223> OTHER INFORMATION: Extended RecD motif I
<220> FEATURE:
<221> NAME/KEY: MISC_FEATURE
<222> LOCATION: (2)..(17)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = T, V or C
<220> FEATURE:
<221> NAME/KEY: MISC_FEATURE
<222> LOCATION: (25)..(25)
<223> OTHER INFORMATION: Xaa = T or S

<400> SEQUENCE: 26

Gln Xaa Xaa Xaa Xaa Xaa Xaa Xaa Xaa Xaa Xaa Xaa Xaa Xaa Xaa Xaa
1 5 10 15

Xaa Gly Gly Pro Gly Xaa Gly Lys Xaa
20 25

<210> SEQ ID NO 27
<211> LENGTH: 26
<212> TYPE: PRT
<213> ORGANISM: Artificial sequence
<220> FEATURE:
<223> OTHER INFORMATION: Extended RecD motif I
<220> FEATURE:
<221> NAME/KEY: MISC_FEATURE
<222> LOCATION: (2)..(18)
<223> OTHER INFORMATION: Xaa = any amino acid
<220> FEATURE:
<221> NAME/KEY: MISC_FEATURE
<222> LOCATION: (23)..(23)
<223> OTHER INFORMATION: Xaa = T, V or C
<220> FEATURE:
<221> NAME/KEY: MISC_FEATURE
<222> LOCATION: (26)..(26)
<223> OTHER INFORMATION: Xaa = T or S

<400> SEQUENCE: 27

Gln Xaa Xaa Xaa Xaa Xaa Xaa Xaa Xaa Xaa Xaa Xaa Xaa Xaa Xaa Xaa
1 5 10 15

Xaa Xaa Gly Gly Pro Gly Xaa Gly Lys Xaa
20 25

<210> SEQ ID NO 28
<211> LENGTH: 27
<212> TYPE: PRT
<213> ORGANISM: Artificial sequence
<220> FEATURE:
<223> OTHER INFORMATION: Extended RecD motif I
<220> FEATURE:
<221> NAME/KEY: MISC_FEATURE
<222> LOCATION: (2)..(19)
<223> OTHER INFORMATION: Xaa = any amino acid
<220> FEATURE:
<221> NAME/KEY: MISC_FEATURE
<222> LOCATION: (24)..(24)
<223> OTHER INFORMATION: Xaa = T, V or C
<220> FEATURE:
<221> NAME/KEY: MISC_FEATURE
<222> LOCATION: (27)..(27)
<223> OTHER INFORMATION: Xaa = T or S

<400> SEQUENCE: 28

Gln Xaa Xaa Xaa Xaa Xaa Xaa Xaa Xaa Xaa Xaa Xaa Xaa Xaa Xaa Xaa
1 5 10 15

Xaa Xaa Xaa Gly Gly Pro Gly Xaa Gly Lys Xaa
20 25

<210> SEQ ID NO 29
<211> LENGTH: 10
<212> TYPE: PRT
<213> ORGANISM: Artificial sequence
<220> FEATURE:
<223> OTHER INFORMATION: RecD-like motif V
<220> FEATURE:

<221> NAME/KEY: MISC_FEATURE
<222> LOCATION: (1)..(1)
<223> OTHER INFORMATION: Xaa = Y, W or F
<220> FEATURE:
<221> NAME/KEY: MISC_FEATURE
<222> LOCATION: (2)..(2)
<223> OTHER INFORMATION: Xaa = A, T, S, M, C or V
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = T, N or S
<220> FEATURE:
<221> NAME/KEY: MISC_FEATURE
<222> LOCATION: (5)..(5)
<223> OTHER INFORMATION: Xaa = A, T, G, S, V or I
<220> FEATURE:
<221> NAME/KEY: MISC_FEATURE
<222> LOCATION: (6)..(8)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa = G or S

<400> SEQUENCE: 29

Xaa Xaa Xaa Xaa Xaa Xaa Xaa Xaa Gln Xaa
1 5 10

<210> SEQ ID NO 30
<211> LENGTH: 10
<212> TYPE: PRT
<213> ORGANISM: Artificial sequence
<220> FEATURE:
<223> OTHER INFORMATION: RecD motif V
<220> FEATURE:
<221> NAME/KEY: MISC_FEATURE
<222> LOCATION: (1)..(1)
<223> OTHER INFORMATION: Xaa = Y, W or F
<220> FEATURE:
<221> NAME/KEY: MISC_FEATURE
<222> LOCATION: (2)..(2)
<223> OTHER INFORMATION: Xaa = A, M, C or V
<220> FEATURE:
<221> NAME/KEY: MISC_FEATURE
<222> LOCATION: (3)..(3)
<223> OTHER INFORMATION: Xaa = I, M or L
<220> FEATURE:
<221> NAME/KEY: MISC_FEATURE
<222> LOCATION: (4)..(4)
<223> OTHER INFORMATION: Xaa = T or S
<220> FEATURE:
<221> NAME/KEY: MISC_FEATURE
<222> LOCATION: (5)..(5)
<223> OTHER INFORMATION: Xaa = V or I

<400> SEQUENCE: 30

Xaa Xaa Xaa Xaa Xaa His Lys Ser Gln Gly
1 5 10

<210> SEQ ID NO 31
<211> LENGTH: 13
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE -continued

```
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(10)
<223> OTHER INFORMATION: Xaa = any amino acid
<220> FEATURE:
<221> NAME/KEY: MISC_FEATURE
<222> LOCATION: (12)..(12)
<223> OTHER INFORMATION: Xaa = any amino acid except D, E, R and K

<400> SEQUENCE: 31

His Xaa Xaa Xaa Arg Xaa Xaa Xaa Xaa Xaa His Xaa His
1               5                   10


<210> SEQ ID NO 32
<211> LENGTH: 14
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(11)
<223> OTHER INFORMATION: Xaa = any amino acid
<220> FEATURE:
<221> NAME/KEY: MISC_FEATURE
<222> LOCATION: (13)..(13)
<223> OTHER INFORMATION: Xaa = any amino acid except D, E, R and K

<400> SEQUENCE: 32

His Xaa Xaa Xaa Arg Xaa Xaa Xaa Xaa Xaa Xaa His Xaa His
1               5                   10


<210> SEQ ID NO 33
<211> LENGTH: 15
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(12)
<223> OTHER INFORMATION: Xaa = any amino acid
<220> FEATURE:
<221> NAME/KEY: MISC_FEATURE
<222> LOCATION: (14)..(14)
<223> OTHER INFORMATION: Xaa = any amino acid except D, E, R and K

<400> SEQUENCE: 33

His Xaa Xaa Xaa Arg Xaa Xaa Xaa Xaa Xaa Xaa Xaa His Xaa His
1               5                   10                  15


<210> SEQ ID NO 34
<211> LENGTH: 16
<212> TYPE: PRT
<213> ORGANISM: Artificial sequence
```

<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(13)
<223> OTHER INFORMATION: Xaa = any amino acid
<220> FEATURE:
<221> NAME/KEY: MISC_FEATURE
<222> LOCATION: (15)..(15)
<223> OTHER INFORMATION: Xaa = any amino acid except D, E, R and K

<400> SEQUENCE: 34

```
His Xaa Xaa Xaa Arg Xaa Xaa Xaa Xaa Xaa Xaa Xaa Xaa His Xaa His
1               5                   10                  15
```

<210> SEQ ID NO 35
<211> LENGTH: 17
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(14)
<223> OTHER INFORMATION: Xaa = any amino acid
<220> FEATURE:
<221> NAME/KEY: MISC_FEATURE
<222> LOCATION: (16)..(16)
<223> OTHER INFORMATION: Xaa = any amino acid except D, E, R and K

<400> SEQUENCE: 35

```
His Xaa Xaa Xaa Arg Xaa Xaa Xaa Xaa Xaa Xaa Xaa Xaa Xaa His Xaa
1               5                   10                  15

His
```

<210> SEQ ID NO 36
<211> LENGTH: 18
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(15)
<223> OTHER INFORMATION: Xaa = any amino acid
<220> FEATURE:
<221> NAME/KEY: MISC_FEATURE
<222> LOCATION: (17)..(17)
<223> OTHER INFORMATION: Xaa = any amino acid except D, E, R and K

<400> SEQUENCE: 36

His Xaa Xaa Xaa Arg Xaa Xaa Xaa Xaa Xaa Xaa Xaa Xaa Xaa Xaa His
1 5 10 15

Xaa His

<210> SEQ ID NO 37
<211> LENGTH: 19
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(16)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid except D, E, R and K

<400> SEQUENCE: 37

His Xaa Xaa Xaa Arg Xaa Xaa Xaa Xaa Xaa Xaa Xaa Xaa Xaa Xaa Xaa
1 5 10 15

His Xaa His

<210> SEQ ID NO 38
<211> LENGTH: 20
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(17)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = any amino acid

<400> SEQUENCE: 38

His Xaa Xaa Xaa Arg Xaa Xaa Xaa Xaa Xaa Xaa Xaa Xaa Xaa Xaa Xaa
1 5 10 15

Xaa His Xaa His
20

<210> SEQ ID NO 39
<211> LENGTH: 17
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(15)
<223> OTHER INFORMATION: Xaa = any amino acid
<220> FEATURE:
<221> NAME/KEY: MISC_FEATURE
<222> LOCATION: (17)..(17)
<223> OTHER INFORMATION: Xaa = any amino acid except D, E, K and R

<400> SEQUENCE: 39

Gly Xaa Xaa Xaa Xaa Xaa Xaa Xaa His Xaa Xaa Xaa Xaa Xaa Xaa His
1               5                   10                  15

Xaa

<210> SEQ ID NO 40
<211> LENGTH: 18
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(16)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid except D, E, K and R

<400> SEQUENCE: 40

Gly Xaa Xaa Xaa Xaa Xaa Xaa Xaa His Xaa Xaa Xaa Xaa Xaa Xaa Xaa
1               5                   10                  15

His Xaa

<210> SEQ ID NO 41
<211> LENGTH: 19
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)

<223> OTHER INFORMATION: Xaa = any amino acid except D, E, K and R
<220> FEATURE:
<221> NAME/KEY: MISC_FEATURE
<222> LOCATION: (10)..(17)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = any amino acid except D, E, K and R

<400> SEQUENCE: 41

Gly Xaa Xaa Xaa Xaa Xaa Xaa Xaa His Xaa Xaa Xaa Xaa Xaa Xaa Xaa
1 5 10 15

Xaa His Xaa

<210> SEQ ID NO 42
<211> LENGTH: 20
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(18)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = any amino acid except D, E, K and R

<400> SEQUENCE: 42

Gly Xaa Xaa Xaa Xaa Xaa Xaa Xaa His Xaa Xaa Xaa Xaa Xaa Xaa Xaa
1 5 10 15

Xaa Xaa His Xaa
20

<210> SEQ ID NO 43
<211> LENGTH: 21
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(19)
<223> OTHER INFORMATION: Xaa = any amino acid
<220> FEATURE:
<221> NAME/KEY: MISC_FEATURE
<222> LOCATION: (21)..(21)

<223> OTHER INFORMATION: Xaa = any amino acid

<400> SEQUENCE: 43

Gly Xaa Xaa Xaa Xaa Xaa Xaa Xaa His Xaa Xaa Xaa Xaa Xaa Xaa Xaa
1               5                   10                  15

Xaa Xaa Xaa His Xaa
            20

<210> SEQ ID NO 44
<211> LENGTH: 22
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(20)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid except D, E, K and R

<400> SEQUENCE: 44

Gly Xaa Xaa Xaa Xaa Xaa Xaa Xaa His Xaa Xaa Xaa Xaa Xaa Xaa Xaa
1               5                   10                  15

Xaa Xaa Xaa Xaa His Xaa
            20

<210> SEQ ID NO 45
<211> LENGTH: 23
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (23)..(23)
<223> OTHER INFORMATION: Xaa = any amino acid except D, E, K and R

<400> SEQUENCE: 45

Gly Xaa Xaa Xaa Xaa Xaa Xaa Xaa His Xaa Xaa Xaa Xaa Xaa Xaa Xaa
1               5                   10                  15

Xaa Xaa Xaa Xaa Xaa His Xaa
20

<210> SEQ ID NO 46
<211> LENGTH: 1756
<212> TYPE: PRT
<213> ORGANISM: Escherichia coli

<400> SEQUENCE: 46

Met Met Ser Ile Ala Gln Val Arg Ser Ala Gly Ser Ala Gly Asn Tyr
1 5 10 15

Tyr Thr Asp Lys Asp Asn Tyr Tyr Val Leu Gly Ser Met Gly Glu Arg
20 25 30

Trp Ala Gly Lys Gly Ala Glu Gln Leu Gly Leu Gln Gly Ser Val Asp
35 40 45

Lys Asp Val Phe Thr Arg Leu Leu Glu Gly Arg Leu Pro Asp Gly Ala
50 55 60

Asp Leu Ser Arg Met Gln Asp Gly Ser Asn Lys His Arg Pro Gly Tyr
65 70 75 80

Asp Leu Thr Phe Ser Ala Pro Lys Ser Val Ser Met Met Ala Met Leu
85 90 95

Gly Gly Asp Lys Arg Leu Ile Asp Ala His Asn Gln Ala Val Asp Phe
100 105 110

Ala Val Arg Gln Val Glu Ala Leu Ala Ser Thr Arg Val Met Thr Asp
115 120 125

Gly Gln Ser Glu Thr Val Leu Thr Gly Asn Leu Val Met Ala Leu Phe
130 135 140

Asn His Asp Thr Ser Arg Asp Gln Glu Pro Gln Leu His Thr His Ala
145 150 155 160

Val Val Ala Asn Val Thr Gln His Asn Gly Glu Trp Lys Thr Leu Ser
165 170 175

Ser Asp Lys Val Gly Lys Thr Gly Phe Ile Glu Asn Val Tyr Ala Asn
180 185 190

Gln Ile Ala Phe Gly Arg Leu Tyr Arg Glu Lys Leu Lys Glu Gln Val
195 200 205

Glu Ala Leu Gly Tyr Glu Thr Glu Val Val Gly Lys His Gly Met Trp
210 215 220

Glu Met Pro Gly Val Pro Val Glu Ala Phe Ser Gly Arg Ser Gln Ala
225 230 235 240

Ile Arg Glu Ala Val Gly Glu Asp Ala Ser Leu Lys Ser Arg Asp Val
245 250 255

Ala Ala Leu Asp Thr Arg Lys Ser Lys Gln His Val Asp Pro Glu Ile
260 265 270

Arg Met Ala Glu Trp Met Gln Thr Leu Lys Glu Thr Gly Phe Asp Ile
275 280 285

Arg Ala Tyr Arg Asp Ala Ala Asp Gln Arg Thr Glu Ile Arg Thr Gln
290 295 300

Ala Pro Gly Pro Ala Ser Gln Asp Gly Pro Asp Val Gln Gln Ala Val
305 310 315 320

Thr Gln Ala Ile Ala Gly Leu Ser Glu Arg Lys Val Gln Phe Thr Tyr
325 330 335

Thr Asp Val Leu Ala Arg Thr Val Gly Ile Leu Pro Pro Glu Asn Gly
340 345 350

Val Ile Glu Arg Ala Arg Ala Gly Ile Asp Glu Ala Ile Ser Arg Glu
355 360 365

-continued

```
Gln Leu Ile Pro Leu Asp Arg Glu Lys Gly Leu Phe Thr Ser Gly Ile
    370                 375                 380

His Val Leu Asp Glu Leu Ser Val Arg Ala Leu Ser Arg Asp Ile Met
385                 390                 395                 400

Lys Gln Asn Arg Val Thr Val His Pro Glu Lys Ser Val Pro Arg Thr
                405                 410                 415

Ala Gly Tyr Ser Asp Ala Val Ser Val Leu Ala Gln Asp Arg Pro Ser
            420                 425                 430

Leu Ala Ile Val Ser Gly Gln Gly Gly Ala Ala Gly Gln Arg Glu Arg
        435                 440                 445

Val Ala Glu Leu Val Met Met Ala Arg Glu Gln Gly Arg Glu Val Gln
    450                 455                 460

Ile Ile Ala Ala Asp Arg Arg Ser Gln Met Asn Leu Lys Gln Asp Glu
465                 470                 475                 480

Arg Leu Ser Gly Glu Leu Ile Thr Gly Arg Arg Gln Leu Leu Glu Gly
                485                 490                 495

Met Ala Phe Thr Pro Gly Ser Thr Val Ile Val Asp Gln Gly Glu Lys
            500                 505                 510

Leu Ser Leu Lys Glu Thr Leu Thr Leu Leu Asp Gly Ala Ala Arg His
        515                 520                 525

Asn Val Gln Val Leu Ile Thr Asp Ser Gly Gln Arg Thr Gly Thr Gly
    530                 535                 540

Ser Ala Leu Met Ala Met Lys Asp Ala Gly Val Asn Thr Tyr Arg Trp
545                 550                 555                 560

Gln Gly Gly Glu Gln Arg Pro Ala Thr Ile Ile Ser Glu Pro Asp Arg
                565                 570                 575

Asn Val Arg Tyr Ala Arg Leu Ala Gly Asp Phe Ala Ala Ser Val Lys
            580                 585                 590

Ala Gly Glu Glu Ser Val Ala Gln Val Ser Gly Val Arg Glu Gln Ala
        595                 600                 605

Ile Leu Thr Gln Ala Ile Arg Ser Glu Leu Lys Thr Gln Gly Val Leu
    610                 615                 620

Gly His Pro Glu Val Thr Met Thr Ala Leu Ser Pro Val Trp Leu Asp
625                 630                 635                 640

Ser Arg Ser Arg Tyr Leu Arg Asp Met Tyr Arg Pro Gly Met Val Met
                645                 650                 655

Glu Gln Trp Asn Pro Glu Thr Arg Ser His Asp Arg Tyr Val Ile Asp
            660                 665                 670

Arg Val Thr Ala Gln Ser His Ser Leu Thr Leu Arg Asp Ala Gln Gly
        675                 680                 685

Glu Thr Gln Val Val Arg Ile Ser Ser Leu Asp Ser Ser Trp Ser Leu
    690                 695                 700

Phe Arg Pro Glu Lys Met Pro Val Ala Asp Gly Glu Arg Leu Arg Val
705                 710                 715                 720

Thr Gly Lys Ile Pro Gly Leu Arg Val Ser Gly Gly Asp Arg Leu Gln
                725                 730                 735

Val Ala Ser Val Ser Glu Asp Ala Met Thr Val Val Val Pro Gly Arg
            740                 745                 750

Ala Glu Pro Ala Ser Leu Pro Val Ser Asp Ser Pro Phe Thr Ala Leu
        755                 760                 765

Lys Leu Glu Asn Gly Trp Val Glu Thr Pro Gly His Ser Val Ser Asp
    770                 775                 780
```

-continued

```
Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
                805                 810                 815

Ser Leu Asp Glu Thr Arg Thr Ala Glu Lys Leu Ala Arg His Pro Ser
            820                 825                 830

Phe Thr Val Val Ser Glu Gln Ile Lys Ala Arg Ala Gly Glu Thr Leu
        835                 840                 845

Leu Glu Thr Ala Ile Ser Leu Gln Lys Ala Gly Leu His Thr Pro Ala
    850                 855                 860

Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
                885                 890                 895

Glu Gly Thr Gly Phe Thr Glu Leu Gly Gly Glu Ile Asn Ala Gln Ile
            900                 905                 910

Lys Arg Gly Asp Leu Leu Tyr Val Asp Val Ala Lys Gly Tyr Gly Thr
        915                 920                 925

Gly Leu Leu Val Ser Arg Ala Ser Tyr Glu Ala Glu Lys Ser Ile Leu
    930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
                965                 970                 975

Thr Arg Met Ile Leu Glu Thr Ser Asp Arg Phe Thr Val Val Gln Gly
            980                 985                 990

Tyr Ala Gly Val Gly Lys Thr Thr  Gln Phe Arg Ala Val  Met Ser Ala
        995                 1000                1005

Val Asn  Met Leu Pro Ala Ser  Glu Arg Pro Arg Val  Val Gly Leu
    1010                1015                1020

Gly Pro  Thr His Arg Ala Val  Gly Glu Met Arg Ser  Ala Gly Val
    1025                1030                1035

Asp Ala  Gln Thr Leu Ala Ser  Phe Leu His Asp Thr  Gln Leu Gln
    1040                1045                1050

Gln Arg  Ser Gly Glu Thr Pro  Asp Phe Ser Asn Thr  Leu Phe Leu
    1055                1060                1065

Leu Asp  Glu Ser Ser Met Val  Gly Asn Thr Glu Met  Ala Arg Ala
    1070                1075                1080

Tyr Ala  Leu Ile Ala Ala Gly  Gly Gly Arg Ala Val  Ala Ser Gly
    1085                1090                1095

Asp Thr  Asp Gln Leu Gln Ala  Ile Ala Pro Gly Gln  Ser Phe Arg
    1100                1105                1110

Leu Gln  Gln Thr Arg Ser Ala  Ala Asp Val Val Ile  Met Lys Glu
    1115                1120                1125

Ile Val  Arg Gln Thr Pro Glu  Leu Arg Glu Ala Val  Tyr Ser Leu
    1130                1135                1140

Ile Asn  Arg Asp Val Glu Arg  Ala Leu Ser Gly Leu  Glu Ser Val
    1145                1150                1155

Lys Pro  Ser Gln Val Pro Arg  Leu Glu Gly Ala Trp  Ala Pro Glu
    1160                1165                1170

His Ser  Val Thr Glu Phe Ser  His Ser Gln Glu Ala  Lys Leu Ala
    1175                1180                1185

Glu Ala  Gln Gln Lys Ala Met  Leu Lys Gly Glu Ala  Phe Pro Asp
```

-continued

```
    1190                1195                1200

Ile Pro  Met Thr Leu Tyr Glu  Ala Ile Val Arg Asp  Tyr Thr Gly
    1205                1210                1215

Arg Thr  Pro Glu Ala Arg Glu  Gln Thr Leu Ile Val  Thr His Leu
    1220                1225                1230

Asn Glu  Asp Arg Arg Val Leu  Asn Ser Met Ile His  Asp Ala Arg
    1235                1240                1245

Glu Lys  Ala Gly Glu Leu Gly  Lys Glu Gln Val Met  Val Pro Val
    1250                1255                1260

Leu Asn  Thr Ala Asn Ile Arg  Asp Gly Glu Leu Arg  Arg Leu Ser
    1265                1270                1275

Thr Trp  Glu Lys Asn Pro Asp  Ala Leu Ala Leu Val  Asp Asn Val
    1280                1285                1290

Tyr His  Arg Ile Ala Gly Ile  Ser Lys Asp Asp Gly  Leu Ile Thr
    1295                1300                1305

Leu Gln  Asp Ala Glu Gly Asn  Thr Arg Leu Ile Ser  Pro Arg Glu
    1310                1315                1320

Ala Val  Ala Glu Gly Val Thr  Leu Tyr Thr Pro Asp  Lys Ile Arg
    1325                1330                1335

Val Gly  Thr Gly Asp Arg Met  Arg Phe Thr Lys Ser  Asp Arg Glu
    1340                1345                1350

Arg Gly  Tyr Val Ala Asn Ser  Val Trp Thr Val Thr  Ala Val Ser
    1355                1360                1365

Gly Asp  Ser Val Thr Leu Ser  Asp Gly Gln Gln Thr  Arg Val Ile
    1370                1375                1380

Arg Pro  Gly Gln Glu Arg Ala  Glu Gln His Ile Asp  Leu Ala Tyr
    1385                1390                1395

Ala Ile  Thr Ala His Gly Ala  Gln Gly Ala Ser Glu  Thr Phe Ala
    1400                1405                1410

Ile Ala  Leu Glu Gly Thr Glu  Gly Asn Arg Lys Leu  Met Ala Gly
    1415                1420                1425

Phe Glu  Ser Ala Tyr Val Ala  Leu Ser Arg Met Lys  Gln His Val
    1430                1435                1440

Gln Val  Tyr Thr Asp Asn Arg  Gln Gly Trp Thr Asp  Ala Ile Asn
    1445                1450                1455

Asn Ala  Val Gln Lys Gly Thr  Ala His Asp Val Leu  Glu Pro Lys
    1460                1465                1470

Pro Asp  Arg Glu Val Met Asn  Ala Gln Arg Leu Phe  Ser Thr Ala
    1475                1480                1485

Arg Glu  Leu Arg Asp Val Ala  Ala Gly Arg Ala Val  Leu Arg Gln
    1490                1495                1500

Ala Gly  Leu Ala Gly Gly Asp  Ser Pro Ala Arg Phe  Ile Ala Pro
    1505                1510                1515

Gly Arg  Lys Tyr Pro Gln Pro  Tyr Val Ala Leu Pro  Ala Phe Asp
    1520                1525                1530

Arg Asn  Gly Lys Ser Ala Gly  Ile Trp Leu Asn Pro  Leu Thr Thr
    1535                1540                1545

Asp Asp  Gly Asn Gly Leu Arg  Gly Phe Ser Gly Glu  Gly Arg Val
    1550                1555                1560

Lys Gly  Ser Gly Asp Ala Gln  Phe Val Ala Leu Gln  Gly Ser Arg
    1565                1570                1575

Asn Gly  Glu Ser Leu Leu Ala  Asp Asn Met Gln Asp  Gly Val Arg
    1580                1585                1590
```

Ile Ala Arg Asp Asn Pro Asp Ser Gly Val Val Val Arg Ile Ala
1595 1600 1605

Gly Glu Gly Arg Pro Trp Asn Pro Gly Ala Ile Thr Gly Gly Arg
1610 1615 1620

Val Trp Gly Asp Ile Pro Asp Asn Ser Val Gln Pro Gly Ala Gly
1625 1630 1635

Asn Gly Glu Pro Val Thr Ala Glu Val Leu Ala Gln Arg Gln Ala
1640 1645 1650

Glu Glu Ala Ile Arg Arg Glu Thr Glu Arg Arg Ala Asp Glu Ile
1655 1660 1665

Val Arg Lys Met Ala Glu Asn Lys Pro Asp Leu Pro Asp Gly Lys
1670 1675 1680

Thr Glu Leu Ala Val Arg Asp Ile Ala Gly Gln Glu Arg Asp Arg
1685 1690 1695

Ser Ala Ile Ser Glu Arg Glu Thr Ala Leu Pro Glu Ser Val Leu
1700 1705 1710

Arg Glu Ser Gln Arg Glu Arg Glu Ala Val Arg Glu Val Ala Arg
1715 1720 1725

Glu Asn Leu Leu Gln Glu Arg Leu Gln Gln Met Glu Arg Asp Met
1730 1735 1740

Val Arg Asp Leu Gln Lys Glu Lys Thr Leu Gly Gly Asp
1745 1750 1755

<210> SEQ ID NO 47
<211> LENGTH: 8
<212> TYPE: PRT
<213> ORGANISM: Artificial sequence
<220> FEATURE:
<223> OTHER INFORMATION: RecD-like motif I of TraI Eco

<400> SEQUENCE: 47

Gly Tyr Ala Gly Val Gly Lys Thr
1 5

<210> SEQ ID NO 48
<211> LENGTH: 10
<212> TYPE: PRT
<213> ORGANISM: Artificial sequence
<220> FEATURE:
<223> OTHER INFORMATION: RecD-like motif V of TraI Eco

<400> SEQUENCE: 48

Tyr Ala Ile Thr Ala His Gly Ala Gln Gly
1 5 10

<210> SEQ ID NO 49
<211> LENGTH: 14
<212> TYPE: PRT
<213> ORGANISM: Artificial sequence
<220> FEATURE:
<223> OTHER INFORMATION: MobF motif III of TraI Eco

<400> SEQUENCE: 49

His Asp Thr Ser Arg Asp Gln Glu Pro Gln Leu His Thr His
1 5 10

<210> SEQ ID NO 50
<211> LENGTH: 9
<212> TYPE: PRT
<213> ORGANISM: Artificial Sequence
<220> FEATURE:

<223> OTHER INFORMATION: XPD motif V
<220> FEATURE:
<221> NAME/KEY: MISC_FEATURE
<222> LOCATION: (1)..(1)
<223> OTHER INFORMATION: Any amino acid except D, E, K or R.  Preferably
      not charged or H. More preferably V, L, I, S or Y.
<220> FEATURE:
<221> NAME/KEY: MISC_FEATURE
<222> LOCATION: (2)..(2)
<223> OTHER INFORMATION: Any amino acid except D, E, K or R.  Preferably
      not charged or H.
<220> FEATURE:
<221> NAME/KEY: MISC_FEATURE
<222> LOCATION: (3)..(3)
<223> OTHER INFORMATION: Any amino acid.
<220> FEATURE:
<221> NAME/KEY: MISC_FEATURE
<222> LOCATION: (5)..(5)
<223> OTHER INFORMATION: Any amino acid.  Preferably K, R or T.
<220> FEATURE:
<221> NAME/KEY: MISC_FEATURE
<222> LOCATION: (6)..(6)
<223> OTHER INFORMATION: Any amino acid except D, E, K or R.  Preferably
      not charged or H. More preferably V, L, I, N or F.
<220> FEATURE:
<221> NAME/KEY: MISC_FEATURE
<222> LOCATION: (7)..(7)
<223> OTHER INFORMATION: Any amino acid except D, E, K or R.  Preferably
      not charged or H. More preferably S or A.

<400> SEQUENCE: 50

Xaa Xaa Xaa Gly Xaa Xaa Xaa Glu Gly
1               5

<210> SEQ ID NO 51
<211> LENGTH: 22
<212> TYPE: PRT
<213> ORGANISM: Artificial Sequence
<220> FEATURE:
<223> OTHER INFORMATION: XPD motif VI
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (3)..(3)
<223> OTHER INFORMATION: Any amino acid except D, E, K, R.  Typically G,
      P, A, V, L, I, M, C, F, Y, W, H, Q, N, S or T.  Preferably not
      charged.  Preferably not H.  More preferably V, A, L, I or M.
<220> FEATURE:
<221> NAME/KEY: MISC_FEATURE
<222> LOCATION: (6)..(6)
<223> OTHER INFORMATION: Any amino acid except D, E, K, R.  Typically G,
      P, A, V, L, I, M, C, F, Y, W, H, Q, N, S or T.  Preferably not
      charged.  Preferably not H.  More preferably V, A, L, I, M or C.
<220> FEATURE:
<221> NAME/KEY: MISC_FEATURE
<222> LOCATION: (7)..(7)
<223> OTHER INFORMATION: Any amino acid except D, E, K, R.  Typically G,
      P, A, V, L, I, M, C, F, Y, W, H, Q, N, S or T.  Preferably not
      charged.  Preferably not H.  More preferably I, H, L, F, M or V.
<220> FEATURE:
<221> NAME/KEY: MISC_FEATURE
<222> LOCATION: (9)..(11)
<223> OTHER INFORMATION: Any amino acid.
<220> FEATURE:
<221> NAME/KEY: MISC_FEATURE
<222> LOCATION: (12)..(12)
<223> OTHER INFORMATION: D or E
<220> FEATURE:
<221> NAME/KEY: MISC_FEATURE
<222> LOCATION: (13)..(13)
<223> OTHER INFORMATION: Any amino acid.
<220> FEATURE:
<221> NAME/KEY: MISC_FEATURE
<222> LOCATION: (14)..(14)

<223> OTHER INFORMATION: Any amino acid.  Preferably G, A, S or C
<220> FEATURE:
<221> NAME/KEY: MISC_FEATURE
<222> LOCATION: (15)..(16)
<223> OTHER INFORMATION: Any amino acid.
<220> FEATURE:
<221> NAME/KEY: MISC_FEATURE
<222> LOCATION: (17)..(17)
<223> OTHER INFORMATION: Any amino acid. Preferably F, V, L, I, M, A, W or Y
<220> FEATURE:
<221> NAME/KEY: MISC_FEATURE
<222> LOCATION: (18)..(18)
<223> OTHER INFORMATION: Any amino acid. Preferably L, F, Y, M, I or V.
<220> FEATURE:
<221> NAME/KEY: MISC_FEATURE
<222> LOCATION: (19)..(19)
<223> OTHER INFORMATION: Any amino acid. Preferably A, C, V, L, I, M or S.

<400> SEQUENCE: 51

```
Gln Xaa Xaa Gly Arg Xaa Xaa Arg Xaa Xaa Xaa Xaa Xaa Xaa Xaa Xaa
1               5                   10                  15

Xaa Xaa Xaa Asp Asn Arg
            20
```

<210> SEQ ID NO 52
<211> LENGTH: 726
<212> TYPE: PRT
<213> ORGANISM: Methanococcoides burtonii

<400> SEQUENCE: 52

```
Met Ser Asp Lys Pro Ala Phe Met Lys Tyr Phe Thr Gln Ser Ser Cys
1               5                   10                  15

Tyr Pro Asn Gln Gln Glu Ala Met Asp Arg Ile His Ser Ala Leu Met
            20                  25                  30

Gln Gln Gln Leu Val Leu Phe Glu Gly Ala Cys Gly Thr Gly Lys Thr
        35                  40                  45

Leu Ser Ala Leu Val Pro Ala Leu His Val Gly Lys Met Leu Gly Lys
    50                  55                  60

Thr Val Ile Ile Ala Thr Asn Val His Gln Gln Met Val Gln Phe Ile
65                  70                  75                  80

Asn Glu Ala Arg Asp Ile Lys Lys Val Gln Asp Val Lys Val Ala Val
                85                  90                  95

Ile Lys Gly Lys Thr Ala Met Cys Pro Gln Glu Ala Asp Tyr Glu Glu
            100                 105                 110

Cys Ser Val Lys Arg Glu Asn Thr Phe Glu Leu Met Glu Thr Glu Arg
        115                 120                 125

Glu Ile Tyr Leu Lys Arg Gln Glu Leu Asn Ser Ala Arg Asp Ser Tyr
    130                 135                 140

Lys Lys Ser His Asp Pro Ala Phe Val Thr Leu Arg Asp Glu Leu Ser
145                 150                 155                 160

Lys Glu Ile Asp Ala Val Glu Glu Lys Ala Arg Gly Leu Arg Asp Arg
                165                 170                 175

Ala Cys Asn Asp Leu Tyr Glu Val Leu Arg Ser Asp Ser Glu Lys Phe
            180                 185                 190

Arg Glu Trp Leu Tyr Lys Glu Val Arg Ser Pro Glu Glu Ile Asn Asp
        195                 200                 205

His Ala Ile Lys Asp Gly Met Cys Gly Tyr Glu Leu Val Lys Arg Glu
    210                 215                 220

Leu Lys His Ala Asp Leu Leu Ile Cys Asn Tyr His His Val Leu Asn
```

-continued

```
225                 230                 235                 240

Pro Asp Ile Phe Ser Thr Val Leu Gly Trp Ile Glu Lys Glu Pro Gln
                245                 250                 255

Glu Thr Ile Val Ile Phe Asp Glu Ala His Asn Leu Glu Ser Ala Ala
            260                 265                 270

Arg Ser His Ser Ser Leu Ser Leu Thr Glu His Ser Ile Glu Lys Ala
        275                 280                 285

Ile Thr Glu Leu Glu Ala Asn Leu Asp Leu Leu Ala Asp Asp Asn Ile
    290                 295                 300

His Asn Leu Phe Asn Ile Phe Leu Glu Val Ile Ser Asp Thr Tyr Asn
305                 310                 315                 320

Ser Arg Phe Lys Phe Gly Glu Arg Glu Arg Val Arg Lys Asn Trp Tyr
                325                 330                 335

Asp Ile Arg Ile Ser Asp Pro Tyr Glu Arg Asn Asp Ile Val Arg Gly
            340                 345                 350

Lys Phe Leu Arg Gln Ala Lys Gly Asp Phe Gly Glu Lys Asp Asp Ile
        355                 360                 365

Gln Ile Leu Leu Ser Glu Ala Ser Glu Leu Gly Ala Lys Leu Asp Glu
    370                 375                 380

Thr Tyr Arg Asp Gln Tyr Lys Lys Gly Leu Ser Ser Val Met Lys Arg
385                 390                 395                 400

Ser His Ile Arg Tyr Val Ala Asp Phe Met Ser Ala Tyr Ile Glu Leu
                405                 410                 415

Ser His Asn Leu Asn Tyr Tyr Pro Ile Leu Asn Val Arg Arg Asp Met
            420                 425                 430

Asn Asp Glu Ile Tyr Gly Arg Val Glu Leu Phe Thr Cys Ile Pro Lys
        435                 440                 445

Asn Val Thr Glu Pro Leu Phe Asn Ser Leu Phe Ser Val Ile Leu Met
    450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
                485                 490                 495

Lys Arg Leu Ser Ile Ala Val Ser Ile Pro Pro Leu Phe Ala Lys Asn
            500                 505                 510

Arg Asp Asp Arg His Val Thr Glu Leu Leu Glu Gln Val Leu Leu Asp
        515                 520                 525

Ser Ile Glu Asn Ser Lys Gly Asn Val Ile Leu Phe Phe Gln Ser Ala
    530                 535                 540

Phe Glu Ala Lys Arg Tyr Tyr Ser Lys Ile Glu Pro Leu Val Asn Val
545                 550                 555                 560

Pro Val Phe Leu Asp Glu Val Gly Ile Ser Ser Gln Asp Val Arg Glu
                565                 570                 575

Glu Phe Phe Ser Ile Gly Glu Glu Asn Gly Lys Ala Val Leu Leu Ser
            580                 585                 590

Tyr Leu Trp Gly Thr Leu Ser Glu Gly Ile Asp Tyr Arg Asp Gly Arg
        595                 600                 605

Gly Arg Thr Val Ile Ile Ile Gly Val Gly Tyr Pro Ala Leu Asn Asp
    610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
                645                 650                 655
```

```
Gln Ala Met Gly Arg Val Val Arg Ser Pro Thr Asp Tyr Gly Ala Arg
            660                 665                 670

Ile Leu Leu Asp Gly Arg Phe Leu Thr Asp Ser Lys Lys Arg Phe Gly
        675                 680                 685

Lys Phe Ser Val Phe Glu Val Phe Pro Pro Ala Glu Arg Ser Glu Phe
    690                 695                 700

Val Asp Val Asp Pro Glu Lys Val Lys Tyr Ser Leu Met Asn Phe Phe
705                 710                 715                 720

Met Asp Asn Asp Glu Gln
                725


<210> SEQ ID NO 53
<211> LENGTH: 9
<212> TYPE: PRT
<213> ORGANISM: Artificial Sequence
<220> FEATURE:
<223> OTHER INFORMATION: Motif V

<400> SEQUENCE: 53

Tyr Leu Trp Gly Thr Leu Ser Glu Gly
1               5


<210> SEQ ID NO 54
<211> LENGTH: 22
<212> TYPE: PRT
<213> ORGANISM: Artificial Sequence
<220> FEATURE:
<223> OTHER INFORMATION: Motif VI

<400> SEQUENCE: 54

Gln Ala Met Gly Arg Val Val Arg Ser Pro Thr Asp Tyr Gly Ala Arg
1               5                   10                  15

Ile Leu Leu Asp Gly Arg
            20


<210> SEQ ID NO 55
<211> LENGTH: 301
<212> TYPE: PRT
<213> ORGANISM: Bacteriophage T4

<400> SEQUENCE: 55

Met Phe Lys Arg Lys Ser Thr Ala Glu Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Asn Ala Gly Asn Gly Gln Ala Val Ile Arg Phe Leu
        35                  40                  45

Pro Ser Lys Asn Asp Glu Gln Ala Pro Phe Ala Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asp Asn Lys Glu Tyr Ser Leu Val Lys Arg Lys
            100                 105                 110

Thr Ser Tyr Trp Ala Asn Ile Leu Val Val Lys Asp Pro Ala Ala Pro
        115                 120                 125

Glu Asn Glu Gly Lys Val Phe Lys Tyr Arg Phe Gly Lys Lys Ile Trp
    130                 135                 140
```

-continued

```
Asp Lys Ile Asn Ala Met Ile Ala Val Asp Val Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Gly Gln Val Met Gly
225                 230                 235                 240

Thr Ala Val Met Gly Gly Ala Ala Ala Thr Ala Ala Lys Lys Ala Asp
                245                 250                 255

Lys Val Ala Asp Asp Leu Asp Ala Phe Asn Val Asp Asp Phe Asn Thr
            260                 265                 270

Lys Thr Glu Asp Asp Phe Met Ser Ser Ser Ser Gly Ser Ser Ser Ser
        275                 280                 285

Ala Asp Asp Thr Asp Leu Asp Asp Leu Leu Asn Asp Leu
    290                 295                 300


<210> SEQ ID NO 56
<211> LENGTH: 299
<212> TYPE: PRT
<213> ORGANISM: Bacteriophage RB69

<400> SEQUENCE: 56

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Ala Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
```

```
    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Ser Asp
        275                 280                 285

Asp Gly Asp Leu Asp Asp Leu Leu Ala Gly Leu
    290                 295


<210> SEQ ID NO 57
<211> LENGTH: 232
<212> TYPE: PRT
<213> ORGANISM: Bacteriophage T7

<400> SEQUENCE: 57

Met Ala Lys Lys Ile Phe Thr Ser Ala Leu Gly Thr Ala Glu Pro Tyr
1               5                   10                  15

Ala Tyr Ile Ala Lys Pro Asp Tyr Gly Asn Glu Glu Arg Gly Phe Gly
            20                  25                  30

Asn Pro Arg Gly Val Tyr Lys Val Asp Leu Thr Ile Pro Asn Lys Asp
        35                  40                  45

Pro Arg Cys Gln Arg Met Val Asp Glu Ile Val Lys Cys His Glu Glu
    50                  55                  60

Ala Tyr Ala Ala Ala Val Glu Glu Tyr Glu Ala Asn Pro Pro Ala Val
65                  70                  75                  80

Ala Arg Gly Lys Lys Pro Leu Lys Pro Tyr Glu Gly Asp Met Pro Phe
                85                  90                  95

Phe Asp Asn Gly Asp Gly Thr Thr Thr Phe Lys Phe Lys Cys Tyr Ala
            100                 105                 110

Ser Phe Gln Asp Lys Lys Thr Lys Glu Thr Lys His Ile Asn Leu Val
        115                 120                 125

Val Val Asp Ser Lys Gly Lys Lys Met Glu Asp Val Pro Ile Ile Gly
    130                 135                 140

Gly Gly Ser Lys Leu Lys Val Lys Tyr Ser Leu Val Pro Tyr Lys Trp
145                 150                 155                 160

Asn Thr Ala Val Gly Ala Ser Val Lys Leu Gln Leu Glu Ser Val Met
                165                 170                 175

Leu Val Glu Leu Ala Thr Phe Gly Gly Gly Glu Asp Asp Trp Ala Asp
            180                 185                 190

Glu Val Glu Glu Asn Gly Tyr Val Ala Ser Gly Ser Ala Lys Ala Ser
        195                 200                 205

Lys Pro Arg Asp Glu Glu Ser Trp Asp Glu Asp Asp Glu Glu Ser Glu
    210                 215                 220

Glu Ala Asp Glu Asp Gly Asp Phe
225                 230


<210> SEQ ID NO 58
<211> LENGTH: 608
<212> TYPE: PRT
<213> ORGANISM: Bacteriophage phi-29

<400> SEQUENCE: 58

Met Lys His Met Pro Arg Lys Met Tyr Ser Cys Ala Phe Glu Thr Thr
```

-continued

```
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430
```

```
Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Gly Ser
            580                 585                 590

Gly Gly Gly Ser Gly Gly Ser Ala Trp Ser His Pro Gln Phe Glu Lys
        595                 600                 605


<210> SEQ ID NO 59
<211> LENGTH: 233
<212> TYPE: PRT
<213> ORGANISM: Bacteriophage RB69

<400> SEQUENCE: 59

Lys Gly Phe Ser Ser Glu Asp Lys Gly Glu Trp Lys Leu Lys Leu Asp
1               5                   10                  15

Ala Ser Gly Asn Gly Gln Ala Val Ile Arg Phe Leu Pro Ala Lys Thr
            20                  25                  30

Asp Asp Ala Leu Pro Phe Ala Ile Leu Val Asn His Gly Phe Lys Lys
        35                  40                  45

Asn Gly Lys Trp Tyr Ile Glu Thr Cys Ser Ser Thr His Gly Asp Tyr
    50                  55                  60

Asp Ser Cys Pro Val Cys Gln Tyr Ile Ser Lys Asn Asp Leu Tyr Asn
65                  70                  75                  80

Thr Asn Lys Thr Glu Tyr Ser Gln Leu Lys Arg Lys Thr Ser Tyr Trp
                85                  90                  95

Ala Asn Ile Leu Val Val Lys Asp Pro Gln Ala Pro Asp Asn Glu Gly
            100                 105                 110

Lys Val Phe Lys Tyr Arg Phe Gly Lys Lys Ile Trp Asp Lys Ile Asn
        115                 120                 125

Ala Met Ile Ala Val Asp Thr Glu Met Gly Glu Thr Pro Val Asp Val
    130                 135                 140

Thr Cys Pro Trp Glu Gly Ala Asn Phe Val Leu Lys Val Lys Gln Val
145                 150                 155                 160

Ser Gly Phe Ser Asn Tyr Asp Glu Ser Lys Phe Leu Asn Gln Ser Ala
                165                 170                 175

Ile Pro Asn Ile Asp Asp Glu Ser Phe Gln Lys Glu Leu Phe Glu Gln
            180                 185                 190

Met Val Asp Leu Ser Glu Met Thr Ser Lys Asp Lys Phe Lys Ser Phe
```

```
        195                 200                 205

Glu Glu Leu Asn Thr Lys Phe Asn Gln Val Leu Gly Thr Ala Ala Leu
    210                 215                 220

Gly Gly Ala Ala Ala Ala Ala Ala Ser
225                 230


<210> SEQ ID NO 60
<211> LENGTH: 210
<212> TYPE: PRT
<213> ORGANISM: Bacteriophage T7

<400> SEQUENCE: 60

Ala Lys Lys Ile Phe Thr Ser Ala Leu Gly Thr Ala Glu Pro Tyr Ala
1               5                   10                  15

Tyr Ile Ala Lys Pro Asp Tyr Gly Asn Glu Glu Arg Gly Phe Gly Asn
            20                  25                  30

Pro Arg Gly Val Tyr Lys Val Asp Leu Thr Ile Pro Asn Lys Asp Pro
        35                  40                  45

Arg Cys Gln Arg Met Val Asp Glu Ile Val Lys Cys His Glu Glu Ala
    50                  55                  60

Tyr Ala Ala Ala Val Glu Glu Tyr Glu Ala Asn Pro Pro Ala Val Ala
65                  70                  75                  80

Arg Gly Lys Lys Pro Leu Lys Pro Tyr Glu Gly Asp Met Pro Phe Phe
                85                  90                  95

Asp Asn Gly Asp Gly Thr Thr Thr Phe Lys Phe Lys Cys Tyr Ala Ser
            100                 105                 110

Phe Gln Asp Lys Lys Thr Lys Glu Thr Lys His Ile Asn Leu Val Val
        115                 120                 125

Val Asp Ser Lys Gly Lys Lys Met Glu Asp Val Pro Ile Ile Gly Gly
    130                 135                 140

Gly Ser Lys Leu Lys Val Lys Tyr Ser Leu Val Pro Tyr Lys Trp Asn
145                 150                 155                 160

Thr Ala Val Gly Ala Ser Val Lys Leu Gln Leu Glu Ser Val Met Leu
                165                 170                 175

Val Glu Leu Ala Thr Phe Gly Gly Gly Glu Asp Asp Trp Ala Asp Glu
            180                 185                 190

Val Glu Glu Asn Gly Tyr Val Ala Ser Gly Ser Ala Lys Ala Ser Lys
        195                 200                 205

Pro Arg
    210


<210> SEQ ID NO 61
<211> LENGTH: 99
<212> TYPE: PRT
<213> ORGANISM: Halorubrum lacusprofundi

<400> SEQUENCE: 61

Ser Gly Glu Glu Leu Leu Asp Leu Ala Gly Val Arg Asn Val Gly Arg
1               5                   10                  15

Lys Arg Ala Arg Arg Leu Phe Glu Ala Gly Ile Glu Thr Arg Ala Asp
            20                  25                  30

Leu Arg Glu Ala Asp Lys Ala Val Val Leu Gly Ala Leu Arg Gly Arg
        35                  40                  45

Glu Arg Thr Ala Glu Arg Ile Leu Glu His Ala Gly Arg Glu Asp Pro
    50                  55                  60

Ser Met Asp Asp Val Arg Pro Asp Lys Ser Ala Ser Ala Ala Ala Thr
```

```
65                  70                  75                  80

Ala Gly Ser Ala Ser Asp Glu Asp Gly Glu Gly Gln Ala Ser Leu Gly
                85                  90                  95

Asp Phe Arg


<210> SEQ ID NO 62
<211> LENGTH: 102
<212> TYPE: PRT
<213> ORGANISM: Haloferax volcanii

<400> SEQUENCE: 62

Ser Gly Glu Glu Leu Leu Asp Leu Ala Gly Val Arg Gly Val Gly Arg
1               5                   10                  15

Lys Arg Ala Arg Arg Leu Phe Glu Ala Gly Val Glu Thr Arg Ala Asp
            20                  25                  30

Leu Arg Glu Ala Asp Lys Pro Arg Val Leu Ala Ala Leu Arg Gly Arg
        35                  40                  45

Arg Lys Thr Ala Glu Asn Ile Leu Glu Ala Ala Gly Arg Lys Asp Pro
    50                  55                  60

Ser Met Asp Ala Val Asp Glu Asp Asp Ala Pro Asp Asp Ala Val Pro
65                  70                  75                  80

Asp Asp Ala Gly Phe Glu Thr Ala Lys Glu Arg Ala Asp Gln Gln Ala
                85                  90                  95

Ser Leu Gly Asp Phe Glu
            100


<210> SEQ ID NO 63
<211> LENGTH: 132
<212> TYPE: PRT
<213> ORGANISM: Homo sapiens

<400> SEQUENCE: 63

Glu Ser Glu Thr Thr Thr Ser Leu Val Leu Glu Arg Ser Leu Asn Arg
1               5                   10                  15

Val His Leu Leu Gly Arg Val Gly Gln Asp Pro Val Leu Arg Gln Val
            20                  25                  30

Glu Gly Lys Asn Pro Val Thr Ile Phe Ser Leu Ala Thr Asn Glu Met
        35                  40                  45

Trp Arg Ser Gly Asp Ser Glu Val Tyr Gln Leu Gly Asp Val Ser Gln
    50                  55                  60

Lys Thr Thr Trp His Arg Ile Ser Val Phe Arg Pro Gly Leu Arg Asp
65                  70                  75                  80

Val Ala Tyr Gln Tyr Val Lys Lys Gly Ser Arg Ile Tyr Leu Glu Gly
                85                  90                  95

Lys Ile Asp Tyr Gly Glu Tyr Met Asp Lys Asn Asn Val Arg Arg Gln
            100                 105                 110

Ala Thr Thr Ile Ile Ala Asp Asn Ile Ile Phe Leu Ser Asp Gln Thr
        115                 120                 125

Lys Glu Lys Glu
    130


<210> SEQ ID NO 64
<211> LENGTH: 123
<212> TYPE: PRT
<213> ORGANISM: Bacteriophage phi-29

<400> SEQUENCE: 64
```

```
Glu Asn Thr Asn Ile Val Lys Ala Thr Phe Asp Thr Glu Thr Leu Glu
1               5                   10                  15

Gly Gln Ile Lys Ile Phe Asn Ala Gln Thr Gly Gly Gly Gln Ser Phe
            20                  25                  30

Lys Asn Leu Pro Asp Gly Thr Ile Ile Glu Ala Asn Ala Ile Ala Gln
        35                  40                  45

Tyr Lys Gln Val Ser Asp Thr Tyr Gly Asp Ala Lys Glu Glu Thr Val
    50                  55                  60

Thr Thr Ile Phe Ala Ala Asp Gly Ser Leu Tyr Ser Ala Ile Ser Lys
65                  70                  75                  80

Thr Val Ala Glu Ala Ala Ser Asp Leu Ile Asp Leu Val Thr Arg His
                85                  90                  95

Lys Leu Glu Thr Phe Lys Val Lys Val Val Gln Gly Thr Ser Ser Lys
            100                 105                 110

Gly Asn Val Phe Phe Ser Leu Gln Leu Ser Leu
        115                 120


<210> SEQ ID NO 65
<211> LENGTH: 177
<212> TYPE: PRT
<213> ORGANISM: Escherichia coli

<400> SEQUENCE: 65

Ala Ser Arg Gly Val Asn Lys Val Ile Leu Val Gly Asn Leu Gly Gln
1               5                   10                  15

Asp Pro Glu Val Arg Tyr Met Pro Asn Gly Gly Ala Val Ala Asn Ile
            20                  25                  30

Thr Leu Ala Thr Ser Glu Ser Trp Arg Asp Lys Ala Thr Gly Glu Met
        35                  40                  45

Lys Glu Gln Thr Glu Trp His Arg Val Val Leu Phe Gly Lys Leu Ala
    50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Val Asn Val Gly Gly Thr Met Gln Met Leu
            100                 105                 110

Gly Gly Arg Gln Gly Gly Gly Ala Pro Ala Gly Gly Asn Ile Gly Gly
        115                 120                 125

Gly Gln Pro Gln Gly Gly Trp Gly Gln Pro Gln Gln Pro Gln Gly Gly
    130                 135                 140

Asn Gln Phe Ser Gly Gly Ala Gln Ser Arg Pro Gln Gln Ser Ala Pro
145                 150                 155                 160

Ala Ala Pro Ser Asn Glu Pro Pro Met Asp Phe Asp Asp Asp Ile Pro
                165                 170                 175

Phe


<210> SEQ ID NO 66
<211> LENGTH: 177
<212> TYPE: PRT
<213> ORGANISM: Artificial sequence
<220> FEATURE:
<223> OTHER INFORMATION: EcoSSB-CterAla

<400> SEQUENCE: 66

Ala Ser Arg Gly Val Asn Lys Val Ile Leu Val Gly Asn Leu Gly Gln
1               5                   10                  15
```

```
Asp Pro Glu Val Arg Tyr Met Pro Asn Gly Gly Ala Val Ala Asn Ile
            20                  25                  30

Thr Leu Ala Thr Ser Glu Ser Trp Arg Asp Lys Ala Thr Gly Glu Met
        35                  40                  45

Lys Glu Gln Thr Glu Trp His Arg Val Val Leu Phe Gly Lys Leu Ala
    50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Val Asn Val Gly Gly Thr Met Gln Met Leu
            100                 105                 110

Gly Gly Arg Gln Gly Gly Gly Ala Pro Ala Gly Gly Asn Ile Gly Gly
        115                 120                 125

Gly Gln Pro Gln Gly Gly Trp Gly Gln Pro Gln Gln Pro Gln Gly Gly
    130                 135                 140

Asn Gln Phe Ser Gly Gly Ala Gln Ser Arg Pro Gln Gln Ser Ala Pro
145                 150                 155                 160

Ala Ala Pro Ser Asn Glu Pro Pro Met Ala Phe Ala Ala Ala Ile Pro
                165                 170                 175

Phe


<210> SEQ ID NO 67
<211> LENGTH: 177
<212> TYPE: PRT
<213> ORGANISM: Artificial sequence
<220> FEATURE:
<223> OTHER INFORMATION: EcoSSB-CterNGGN

<400> SEQUENCE: 67

Ala Ser Arg Gly Val Asn Lys Val Ile Leu Val Gly Asn Leu Gly Gln
1               5                   10                  15

Asp Pro Glu Val Arg Tyr Met Pro Asn Gly Gly Ala Val Ala Asn Ile
            20                  25                  30

Thr Leu Ala Thr Ser Glu Ser Trp Arg Asp Lys Ala Thr Gly Glu Met
        35                  40                  45

Lys Glu Gln Thr Glu Trp His Arg Val Val Leu Phe Gly Lys Leu Ala
    50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Val Asn Val Gly Gly Thr Met Gln Met Leu
            100                 105                 110

Gly Gly Arg Gln Gly Gly Gly Ala Pro Ala Gly Gly Asn Ile Gly Gly
        115                 120                 125

Gly Gln Pro Gln Gly Gly Trp Gly Gln Pro Gln Gln Pro Gln Gly Gly
    130                 135                 140

Asn Gln Phe Ser Gly Gly Ala Gln Ser Arg Pro Gln Gln Ser Ala Pro
145                 150                 155                 160

Ala Ala Pro Ser Asn Glu Pro Pro Met Asn Phe Gly Gly Asn Ile Pro
                165                 170                 175

Phe
```

```
<210> SEQ ID NO 68
<211> LENGTH: 152
<212> TYPE: PRT
<213> ORGANISM: Artificial sequence
<220> FEATURE:
<223> OTHER INFORMATION: EcoSSB-Q152del

<400> SEQUENCE: 68

Ala Ser Arg Gly Val Asn Lys Val Ile Leu Val Gly Asn Leu Gly Gln
1               5                   10                  15

Asp Pro Glu Val Arg Tyr Met Pro Asn Gly Gly Ala Val Ala Asn Ile
            20                  25                  30

Thr Leu Ala Thr Ser Glu Ser Trp Arg Asp Lys Ala Thr Gly Glu Met
        35                  40                  45

Lys Glu Gln Thr Glu Trp His Arg Val Val Leu Phe Gly Lys Leu Ala
    50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Val Asn Val Gly Gly Thr Met Gln Met Leu
            100                 105                 110

Gly Gly Arg Gln Gly Gly Gly Ala Pro Ala Gly Gly Asn Ile Gly Gly
        115                 120                 125

Gly Gln Pro Gln Gly Gly Trp Gly Gln Pro Gln Gln Pro Gln Gly Gly
    130                 135                 140

Asn Gln Phe Ser Gly Gly Ala Gln
145                 150


<210> SEQ ID NO 69
<211> LENGTH: 117
<212> TYPE: PRT
<213> ORGANISM: Artificial sequence
<220> FEATURE:
<223> OTHER INFORMATION: EcoSSB-G117del

<400> SEQUENCE: 69

Ala Ser Arg Gly Val Asn Lys Val Ile Leu Val Gly Asn Leu Gly Gln
1               5                   10                  15

Asp Pro Glu Val Arg Tyr Met Pro Asn Gly Gly Ala Val Ala Asn Ile
            20                  25                  30

Thr Leu Ala Thr Ser Glu Ser Trp Arg Asp Lys Ala Thr Gly Glu Met
        35                  40                  45

Lys Glu Gln Thr Glu Trp His Arg Val Val Leu Phe Gly Lys Leu Ala
    50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Val Asn Val Gly Gly Thr Met Gln Met Leu
            100                 105                 110

Gly Gly Arg Gln Gly
        115


<210> SEQ ID NO 70
<211> LENGTH: 5206
<212> TYPE: DNA
<213> ORGANISM: Artificial sequence
<220> FEATURE:
```

<223> OTHER INFORMATION: Polynucleotide used in the Examples

<400> SEQUENCE: 70
ggttgtttct gttggtgctg atattgcccg gtggtacctt acgcgttgga tgaggagaag 60
tggcttaata tgcttggcac gttcgtcaag gactggttta gatatgagtc acattttgtt 120
catggtagag attctcttgt tgacatttta aaagagcgtg gattactatc tgagtccgat 180
gctgttcaac cactaatagg taagaaatca tgagtcaagt tactgaacaa tccgtacgtt 240
tccagaccgc tttggcctct attaagctca ttcaggcttc tgccgttttg gatttaaccg 300
aagatgattt cgattttctg acgagtaaca aagtttggat tgctactgac cgctctcgtg 360
ctcgtcgctg cgttgaggct tgcgtttatg gtacgctgga ctttgtagga taccctcgct 420
ttcctgctcc tgttgagttt attgctgccg tcattgctta ttatgttcat cccgtcaaca 480
ttcaaacggc ctgtctcatc atggaaggcg ctgaatttac ggaaaacatt attaatggcg 540
tcgagcgtcc ggttaaagcc gctgaattgt tcgcgtttac cttgcgtgta cgcgcaggaa 600
acactgacgt tcttactgac gcagaagaaa acgtgcgtca aaaattacgt gcagaaggag 660
tgatgtaatg tctaaaggta aaaaacgttc tggcgctcgc cctggtcgtc cgcagccgtt 720
gcgaggtact aaaggcaagc gtaaaggcgc tcgtctttgg tatgtaggtg gtcaacaatt 780
ttaattgcag gggcttcggc cccttacttg aggataaatt atgtctaata ttcaaactgg 840
cgccgagcgt atgccgcatg acctttccca tcttggcttc cttgctggtc agattggtcg 900
tcttattacc atttcaacta ctccggttat cgctggcgac tccttcgaga tggacgccgt 960
tggcgctctc cgtctttctc cattgcgtcg tggccttgct attgactcta ctgtagacat 1020
ttttactttt tatgtccctc atcgtcacgt ttatggtgaa cagtggatta agttcatgaa 1080
ggatggtgtt aatgccactc ctctcccgac tgttaacact actggttata ttgaccatgc 1140
cgcttttctt ggcacgatta accctgatac caataaaatc cctaagcatt tgtttcaggg 1200
ttatttgaat atctataaca actattttaa agcgccgtgg atgcctgacc gtaccgaggc 1260
taaccctaat gagcttaatc aagatgatgc tcgttatggt ttccgttgct gccatctcaa 1320
aaacatttgg actgctccgc ttcctcctga gactgagctt tctcgccaaa tgacgacttc 1380
taccacatct attgacatta tgggtctgca agctgcttat gctaatttgc atactgacca 1440
agaacgtgat tacttcatgc agcgttacca tgatgttatt tcttcatttg gaggtaaaac 1500
ctcttatgac gctgacaacc gtcctttact tgtcatgcgc tctaatctct gggcatctgg 1560
ctatgatgtt gatggaactg accaaacgtc gttaggccag ttttctggtc gtgttcaaca 1620
gacctataaa cattctgtgc cgcgtttctt tgttcctgag catggcacta tgtttactct 1680
tgcgcttgtt cgttttccgc ctactgcgac taaagagatt cagtacctta acgctaaagg 1740
tgctttgact tataccgata ttgctggcga ccctgttttg tatggcaact tgccgccgcg 1800
tgaaatttct atgaaggatg ttttccgttc tggtgattcg tctaagaagt ttaagattgc 1860
tgagggtcag tggtatcgtt atgcgccttc gtatgtttct cctgcttatc accttcttga 1920
aggcttccca ttcattcagg aaccgccttc tggtgatttg caagaacgcg tacttattcg 1980
ccaccatgat tatgaccagt gtttccagtc cgttcagttg ttgcagtgga atagtcaggt 2040
taaatttaat gtgaccgttt atcgcaatct gccgaccact cgcgattcaa tcatgacttc 2100
gtgataaaag attgagtgtg aggttataac gccgaagcgg taaaaatttt aatttttgcc 2160
gctgaggggt tgaccaagcg aagcgcggta ggttttctgc ttaggagttt aatcatgttt 2220
cagactttta tttctcgcca taattcaaac ttttttttctg ataagctggt tctcacttct 2280

-continued

```
gttactccag cttcttcggc acctgtttta cagacaccta aagctacatc gtcaacgtta   2340
tattttgata gtttgacggt taatgctggt aatggtggtt ttcttcattg cattcagatg   2400
gatacatctg tcaacgccgc taatcaggtt gtttctgttg gtgctgatat tgcttttgat   2460
gccgacccta aatttttgc ctgtttggtt cgctttgagt cttcttcggt tccgactacc   2520
ctcccgactg cctatgatgt ttatcctttg gatggtcgcc atgatggtgg ttattatacc   2580
gtcaaggact gtgtgactat tgacgtcctt ccccgtacgc cgggcaataa tgtttatgtt   2640
ggtttcatgg tttggtctaa ctttaccgct actaaatgcc gcggattggt ttcgctgaat   2700
caggttatta aagagattat ttgtctccag ccacttaagt gaggtgattt atgtttggtg   2760
ctattgctgg cggtattgct tctgctcttg ctggtggcgc catgtctaaa ttgtttggag   2820
gcggtcaaaa agccgcctcc ggtggcattc aaggtgatgt gcttgctacc gataacaata   2880
ctgtaggcat gggtgatgct ggtattaaat ctgccattca aggctctaat gttcctaacc   2940
ctgatgaggc cgtccctagt tttgtttctg gtgctatggc taaagctggt aaaggacttc   3000
ttgaaggtac gttgcaggct ggcacttctg ccgtttctga taagttgctt gatttggttg   3060
gacttggtgg caagtctgcc gctgataaag gaaaggatac tcgtgattat cttgctgctg   3120
catttcctga gcttaatgct tgggagcgtg ctggtgctga tgcttcctct gctggtatgg   3180
ttgacgccgg atttgagaat caaaaagagc ttactaaaat gcaactggac aatcagaaag   3240
agattgccga gatgcaaaat gagactcaaa aagagattgc tggcattcag tcggcgactt   3300
cacgccagaa tacgaaagac caggtatatg cacaaaatga gatgcttgct tatcaacaga   3360
aggagtctac tgctcgcgtt gcgtctatta tggaaaacac caatctttcc aagcaacagc   3420
aggtttccga gattatgcgc caaatgctta ctcaagctca aacggctggt cagtatttta   3480
ccaatgacca aatcaaagaa atgactcgca aggttagtgc tgaggttgac ttagttcatc   3540
agcaaacgca gaatcagcgg tatggctctt ctcatattgg cgctactgca aaggatattt   3600
ctaatgtcgt cactgatgct gcttctggtg tggttgatat ttttcatggt attgataaag   3660
ctgttgccga tacttggaac aatttctgga aagacggtaa agctgatggt attggctcta   3720
atttgtctag gaaataaccg tcaggattga caccctccca attgtatgtt ttcatgcctc   3780
caaatcttgg aggctttttt atggttcgtt cttattaccc ttctgaatgt cacgctgatt   3840
attttgactt tgagcgtatc gaggctctta aacctgctat tgaggcttgt ggcatttcta   3900
ctctttctca atccccaatg cttggcttcc ataagcagat ggataaccgc atcaagctct   3960
tggaagagat tctgtctttt cgtatgcagg gcgttgagtt cgataatggt gatatgtatg   4020
ttgacggcca taaggctgct tctgacgttc gtgatgagtt tgtatctgtt actgagaagt   4080
taatggatga attggcacaa tgctacaatg tgctccccca acttgatatt aataacacta   4140
tagaccaccg ccccgaaggg gacgaaaaat ggtttttaga gaacgagaag acggttacgc   4200
agttttgccg caagctggct gctgaacgcc ctcttaagga tattcgcgat gagtataatt   4260
accccaaaaa gaaaggtatt aaggatgagt gttcaagatt gctggaggcc tccactatga   4320
aatcgcgtag aggctttgct attcagcgtt tgatgaatgc aatgcgacag gctcatgctg   4380
atggttggtt tatcgttttt gacactctca cgttggctga cgaccgatta gaggcgtttt   4440
atgataatcc caatgctttg cgtgactatt ttcgtgatat tggtcgtatg gttcttgctg   4500
ccgagggtcg caaggctaat gattcacacg ccgactgcta tcagtatttt tgtgtgcctg   4560
agtatggtac agctaatggc cgtcttcatt tccatgcggt gcactttatg cggacacttc   4620
```

```
ctacaggtag cgttgaccct aattttggtc gtcgggtacg caatcgccgc cagttaaata   4680

gcttgcaaaa tacgtggcct tatggttaca gtatgcccat cgcagttcgc tacacgcagg   4740

acgctttttc acgttctggt tggttgtggc ctgttgatgc taaaggtgag ccgcttaaag   4800

ctaccagtta tatggctgtt ggtttctatg tggctaaata cgttaacaaa aagtcagata   4860

tggaccttgc tgctaaaggt ctaggagcta aagaatggaa caactcacta aaaaccaagc   4920

tgtcgctact tcccaagaag ctgttcagaa tcagaatgag ccgcaacttc gggatgaaaa   4980

tgctcacaat gacaaatctg tccacggagt gcttaatcca acttaccaag ctgggttacg   5040

acgcgacgcc gttcaaccag atattgaagc agaacgcaaa aagagagatg agattgaggc   5100

tgggaaaagt tactgtagcc gacgttttgg cggcgcaacc tgtgacgaca aatctgctca   5160

aatttatgcg cgcttcgata aaaatgattg gcgtatccaa cctgca                 5206
```

<210> SEQ ID NO 71
<211> LENGTH: 5175
<212> TYPE: DNA
<213> ORGANISM: Artificial sequence
<220> FEATURE:
<223> OTHER INFORMATION: Polynucleotide used in the Examples

<400> SEQUENCE: 71

```
ccggtggtac cttacgcgtt ggatgaggag aagtggctta atatgcttgg cacgttcgtc     60

aaggactggt ttagatatga gtcacatttt gttcatggta gagattctct tgttgacatt    120

ttaaaagagc gtggattact atctgagtcc gatgctgttc aaccactaat aggtaagaaa    180

tcatgagtca agttactgaa caatccgtac gtttccagac cgctttggcc tctattaagc    240

tcattcaggc ttctgccgtt ttggatttaa ccgaagatga tttcgatttt ctgacgagta    300

acaaagtttg gattgctact gaccgctctc gtgctcgtcg ctgcgttgag gcttgcgttt    360

atggtacgct ggactttgta ggataccctc gctttcctgc tcctgttgag tttattgctg    420

ccgtcattgc ttattatgtt catcccgtca acattcaaac ggcctgtctc atcatggaag    480

gcgctgaatt tacggaaaac attattaatg gcgtcgagcg tccggttaaa gccgctgaat    540

tgttcgcgtt taccttgcgt gtacgcgcag gaaacactga cgttcttact gacgcagaag    600

aaaacgtgcg tcaaaaatta cgtgcagaag gagtgatgta atgtctaaag gtaaaaaacg    660

ttctggcgct cgccctggtc gtccgcagcc gttgcgaggt actaaaggca agcgtaaagg    720

cgctcgtctt tggtatgtag gtggtcaaca attttaattg caggggcttc ggccccttac    780

ttgaggataa attatgtcta atattcaaac tggcgccgag cgtatgccgc atgacctttc    840

ccatcttggc ttccttgctg gtcagattgg tcgtcttatt accatttcaa ctactccggt    900

tatcgctggc gactccttcg agatggacgc cgttggcgct ctccgtcttt ctccattgcg    960

tcgtggcctt gctattgact ctactgtaga catttttact ttttatgtcc ctcatcgtca   1020

cgtttatggt gaacagtgga ttaagttcat gaaggatggt gttaatgcca ctcctctccc   1080

gactgttaac actactggtt atattgacca tgccgctttt cttggcacga ttaaccctga   1140

taccaataaa atccctaagc atttgtttca gggttatttg aatatctata acaactattt   1200

taaagcgccg tggatgcctg accgtaccga ggctaaccct aatgagctta atcaagatga   1260

tgctcgttat ggtttccgtt gctgccatct caaaaacatt tggactgctc cgcttcctcc   1320

tgagactgag ctttctcgcc aaatgacgac ttctaccaca tctattgaca ttatgggtct   1380

gcaagctgct tatgctaatt tgcatactga ccaagaacgt gattacttca tgcagcgtta   1440

ccatgatgtt atttcttcat ttggaggtaa aacctcttat gacgctgaca accgtccttt   1500
```

```
acttgtcatg cgctctaatc tctgggcatc tggctatgat gttgatggaa ctgaccaaac   1560
gtcgttaggc cagttttctg gtcgtgttca acagacctat aaacattctg tgccgcgttt   1620
ctttgttcct gagcatggca ctatgtttac tcttgcgctt gttcgttttc cgcctactgc   1680
gactaaagag attcagtacc ttaacgctaa aggtgctttg acttataccg atattgctgg   1740
cgaccctgtt ttgtatggca acttgccgcc gcgtgaaatt tctatgaagg atgttttccg   1800
ttctggtgat tcgtctaaga agtttaagat tgctgagggt cagtggtatc gttatgcgcc   1860
ttcgtatgtt tctcctgctt atcaccttct tgaaggcttc ccattcattc aggaaccgcc   1920
ttctggtgat ttgcaagaac gcgtacttat tcgccaccat gattatgacc agtgtttcca   1980
gtccgttcag ttgttgcagt ggaatagtca ggttaaattt aatgtgaccg tttatcgcaa   2040
tctgccgacc actcgcgatt caatcatgac ttcgtgataa aagattgagt gtgaggttat   2100
aacgccgaag cggtaaaaat tttaattttt gccgctgagg ggttgaccaa gcgaagcgcg   2160
gtaggttttc tgcttaggag tttaatcatg tttcagactt ttatttctcg ccataattca   2220
aactttttttt ctgataagct ggttctcact tctgttactc cagcttcttc ggcacctgtt   2280
ttacagacac ctaaagctac atcgtcaacg ttatattttg atagtttgac ggttaatgct   2340
ggtaatggtg gttttcttca ttgcattcag atggatacat ctgtcaacgc cgctaatcag   2400
gttgtttctg ttggtgctga tattgctttt gatgccgacc ctaaattttt tgcctgtttg   2460
gttcgctttg agtcttcttc ggttccgact accctcccga ctgcctatga tgtttatcct   2520
ttggatggtc gccatgatgg tggttattat accgtcaagg actgtgtgac tattgacgtc   2580
cttccccgta cgccgggcaa taatgtttat gttggtttca tggtttggtc taactttacc   2640
gctactaaat gccgcggatt ggtttcgctg aatcaggtta ttaaagagat tatttgtctc   2700
cagccactta agtgaggtga tttatgtttg gtgctattgc tggcggtatt gcttctgctc   2760
ttgctggtgg cgccatgtct aaattgtttg gaggcggtca aaaagccgcc tccggtggca   2820
ttcaaggtga tgtgcttgct accgataaca atactgtagg catgggtgat gctggtatta   2880
aatctgccat tcaaggctct aatgttccta accctgatga ggccgtccct agttttgttt   2940
ctggtgctat ggctaaagct ggtaaaggac ttcttgaagg tacgttgcag gctggcactt   3000
ctgccgtttc tgataagttg cttgatttgg ttggacttgg tggcaagtct gccgctgata   3060
aaggaaagga tactcgtgat tatcttgctg ctgcatttcc tgagcttaat gcttgggagc   3120
gtgctggtgc tgatgcttcc tctgctggta tggttgacgc cggatttgag aatcaaaaag   3180
agcttactaa aatgcaactg gacaatcaga aagagattgc cgagatgcaa aatgagactc   3240
aaaaagagat tgctggcatt cagtcggcga cttcacgcca gaatacgaaa gaccaggtat   3300
atgcacaaaa tgagatgctt gcttatcaac agaaggagtc tactgctcgc gttgcgtcta   3360
ttatggaaaa caccaatctt tccaagcaac agcaggtttc cgagattatg cgccaaatgc   3420
ttactcaagc tcaaacggct ggtcagtatt ttaccaatga ccaaatcaaa gaaatgactc   3480
gcaaggttag tgctgaggtt gacttagttc atcagcaaac gcagaatcag cggtatggct   3540
cttctcatat tggcgctact gcaaaggata tttctaatgt cgtcactgat gctgcttctg   3600
gtgtggttga tatttttcat ggtattgata aagctgttgc cgatacttgg aacaatttct   3660
ggaaagacgg taaagctgat ggtattggct ctaatttgtc taggaaataa ccgtcaggat   3720
tgacaccctc ccaattgtat gttttcatgc ctccaaatct tggaggcttt tttatggttc   3780
gttcttatta cccttctgaa tgtcacgctg attattttga ctttgagcgt atcgaggctc   3840
```

ttaaacctgc tattgaggct tgtggcattt ctactctttc tcaatcccca atgcttggct 3900
tccataagca gatggataac cgcatcaagc tcttggaaga gattctgtct tttcgtatgc 3960
agggcgttga gttcgataat ggtgatatgt atgttgacgg ccataaggct gcttctgacg 4020
ttcgtgatga gtttgtatct gttactgaga agttaatgga tgaattggca caatgctaca 4080
atgtgctccc ccaacttgat attaataaca ctatagacca ccgccccgaa ggggacgaaa 4140
aatggttttt agagaacgag aagacggtta cgcagttttg ccgcaagctg gctgctgaac 4200
gccctcttaa ggatattcgc gatgagtata attaccccaa aaagaaaggt attaaggatg 4260
agtgttcaag attgctggag gcctccacta tgaaatcgcg tagaggcttt gctattcagc 4320
gtttgatgaa tgcaatgcga caggctcatg ctgatggttg gtttatcgtt tttgacactc 4380
tcacgttggc tgacgaccga ttagaggcgt tttatgataa tcccaatgct ttgcgtgact 4440
attttcgtga tattggtcgt atggttcttg ctgccgaggg tcgcaaggct aatgattcac 4500
acgccgactg ctatcagtat ttttgtgtgc ctgagtatgg tacagctaat ggccgtcttc 4560
atttccatgc ggtgcacttt atgcggacac ttcctacagg tagcgttgac cctaattttg 4620
gtcgtcgggt acgcaatcgc cgccagttaa atagcttgca aaatacgtgg ccttatggtt 4680
acagtatgcc catcgcagtt cgctacacgc aggacgcttt ttcacgttct ggttggttgt 4740
ggcctgttga tgctaaaggt gagccgctta aagctaccag ttatatggct gttggtttct 4800
atgtggctaa atacgttaac aaaaagtcag atatggacct tgctgctaaa ggtctaggag 4860
ctaaagaatg gaacaactca ctaaaaacca agctgtcgct acttcccaag aagctgttca 4920
gaatcagaat gagccgcaac ttcgggatga aaatgctcac aatgacaaat ctgtccacgg 4980
agtgcttaat ccaacttacc aagctgggtt acgacgcgac gccgttcaac cagatattga 5040
agcagaacgc aaaaagagag atgagattga ggctgggaaa agttactgta gccgacgttt 5100
tggcggcgca acctgtgacg acaaatctgc tcaaatttat gcgcgcttcg ataaaaatga 5160
ttggcgtatc caacc 5175

<210> SEQ ID NO 72
<211> LENGTH: 29
<212> TYPE: DNA
<213> ORGANISM: Artificial sequence
<220> FEATURE:
<223> OTHER INFORMATION: Polynucleotide used in the Examples

<400> SEQUENCE: 72
gcaatatcag caccaacaga aacaacctt 29

<210> SEQ ID NO 73
<211> LENGTH: 88
<212> TYPE: DNA
<213> ORGANISM: Artificial sequence
<220> FEATURE:
<223> OTHER INFORMATION: Polynucleotide used in the Examples

<400> SEQUENCE: 73
cgtggtcacg aggagctcgt cctcacctcg acgtctgcac gagctttttt tttttttttt 60
tttttttttt tttttttttt tttttttt 88

<210> SEQ ID NO 74
<211> LENGTH: 55
<212> TYPE: PRT
<213> ORGANISM: Artificial sequence
<220> FEATURE:
<223> OTHER INFORMATION: (HhH)2 domain

<400> SEQUENCE: 74

Trp Lys Glu Trp Leu Glu Arg Lys Val Gly Glu Gly Arg Ala Arg Arg
1 5 10 15

Leu Ile Glu Tyr Phe Gly Ser Ala Gly Glu Val Gly Lys Leu Val Glu
20 25 30

Asn Ala Glu Val Ser Lys Leu Leu Glu Val Pro Gly Ile Gly Asp Glu
35 40 45

Ala Val Ala Arg Leu Val Pro
50 55

<210> SEQ ID NO 75
<211> LENGTH: 107
<212> TYPE: PRT
<213> ORGANISM: Artificial sequence
<220> FEATURE:
<223> OTHER INFORMATION: (HhH)2-(HhH)2 domain

<400> SEQUENCE: 75

Trp Lys Glu Trp Leu Glu Arg Lys Val Gly Glu Gly Arg Ala Arg Arg
1 5 10 15

Leu Ile Glu Tyr Phe Gly Ser Ala Gly Glu Val Gly Lys Leu Val Glu
20 25 30

Asn Ala Glu Val Ser Lys Leu Leu Glu Val Pro Gly Ile Gly Asp Glu
35 40 45

Ala Val Ala Arg Leu Val Pro Gly Tyr Lys Thr Leu Arg Asp Ala Gly
50 55 60

Leu Thr Pro Ala Glu Ala Glu Arg Val Leu Lys Arg Tyr Gly Ser Val
65 70 75 80

Ser Lys Val Gln Glu Gly Ala Thr Pro Asp Glu Leu Arg Glu Leu Gly
85 90 95

Leu Gly Asp Ala Lys Ile Ala Arg Ile Leu Gly
100 105

<210> SEQ ID NO 76
<211> LENGTH: 318
<212> TYPE: PRT
<213> ORGANISM: Herpes simplex virus 1

<400> SEQUENCE: 76

Thr Asp Ser Pro Gly Gly Val Ala Pro Ala Ser Pro Val Glu Asp Ala
1 5 10 15

Ser Asp Ala Ser Leu Gly Gln Pro Glu Glu Gly Ala Pro Cys Gln Val
20 25 30

Val Leu Gln Gly Ala Glu Leu Asn Gly Ile Leu Gln Ala Phe Ala Pro
35 40 45

Leu Arg Thr Ser Leu Leu Asp Ser Leu Leu Val Met Gly Asp Arg Gly
50 55 60

Ile Leu Ile His Asn Thr Ile Phe Gly Glu Gln Val Phe Leu Pro Leu
65 70 75 80

Glu His Ser Gln Phe Ser Arg Tyr Arg Trp Arg Gly Pro Thr Ala Ala
85 90 95

Phe Leu Ser Leu Val Asp Gln Lys Arg Ser Leu Leu Ser Val Phe Arg
100 105 110

Ala Asn Gln Tyr Pro Asp Leu Arg Arg Val Glu Leu Ala Ile Thr Gly
115 120 125

Gln Ala Pro Phe Arg Thr Leu Val Gln Arg Ile Trp Thr Thr Thr Ser

-continued

```
    130                 135                 140

Asp Gly Glu Ala Val Glu Leu Ala Ser Glu Thr Leu Met Lys Arg Glu
145                 150                 155                 160

Leu Thr Ser Phe Val Val Leu Val Pro Gln Gly Thr Pro Asp Val Gln
                165                 170                 175

Leu Arg Leu Thr Arg Pro Gln Leu Thr Lys Val Leu Asn Ala Thr Gly
            180                 185                 190

Ala Asp Ser Ala Thr Pro Thr Thr Phe Glu Leu Gly Val Asn Gly Lys
        195                 200                 205

Phe Ser Val Phe Thr Thr Ser Thr Cys Val Thr Phe Ala Ala Arg Glu
    210                 215                 220

Glu Gly Val Ser Ser Ser Thr Ser Thr Gln Val Gln Ile Leu Ser Asn
225                 230                 235                 240

Ala Leu Thr Lys Ala Gly Gln Ala Ala Ala Asn Ala Lys Thr Val Tyr
                245                 250                 255

Gly Glu Asn Thr His Arg Thr Phe Ser Val Val Val Asp Asp Cys Ser
            260                 265                 270

Met Arg Ala Val Leu Arg Arg Leu Gln Val Gly Gly Gly Thr Leu Lys
        275                 280                 285

Phe Phe Leu Thr Thr Pro Val Pro Ser Leu Cys Val Thr Ala Thr Gly
    290                 295                 300

Pro Asn Ala Val Ser Ala Val Phe Leu Leu Lys Pro Gln Lys
305                 310                 315


<210> SEQ ID NO 77
<211> LENGTH: 293
<212> TYPE: PRT
<213> ORGANISM: Staphylococcus aureus

<400> SEQUENCE: 77

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190
```

```
Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290


<210> SEQ ID NO 78
<211> LENGTH: 15
<212> TYPE: DNA
<213> ORGANISM: Artificial sequence
<220> FEATURE:
<223> OTHER INFORMATION: Polynucleotide used in the Examples

<400> SEQUENCE: 78

ccuagtctcc guagc                                                    15


<210> SEQ ID NO 79
<211> LENGTH: 354
<212> TYPE: DNA
<213> ORGANISM: Artificial sequence
<220> FEATURE:
<223> OTHER INFORMATION: Polynucleotide used in the Examples

<400> SEQUENCE: 79

aggttttttt tttttttttt tttttttttt tttttttttt tttttttttt tttttttttt     60

tttttttttt tttttttttt tttttttttt tttttttttt tttttttttt tttttttttt    120

tttttttttt tttttttttt tttttttttt tttttttttt tttttttttt tttttttttt    180

tttttttttt tttttttttt tttttttttt tttttttttt tttttttttt tttttttttt    240

tttttttttt tttttttttt tttttttttt tttttttttt tttttttttt tttttttttt    300

tttttttttt tttttttttt tttttttttt tttttttttt tttttttttt tttt          354


<210> SEQ ID NO 80
<211> LENGTH: 508
<212> TYPE: PRT
<213> ORGANISM: Artificial sequence
<220> FEATURE:
<223> OTHER INFORMATION: EcoExoI with all natural cysteines removed,
      A83C and two Strep tags

<400> SEQUENCE: 80

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Ala Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
```

```
65                  70                  75                  80

Glu Ala Cys Phe Ala Ala Arg Ile His Ser Leu Phe Thr Val Pro Lys
                85                  90                  95

Thr Thr Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Thr
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Thr Pro Val Leu Ala Gln Ala Asn Thr Leu Arg Pro Glu Asp Ala
305                 310                 315                 320

Asp Arg Leu Gly Ile Asn Arg Gln His Thr Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val Ser Gly Gly Ser Ala
465                 470                 475                 480

Trp Ser His Pro Gln Phe Glu Lys Gly Gly Gly Ser Gly Gly Gly Ser
                485                 490                 495
```

Gly Gly Ser Ala Trp Ser His Pro Gln Phe Glu Lys
500 505

<210> SEQ ID NO 81
<211> LENGTH: 89
<212> TYPE: DNA
<213> ORGANISM: Artificial sequence
<220> FEATURE:
<223> OTHER INFORMATION: Polynucleotide used in the Examples

<400> SEQUENCE: 81
aggttttttt tttttttttt tttttttttt tttttttttt tttttttttt tttttttttt 60
tttttttttt tttttttttt ttttttttt 89

<210> SEQ ID NO 82
<211> LENGTH: 608
<212> TYPE: PRT
<213> ORGANISM: Artificial sequence
<220> FEATURE:
<223> OTHER INFORMATION: PhiE T373C/C22A/C455A/C503A-STrEP

<400> SEQUENCE: 82

Met Lys His Met Pro Arg Lys Met Tyr Ser Cys Asp Phe Glu Thr Thr
1 5 10 15

Thr Lys Val Glu Asp Ala Arg Val Trp Ala Tyr Gly Tyr Met Asn Ile
20 25 30

Glu Asp His Ser Glu Tyr Lys Ile Gly Asn Ser Leu Asp Glu Phe Met
35 40 45

Ala Trp Val Leu Lys Val Gln Ala Asp Leu Tyr Phe His Asn Leu Lys
50 55 60

Phe Asp Gly Ala Phe Ile Ile Asn Trp Leu Glu Arg Asn Gly Phe Lys
65 70 75 80

Trp Ser Ala Asp Gly Leu Pro Asn Thr Tyr Asn Thr Ile Ile Ser Arg
85 90 95

Met Gly Gln Trp Tyr Met Ile Asp Ile Cys Leu Gly Tyr Lys Gly Lys
100 105 110

Arg Lys Ile His Thr Val Ile Tyr Asp Ser Leu Lys Lys Leu Pro Phe
115 120 125

Pro Val Lys Lys Ile Ala Lys Asp Phe Lys Leu Thr Val Leu Lys Gly
130 135 140

Asp Ile Asp Tyr His Lys Glu Arg Pro Val Gly Tyr Lys Ile Thr Pro
145 150 155 160

Glu Glu Tyr Ala Tyr Ile Lys Asn Asp Ile Gln Ile Ile Ala Glu Ala
165 170 175

Leu Leu Ile Gln Phe Lys Gln Gly Leu Asp Arg Met Thr Ala Gly Ser
180 185 190

Asp Ser Leu Lys Gly Phe Lys Asp Ile Ile Thr Thr Lys Lys Phe Lys
195 200 205

Lys Val Phe Pro Thr Leu Ser Leu Gly Leu Asp Lys Glu Val Arg Tyr
210 215 220

Ala Tyr Arg Gly Gly Phe Thr Trp Leu Asn Asp Arg Phe Lys Glu Lys
225 230 235 240

Glu Ile Gly Glu Gly Met Val Phe Asp Val Asn Ser Leu Tyr Pro Ala
245 250 255

Gln Met Tyr Ser Arg Leu Leu Pro Tyr Gly Glu Pro Ile Val Phe Glu
260 265 270

-continued

```
Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Cys Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Ala Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Ala Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Gly Ser
            580                 585                 590

Gly Gly Gly Ser Gly Gly Ser Ala Trp Ser His Pro Gln Phe Glu Lys
        595                 600                 605
```

<210> SEQ ID NO 83
<211> LENGTH: 70
<212> TYPE: DNA
<213> ORGANISM: Artificial sequence
<220> FEATURE:
<223> OTHER INFORMATION: Polynucleotide used in the Examples

<400> SEQUENCE: 83

```
tttttttttt tttttttttt tttttttttt tttttttttt tttttttttt tttttttttt      60

tttttttttt                                                             70
```

<210> SEQ ID NO 84

<211> LENGTH: 6
<212> TYPE: PRT
<213> ORGANISM: Artificial sequence
<220> FEATURE:
<223> OTHER INFORMATION: Linker

<400> SEQUENCE: 84

Gly Thr Gly Ser Gly Ala
1               5

<210> SEQ ID NO 85
<211> LENGTH: 6
<212> TYPE: PRT
<213> ORGANISM: Artificial sequence
<220> FEATURE:
<223> OTHER INFORMATION: Linker

<400> SEQUENCE: 85

Gly Thr Gly Ser Gly Thr
1               5

<210> SEQ ID NO 86
<211> LENGTH: 970
<212> TYPE: PRT
<213> ORGANISM: Citromicrobium bathyomarinum JL354

<400> SEQUENCE: 86

```
Met Leu Ser Val Ala Asn Val Arg Ser Pro Ser Ala Ala Ala Ser Tyr
1               5                   10                  15

Phe Ala Ser Asp Asn Tyr Tyr Ala Ser Ala Asp Ala Asp Arg Ser Gly
            20                  25                  30

Gln Trp Ile Gly Asp Gly Ala Lys Arg Leu Gly Leu Glu Gly Lys Val
        35                  40                  45

Glu Ala Arg Ala Phe Asp Ala Leu Leu Arg Gly Glu Leu Pro Asp Gly
    50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
            100                 105                 110

His Trp Ala Glu Lys Asn Ala Ala Glu Thr Arg Val Val Glu Lys Gly
        115                 120                 125

Met Val Val Thr Gln Ala Thr Gly Asn Leu Ala Ile Gly Leu Phe Gln
    130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
        195                 200                 205

Val Leu Lys His Gly Asn Phe Glu Ala Arg Gly Ile Ser Arg Glu Gln
    210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
                245                 250                 255
```

-continued

```
Ser Lys Glu Gly Ile Glu Asp Arg Ala Thr Leu Ser Lys Gln Trp Ser
            260                 265                 270

Glu Ala Ala Gln Ser Ile Gly Leu Asp Leu Lys Pro Leu Val Asp Arg
        275                 280                 285

Ala Arg Thr Lys Ala Leu Gly Gln Gly Met Glu Ala Thr Arg Ile Gly
    290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Pro Ser Val Leu Lys
                325                 330                 335

Gln Asp Arg Gln Thr Ile Ala Ala Ala Gln Ala Val Ala Ser Ala Val
            340                 345                 350

Arg His Leu Ser Gln Arg Glu Ala Ala Phe Glu Arg Thr Ala Leu Tyr
        355                 360                 365

Lys Ala Ala Leu Asp Phe Gly Leu Pro Thr Thr Ile Ala Asp Val Glu
    370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
                405                 410                 415

Gln Arg Ile Leu Ser Glu Val Ala Ala Gly Lys Gly Asp Ser Ser Pro
            420                 425                 430

Ala Ile Thr Pro Gln Lys Ala Ala Ala Ser Val Gln Ala Ala Ala Leu
        435                 440                 445

Thr Gly Gln Gly Phe Arg Leu Asn Glu Gly Gln Leu Ala Ala Ala Arg
    450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
                485                 490                 495

Asp Glu Gly His Pro Val Ile Gly Leu Ala Ile Gln Asn Thr Leu Val
            500                 505                 510

Gln Met Leu Glu Arg Asp Thr Gly Ile Gly Ser Gln Thr Leu Ala Arg
        515                 520                 525

Phe Leu Gly Gly Trp Asn Lys Leu Leu Asp Asp Pro Gly Asn Val Ala
    530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
        595                 600                 605

Arg Ala Gly Ile Ala Arg Ala Glu Met Ala Thr Asn Leu Arg Ala Arg
    610                 615                 620

Asp Pro Val Val Arg Glu Ala Gln Ala Ala Ala Gln Ala Gly Asp Val
625                 630                 635                 640

Arg Lys Ala Leu Arg His Leu Lys Ser His Thr Val Glu Ala Arg Gly
                645                 650                 655

Asp Gly Ala Gln Val Ala Ala Glu Thr Trp Leu Ala Leu Asp Lys Glu
            660                 665                 670
```

```
Thr Arg Ala Arg Thr Ser Ile Tyr Ala Ser Gly Arg Ala Ile Arg Ser
        675                 680                 685

Ala Val Asn Ala Ala Val Gln Gln Gly Leu Leu Ala Ser Arg Glu Ile
    690                 695                 700

Gly Pro Ala Lys Met Lys Leu Glu Val Leu Asp Arg Val Asn Thr Thr
705                 710                 715                 720

Arg Glu Glu Leu Arg His Leu Pro Ala Tyr Arg Ala Gly Arg Val Leu
                725                 730                 735

Glu Val Ser Arg Lys Gln Gln Ala Leu Gly Leu Phe Ile Gly Glu Tyr
            740                 745                 750

Arg Val Ile Gly Gln Asp Arg Lys Gly Lys Leu Val Glu Val Glu Asp
        755                 760                 765

Lys Arg Gly Lys Arg Phe Arg Phe Asp Pro Ala Arg Ile Arg Ala Gly
    770                 775                 780

Lys Gly Asp Asp Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Glu Ile Ala Asn Gly Lys
            820                 825                 830

Val Thr Phe Glu Thr Ser Lys Gly Asp Leu Val Glu Leu Lys Lys Asp
        835                 840                 845

Asp Pro Met Leu Lys Arg Ile Asp Leu Ala Tyr Ala Leu Asn Val His
    850                 855                 860

Met Ala Gln Gly Leu Thr Ser Asp Arg Gly Ile Ala Val Met Asp Ser
865                 870                 875                 880

Arg Glu Arg Asn Leu Ser Asn Gln Lys Thr Phe Leu Val Thr Val Thr
                885                 890                 895

Arg Leu Arg Asp His Leu Thr Leu Val Val Asp Ser Ala Asp Lys Leu
            900                 905                 910

Gly Ala Ala Val Ala Arg Asn Lys Gly Glu Lys Ala Ser Ala Ile Glu
        915                 920                 925

Val Thr Gly Ser Val Lys Pro Thr Ala Thr Lys Gly Ser Gly Val Asp
    930                 935                 940

Gln Pro Lys Ser Val Glu Ala Asn Lys Ala Glu Lys Glu Leu Thr Arg
945                 950                 955                 960

Ser Lys Ser Lys Thr Leu Asp Phe Gly Ile
                965                 970
```

<210> SEQ ID NO 87
<211> LENGTH: 8
<212> TYPE: PRT
<213> ORGANISM: Artificial sequence
<220> FEATURE:
<223> OTHER INFORMATION: RecD-like motif I of TrwC Cba

<400> SEQUENCE: 87

```
Gly Ile Ala Gly Ala Gly Lys Ser
1               5
```

<210> SEQ ID NO 88
<211> LENGTH: 10
<212> TYPE: PRT
<213> ORGANISM: Artificial sequence
<220> FEATURE:
<223> OTHER INFORMATION: RecD-like motif V of TrwC Cba

<400> SEQUENCE: 88

```
Tyr Ala Leu Asn Val His Met Ala Gln Gly
1               5                   10


<210> SEQ ID NO 89
<211> LENGTH: 14
<212> TYPE: PRT
<213> ORGANISM: Artificial sequence
<220> FEATURE:
<223> OTHER INFORMATION: MobF motif III of TrwC Cba

<400> SEQUENCE: 89

His Asp Thr Asn Arg Asn Gln Glu Pro Asn Leu His Phe His
1               5                   10


<210> SEQ ID NO 90
<211> LENGTH: 943
<212> TYPE: PRT
<213> ORGANISM: Halothiobacillus neapolitanus c2

<400> SEQUENCE: 90

Met Leu Arg Ile Lys Asn Leu Lys Gly Asp Pro Ser Ala Ile Ile Asp
1               5                   10                  15

Tyr Ala Glu Asn Lys Lys Asn His Pro Asp Gln Lys Ser Gly Tyr Tyr
            20                  25                  30

Asp Ala Lys Gly Ala Pro Ser Ala Trp Gly Gly Ala Leu Ala Ala Asp
        35                  40                  45

Leu Gly Leu Ser Gly Ser Val Gln Ala Ala Asp Leu Lys Lys Leu Leu
    50                  55                  60

Ser Gly Glu Leu Ser Asp Gly Thr Arg Phe Ala Lys Glu Asp Pro Asp
65                  70                  75                  80

Arg Arg Leu Gly Ile Asp Met Ser Phe Ser Ala Pro Lys Ser Val Ser
                85                  90                  95

Leu Ala Ala Leu Val Gly Gly Asp Glu Arg Ile Ile Gln Ala His Asp
            100                 105                 110

Ala Ala Val Arg Thr Ala Met Ser Met Ile Glu Gln Glu Tyr Ala Thr
        115                 120                 125

Ala Arg Phe Gly His Ala Gly Arg Asn Val Val Cys Ser Gly Lys Leu
    130                 135                 140

Val Tyr Ala Ala Tyr Arg His Glu Asp Ala Arg Thr Val Asp Asp Ile
145                 150                 155                 160

Ala Asp Pro Gln Leu His Thr His Cys Ile Val Ser Asn Ile Thr Ile
                165                 170                 175

Asp Pro Glu Thr Gly Lys Pro Arg Ser Ile Asp Phe Ala Trp Gly Gln
            180                 185                 190

Asp Gly Ile Lys Leu Ala Gly Ala Met Tyr Arg Ala Glu Leu Ala Arg
        195                 200                 205

Arg Leu Lys Glu Met Gly Tyr Glu Leu Arg Lys Ser Glu Glu Gly Phe
    210                 215                 220

Glu Leu Ala Gln Ile Ser Asp Glu Gln Val Glu Thr Phe Ser Arg Arg
225                 230                 235                 240

Arg Val Gln Val Asp Gln Ala Leu Glu Gln Gln Gly Thr Asp Arg Glu
                245                 250                 255

His Ala Ser Ser Glu Leu Lys Thr Ala Val Thr Leu Ala Thr Arg Gln
            260                 265                 270

Gly Lys Ala Gln Leu Ser Ala Glu Asp Gln Tyr Glu Glu Trp Gln Gln
        275                 280                 285
```

```
Arg Ala Ala Glu Ala Glu Leu Asp Leu Ser Gln Pro Val Gly Pro Arg
    290                 295                 300

Val Ser Val Thr Pro Pro Glu Ile Asp Leu Asp His Thr Phe Glu His
305                 310                 315                 320

Leu Ser Glu Arg Ala Ser Val Ile Asn Lys Asp Ala Val Arg Leu Asp
                325                 330                 335

Ala Leu Ile Asn His Met Ser Glu Gly Ala Thr Leu Ser Thr Val Asp
            340                 345                 350

Lys Ala Ile Gln Gly Ala Ala Val Thr Gly Asp Val Phe Glu Ile Glu
        355                 360                 365

Asp Gly Ile Lys Arg Lys Ile Ile Thr Arg Glu Thr Leu Lys Arg Glu
    370                 375                 380

Gln Gln Ile Leu Leu Leu Ala Gln Gln Gly Arg Gly Val Asn Ser Val
385                 390                 395                 400

Leu Ile Gly Val Gly Asp Thr Lys His Leu Ile Glu Asp Ala Glu Gln
                405                 410                 415

Ala Gln Gly Phe Arg Phe Ser Glu Gly Gln Arg Arg Ala Ile Asn Leu
            420                 425                 430

Thr Ala Thr Thr Thr Asp Gln Val Ser Gly Ile Val Gly Ala Ala Gly
        435                 440                 445

Ala Gly Lys Thr Thr Ala Met Lys Thr Val Ala Asp Leu Ala Lys Ser
    450                 455                 460

Gln Gly Leu Thr Val Val Gly Ile Ala Pro Ser Ser Ala Ala Ala Asp
465                 470                 475                 480

Glu Leu Lys Ser Ala Gly Ala Asp Asp Thr Met Thr Leu Ala Thr Phe
                485                 490                 495

Asn Leu Lys Gly Glu Ala Ala Gly Pro Arg Leu Leu Ile Leu Asp Glu
            500                 505                 510

Ala Gly Met Val Ser Ala Arg Asp Gly Glu Ala Leu Leu Lys Lys Leu
        515                 520                 525

Gly Lys Glu Asp Arg Leu Ile Phe Val Gly Asp Pro Lys Gln Leu Ala
    530                 535                 540

Ala Val Glu Ala Gly Ser Pro Phe Ala Gln Leu Met Arg Ser Gly Ala
545                 550                 555                 560

Ile Gln Tyr Ala Glu Ile Thr Glu Ile Asn Arg Gln Lys Asp Gln Lys
                565                 570                 575

Leu Leu Asp Ile Ala Gln His Phe Ala Lys Gly Lys Ala Glu Glu Ala
            580                 585                 590

Val Ala Leu Ala Thr Lys Tyr Val Thr Glu Val Pro Val Thr Leu Pro
        595                 600                 605

Asp Lys Pro Glu His Lys Ile Thr Arg Gln Ala Lys Thr Glu Ala Arg
    610                 615                 620

Arg Leu Ala Ile Ala Ser Ala Thr Ala Lys Arg Tyr Leu Glu Leu Ser
625                 630                 635                 640

Gln Glu Glu Arg Ala Thr Thr Leu Val Leu Ser Gly Thr Asn Ala Val
                645                 650                 655

Arg Lys Gln Val Asn Glu Gln Val Arg Lys Gly Leu Ile Asp Lys Gly
            660                 665                 670

Glu Ile Asn Gly Glu Ser Phe Thr Val Ser Thr Leu Asp Lys Ala Asp
        675                 680                 685

Met Thr Arg Ala Lys Met Arg Lys Ala Gly Asn Tyr Lys Pro Gly Gln
    690                 695                 700

Val Ile Lys Thr Ala Gly Lys Gln Ala Glu Gln Ser Glu Val Val Ala
```

```
705                 710                 715                 720

Val Asn Leu Asp Gln Asn Leu Ile Gln Val Lys Leu Ser Asp Gly Thr
                725                 730                 735

Leu Lys Ser Ile Asp Ala Ser Arg Phe Asp Val Lys Lys Thr Gln Val
            740                 745                 750

Phe Asn Pro Arg Gln Ile Asp Ile Ala Ala Gly Asp Lys Ile Ile Phe
        755                 760                 765

Thr Asn Asn Asp Gln Ala Thr Glu Thr Lys Asn Asn Gln Ile Gly Leu
    770                 775                 780

Ile Glu Glu Ile Lys Asp Gly Lys Ala Ile Ile Asn Ser Asn Gly Ala
785                 790                 795                 800

Lys Val Glu Ile Asp Ile Gln Arg Lys Leu His Ile Asp His Ala Tyr
                805                 810                 815

Cys Ile Thr Ile His Arg Ser Gln Gly Gln Thr Val Asp Ser Val Ile
            820                 825                 830

Val Ala Gly Glu Ala Ser Arg Thr Thr Thr Ala Glu Ala Ala Tyr Val
        835                 840                 845

Ala Cys Thr Arg Glu Arg Tyr Lys Leu Glu Ile Ile Thr Asp Asn Thr
    850                 855                 860

Glu Arg Leu Ser Lys Asn Trp Val Arg Tyr Ala Asp Arg Gln Thr Ala
865                 870                 875                 880

Ala Glu Ala Leu Lys Ser Ser Glu Glu Lys Tyr Pro His Leu Asp Glu
                885                 890                 895

Ile Arg Glu Glu Leu Arg Arg Glu Leu Gln Gln Glu Leu Glu Arg Gln
            900                 905                 910

Glu Pro Thr Asn Ile Thr Pro Glu Leu Glu Ile Glu Met Glu Arg Ser
        915                 920                 925

Met Phe Asp Gln Tyr Thr Leu His Ser Arg Gln Pro Arg Ser Tyr
    930                 935                 940
```

<210> SEQ ID NO 91
<211> LENGTH: 8
<212> TYPE: PRT
<213> ORGANISM: Artificial sequence
<220> FEATURE:
<223> OTHER INFORMATION: RecD-like motif I of TrwC Hne

<400> SEQUENCE: 91

```
Gly Ala Ala Gly Ala Gly Lys Thr
1               5
```

<210> SEQ ID NO 92
<211> LENGTH: 10
<212> TYPE: PRT
<213> ORGANISM: Artificial sequence
<220> FEATURE:
<223> OTHER INFORMATION: RecD-like motif V of TrwC Hne

<400> SEQUENCE: 92

```
Tyr Cys Ile Thr Ile His Arg Ser Gln Gly
1               5                   10
```

<210> SEQ ID NO 93
<211> LENGTH: 18
<212> TYPE: PRT
<213> ORGANISM: Artificial sequence
<220> FEATURE:
<223> OTHER INFORMATION: MobF motif III of TrwC Hne

<400> SEQUENCE: 93

```
His Glu Asp Ala Arg Thr Val Asp Asp Ile Ala Asp Pro Gln Leu His
1               5                   10                  15

Thr His


<210> SEQ ID NO 94
<211> LENGTH: 960
<212> TYPE: PRT
<213> ORGANISM: Erythrobacter litoralis HTCC2594

<400> SEQUENCE: 94

Met Leu Ser Val Ala Asn Val Arg Ser Pro Thr Ala Ala Ala Ser Tyr
1               5                   10                  15

Phe Ala Ser Asp Asn Tyr Tyr Ala Ser Ala Asp Ala Asp Arg Ser Gly
            20                  25                  30

Gln Trp Ile Gly Gly Gly Ala Lys Arg Leu Gly Leu Glu Gly Lys Val
        35                  40                  45

Glu Ala Lys Ala Phe Asp Ala Leu Leu Arg Gly Glu Leu Pro Asp Gly
    50                  55                  60

Ser Ser Val Gly Asn Pro Gly Gln Ala His Arg Pro Gly Thr Asp Leu
65                  70                  75                  80

Ser Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
            100                 105                 110

Gln Trp Ala Glu Lys Asn Ala Ala Glu Thr Arg Ile Val Glu Lys Gly
        115                 120                 125

Lys Met Val Thr Gln Ala Thr Gly Asn Leu Ala Val Gly Leu Phe Gln
    130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
        195                 200                 205

Val Leu Lys His Gly Asn Phe Glu Ala Arg Gly Ile Ser Arg Glu Gln
    210                 215                 220

Ile Met Ala Phe Ser Thr Arg Arg Lys Glu Val Leu Glu Ala Arg Arg
225                 230                 235                 240

Gly Pro Gly Leu Glu Ala Gly Arg Ile Ala Ala Leu Asp Thr Arg Ala
                245                 250                 255

Ser Lys Glu Glu Ile Glu Asp Arg Ala Thr Leu Gly Lys Gln Trp Ser
            260                 265                 270

Glu Thr Ala Gln Ser Ile Gly Leu Asp Leu Thr Pro Leu Val Asp Arg
        275                 280                 285

Ala Arg Thr Asn Ala Leu Gly Gln Ser Met Glu Ala Thr Arg Ile Gly
    290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Pro Ser Val Leu Lys
                325                 330                 335

Gln Asp Arg Gln Thr Ile Ala Ala Ala Gln Ala Val Ala Ser Ala Ile
            340                 345                 350
```

-continued

```
Arg His Leu Ser Gln Arg Glu Ala Ala Phe Glu Arg Thr Ala Leu Tyr
        355                 360                 365

Lys Ala Ala Leu Asp Phe Gly Leu Pro Ala Thr Ile Ala Asp Val Glu
    370                 375                 380

Lys Arg Thr Arg Ala Leu Val Arg Ser Gly Asp Leu Ile Ser Gly Lys
385                 390                 395                 400

Gly Glu His Lys Gly Trp Leu Ala Ser Arg Glu Ala Val Val Thr Glu
                405                 410                 415

Gln Arg Ile Leu Ser Glu Val Ala Ala Gly Lys Gly Asn Ser Ser Pro
            420                 425                 430

Ala Ile Glu Pro Gln Lys Ala Ala Ala Ser Val Gln Ala Ala Ala Ala
        435                 440                 445

Thr Gly Gln Gly Phe Arg Leu Asn Glu Gly Gln Leu Ala Ala Ala Glu
    450                 455                 460

Leu Ile Leu Thr Ser Lys Asp Arg Thr Ile Ala Ile Gln Gly Ile Ala
465                 470                 475                 480

Gly Ala Gly Lys Ser Ser Val Leu Lys Pro Val Ala Glu Val Leu Arg
                485                 490                 495

Asp Glu Gly His Pro Val Ile Gly Leu Ala Ile Gln Asn Thr Leu Val
            500                 505                 510

Gln Met Leu Glu Arg Glu Thr Gly Ile Gly Ser Gln Thr Leu Ala Arg
        515                 520                 525

Phe Leu Arg Gly Trp Thr Lys Leu Leu Gly Asp Pro Gly Asn Val Ala
    530                 535                 540

Leu Arg Thr Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
        595                 600                 605

Arg Ala Gly Ile Ala Arg Ala Glu Met Ala Thr Asn Leu Arg Ala Arg
    610                 615                 620

Asp Pro Val Val Arg Glu Ala Gln Ala Ser Ala Gln Ala Gly Asp Val
625                 630                 635                 640

Arg Asn Ala Leu Arg His Leu Lys Ser His Thr Val Glu Ala Lys Gly
                645                 650                 655

Asp Gly Ala Gln Val Ala Ala Glu Thr Trp Leu Ala Leu Asp Lys Glu
            660                 665                 670

Thr Arg Ala Arg Thr Ser Ile Tyr Ala Ser Gly Arg Ala Ile Arg Ser
        675                 680                 685

Ala Val Asn Ala Ala Val Gln Gln Gly Leu Leu Ala Asn Arg Glu Ile
    690                 695                 700

Gly Pro Gly Met Met Lys Leu Asp Val Leu Asp Arg Val Asn Ala Thr
705                 710                 715                 720

Arg Glu Glu Leu Arg His Leu Pro Ala Tyr Arg Ala Gly Gln Val Leu
                725                 730                 735

Glu Ile Ser Arg Lys Gln Gln Ala Leu Gly Leu Ser Val Gly Glu Tyr
            740                 745                 750

Arg Val Leu Gly Gln Asp Arg Lys Gly Arg Leu Val Glu Val Glu Asp
        755                 760                 765
```

-continued

```
Lys Arg Gly Lys Arg Phe Arg Phe Asp Pro Ala Arg Ile Lys Ala Gly
    770                 775                 780

Lys Gly Asp Glu Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Ala Ile Ala Gly Gly Lys
            820                 825                 830

Ile Thr Phe Glu Thr Ser Gln Gly Asp Gln Val Glu Leu Lys Arg Asp
        835                 840                 845

Asp Pro Met Leu Lys Arg Ile Asp Leu Ala Tyr Ala Leu Asn Ala His
    850                 855                 860

Met Ala Gln Gly Leu Thr Ser Asp Arg Gly Ile Ala Val Met Thr Ser
865                 870                 875                 880

Ser Glu Arg Asn Leu Ser Asn Gln Lys Thr Phe Met Val Thr Val Thr
                885                 890                 895

Arg Leu Arg Asp His Leu Thr Leu Val Val Asp Asn Ala Glu Lys Leu
            900                 905                 910

Gly Ala Ala Val Ala Arg Asn Lys Gly Glu Lys Ala Ser Ala Leu Glu
        915                 920                 925

Val Thr Gly Ser Val Lys Ser Thr Ala Ala Lys Gly Ser Gly Val Asp
    930                 935                 940

Gln Leu Lys Pro Glu Glu Ala Asn Lys Ala Glu Lys Glu Leu Thr Arg
945                 950                 955                 960


<210> SEQ ID NO 95
<211> LENGTH: 10
<212> TYPE: PRT
<213> ORGANISM: Artificial sequence
<220> FEATURE:
<223> OTHER INFORMATION: RecD-like motif V of TrwC Eli

<400> SEQUENCE: 95

Tyr Ala Leu Asn Ala His Met Ala Gln Gly
1               5                   10
```

SSB METHOD

RELATED APPLICATIONS

This Application is a continuation of U.S. application Ser. No. 14/415,459, filed Jan. 16, 2015, which is a national stage filing under 35 U.S.C. § 371 of international application number PCT/GB2013/051924, filed Jul. 18, 2013, which claims the benefit of priority under 35 U.S.C. § 119(e) to U.S. provisional application No. 61/774,688, filed Mar. 8, 2013, and U.S. provisional application No. 61/673,457, filed Jul. 19, 2012, the entire contents of each of which are incorporated herein by reference.

FIELD OF THE INVENTION

The invention relates to a method of characterising a target polynucleotide using a single-stranded binding protein (SSB). The SSB is either an SSB comprising a carboxy-terminal (C-terminal) region which does not have a net negative charge or a modified SSB comprising one or more modifications in its C-terminal region which decreases the net negative charge of the C-terminal region.

BACKGROUND OF THE INVENTION

There is currently a need for rapid and cheap polynucleotide (e.g DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identity of the nucleotides are derived. Strand sequencing can involve the use of a nucleotide handling protein to control the movement of the polynucleotide through the pore.

SUMMARY OF THE INVENTION

The inventors have surprisingly demonstrated that certain SSBs may be used, for example, to prevent a target polynucleotide from forming secondary structure or as a molecular brake when the polynucleotide is characterized, such as sequenced, using a transmembrane pore. In particular, the inventors have surprisingly demonstrated that SSBs which lack a negatively charged carboxy-terminal (C-terminal) region will bind to a target polynucleotide and prevent secondary structure formation or act as a molecular brake without blocking the transmembrane pore The absence of pore block is advantageous because it allows the polynucleotide to be characterised by measuring the current flowing through the pore as the polynucleotide moves through the pore. For strand sequencing, it is preferred that the pore has a high duty cycle, i.e. the pore has a polynucleotide within it as much as possible and is sequencing as much as possible Pore block by something other than the analyte of interest lowers the duty cycle and so also lowers data output. Hence, an absence of pore block helps to maintain a high duty cycle and a high data output. Pore block could also happen when a polynucleotide strand is present in the pore and thus attenuate sequencing.

Pore block can be transient (i.e. the block reverses itself during the experiment) or permanent (i.e. the block is maintained for the duration of the experiment without some sort of intervention). If the block is permanent, then a change in potential may be needed to clear the block. This can be problematic, especially for a sequencing array. If each electrode in the army is not individually addressable, it would be necessary to change the potential in all channels to clear the block in one channel or a few channels. This would of course interrupt any sequencing using the array. An absence of pore block therefore helps sequencing arrays to function effectively.

Accordingly, the invention provides a method of characterising a target polynucleotide, comprising.

a) contacting the target polynucleotide with a transmembrane pore and a single-stranded binding protein (SSB) such that the target polynucleotide moves through the pore and the SSB does not move through the pore, wherein the SSB is (i) an SSB comprising a carboxy-terminal (C-terminal) region which does not have a net negative charge or (ii) a modified SSB comprising one or more modifications in its C-terminal region which decreases the net negative charge of the C-terminal region, and
b) taking one or more measurements as the polynucleotide moves with respect to the pore wherein the measurements are indicative of one or more characteristics of the target polynucleotide and thereby characterising the target polynucleotide.

The invention also provides:

- a method of forming a sensor for characterising a target polynucleotide, comprising forming a complex between a pore and an SSB as defined above and thereby forming a sensor for characterising the target polynucleotide.
- a sensor for characterising a target polynucleotide, comprising a complex between (a) a pore and (b) a SSB as defined above,
- use of a SSB as defined above in the characterisation of a target polynucleotide using a transmembrane pore;
- a kit for characterising a target polynucleotide comprising (a) a transmembrane pore and (b) a SSB as defined above;
- an apparatus for characterising target polynucleotides in a sample, comprising (a) a plurality of transmembrane pores and (b) a plurality of SSBs as defined above;
- a construct comprising at least one helicase and an SSB as defined above, wherein the helicase is attached to the SSB and the construct has the ability to control the movement of a polynucleotide; and
- a method of forming a construct of the invention, comprising attaching an SSB as defined above to at least one helicase and thereby producing a construct of the invention.

Description of the Sequence Listing

Figure 1:
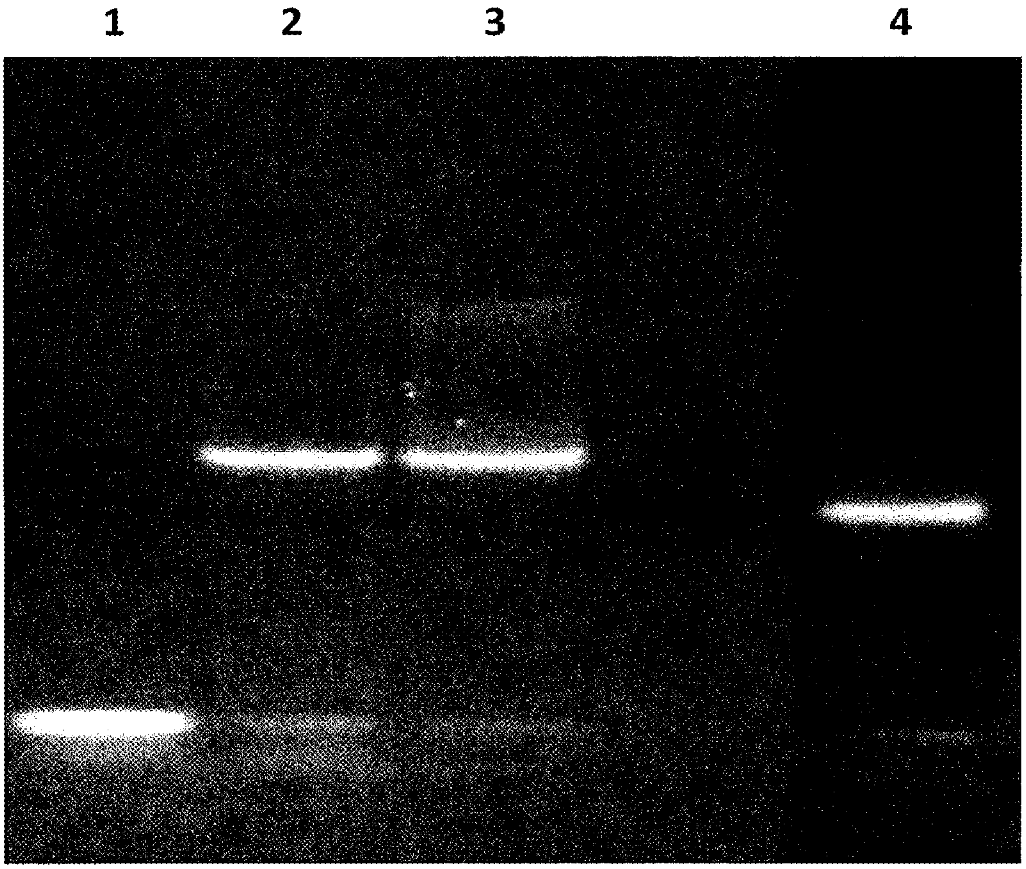
FIG. 1 shows an electrophoretic mobility bandshift assay for ssDNA:SSB complexes. Column 1 contains the 70-polyT (SEQ ID NO: 83), column 2 contains commercial EcoSSB-WT (SEQ ID NO. 65), column 3 contains WT-SSB (SEQ ID NO: 65) and column 4 contains EcoSSB-Q152del (SEQ ID NO. 68). It can be seen that the EcoSSB-Q152del mutant (SEQ ID NO. 68) is not impaired in its ability to form a complex with the 70mer polyT (SEQ ID NO: 83), when compared to the wild-type SSB (SEQ ID NO: 65). The slight shift in position of the protein DNA complex is likely due to the deletion of the C-terminus and charge removal.

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D18R, D134R and E139K SEQ ID NO: 3 shows the polynucleotide sequence encoding one monomer of α-hemolysin-E111N/K 147N (α-HL-NN; Stoddart el at., PNAS, 2009; 106(19) 7702-7707).

SEQ ID NO: 4 shows the amino acid sequence of one monomer of 0-1HL-NN.

SEQ ID NO: 5 to 7 show the amino acid sequences of MspB, C and D

SEQ ID NO 8 shows the amino acid sequence of the Hel308 motif.

SEQ ID NO: 9 shows the amino acid sequence of the extended Hel308 motif.

SEQ ID NO. 10 shows the amino acid sequence of Hel308 Mbu.

SEQ ID NO: 11 shows the Hel308 motif of Hel308 Mbu and Hel308 Mhu.

SEQ ID NO. 12 shows the extended Hel308 motif of Hel308 Mbu and Hel308 Mhu.

SEQ ID NO: 13 shows the amino acid sequence of Hel308 Csy.

SEQ ID NO: 14 shows the Hel308 motif of Hel308 Csy.

SEQ ID NO 15 shows the extended Hel308 motif of Hel308 Cay.

SEQ ID NO: 16 shows the amino acid sequence of Hel308 Tga.

SEQ ID NO. 17 shows the Hel308 motif of Hel308 Tga.

SEQ ID NO: 18 shows the extended Hel308 motif of Hel308 Tga.

SEQ ID NO 19 shows the amino acid sequence of Hel308 Mbu.

SEQ ID NO: 20 shows the RecD-like motif I.

SEQ ID NOs: 21 to 23 show the extended RecD-like motif 1.

SEQ ID NO: 24 shows the RecD motif I

SEQ ID NO: 25 shows a preferred RecD motif 1, namely G-G-P-G-T-G-K-T.

SEQ ID NOs: 26 to 28 show the extended RecD motif I.

SEQ ID NO: 29 shows the RecD-like motif V.

SEQ ID NO: 30 shows the RecD motif V.

SEQ ID NOs: 31 to 38 show the MobF motif III.

SEQ ID NOs: 39 to 45 show the MobQ motif III.

SEQ ID NO: 46 shows the amino acid sequence of TraI Eco.

SEQ ID NO 47 shows the RecD-like motif I of TraI Eco.

SEQ ID NO: 48 shows the RecD-like motif V of TraI Eco.

SEQ ID NO. 49 shows the the MobF motif Ill of TraI Eco.

SEQ ID NO: 50 shows the XPD motif V.

SEQ ID NO: 51 shows XPD motif VI.

SEQ ID NO: 52 shows the amino acid sequence of XPD Mbu.

SEQ ID NO: 53 shows the XPD motif V of XPD Mbu.

SEQ ID NO: 54 shows XPD motif VI of XPD Mbu

SEQ ID NO: 55 shows the amino acid sequence of the ssb from the bacteriophage T4, which is encoded by the gp32 gene SEQ ID NO: 56 shows the amino acid sequence of the ssb from the bacteriophage RB69, which is encoded by the gp32 gene SEQ ID NO: 57 shows the amino acid sequence of the ssb from the bacteriophage T7, which is encoded by the gp2.5 gene.

SEQ ID NO: 58 shows the amino acid sequence of Phi29 DNA polymerase.

SEQ ID NO: 59 shows the amino acid sequence of the ssb from the bacteriophage RB69, i.e. SEQ ID NO: 56, with its C terminus deleted (gp32RB69CD).

SEQ ID NO: 60 shows the amino acid sequence (from 1 to 210) of the ssb from the bacteriophage T7 (gp2.5T7-R211Del) The full length protein is shown in SEQ ID NO: 57.

SEQ ID NO: 61 shows the amino acid sequence of the $5^{th}$ domain of Hel308 Hla.

SEQ ID NO: 62 shows the amino acid sequence of the $5^{th}$ domain of Hel308 Hvo.

SEQ ID NO: 63 shows the amino acid sequence of the human mitochondrial SSB (HmtSSB)

SEQ ID NO: 64 shows the amino acid sequence of the p5 protein from Phi29 DNA polymerase.

SEQ ID NO: 65 shows the amino acid sequence of the wild-type SSB from *E. coli* (EcoSSB-WT).

SEQ ID NO: 66 shows the amino acid sequence of EcoSSB-CterAla.

SEQ ID NO. 67 shows the amino acid sequence of EcoSSB-CterNGGN.

SEQ ID NO: 68 shows the amino acid sequence of EcoSSB-Q152del.

SEQ ID NO: 69 shows the amino acid sequence of EcoSSB-G117del

SEQ ID NO: 70 shows the polynucleotide sequence, for PhiX 5 kB sense strand, which is used in Example 4.

SEQ ID NO: 71 shows the polynucleotide sequence, for PhiX 5 kB anti-sense strand, which is used in Example 4.

SEQ ID NO 72 shows the polynucleotide sequence of a short strand of DNA which is used in Example 4.

SEQ ID NO. 73 shows the polynucleotide sequence of a DNA strand used in a transport control protein fluorescent assay.

SEQ ID NO: 74 shows the amino acid sequence of the (HhH)2 domain.

SEQ ID NO: 75 shows the amino acid sequence of the (HhH)2-(HhH)2 domain.

SEQ 1D NO: 76 shows the amino acid sequence (from 1 to 319) of the UL42 processivity factor from the Herpes virus 1

SEQ ID NO: 77 shows the amino acid sequence of one subunit of wild-type (WT) α-hemolysin.

SEQ ID NO: 78 shows a polynucleotide sequence that contains two uracils which are labelled with azido-hexanoic acid and is used in Examples 3a and 3b.

SEQ ID NO: 79 shows a polynucleotide sequence which is used in Example 3a.

SEQ ID NO. 80 shows the amino acids sequence of a mutant EcoExoI with all of its natural cysteines removed, an additional cysteine mutation included at A83C and two Strep tags for purification.

SEQ ID NO: 81 shows a polynucleotide sequence, that contains two alkyne residues (shown as n in sequence), which is used in Example 3b.

SEQ ID NO: 82 shows the amino acid sequence of a PhiE DNA polymerase mutant (PhiE T373C/C22A/C455A/C530A) with a STrEP tag at the C-terminal end.

SEQ ID NO: 83 shows a polynucleotide sequence used in Example 2.

SEQ ID NO: 84 shows the GTGSGA linker.

SEQ ID NO: 85 shows the GTGSGT linker.

SEQ ID NOs: 86 to 95 show the TraI sequences shown in Table 5.

Detailed Description of the Invention

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms “a”, “an”, and “the” include plural referents unless the content clearly dictates otherwise. Thus, for example, reference to “a SSB” includes “SSBs”, reference to “a helicase” includes two or more such helicases, reference to “a transmembrane pore” includes two or more such pores, and the like.

All publications, patents and patent applications cited herein, whether supra or infra, are hereby incorporated by reference in their entirety.

Method of the Invention

The invention provides a method of characterising a target polynucleotide. The method comprises contacting the target polynucleotide with a transmembrane pore and a SSB such that the target polynucleotide moves through the pore and the SSB does not move through the pore. The SSB is either an SSB comprising a carboxy-terminal (C-terminal) region which does not have a net negative charge or a modified SSB comprising one or more modifications in its C-terminal region which decreases the net negative charge of the C-terminal region. Such SSBs are described in more detail below. The method then comprises taking one or more measurements as the polynucleotide moves with respect to the pore wherein the measurements are indicative of one or more characteristics of the target polynucleotide and thereby characterising the target polynucleotide. The target polynucleotide is preferably contacted with the pore and the SSB on the same side of the membrane.

The method of the invention is advantageous. Specifically, the ability of the SSB to bind the target polynucleotide without blocking the pore is advantageous for maintaining a high rate of experimental throughput. A target polynucleotide is unlikely to pass through a blocked pore. In an experiment which uses an array of multiple pores, the throughput is reduced by each blocked pore. The pores may be “permanently” blocked, ie. for the duration of the experiment without intervention, but it may be possible to unblock the pores by altering experimental conditions, such as reversing the potential. However, the alteration of conditions increases the length and complexity of the experiment and may not successfully unblock the pores. In a single pore experiment, the permanent blocking of the pore results in a failure to acquire any characterizing data.

The method is preferably carried out with a potential applied across the pore. As discussed in more detail below, the applied potential typically results in the formation of a complex between the pore and the SSB. The applied potential may be a voltage potential. Alternatively, the applied potential may be a chemical potential An example of this is using a salt gradient across an amphiphilic layer. A salt gradient is disclosed in Holden et al., J Am Chem Soc 2007 Jul 11; 129(27):8650-5

In some instances, the current passing through the pore as the polynucleotide moves with respect to the pore is used to determine the sequence of the target polynucleotide. This is Strand Sequencing.

Target Polynucleotide

The method of the invention is for characterising a target polynucleotide. A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated One or more nucleotides in the target polynucleotide may be damaged. For instance, the polynucleotide may comprise a pyrimidine dimer Such dimers are typically associated with damage by ultraviolet light and are the primary cause of skin melanomas One or more nucleotides in the target polynucleotide may be modified, for instance with a label or a tag. Suitable labels are described above. The target polynucleotide may comprise one or more spacers.

A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), guanosine monophosphate (GMP), thymidine monophosphate (TMP). uridine monophosphate (UMP), cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably single stranded.

The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

The whole or only pan of the target polynucleotide may be characterised using this method. The target polynucleotide can be any length. For example, the polynucleotide can be at least 10, at least 50, at least 100, at least 150, at least 200, at least 250, at least 300, at least 400 or at least 500 nucleotide pairs in length The polynucleotide can be 1000 or more nucleotide pairs, 5000 or more nucleotide pairs in length or 100000 or more nucleotide pairs in length.

The target polynucleotide is present in any suitable sample. The invention is typically carried out on a sample that is known to contain or suspected to contain the target polynucleotide Alternatively, the invention may be carried out on a sample to confirm the identity of one or more target polynucleotides whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms. plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids. water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken The sample may also be typically stored prior to assay, preferably below −70° C.

Transmembrane Pore

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane It may be closed at one end. For instance, the pore may be a well in the membrane along which or into which hydrated ions may flow.

The pore may be biological or artificial. Suitable pores include, but are not limited to, protein pores, polynucleotide pores and solid state pores.

The pore allows the target polynucleotide, but not the SSB to move through it. The barrel or channel of the pore preferably has a diameter of less than 10 nm, such as less than 7 nm or less than 5 nm, at its narrowest point.

Any membrane may be used in accordance with the invention. Suitable membranes are well-known in the art The membrane is preferably an amphiphilic layer An amphiphilic layer is a layer formed from amphiphilic molecules, such as phospholipids, which have both at least one hydrophilic portion and at least one lipophilic or hydrophobic portion. The amphiphilic layer may be a monolayer or a bilayer. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer.

The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Nati Acad Sci. USA. 1972; 69 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore. (ii) an isolated. naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below The method of the invention is typically carried out in vitro.

The polynucleotide may be coupled to the membrane This may be done using any known method. If the membrane is an amphiphilic layer, such as a lipid bilayer (as discussed in detail above), the polynucleotide is preferably coupled to the membrane via a polypeptide present in the membrane or a hydrophobic anchor present in the membrane. The hydrophobic anchor is preferably a lipid, fatty acid, sterol, carbon nanotube or amino acid.

The polynucleotide may be coupled directly to the membrane. The polynucleotide is preferably coupled to the membrane via a linker. Preferred linkers include, but are not limited to, polymers. such as polynucleotides, polyethylene glycols (PEGs) and polypeptides. If a polynucleotide is coupled directly to the membrane, then some data will be lost as the characterising run cannot continue to the end of the polynucleotide due to the distance between the membrane and the helicase. If a linker is used, then the polynucleotide can be processed to completion. If a linker is used, the linker may be attached to the polynucleotide at any position. The linker is preferably attached to the polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the bilayer and the helicase's active site. If the coupling is transient, then when the coupled end randomly becomes free of the bilayer, then the polynucleotide can be processed to completion. Chemical groups that form stable or transient links with the membrane are discussed in more detail below. The polynucleotide may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

In preferred embodiments, the polynucleotide is coupled to an amphiphilic layer Coupling of polynucleotides to synthetic lipid bilayers has been carried out previously with various different tethering strategies. These are summarised in Table 1 below

TABLE 1

| Attachment group | Type of coupling | Reference |
|---|---|---|
| Thiol | Stable | Yoshina-Ishii, C. and S. G. Boxer (2003). "Arrays of mobile tethered vesicles on supported lipid bilayers." J Am Chem Soc 125(13): 3696-7. |
| Biotin | Stable | Nikolov, V., R. Lipowsky, et al. (2007). "Behavior of giant vesicles with anchored DNA molecules." Biophys J 92(12): 4356-68 |
| Cholestrol | Transient | Pfeiffer, I. and F. Hook (2004). "Bivalent cholesterol-based coupling of oligonucletides to lipid membrane assemblies." J Am Chem Soc 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." Langmuir 26(11): 8666-72 |

Polynucleotides may be functionalized using a modified phosphoramidite in the synthesis reaction, which is easily compatible for the addition of reactive groups. such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the bilayer. The advantages of transient coupling are discussed above.

Coupling of polynucleotides can also be achieved by a number of other means provided that a reactive group can be added to the polynucleotide. The addition of reactive groups to either end of DNA has been reported previously. A thiol group can be added to the 5' of ssDNA using polynucleotide kinase and ATPγS (Grant. G. P. and P. Z. Qin (2007). "A facile method for attaching nitroxide spin labels at the 5' terminus of nucleic acids." *Nucleic Acids Recs* 35(10): e77). A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82)

Alternatively, the reactive group could be considered to be the addition of a short piece of DNA complementary to one already coupled to the bilayer, so that attachment can be achieved via hybridisation. Ligation of short pieces of ssDNA have been reported using T4 RNA ligase 1 (Troutt, A. B., M. G. McHeyzer-Williams, et al. (1992). "Ligation-anchored PCR: a simple amplification technique with single-sided specificity." *Proc Natl Acad Sci USA* 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the S' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer with a reactive group attached to it.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the amplified target DNA will contain a reactive group for coupling The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, die transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other The transmembrane protein pore allows a polynucleotide, such as DNA or RNA, to be moved through the pore.

The transmembrane protein pore may be a monomer or an oligomer The pore is preferably made up of several repeating subunits, such as 6, 7, 8 or 9 subunits The pore is preferably a hexameric, heptameric, octameric or nonameric pore.

The transmembrane protein pore typically comprises a barrel or channel through which the ions may flow The subunits of the pore typically surround a central axis and contribute strands to a transmembrane β barrel or channel or a transmembrane α-helix bundle or channel The barrel or channel of the transmembrane protein pore typically comprises amino acids that facilitate interaction with analyte, such as nucleotides, polynucleotides or nucleic acids These amino acids are preferably located near a constriction of the barrel or channel The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA MspB, MspC or MspD, outer membrane porin F (OmpF), outer membrane porin G (OmpG), outer membrane phospholipase A and *Neisseria* autotransporter lipoprotein (NalP) α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A. monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D911N, D93N, DI 18R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M.A. Holden, H. Bayley. J. Am. Chem. Soc. 2005, 127, 6502-6503 and International Application No. PCT/GB2006/001057 (published as WO 206/100484).

Over the entire length of the amino acid sequence of SEQ LD NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology information (http://www.ncbi.nlm.nih gov/).

SEQ ID NO: 2 is the MS-(B1)8 mutant of the MspA monomer. The variant may comprise any of the mutations in the MspB, C or D monomers compared with MspA. The mature forms of MspB. C and D are shown in SEQ ID NOs: 5 to 7. In particular, the variant may comprise the following substitution present in MspB: A138P. The variant may comprise one or more of the following substitutions present in MspC: A96G. N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation LSSN. A variant of SEQ ID NO: 2 has the mutation L88N in addition to all the mutations of MS-B1 and is called MS-(B2)8. The pore used in the invention is preferably MS-(B2)8. A variant of SEQ ID NO: 2 has the mutations G75S/G77S/L88N/Q126R in addition to all the mutations of MS-B1 and is called MS-B2C. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions Conservative substitutions replace amino acids with other amino acids of similar chemical structure. similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3.

TABLE 2

Chemical properties of amino acids

| | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, | Thr | polar, hydrophilic, neutral |
| | charged (+) | Val | aliphatic, hydrophobic, neutral |
| Ile | aliphatic, hydrophobic, neutral | Trp | aromatic, hydrophobic, neutral |
| Lys | polar, hydrophilic, charged(+) | Tyr | aromatic, polar, hydrophobic |
| Leu | aliphatic, hydrophobic, neutral | | |

TABLE 3

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively. the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a 0-barrel, is provided by β-sheets in each subunit. A variant of SEQ ID NO: 2 typically comprises the regions in SEQ ID NO: 2 that form (i-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol 1997 Jul; 4(7):497-505)

The monomer derived from Msp may be labelled with a revealing label. The revealing label may be any suitable label which allows the pore to be detected. Suitable labels are described above.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include. for example, reductive alkylation of amino acids by reaction with an aldehyde followed by reduction with $NaBH_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB091001679 (published as WO 20101004265) or PCT/GB10/000133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of r-hemolysin-NN is shown in SEQ ID NO. 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ IT) NO 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homo-heptamer) or different (hetero-heptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with the construct. The variant preferably comprises one or more reactive cysteine residues that facilitate attachment to the construct. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C) The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135, 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO. 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its ox-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive $S^-$ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

The construct may be covalently attached to the pore. The construct is preferably not covalently attached to the pore. The application of a voltage to the pore and construct typically results in the formation of a sensor that is capable of sequencing target polynucleotides. This is discussed in more detail below.

Any of the proteins described herein, i.e. the transmembrane protein pores or constructs, may be modified to assist their identification or purification, for example by the addition of histidine residues (a his tag). aspartic acid residues (an asp tag), a streptavidin tag. a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or construct An example of this would be to react a gel-shift reagent to a cysteine engineered on the outside of the pore This has been demonstrated as a method for separating hemolysin hetero-oligomers (Chem Biol. 1997 Jul; 4(7): 497-505).

The pore and/or construct may be labelled with a revealing label The revealing label may be any suitable label which allows the pore to be detected Suitable labels include, but are not limited to, fluorescent molecules, radioisotopes, e.g. $^{125}I$, $^{35}S$, enzymes, antibodies, antigens. polynucleotides and ligands such as biotin.

Proteins may be made synthetically or by recombinant means. For example, the pore and/or construct may be synthesized by in vitro translation and transcription (IVTT). The amino acid sequence of the pore and/or construct may be modified to include non-naturally occurring amino acids or to increase the stability of the protein. When a protein is produced by synthetic means, such amino acids may be introduced during production. The pore and/or construct may also be altered following either synthetic or recombinant production.

The pore and/or construct may also be produced using D-amino acids For instance, the pore or construct may comprise a mixture of L-amino acids and D-amino acids. This is conventional in the art for producing such proteins or peptides.

The pore and/or construct may also contain other non-specific modifications as long as they do not interfere with pore formation or construct function. A number of non-specific side chain modifications are known in the art and may be made to the side chains of the protein(s). Such modifications include, for example, reductive alkylation of amino acids by reaction with an aldehyde followed by reduction with $NaBH_4$, amidination with methylacetimidate or acylation with acetic anhydride.

The pore and construct can be produced using standard methods known in the art. Polynucleotide sequences encoding a pore or construct may be derived and replicated using standard methods in the art Polynucleotide sequences encoding a pore or construct may be expressed in a bacterial host cell using standard techniques in the art. The pore and/or construct may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning A Laboratory Manual. 3rd Edition. Cold Spring Harbor Laboratory Press, Cold Spring Harbor, NY.

The pore and/or construct may be produced in large scale following purification by any protein liquid chromatography system from protein producing organisms or after recombinant expression. Typical protein liquid chromatography systems include FPLC, AKTA systems. the Bio-Cad system, the Bio-Rad BioLogic system and the Gilson HPLC system.

SSB

The method of the invention comprises contacting the target polynucleotide with a SSB. SSBs bind single stranded DNA with high affinity in a sequence non-specific manner. They exist in all domains of life in a variety of forms and bind DNA either as monomers or multimers. Using amino acid sequence alignment and logorithms (such as Hidden Markov models) SSBs can be classified according to their sequence homology. The Pfam family, PF00436, includes proteins that all show sequence similarity to known SSBs. This group of SSBs can then be further classified according to the Structural Classification of Proteins (SCOP). SSBs fall into the following lineage: Class. All beta proteins, Fold; OB-fold. Superfamily: Nucleic acid-binding proteins. Family: Single strand DNA-binding domain. SSB. Within this family SSBs can be classified according to subfamilies, with several type species often characterised within each subfamily.

The SSB may be from a eukaryote, such as from humans, mice, rats, fungi, protozoa or plants, from a prokaryote, such as bacteria and archaea, or from a virus.

Eukariotic SSBs are known as replication protein A (RPAs). In most cases, they are hetero-trimers formed of different size units. Some of the larger units (e.g. RPA70 of *Saccharomyces cerevisiae*) are stable and bind ssDNA in monomeric form.

Bacterial SSBs bind DNA as stable homo-tetramers (e.g. *E. coli, Mycobacterium smegmatis* and *Helicobacter pylori*) or homo-dimers (e.g. *Deinococcus radiodurans* and *Thermotoga maritima*). The SSBs from archaeal genomes are considered to be related with eukaryotic RPAs. Few of them, such as the SSB encoded by the crenarchaeote *Sulfolobus solfataricus*, are homo-tetramers. The SSBs from most other species are closer related to the replication proteins from eukaryotes and are referred to as RPAs in some of these species they have been shown to be monomeric (*Methanococcus* jamaschii and *Methanothermobacter* thermoautotrophicum). Still. other species of Archaea, including *Archaeoglobus fulgidus* and *Methanococcoides burtonii*, appear to each contain two open reading frames with sequence similarity to RPAs. There is no evidence at protein level and no published data regarding their DNA binding capabilities or oligomeric state. However, the presence of two oligonucleotide/oligosaccharide (OB) folds in each of these genes (three OB folds in the case of one of the *M. burtonii* ORFs) suggests that they also bind single stranded DNA.

Viral SSBs bind DNA as monomers. This, as well as their relatively small size renders them amenable to genetic fusion to other proteins, for instance via a flexible peptide linker. Alternatively, the SSBs can be expressed separately and attached to other proteins by chemical methods (e g. cysteines, unnatural amino-acids). This is discussed in more detail below.

The SSB used in the method of the invention is either (i) an SSB comprising a carboxy-terminal (C-terminal) region which does not have a net negative charge or (ii) a modified SSB comprising one or more modifications in its C-terminal region which decreases the net negative charge of the C-terminal region. Such SSBs do not block the transmembrane pore and therefore allow characterization of the target polynucleotide.

Examples of SSBs comprising a C-terminal region which does not have a net negative charge include, but are not limited to, the human mitochondrial SSB (HsmtSSB; SEQ ID NO: 63), the human replication protein A 70 kDa subunit, the human replication protein A 14 kDa subunit, the telomere end binding protein alpha subunit from *Oxytricha nova*, the core domain of telomere end binding protein beta subunit from *Oxytricha nova*, the protection of telomeres protein 1 (Pot 1) from *Schizosaccharomyces pombe*, the human Pot1. the OB-fold domains of BRCA2 from mouse or rat, the p5 protein from phi29 (SEQ ID NO: 64) or a variant of any of those proteins. A variant is a protein that has an amino acid sequence which varies from that of the wild-type protein and which retains single stranded polynucleotide binding activity. Polynucleotide binding activity can be determined using methods known in the art. Suitable methods include, but are not limited to, fluorescence anisotropy, tryptophan fluorescence and electrophoretic mobility shift assay (EMSA). For instance, the ability of a variant to bind a single stranded polynucleotide can be determined as described in the Examples.

A variant of SEQ ID NO 63 or 64 typically has at least 50% homology to SEQ ID NO. 63 or 64based on amino acid identity over its entire sequence (or any of the % homologies discussed above in relation to pores) and retains single stranded polynucleoside binding activity. A variant may differ from SEQ ID NO: 63 or 64in any of the ways discussed above in relation to pores. In particular, a variant may have one or more conservative substitutions as shown in Tables 2 and 3.

Examples of SSBs which require one or more modifications in their C-terminal region to decrease the net negative charge include, but are not limited to, the SSB of *E. coli* (EcoSSB-WT; SEQ ID NO: 65), the SSB of *Mycobacterium tuberculosis*, the SSB of *Deinococcus radiodurans*, the SSB of *Thermus* thermophiles, the SSB from *Sulfolobus solfataricus*, the human replication protein A 32 kDa subunit (RPA32) fragment, the CDC13 SSB from *Saccharomyces cerevisiae*, the Primosomal replication protein N (PriB) from *E. coli*, the PriB from Arahidopsis thahana, the hypothetical protein At4g28440, the SSB from T4 (gp32; SEQ ID NO: 55), the SSB from RB69 (gp32; SEQ ID NO: 56), the SSB from T7 (gp2.5; SEQ ID NO: 57) or a variant of any of these proteins. Hence, the SSB used in the method of the invention may be derived from any of these proteins in addition to the one or or more modifications in the C-terminal region, the SSB used in the method may include additional modifications which are outside the C-terminal region or do not decrease the net negative charge of the C-terminal region. In other words, the SSB used in the method of the invention is derived from a variant of a wild-type protein. A variant is a protein that has an amino acid sequence which varies from that of the wild-type protein and which retains single stranded polynucleotide binding activity Polynucleotide binding activity can be determined as discussed above.

The SSB used in the invention may be derived from a variant of SEQ ID NO: 55, 56, 57 or 65. In other words, a variant of SEQ ID NO: 55, 56, 57 or 65 may be used as the starting point for the SSB used in the invention, but the SSB actually used further includes one or more modifications in its C-terminal region which decreases the net negative charge of the C-terminal region. A variant of SEQ ID NO: 55, 56, 57 or 65 typically has at least 50% homology to SEQ ID NO: 55, 56, 57 or 65 based on amino acid identity over its entire sequence (or any of the % homologies discussed above in relation to pores) and retains single stranded polynucleotide binding activity. A variant may differ from SEQ ID NO: 55, 56, 57 or 65 in any of the ways discussed above in relation to pores. In particular, a variant may have one or more conservative substitutions as shown in Tables 2 and 3.

It is straightforward to identify the C-terminal region of the SSB in accordance with normal protein N to C nomenclature. The C-terminal region of the SSB is preferably about the last third of the SSB at the C-terminal end, such as the last third of the SSB at the C-terminal end. The C-terminal region of the SSB is more preferably about the last quarter, fifth or eighth of the SSB at the C-terminal end, such as the last quarter, fifth or eighth of the SSB at the C-terminal end. The last third, quarter, fifth or eighth of the SSB may be measured in terms of numbers of amino acids or in terms of actual length of the primary structure of the SSB protein. The length of the various amino acids in the N to C direction are known in the art.

The C-terminal region is preferably from about the last 10 to about the last 60 amino acids of the C-terminal end of the SSB. The C-terminal region is more preferably about the last 15, about the last 20, about the last 25, about the last 30, about the last 35, about the last 40, about the last 45, about the last 50 or about the last 55 amino acids of the C-terminal end of the SSB.

The C-terminal region typically comprises a glycine and/or proline rich region. This proline/glycine rich region gives the C-terminal region flexibility and can be used to identify the C-terminal region.

The method of the invention may use a SSB comprising a C-terminal region which does not have a net negative charge. The C-terminal region may have a net positive charge or a net neutral charge. The net charge of the C-terminal region can be measured using methods known in the art. For instance, the isolectric point may be used to define the net charge of the C-terminal region. The C-terminal region typically lacks negatively charged amino acids, has the same number of negatively charged and positively charged amino acids or has fewer negatively charged amino acids than positively charged amino acids.

The method of the invention may use a modified SSB comprising one or more modifications in its C-terminal region which decreases the net negative charge of the C-terminal region. In such instances, the C-terminal region is the C-terminal region of the SSB before the one or more modification are made to decrease its negative charge. Before the one or more modifications are made, the C-terminal region has a net negative charge. C-terminal regions having a net negative charge can be identified as discussed above. The C-terminal region typically comprises negatively charged amino acids and/or has more negatively charged amino acids than positively charged amino acids.

The net negative charge of the C-terminal region may be decreased by any means known in the art. The net negative charge of the C-terminal region is decreased in a manner that does not interfere with binding of the modified SSB to the target polynucleotide. A decrease in net negative charge may be measured as discussed above.

The net negative charge is decreased by one or more modifications in the C-terminal region. Any number of modifications, such as 2, 3, 4, 5, 10, 15, 20, 30, 40, 50 or more modifications, may be made.

The one or more modifications are preferably one or more deletions of negatively charged amino acids. Removal of one or more negatively charged amino acids reduces the net negative charge of the C-terminal region A negatively charged amino acid is an amino acid with a net negative charge. Negatively charged amino acids include, but are not limited to, aspartic acid (D) and glutamic acid (E). Methods for deleting amino acids from proteins, such as SSBs, are well known in the art.

The one or more modifications are preferably deletion of the C-terminal region. Removal of a C-terminal region having a net negative charge decreases the net negative charge at the C-terminus of the resulting modified SSB.

The one or more modifications are preferably one or more substitutions of negatively charged amino acids with one or more positively charged, uncharged, non-polar and/or aromatic amino acids. A positively charged amino acid is an amino acid with a net positive charge. The positively charged amino acid(s) can be naturally-occurring or non-naturally-occurring. The positively charged amino acid(s) may be synthetic or modified. For instance, modified amino acids with a net positive charge may be specifically designed for use in the invention. A number of different types of modification to amino acids are well known in the art Preferred naturally-occurring positively charged amino acids include, but are not limited to, histidine (H). lysine (K) and arginine (R). Any number and combination of H K and/or R may be substituted into the C-terminal region of the SSB.

The uncharged amino acids, non-polar amino acids and/or aromatic amino acids can be naturally occurring or non-naturally-occurring. They may be synthetic or modified. Uncharged amino acids have no net charge. Suitable uncharged amino acids include, but are not limited to, cysteine (C), serine (S), threonine (T), methionine (M), asparagines (N) and glutamine (Q). Non-polar amino acids have non-polar side chains. Suitable non-polar amino acids include, but are not limited to, glycine (G), alanine (A). proline (P), isoleucine (I), leucine (L) and valine (V). Aromatic amino acids have an aromatic side chain. Suitable aromatic amino acids include, but are not limited to, histidine (H), phenylyalanine (F), tryptophan (W) and tyrosine (Y). Any number and combination of these amino acids may be substituted into the C-terminal region of the SSB.

The one or more negatively charged amino acids are preferably substituted with alanine (A), valine (V), asparagine (N) or glycine (G). Preferred substitutions include, but are not limited to, substitution of D with A, substitution of D with V, substitution of D with N and substitution of D with G.

The one or more modifications are preferably one or more introductions of positively charged amino acids which neutralise one or more negatively charged amino acids The neutralisation of negative charge from the C-terminal region of the SSB decreases the net negative charge. The one or more positively charged amino acids may be introduced by addition or substitution. Any amino acid may be substituted with a positively charged amino acid. One or more uncharged amino acids, non-polar amino acids and/or aromatic amino acids may be substituted with one or more positively charged amino acids. Any number of positively charged amino acids may be introduced. The number is typically the same as the number of negatively charged amino acids in the C-terminal region.

The one or more positively charged amino acids may be introduced at any position in the C-terminal region as long as they neutralise the negative charge of the one or more negatively charged amino acids. To effectively neutralise the negative charge, there is typically 5 or fewer amino acids between each positively charged amino acid that is introduced and the negatively charged amino acid it is neutralising. There is preferably 4 or fewer, 3 or fewer or 2 or fewer amino acids between each positively charged amino acid that is introduced and the negatively charged amino acid it is neutralising. There is more preferably one amino acid between each positively charged amino acid that is introduced and the negatively charged amino acid it is neutralising. Each positively charged amino acid is most preferably introduced adjacent to the negatively charged amino acid it is neutralising. Methods for introducing or substituting naturally-occurring amino acids are well known in the art. For instance, methionine (M) may be substituted with arginine (R) by replacing the codon for aspartic acid (GAC) with a codon for alanine (GCC) at the relevant position in a polynucleotide encoding the SSB. The polynucleotide can then be expressed as discussed above.

Methods for introducing or substituting non-naturally-occurring amino acids are also well known in the art. For instance. non-naturally-occurring amino acids may be introduced by including synthetic aminoacyl-tRNAs in the IVTT system used to express the SSB. Alternatively, they may be introduced by expressing the SSB in *E. coli* that are auxotrophic for specific amino acids in the presence of synthetic (i.e. non-naturally-occurring) analogues of those specific amino acids. They may also be produced by naked ligation if the SSB is produced using partial peptide synthetisis.

The one or more modifications are preferably one or more chemical modifications of one or more negatively charged amino acids which neutralise their negative charge. For instance, the one or more negatively charged amino acids may be reacted with a carbodiimide.

If the modified SSB is oligomeric, the one or more modifications may be made in one or more of the monomer subunits of the SSB. The one or more modifications are preferably made in all monomer subunits of the SSB.

As discussed above, the modified SSB is preferably derived from the sequence shown in SEQ ID NO: 65 or a variant thereof. The C-terminal region of SEQ ID NO. 65 is typically its last 10 amino acids (amino acids 168 to 177), which comprises four negatively amino acids (four aspartic acids Ds). The four aspartic acids are at positions 170, 172, 173 and 174 of SEQ ID NO: 65.

The general structure of SEQ ID NO: 65's C-terminal region is relatively conserved amongst SSBs which have a C-terminal region having a net negative charge, such as those discussed above. In particular, the C-terminal region of various SSBs comprises a flexible glycine and/or proline rich region followed (in the N to C direction) by several negatively charged amino acids. The C-terminal regions of the SSB from T4 (gp32; SEQ ID NO: 55), the SSB from RB69 (gp32; SEQ ID NO: 56) and the SSB from T7 (gp2.5; SEQ ID NO: 57) are discussed in more detail below.

The modified SSB is more preferably derived from the sequence shown in SEQ ID NO: 65 or a variant thereof and comprises the following modification(s):

a) deletion of one or more of, such as 2, 3 or 4 of, amino acids 170, 172, 173 and 174 in SEQ ID NO: 65;
b) deletion of amino acids 168 to 177 of SEQ ID NO: 65 (i e. deletion of the C-terminal region);
c) substitution of one or more of, such as 2, 3 or 4 of, amino acids 170, 172, 173 and 174 in SEQ ID NO: 65 with a positively charged, uncharged, non-polar or aromatic amino acid; or
d) substitution of one or more of, such as 2, 3 or 4 of, amino acids 168, 169, 171, 175, 176 and 177 in SEQ ID NO: 65 with a positively charged amino acid. Possible combinations of modifications include (a) and (c). (a) and (d) and (c) and (d).

As discussed above, the modified SSB is preferably derived from the sequence shown in SEQ ID NO: 55 or a variant thereof. The C-terminal region of SEQ ID NO: 55 is typically its last 13 amino acids (amino acids 289 to 301). which comprises six negatively charged amino acids (six aspartic acids Ds) The six aspartic acids are at positions 290, 291, 293, 295, 296 and 300 of SEQ ID NO: 55.

The modified SSB is more preferably derived from the sequence shown in SEQ ID NO: 55 or a variant thereof and comprises the following modification(s):

a) deletion of one or more of, such as 2, 3, 4, 5 or 6 of, amino acids 290, 291, 293, 295, 296 and 300 in SEQ 11) NO: 55;
b) deletion of amino acids 289 to 301 of SEQ ID NO: 55 (i.e. deletion of the C-terminal region);
c) substitution of one or more of, such as 2, 3, 4, 5 or 6 of amino acids 290, 291, 293, 295, 296 and 300 in SEQ ID NO: 55 with a positively charged, uncharged, non-polar or aromatic amino acid; or
d) substitution of one or more of, such as 2, 3, 4, 5, 6 or 7 of, amino acids 289, 292, 294, 297, 298, 299 and 301 in SEQ ID NO: 55 with a positively charged amino acid.

As discussed above, the modified SSB is preferably derived from the sequence shown in SEQ ID NO. 56 or a variant thereof. The C-terminal region of SEQ ID NO: 56 is typically its last 12 amino acids (amino acids 288 to 299). which comprises five negatively charged amino acids (five aspartic acids Ds) The five aspartic acids are at positions 288, 289, 291, 293 and 294 of SEQ ID NO 56.

The modified SSB is more preferably derived from the sequence shown in SEQ ID NO: 56 or a variant thereof and comprises the following modification(s):

a) deletion of one or more of, such as 2, 3, 4 or 5 of, amino acids 288, 289, 291, 293 and 294 in SEQ ID NO: 56;
b) deletion of amino acids 288 to 299 of SEQ ID NO: 56 (i e. deletion of the C-terminal region);
c) substitution of one or more of, such as 2, 3, 4, 5, 6 or 7 of, amino acids 290, 292, 295, 296, 297, 298 and 299 in SEQ ID NO: 56 with a positively charged, uncharged, non-polar or aromatic amino acid; or
d) substitution of one or more of, such as 2, 3, 4, 5, 6 or 7 of, amino acids 290, 292, 295, 296, 297, 298 and 299 in SEQ ID NO: 56 with a positively charged amino acid.

As discussed above, the modified SSB is preferably derived from the sequence shown in SEQ ID NO: 57 or a variant thereof. The C-terminal region of SEQ ID NO: 57 is typically its last 21 amino acids (amino acids 212 to 232), which comprises seven negatively charged amino acids (seven aspartic acids Ds). The seven aspartic acids are at positions 212, 217, 219, 220, 227, 229 and 231 of SEQ ID NO: 57.

The modified SSB is more preferably derived from the sequence shown in SEQ ID NO: 57 or a variant thereof and comprises the following modification(s):

a) deletion of one or more of, such as 2, 3, 4, 5, 6 or 7 of, amino acids 212, 217, 219, 220, 227, 229 and 231 in SEQ ID NO: 57;
b) deletion of amino acids 212 to 232 of SEQ ID NO: 57 (i.e. deletion of the C-terminal region);
c) substitution of one or more of, such as 2, 3, 4, 5, 6, 7, 8, 9, 10, 11, 12, 13 or 14 of, amino acids 213, 214, 215, 216, 218, 221, 222, 223, 224, 225, 226, 228, 230 and 232 in SEQ ID NO: 57 with a positively charged, uncharged, non-polar or aromatic amino acid; or
d) substitution of one or more of, such as 2, 3, 4, 5, 6 or 7 of, amino acids 212, 217, 219, 220, 227, 229 and 231 in SEQ ID NO: 57 with a positively charged amino acid.

The modified SSB most preferably comprises a sequence selected from those shown in SEQ ID NOs: 59, 60 and 66 to 69.

Measuring Characteristics

The method of the invention involves measuring one or more characteristics of the target polynucleotide. The method may involve measuring two, three, four or five or more characteristics of the target polynucleotide. The one or more characteristics are preferably selected from (i) the length of the target polynucleotide, (ii) the identity of the target polynucleotide, (iii) the sequence of the target polynucleoside, (iv) the secondary structure of the target polynucleotide and (v) whether or not the target polynucleotide is modified. Any combination of (i) to (v) may be measured in accordance with the invention.

For (i), the length of the polynucleotide may be measured for example by determining the number of interactions between the target polynucleotide and the pore or the duration of interaction between the target polynucleotide and the pore.

For (ii), the identity of the polynucleotide may be measured in a number of ways. The identity of the polynucleotide may be measured in conjunction with measurement of the sequence of the target polynucleotide or without measurement of the sequence of the target polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the target polynucleotide as coming from a particular source.

For (iii), the sequence of the polynucleotide can be determined as described previously. Suitable sequencing methods, particularly those using electrical measurements, are described in Stoddart D et at, *Proc Natl Acad Sci,* 12; 106(19)7702-7, Lieberman K R et al. J Am Chem Soc 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the target polynucleotide is modified by methylation, by oxidation. by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interation with each nucleotide.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 Jan.; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50) 17961-72, and International Application WO-2000/28312. Alternatively, electrical measurements may be made using a multi-channel system, for example as described in International Application WO-2009/077734 and International Application WO-2011/067559.

Transport Control Protein

Step (a) of the method of the invention preferably further comprises contacting the polynucleotide with a transport control protein such that the transport control protein controls the movement of the target polynucleotide through the pore and wherein the transport control protein does not move through the pore The transport control protein is preferably derived from a polynucleotide binding enzyme. A polynucleotide binding enzyme is a polypeptide that is capable of binding to a polynucleotide and interacting with and modifying at least one property of the polynucleotide The enzyme may modify the polynucleotide by cleaving it to form individual nucleotides or shorter chains of nucleotides, such as di- or trinucleotides The enzyme may modify the polynucleotide by orienting it or moving it to a specific position. The transport control protein does not need to display enzymatic activity as long as it is capable of binding the polynucleotide and controlling its movement. For instance, the protein may be derived from an enzyme that has been modified to remove its enzymatic activity or may be used under conditions which prevent it from acting as an enzyme.

The transport control protein is preferably derived from a nucleolytic enzyme. The enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in international Application No. PCT/GB10/000133 (published as WO 2010/086603).

Preferred enzymes are exonucleases, polymerases, helicases and topoisomerases, such as gyrases Suitable exonucleases include, but are not limited to, exonuclease 1 from *E. coli*, exonuclease III enzyme from *E. coli*, RecJ from *T. thermophilus* and bacteriophage lambda exonuclease and variants thereof.

The transport control protein may additionally comprise one or more nucleic acid binding domains or motifs, such as a helix-hairpin-helix (HhH) motif. For example the transport control protein may be a helicase coupled to one, two, three, four or more nucleic acid binding domains such as HhH motifs.

The transport control protein may comprise two or more enzymes coupled together, where the enzymes are the same or different. The transport control protein may additionally comprise a protein which is not an SSB but which is capable of binding to nucleic acid, such as a processivity factor.

The polymerase is preferably a member of any of the Moiety Classification (EC) groups 2.7.7.6, 2.7.7 7, 2.7 7.19, 2 7.7.48 and 2.7.7.49. The polymerase is preferably a DNA-dependent DNA polymerase, an RNA-dependent DNA polymerase, a DNA-dependent RNA polymerase or an RNA-dependent RNA polymerase. The transport control protein is preferably derived from Phi29 DNA polymerase (SEQ ID NO 58). The transport control protein may comprise the sequence shown in SEQ ID NO. 58 or a variant thereof. A variant of SEQ ID NO: 58 is an enzyme that has an amino acid sequence which varies from that of SEQ ID NO: 58 and which retains polynucleotide binding activity The variant may include modifications that facilitate binding of the polynucleotide and/or facilitate its activity at high salt concentrations and/or room temperature.

Over the entire length of the amino acid sequence of SEQ ID NO: 58, a variant will preferably be at least 50% homologous to that sequence based on amino acid identity. More preferably, the variant polypeptide may be at least 55%, at least 60%, at least 65%, at least 70%/c, at least 75%, at least 80%, at least 85%., at least 90% and more preferably at least 95%, 97% or 99% homologous based on amino acid identity to the amino acid sequence of SEQ ID NO. 58 over the entire sequence. There may be at least 80%, for example at least 85%, 9% or 95%, amino acid identity over a stretch of 200 or more, for example 230, 250, 270 or 280 or more, contiguous amino acids ("hard homology"). Homology is determined as described above. The variant may differ from the wild-type sequence in any of the ways discussed below with reference to SEQ ID NOs: 2 and 4.

Any helicase may be used in the invention Helicases are often known as translocases and the two terms may be used interchangeably. Suitable helicases are well-known in the art (M. E Fairman-Williams et al., Curr Opin Struct Biol., 2010, 20 (3), 313-324, T. M. Lohman et al, Nature Reviews Molecular Cell Biology, 2008, 9, 391-401) The helicase is typically a member of one of superfamilies 1 to 6. The helicase is preferably a member of any of the Moiety Classification (EC) groups 3.6.1.- and 2.7.7.-. The helicase is preferably an ATP-dependent DNA helicase (EC group 3.6.4.12), an ATP-dependent RNA helicase (EC group 3.6 4.13) or an ATP-independent RNA helicase.

The helicase is preferably capable of binding to the target polynucleotide at an internal nucleotide. An internal nucleotide is a nucleotide which is not a terminal nucleotide in the target polynucleotide. For example, it is not a 3' terminal nucleotide or a 5' terminal nucleotide. All nucleotides in a circular polynucleotide are internal nucleotides.

Generally, a helicase which is capable of binding at an internal nucleotide is also capable of binding at a terminal nucleotide, but the tendency for some helicases to bind at an internal nucleotide will be greater than others. For a helicase suitable for use in the invention, typically at least 10% of its binding to a polynucleotide will be at an internal nucleotide. Typically, at least 20%, at least 30%, at least 40% or at least 50% of its binding will be at an internal nucleotide. Binding at a terminal nucleotide may involve binding to both a terminal nucleotide and adjacent internal nucleotides at the same time. For the purposes of the invention, this is not binding to the target polynucleotide at an internal nucleotide. In other words, the helicase used in the invention is not only capable of binding to a terminal nucleotide in combination with one or more adjacent internal nucleotides. The helicase must be capable of binding to an internal nucleotide without concurrent binding to a terminal nucleotide.

A helicase which is capable of binding at an internal nucleotide may bind to more than one internal nucleotide. Typically, the helicase binds to at least 2 internal nucleotides, for example at least 3, at least 4, at least 5. at least 10 or at least 15 internal nucleotides. Typically the helicase binds to at least 2 adjacent internal nucleotides, for example at least 3, at least 4, at least 5, at least 10 or at least 15 adjacent internal nucleotides. The at least 2 internal nucleotides may be adjacent or non-adjacent.

The ability of a helicase to bind to a polynucleotide at an internal nucleotide may be determined by carrying out a comparative assay. The ability of a motor to bind to a control polynucleotide A is compared to the ability to bind to the same polynucleotide but with a blocking group attached at the terminal nucleotide (polynucleotide B). The blocking group prevents any binding at the terminal nucleotide of strand B. and thus allows only internal binding of a helicase.

Examples of helicases which are capable of binding at an internal nucleotide include, but are not limited to, Hel308 Tga, Hel308 Mhu and Hel308 Csy Hence, the molecular motor preferably comprises (a) the sequence of Hel308 Tga (i.e. SEQ ID NO: 16) or a variant thereof or (b) the sequence of Hel308 Cay (i e. SEQ ID NO: 13) or a variant thereof or (c) the sequence of Hel308 Mhu (i.e. SEQ ID NO: 19) or a variant thereof. Variants of these sequences are discussed in more detail below. Variants preferably comprise one or more substituted cysteine residues and/or one or more substituted Faz residues to facilitate attachment as discussed above.

The helicase is preferably a Hel308 helicase. Any Hel308 helicase may be used in accordance with the invention. Hel308 helicases are also known as ski2-like helicases and the two terms can be used interchangeably. Suitable Hel308 helicases are disclosed in Table 4 of US Patent Application Nos. 61,549,998 and 61/599,244 and International Application No. PCT/GB2012/052579 (published as WO 2013/057495).

The Hel308 helicase typically comprises the amino acid motif Q-X1-X2-G-R-A-G-R (hereinafter called the Hel308 motif; SEQ ID NO: 8). The Hel308 motif is typically part of the helicase motif VI (Tuteja and Tuteja, Eur. J Biochem 271, 1849-1863 (2004)) X1 may be C. M or L. X1 is preferably C. X2 may be any amino acid residue X2 is typically a hydrophobic or neutral residue. X2 may be A, F, M, C, V, L, 1, S, T, P or R. X2 is preferably A, F, M, C, V, L, I, S, T or P. X2 is more preferably A. M or L. X2 is most preferably A or M.

The Hel308 helicase prferably comprises the motifQ-X 1--X2-G-R-A-G-R-P (hereinafter called the extended Hel308 motif, SEQ ID NO: 9) wherein X1 and X2 are as described above.

The most preferred Hel308 motifs and extended Hel308 motifs are shown in the Table 4 below

TABLE 4

Preferred Hel308 helicases and their motifs

| SEQ ID NO: | Helicase | Names | % Identity to Hel308 Mbu | Hel308 motif | Extended Hel308 motif |
|---|---|---|---|---|---|
| 10 | Hel308 Mbu | *Methanococcoides burtonii* | — | QMAGRAGR (SEQ ID NO: 11) | QMAGRAGRP (SEQ ID NO: 12) |
| 13 | Hel308 Csy | *Cenarchaeum symbiosum* | 34% | QLCGRAGR (SEQ ID NO: 14) | QLCGRAGRP (SEQ ID NO: 15) |
| 16 | Hel308 Tga | *Thermococcus gammatolerans* EJ3 | 38% | QMMGRAGR (SEQ ID NO: 17) | QMMGRAGRP (SEQ ID NO: 18) |
| 19 | Hel308 Mhu | *Methanospirillum hungatei* JF-1 | 40% | QMAGRAGR (SEQ ID NO: 11) | QMAGRAGRP (SEQ ID NO: 12) |

The most preferred Hel308 motif is shown in SEQ ID NO: 17. The most preferred extended Hel308 motif is shown in SEQ ID NO: 18. Other preferred Hel308 motifs and extended Hel308 motifs are found in Table 5 of US Patent Application Nos 61,549,998 and 61/599,244 and International Application No. PCT/GB2012/052579 (published as WO 2013/057495).

The Hel308 helicase preferably comprises the sequence of Hel308 Mbu (i.e. SEQ ID NO. 10) or a variant thereof. The He308 helicase more preferably comprises (a) the sequence of Hel308 Tga (i.e. SEQ ID NO. 16) or a variant thereof, (b) the sequence of Hel308 Csy (i.e. SEQ ID NO: 13) or a variant thereof or (c) the sequence of Hel308 Mhu (i.e. SEQ ID NO: 19) or a variant thereof. The Hel308 helicase most preferably comprises the sequence shown in SEQ ID NO: 16 or a variant thereof.

A variant of a Hel308 helicase is an enzyme that has an amino acid sequence which varies from that of the wild-type helicase and which retains polynucleotide binding activity. This can be measured as described above. In particular, a variant of SEQ ID NO: 10, 13, 16 or 19 is an enzyme that has an amino acid sequence which varies from that of SEQ ID NO: 10, 13, 16 or 19 and which retains polynucleotide binding activity.

The variant retains helicase activity. This can be measured in various ways. For instance, the ability of the variant to translocate along a polynucleotide can be measured using electrophysiology, a fluorescence assay or ATP hydrolysis.

The variant may include modifications that facilitate handling of the polynucleotide encoding the helicase and/or facilitate its activity at high salt concentrations and/or room temperature. Variants typically differ from the wild-type helicase in regions outside of the Hel308 motif or extended Hel308 motif discussed above. However. variants may include modifications within these motif(s).

Over the entire length of the amino acid sequence of SEQ ID NO: 10, 13, 16 or 19, a variant will preferably be at least 30% homologous to that sequence based on amino acid identity. More preferably, the variant polypeptide may be at least 40%, at least 45%, at least 50%, at least 55%, at least 60%, at least 65%, at least 70%, at least 75%, at least 80%., at least 85%, at least 90% and more preferably at least 95%, 97% or 99% homologous based on amino acid identity to the amino acid sequence of SEQ ID NO. 10, 13, 16 or 19 over the entire sequence. There may be at least 70%, for example at least 80%, at least 85%, at least 90% or at least 95%. amino acid identity over a stretch of 150 or more, for example 200, 300, 400, 500, 600, 700, 800, 900 or 1000 or more, contiguous amino acids ("hard homology"). Homology is determined as described above The variant may differ from the wild-type sequence in any of the ways discussed below with reference to SEQ ID NOs: 2 and 4.

A variant of SEQ ID NO: 10, 13, 16 or 19 preferably comprises the Hel308 motif or extended Hel308 motif of the wild-type sequence as shown in Table 4 above. However, a variant may comprise the 1Hel308 motif or extended Hel308 motif from a deferent wild-type sequence. For instance, a variant of SEQ ID NO: 12 may comprise the Hel308 motif or extended Hel308 motif from SEQ ID NO: 13 (i.e. SEQ ID NO: 14 or 15). Variants of SEQ ID NO: 10, 13, 16 or 19 may also include modifications within the Hel308 motif or extended Hel308 motif of the relevant wild-type sequence. Suitable modifications at X1 and X2 are discussed above when defining the two motifs. A variant of SEQ ID NO: 10, 13, 16 or 19 preferably comprises one or more substituted cysteine residues and/or one or more substituted Faz residues to facilitate attachment as discussed above.

A variant of SEQ ID NO: 10 may lack the first 19 amino acids of SEQ ID NO: 10 and/or lack the last 33 amino acids of SEQ 1D NO: 10. A variant of SEQ ID NO: 10 preferably comprises a sequence which is at least 70%, at least 75%, at least 80%, at least 85%, at least 90% or more preferably at least 95%, at least 97% or at least 99% homologous based on amino acid identity with amino acids 20 to 211 or 20 to 727 of SEQ ID NO: 10.

SEQ ID NO: 10 (Hel308 Mbu) contains five natural cysteine residues. However, all of these residues are located within or around the DNA binding grove of the enzyme. Once a DNA strand is bound within the enzyme, these natural cysteine residues become less accessible for external modifications. This allows specific cysteine mutants of SEQ ID NO: 10 to be designed and attached to the SSB using cysteine linkage as discussed above. Preferred variants of SEQ ID NO. 10 have one or more of the following substitutions- A29C, Q221C, Q442C, T569C, A577C, A700C and S708C. The introduction of a cysteine residue at one or more of these positions facilitates cysteine linkage as discussed above Other preferred variants of SEQ 1D NO: 10 have one or more of the following substitutions: M2Faz, R10Faz, F15Faz, A29Faz, R185Faz, A268Faz, E284Faz, Y387Faz, F400Faz, Y455Faz, E464Faz, E573Faz, A577Faz, E649Faz, A700Faz, Y720Faz, Q442Faz. and S708Faz. The introduction of a Faz residue at one or more of these positions facilitates Faz linkage as discussed above.

The helicase is preferably a RecD helicase. Any RecD helicase may be used in accordance with the invention. The structures of RecD helicases are known in the art (FEBS J. 2008 Apr; 275(8).-1835-51. Epub 2008 Mar 9. ATPase activity of RecD is essential for growth of the Antarctic *Pseudomonas syringae* Lz4W at low temperature. Satapathy A K, Pavankumar T L, Bhattacharjya S, Sankaranarayanan R, Ray M K; EMS Microbiol Rev. 2009 May; 33(3):657-87. The diversity of conjugative relaxases and its application in plasmid classification. Garcillán-Barcia NIP, Francia MV, de la Cruz F; J Biol Chem 2011 Apr 8; 286(14):12670-82. Epub 2011 Feb 2. Functional characterization of the multidomain F plasmid TraI relaxase-helicase Cheng Y, McNamara D E, Miley M J, Nash R P, Redinbo M R).

The RecD helicase typically comprises the amino acid motif X1-X2-X3-G-X4-X5-X6-X7 (hereinafter called the RecD-like motif 1; SEQ ID NO 20), wherein X1 is G, S or A, X2 is any amino acid, X3 is P, A, S or G, X4 is T, A, V, S or C, X5 is G or A, X6 is K or R and X7 is T or S. X1 is preferably G. X2 is preferably G, I, Y or A. X2 is more preferably G. X3 is preferably P or A. X4 is preferably T, A, V or C. X4 is preferably T, V or C. X5 is preferably G. X6 is preferably K. X7 is preferably T or S. The RecD helicase preferably comprises Q-$(X8)_{16-18}$-X1-X2-X3-C-X4-X5-X6-X7 (hereinafter called the extended RecD-like motif I; SEQ ID NOs: 21 to 23), wherein X1 to X7 are as defined above and X8 is any amino acid. There are preferably 16 X8 residues (i.e. $(X8)_{16}$) in the extended RecD-like motif 1. Suitable sequences for $(X8)_{16}$ can be identified in SEQ 11 NOs: 14, 17, 20, 23, 26, 29, 32, 35, 38, 41, 44, 47 and 50 of U.S. Patent Application No. 61/581,332 and SEQ 1D NOs: 18, 21, 24, 25, 28, 30, 32, 35, 37, 39, 41, 42 and 44 of International Application No PCT/GB2012/053274 (published as WO 2012/098562).

The RecD helicase preferably comprises the amino acid motif G-G-P-G-Xa-G-K-Xb (hereinafter called the RecD motif 1; SEQ ID NO. 24) wherein Xa is T, V or C and Xb is T or S. Xa is preferably T. Xb is preferably T. The Rec-D helicase preferably comprises the sequence G-G-P-G-T-G-K-T (SEQ ID NO: 25). The RecD helicase more preferably comprises the amino acid motif Q-$(X8)_{16-18}$-G-G-P-G-Xa-G-K-Xb (hereinafter called the extended RecD motif 1: SEQ ID NOs: 26 to 28), wherein Xa and Xb are as defined above and X8 is any amino acid. There are preferably 16 X8 residues (i.e. $(X8)_{16}$) in the extended RecD motif I. Suitable sequences for $(X8)_{16}$ can be identified in SEO ID NOs: 14, 17, 20, 23, 26, 29, 32, 35, 38, 41, 44, 47 and 50 of U.S. Patent Application No. 61/581,332 and SEQ ID NOs: 18, 21, 24, 25, 28, 30, 32, 35, 37, 39, 41, 42 and 44 of International Application No PCT/GB2012/053274 (published as WO 2012/098562).

The RecD helicase typically comprises the amino acid motif X1-X2-X3-X4-X5-(X6).;-Q-X7 (hereinafter called the RecD-like motif V; SEQ ID NO: 29), wherein X1 is V, W or F, X2 is A, T, S, M. C or V, X3 is any amino acid, X4 is T, N or S, X5 is A, T, G, S, V or 1, X6 is any amino acid and X7 is G or S X1 is preferably Y. X2 is preferably A, M. C or V. X2 is more preferably A. X3 is preferably 1, M or L. X3 is more preferably I or L. X4 is preferably T or S. X4 is more preferably T. X5 is preferably A. V or 1. X5 is more preferably V or 1. X5 is most preferably V. (X6) is preferably H—K-S. H-M-A, H-G-A or H—R-S. (X6), is more preferably H—K-S. X7 is preferably G. The RecD helicase preferably comprises the amino acid motif Xa-Xb-Xc-Xd-Xe-lH—K-S-Q-G (hereinafter called the RecD motif V. SEQ UD NO: 30), wherein Xa is Y, W or F, Xb is A, M, C or V, Xc is 1, M or L, Xd is T or S and Xe is V or 1. Xa is preferably Y Xb is preferably A. Xd is preferably T Xd is preferably V. Preferred RecD motifs I are shown in Table 5 of U.S. Patent Application No. 61/581,332 and International Application No. PCT/GB2012/053274 (published as WO 2012/098562). Preferred RecD-like motifs I are shown in Table 7 of U.S. Patent Application No. 61/581,332 and international Application No. PCT/GB2012/053274 (published as WO 2012/098562). Preferred RecD-like motifs V are shown in Tables 5 and 7 of U.S. Patent Application No. 61/581,332 and international Application No. PCT/GB2012/053274 (published as WO 2012/098562).

The RecD helicase is preferably one of the helicases shown in Table 4 or 5 of US Patent Application No. 61/581,332 and International Application No. PCT/GB2012/053274 (published as WO 2012/098562) or a variant thereof. Variants are described in U.S. Patent Application No. 61/581,332 and International Application No. PCT/G1B2012/053274 (published as WO 2012/098562).

The RecD helicase is preferably a TraI helicase or a TraI subgroup helicase. TraI helicases and TraI subgroup helicases may contain two RecD helicase domains, a relaxase domain and a C-terminal domain The TraI subgroup helicase is preferably a TrwC helicase. The TraI helicase or TraI subgroup helicase is preferably one of the helicases shown in Table 6 of US Patent Application No 61/581.332 and International Application No. PCT/GB2012/053274 (published as WO 2012/098562) or a variant thereof. Variants are described in U.S. Patent Application No. 61/581,332 and International Application No PCT/GB2012/053274 (published as WO 2012/098562)

The TraI helicase or a TraI subgroup helicase typically comprises a RecD-like motif I as defined above (SEQ ID NO: 20) and/or a RecD-like motif V as defined above (SEQ 1D NO: 27). The TraI helicase or a TraI subgroup helicase preferably comprises both a RecD-like motif I (SEQ ID NO: 22) and a RecD-like motif V (SEQ ID NO: 29) The TraI helicase or a TraT subgroup helicase typically Further comprises one of the following two motifs:

The amino acid motif H-$(X1)_2$-X2-R-$(X3)_{5-12}$-H-X4-H (hereinafter called the MobF motif III; SEQ ID NOs: 31 to 38), wherein X1 and X2 are any amino acid and X2 and X4 are independently selected from any amino acid except D, E, K and R. $(X1)_2$ is of course X1a-X1b. X1a and X1b can be the same of different amino acid. X1a is preferably D or E. X1b is preferably T or D. $(X1)_2$ is preferably DT or ED. $(X1)_2$ is most preferably DT. The 5 to 12 amino acids in $(X3)_{5-12}$, can be the same or different. X2 and X4 are independently selected from G, P, A, V, L, I, M, C, F, Y, W, I, Q, N, S and T. X2 and X4 are preferably not charged. X2 and X4 are preferably not H. X2 is more preferably N, S or A. X2 is most preferably N. X4 is most preferably F or T. $(X3)_{5-12}$ is preferably 6 or 10 residues in length. Suitable embodiments of $(X3)_{5-12}$ can be derived from SEQ ID NOs: 58, 62, 66 and 70 shown in Table 7 of U.S. Patent Application No. 61/581,332 and SEQ ID NOs: 61, 65, 69, 73, 74, 82, 86, 90, 94, 98, 102, 110, 112, 113, 114, 117, 121, 124, 125, 129, 133, 136, 140, 144, 147, 151, 152, 156, 160, 164 and 168 of International Application No PCT/GB2012/053274 (published as WO 2012/098562).

The amino acid motif G-X1-X2-X3-X4-X5-X6-X7-1-$(X8)_{6-12}$-H-X9 (hereinafter called the MobQ motif III; SEQ ID NOs: 39 to 45), wherein X1, X2, X3, X5, X6, X7 and X9 are independently selected from any amino acid except D, E. K and R, X4 is D or E and X8 is any amino acid. X1, X2, X3, X5, X6. X7 and X9 are independently selected from G, P, A, V, L, I, M, C, F, Y, W, H, Q, N, S and T. X1, X2, X3, X5, X6, X7 and X9 are preferably not charged. X1, X2, X1. X5, X6, X7 and X9 are preferably not H. The 6 to 12 amino acids in $(X8)_{6-12}$ can be the same or different. Preferred MobF motifs III are shown in Table 7 of U.S. Patent Application No. 61/581,332 and International Application No. PCT/GB2012/053274 (published as WO 2012/098562).

The TraI helicase or Trail subgroup helicase is more preferably one of the helicases shown in Table 6 or 7 of U.S. Patent Application No. 61/581,332 and International Application No. PCT/GB2012/053274 (published as WO 2012/098562) or a variant thereof. The TraI helicase most preferably comprises the sequence shown in SEQ ID NO: 46 or a variant thereof. SEQ ID NO. 46 is TraI Eco (NCBI Reference Sequence: NP 061483.1; Genbank AAQ98619.1. SEQ ID NO: 46). TraI Eco comprises the following motifs: RecD-like motif I (GYAGVGKT; SEQ ID NO: 47). RecD-like motif V (YAJTAIGAQG; SEQ ID NO: 48) and Mob F motif III (HDTSRDQEPQLHTH; SEQ ID NO: 49).

The TraT helicase or TraI subgroup helicase more preferably comprises the sequence of one of the helicases shown in Table 5 below, i e. one of SEQ. ID NOs: 46, 86, 90 and 94, or a variant thereof.

TABLE 5

More preferred TraI helicase and TraI subgroup helicases

| SEQ ID NO | Name | Strain | NCBI ref | % Identity to TraI Eco | RecD-like motif I (SEQ ID NO:) | RecD-like motif V (SEQ ID NO:) | Mob F motif III (SEQ ID NO:) |
|---|---|---|---|---|---|---|---|
| 46 | TraI Eco | *Escherichia coli* | NCBI Reference Sequence: NP_061483.1 Genbank AAQ98619.1 | — | GYAGV GKT (47) | YAITA HGAQG (48) | HDTSR DQEPQ LHTH 49) |
| 86 | TrwC Cba | *Citro-microbium bathyo-marinum* JL354 | NCBI Reference Sequence: ZP_06861556.1 | 15% | GIAGA GKS (87) | YALNV HMAQG (88) | HDTNR NQEPN LHFH (89) |

TABLE 5-continued

More preferred TraI helicase and TraI subgroup helicases

| SEQ ID NO | Name | Strain | NCBI ref | % Identity to TraI Eco | RecD-like motif I (SEQ ID NO:) | RecD-like motif V (SEQ ID NO:) | Mob F motif III (SEQ ID NO:) |
|---|---|---|---|---|---|---|---|
| 90 | TrwC Hne | *Halothiobacillus neapolitanus* c2 | NCBI Reference Sequence: YP_003262832.1 | 11.5% | GAAGA GKT (91) | YCITIH RSQG (92) | HEDAR TVDDI ADPQL HTH (93) |
| 94 | TrwC Eli | *Erythrobacter litoralis* HTCC2594 | NCBI Reference Sequence: YP_457045.1 | 16% | GIAGA GKS (87) | YALNA HMAQG (95) | HDTNR NQEPN LHFH (89) |

A variant of a Reel) helicase, TraI helicase or TraI subgroup helicase is an enzyme that has an amino acid sequence which varies from that of the wild-type helicase and which retains polynucleotide binding activity. In particular, a variant of SEQ ID NO: 46 is an enzyme that has an amino acid sequence which varies from that of SEQ ID NO: 46 and which retains polynucleotide binding activity. This can be measured as described above. The variant retains helicase activity. The variant must work in at least one of the two modes discussed below Preferably, the variant works in both modes. The variant may include modifications that facilitate handling of the polynucleotide encoding the helicase and/or facilitate its activity at high salt concentrations and/or room temperature. Variants typically differ from the wild-type helicase in regions outside of the motif-s discussed above. However, variants may include modifications within these motif(s).

Over the entire length of the amino acid sequence of any one of SEQ ID NO: 46, 86, 90 and 94, a variant will preferably be at least 10% homologous to that sequence based on amino acid identity. More preferably, the variant polypeptide may be at least 20%, at least 25%, at least 30%, at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of any one of SEQ ID NOs: 46, 86, 90 and 94 over the entire sequence. There may be at least 70%, for example at least 80%, at least 85%, at least 90% or at least 95%, amino acid identity over a stretch of 150 or more, for example 200, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NOs: 2 and 4

A variant of any one of SEQ ID NOs: 46, 86, 90 and 94 preferably comprises the RecD-like motif I and/or RecD-like motif V of the wild-type sequence. However, a variant of SEQ ID NO 46, 86, 90 or 94 may comprise the RecD-like motif I and/or extended RecD-like motif V from a different wild-type sequence. For instance, a variant may comprise any one of the preferred motifs shown in Tables 5 and 7 of U.S. Patent Application No. 61/581,332. Variants of SEQ ID NOs: 46, 86, 90 and 94 may also include modifications within the RecD-like motifs I and V of the wild-type sequence. A variant of SEQ ID NO: 46, 86, 90 or 94 preferably comprises one or more substituted cysteine residues and/or one or more substituted Faz residues to facilitate attachment as discussed above.

The helicase is preferably an XPD helicase. Any XPD helicase may be used in accordance with the invention. XPD helicases are also known as Rad3 helicases and the two terms can be used interchangeably.

The structures of XPD helicases are known in the art (Cell. 2008 May 30; 133(5):801-12. Structure of the DNA repair helicase XPD. Liu H, Rudolf J, Johnson K A, McMahon S A, Oke M, Carter L, McRobbie A M, Brown S E, Naismith J H, White M F). The XPD helicase typically comprises the amino acid motif X1-X2-X3-G-X4-X5-X6-E-G (hereinafter called XPD motif V; SEQ ID NO: 50). X1, X2, X5 and X6 are independently selected from any amino acid except D, E, K and R, X1, X2, X5 and X6 are independently selected from G, P, A, V, L, I, M, C, F, Y, W, H, Q, N, S and T. X1, X2, X5 and X6 are preferably not charged. X 1, X2, X5 and X6 are preferably not H. X1 is more preferably V, L, I, S or Y X5 is more preferably V. L, 1, N or F. X6 is more preferably S or A. X3 and X4 may be any amino acid residue. X4 is preferably K, R or T.

The XPD helicase typically comprises the amino acid motif Q-Xa-Xb-G-R-Xc-Xd-R-$(Xe)_3$-Xf-$(Xg)_7$-D-Xh-R (hereinafter called XPD motif VI; SEQ ID NO: 51). Xa. Xe and Xg may be any amino acid residue. Xb, Xc and Xd are independently selected from any amino acid except D, E, K and R. Xb, Xc and Xd are typically independently selected from G, P, A, V, L. 1, M, C, F, Y, W, H, Q, N. S and T. Xb, Xc and Xd are preferably not charged. Xb. Xc and Xd are preferably not H. Xb is more preferably V, A, L, I or M. Xc is more preferably V, A, L, I, M or C. Xd is more preferably 1, H, L, F, M or V. Xf may be D or E. $(Xg)_7$ is $X_{g1}$, $X_{g2}$, $X_{g3}$, $X_{g4}$, $X_{g5}$, $X_{g6}$, and $X_{g7}$. $X_{g2}$ is preferably G, A, S or C. $X_{g5}$ is preferably F, V, L, I, M, A, W or Y. $X_{g6}$, is preferably L, F, Y, M, I or V. $X_{g7}$ is preferably A, C, V, L, I, M or S.

The XPD helicase preferably comprises XPD motifs V and VI. The most preferred XPD motifs V and V1 are shown in Table 5 of U.S. Patent Application No. 61/581,340 and International Application No. PCT/GB2012/053273 (published as WO 2012/098561).

The XPD helicase preferably further comprises an iron sulphide (FeS) core between two Walker A and B motifs (motifs 1 and II). An FeS core typically comprises an iron atom coordinated between the sulphide groups of cysteine residues. The FeS core is typically tetrahedral.

The XPD helicase is preferably one of the helicases shown in Table 4 or 5 of U.S. Patent Application No.

61/581,340 and International Application No. PCT/GB2012/053273 (published as WO 2012/098561) or a variant thereof. The XPD helicase most preferably comprises the sequence shown in SEQ ID NO: 52 or a variant thereof. SEQ ID NO: 52 is XPD Mbu (*Methanococcoides burtonii*; YP_566221.1; GI:91773529). XPD Mbu comprises YLWGTLSEG (Motif V, SEQ ID NO. 53) and QAMGRVVRSPTDYGARILLDGR (Motif V1; SEQ ID NO: 54).

A variant of a XPD helicase is an enzyme that has an amino acid sequence which varies from that of the wild-type helicase and which retains polynucleotide binding activity. In particular, a variant of SEQ ID NO: 52 is an enzyme that has an amino acid sequence which varies from that of SEQ ID NO: 52 and which retains polynucleotide binding activity. This can be measured as described above. The variant retains helicase activity. The variant must work in at least one of the two modes discussed below. Preferably, the variant works in both modes. The variant may include modifications that facilitate handling of the polynucleotide encoding the helicase and/or facilitate its activity at high salt concentrations and/or room temperature. Variants typically differ from the wild-type helicase in regions outside of XPD motifs V and VI discussed above. However, variants may include modifications within one or both of these motifs.

Over the entire length of the amino acid sequence of SEQ ID NO: 52, a variant will preferably be at least 10%, preferably 30% homologous to that sequence based on amino acid identity More preferably, the variant polypeptide may be at least 40%, at least 45%, at least 50%, at least 55%, at least 60%, at least 65%, at least 70%, at least 75%, at least 80%, at least 85%, at least 90% and more preferably at least 95, 97% or 99% homologous based on amino acid identity to the amino acid sequence of SEQ ID NO: 52 over the entire sequence. There may be at least 700, for example at least 80%, at least 85%, at least 900 or at least 95%, amino acid identity over a stretch of 150 or more, for example 200, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NOs: 2 and 4.

A variant of SEQ 1D NO: 52 preferably comprises the XPD motif V and/or the XPD motif VT of the wild-type sequence. A variant of SEQ ID NO: 52 more preferably comprises both XPD motifs V and VI of SEQ ID NO: 52 However, a variant of SEQ ID NO: 52 may comprise XPD motifs V and/or VI from a different wild-type sequence. For instance, a variant of SEQ TD NO: 52 may comprise any one of the preferred motifs shown in Table 5 of U.S. Patent Application No. 61/581,340 and International Application No. PCT/GB2012/053273 (published as WO 2012/098561). Variants of SEQ ID NO: 52 may also include modifications within XPD motif V and/or XPD motif VI of the wild-type sequence. Suitable modifications to these motifs are discussed above when defining the two motifs. A variant of SEQ ID NO: 52 preferably comprises one or more substituted cysteine residues and/or one or more substituted Faz residues to facilitate attachment as discussed above.

The helicase may be any of the modified helicases described and claimed in U.S. Provisional Application Nos. 61/673,446 and 61/673,452 (filed 19 Jul. 2012), US Provisional Application Nos. 61/774,694and 61/774,862 (filed 8 Mar. 2013) and the two International Applications being filed concurrently with this application (Oxford Nanopore Refs: ONT IP 028 and ONT IP 033).

The helicase is more preferably a Hel308 helicase in which one or more cysteine residues and/or one or more non-natural amino acids have been introduced at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10), wherein the helicase retains its ability to control the movement of a polynucleotide.

The Hel308 helicase preferably comprises a variant of one of SEQ ID NOs: 10, 13, 16 or 19 which comprises one or more cysteine residues and/or one or more non-natural amino acids at one or more of the positions which correspond to D272, N273, 274, G281, 284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10).

The Hel308 helicase preferably comprises a variant of one of SEQ ID NOs: 10, 13, 16 or 19 which comprises one or more cysteine residues and/or one or more non-natural amino acids at one or more of the positions which correspond to D274, E284, E285, S288, S615, K717, Y720, 287, T289, G290, E291, N316 and K319 in Hel308 Mbu (SEQ ID NO: 10).

Tables 6a and 6b below show the positions in other Hel308 helicases which correspond to D274D E284, E285, S288. S615, K717 Y720, E287, T289, G290, E291, N316 and K319 in Hel308 Mbu (SEQ ID NO: 10). The lack of a corresponding position in another Hel308 helicase is marked as a "-".

TABLE 6a

| Positions which correspond to D274, E284, E285, S288, S615, K717 and Y720 in Hel308 Mbu (SEQ ID NO: 10) | | | | | | | | |
|---|---|---|---|---|---|---|---|---|
| SEQ ID NO: | Hel308 homologue | A | B | C | D | E | F | G |
| 10 | Mbu | D274 | E284 | E285 | S288 | S615 | K717 | Y720 |
| 13 | Csy | D280 | K290 | I291 | S294 | P589 | T694 | N697 |
| 16 | Tga | L266 | S276 | L277 | Q280 | P583 | K689 | D692 |
| 19 | Mhu | S269 | Q277 | E278 | R281 | S583 | G685 | R688 |

TABLE 6b

| Positions which correspond to E287, T289, G290, E291, N316 and K319 in Hel308 Mbu (SEQ ID NO: 10). | | | | | | | |
|---|---|---|---|---|---|---|---|
| SEQ ID NO: | Hel308 homologue | H | I | J | K | L | M |
| 10 | Mbu | E287 | T289 | G290 | E291 | N316 | K319 |
| 13 | Csy | S293 | G295 | G296 | E297 | D322 | S325 |
| 16 | Tga | S279 | L281 | E282 | D283 | V308 | T311 |
| 19 | Mhu | R280 | L282 | R283 | D284 | Q309 | T312 |

The Hel308 helicase preferably comprises a variant of one of SEQ ID NOs 10, 13, 16 or 19 which comprises one or more cysteine residues and/or one or more non-natural amino acids at one or more of the positions which correspond to D274, E284, E285, S288, S615, K717 and Y720 in Hel308 Mbu (SEQ ID NO: 10). The helicase may comprise one or more cysteine residues and/or one or more non-natural amino acids at any of the following combinations of the positions labelled A to G in each row of Table 6a. {A}, {B}, {C}, {D}, {G}, {E}, {F}, {A and B}, {A and C}, {A and D}, {A and G}, {A and E}, {A and F}, {B and C}, {B and D}, {B and G}, {B and E}, {B and F}, {C and D}, {C and G}, {C and E}, {C and F}, {D and G}, {D and E}, {D and F}, {G and E}, {G and F}, {E and F}, {A, B and C}, {A, B and D}, {A, B and G}, {A, Band E}, {A, B and F}. {A, C and D}, {A, C and G}, {A, C and E}, {A, C and F}, {A, D and G}, {A, D and E}{A, D and F}, {A, G and E}, {A, G and F}, {A, E and F}, {B, C and D}, {B, C and G}, {B, C and E}, {B, C and F}, {B, D and G}, {B, D and E}, {B, D and F}, {B, G and E}, {B, G and F}, {B, E and F}, {C, D and G}, {C, D and E}, {C, D and F}, {C, G and E}, {C, G and F}, {C, E and F}, {D, G and E}, {D, G and F}, {D, E and F}, {G, E and F}, {A, B, C and D}, {A, B, C and G}, {A, B, C and E}, {A, B, C and F}, {A, B, D and G}, {A, B, D and E}, {A, B, D and F}, {A, B, G and E}, {A, B, G and F}, {A, B, E and F}, {A, C, D and G}, {A, C, D and E}, {A, C, D and F}, {A, C, G and E}, {A, C, G and F}, {A, C, E and F}, {A, D, G and E}, {A, D, G and F}, {A, D, E and F}, {A, G, E and F}, {B, C, D and G}, {B, C, D and E}, {B, C, D and F}, {B, C, G and E}, {B, C, G and F}, {B, C, E and F}, {B, D, G and E}, {B, D, G and F}, {B, D, E and F}, {B, G, E and F}, {C, D, G and E}, {C, D, G and F}, {C, D, E and F}, {C, G, E and F}, {D, G, E and F}, {A, B, C, D and G}, {A, B, C, D and E}, {A, B, C, D and F}, {A, B, C, G and E}, {A, B, C, G and F}, {A, B, C, E and F}, {A, B, D, G and E}, {A, B, D, G and F}, {A, B, D, E and F}, {A, B, G, E ard F}, {A, C, D, G and E}, {A, C, D, G and F}, {A, C, D, E and F}, {A, C, G, E and F}, {A, D, G, E and F}, {B, C, D, G and E}, {B, C, D, G and F}, {B, C, D, E and F}, {B, C, G, E and F}, {B, D, G, E and F}, {C, D, G, E and F}, {A, B, C, D, G and E}, {A, B, C, D, G and F}, {A, B, C, D, E and F}, {A, B, C, G, E and F}, {A, B, D, G, E and F}, {A, C, D, G, E and F}, {B, C, D, G, E and F}, or {A, B, C, D, G, E and F}

The Hel308 helicase more preferably comprises a variant of one of SEQ ID NOs: 10, 13, 16 or 19 which comprises one or more cysteine residues and/or one or more non-natural amino acids at one or more of the positions which correspond to D274, E284, E285, S288 and S615 in Hel308 Mbu (SEQ ID NO. 10).

In particular, the transport control protein may comprise a helicase dimer or a helicase multimer. A helicase multimer comprises two or more helicases attached together. The transport control protein may comprise two, three, four, five or more helicases. In other words, the transport control protein may comprise a helicase dimer, a helicase trimer, a helicase tetramer, a helicase pentamer and the like.

The two or more helicases can be attached together in any orientation. Identical or similar helicases may be attached via the same amino acid residue (i.e. same position) or spatially proximate amino acid residues (i e spatially proximate positions) in each helicase. This is termed the "head-to-head" formation. Alternatively, identical or similar helicases may be attached via amino acid residues (or positions) on opposite or different sides of each helicase. This is termed the "head-to-tail" formation. Helicase trimers comprising three identical or similar helicases may comprise both the head-to-bead and head-to-tail formations.

The two or more helicases may be different from one another (i.e. the construct is a hetero-dimer, -trimer, -tetramer or -pentamer etc.). For instance, the transport control protein may comprise: (a) one or more Hel308 helicases and one or more XPD helicases; (b) one or more Hel308 helicases and one or more RecD helicases; (c) one or more Hel308 helicases and one or more TraI helicases; (d) one or more XPD helicases and one or more RecD helicases; (e) one or more XPD helicases and one or more TraI helicases; or (f) one or more RecD helicases and one or more TraI helicases. The transport control protein may comprise two different variants of the same helicase. For instance, the transport control protein may comprise two variants of one of the helicases discussed above with one or more cysteine residues or Faz residues introduced at different positions in each variant in this instance, the helicases can be in a head-to-tail formation. In a preferred embodiment, a variant of SEQ ID NO: 10 comprising Q442C may be attached via cysteine linkage to a variant of SEQ ID NO: 10 comprising Q557C. Cys mutants of Hel308Mbu can also be made into hetero-dimers if necessary. In this approach, two different Cys mutant pairs such as Hel308Mbu-Q442C and Hel308Mbu-Q577C can be linked in head-to-tail fashion. Hetero-dimers can be formed in two possible ways. The first involves the use of a homo-bifunctional linker as discussed above. One of the helicase variants can be modified with a large excess of linker in such a way that one linker is attached to one molecule of the protein This linker modified variant can then be purified away from unmodified proteins, possible homo-dimers and unreacted linkers to react with the other helicase variant. The resulting dimer can then be purified away from other species.

The second involves the use of hetero-bifunctional linkers For example, one of the helicase variants can be modified with a first PEG linker containing maleimide or iodoacetamide functional group at one end and a cyclooctyne functional group (DIBO) at the other end. An example of this is shown below:

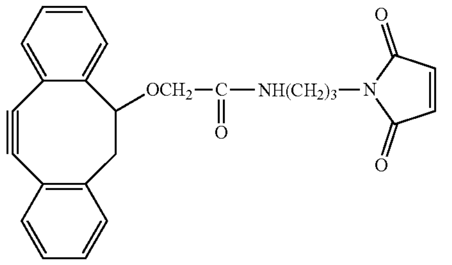

The second helicase variant can be modified with a second PEG linker containing maleimide or iodoacetamide functional group at one end and an azide functional group at the other end. An example is show below:

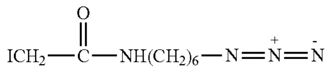

S The two helicase variants with two different linkers can then be purified and clicked together (using $Cu^{2+}$ free click chemistry) to make a dimer. Copper free click chemistry has been used in these applications because of its desirable properties. For example, it is fast, clean and not poisonous towards proteins. However, other suitable bio-orthogonal chemistries include, but are not limited to. Staudinger chemistry, hydrazine or hydrazide/aldehyde or ketone reagents (HyNic+4FB chemistry, including all Solulink™ reagents), Diels-Alder reagent pairs and boronic acid/salicyhydroxamate reagents.

Similar methodology may also be used for linking different Faz variants One Faz variant (such as SEQ TD NO 10 comprising Q442C) can be modified with a large excess of linker in such a way that one linker is attached to one molecule of the protein. This linker modified Faz variant can then be puri fed away from unmodified proteins, possible homo-dimers and unreacted linkers to react with the second Faz variant (such as SEQ ID NO: 10 comprising Q577Faz). The resulting dimer can then be purified away from other species.

Hetero-dimers can also be made by linking cysteine variants and Faz variants of the same helicase or different helicases. For example, any of the above cysteine variants (such as SEQ ID NO. 10 comprising Q442C) can be used to make dimers with any of the above Faz variants (such SEQ ID NO: 10 comprising Q577Faz). Hetero-bifunctional PEG linkers with maleimide or iodoacetamide functionalities at one end and DBCO functionality at the other end can be used in this combination of mutants An example of such a linker is shown below (DBCO-PEG4-maleimide):

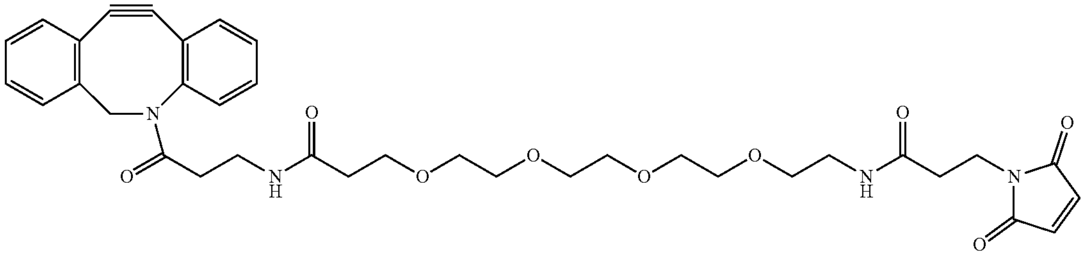 [SMILES: O=C(CCOCCOCCOCCOCCNC(=O)CCN1C(=O)C=CC1=O)NCCC(=O)N1Cc2ccccc2C#Cc2ccccc21]

The length of the linker can be varied by changing the number of PEG units between the two functional groups.

Helicase hetero-trimers can comprise three different types of helicases selected from Hel308 helicases, XPD helicases, RecD helicasess, TraI helicases and variants thereof. The same is true for oligomers comprising more than three helicases. The two or more helicases may be different variants of the same helicase, such as different variants of SEQ ID NO: 10, 13, 16 or 19. The different variants may be modified at different positions to facilitate attachment via the different positions. The hetero-trimers may therefore be in a head-to-tail and head-to-headformation.

The two or more helicases may be the same as one another (i.e. the transport control protein is a homo-dimer, -trimer, -tetramer or -pentamer etc.) Homo-oligomers can comprise two or more Hel308 helicases, two or more XPD helicases, two or more RecD helicases, two or more TraI helicases or two or more of any of the variants discussed above. In such embodiments, the helicases are preferably attached using the same amino acid residue (i.e. same position) in each helicase. The helicases are therefore attached head-to-head. The helicases may be linked using a cysteine residue or a Faz residue that has been substituted into the helicases at the same position. Cysteine residues in identical helicase variants can be linked using a homo-bifunctional linker containing thiol reactive groups such as maleimide or iodoacetamide. These functional groups can be at the end of a polyethyleneglycol (PEG) chain as in the following example:

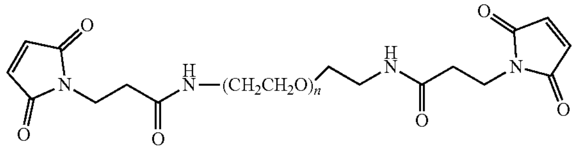

The length of the linker can be varied to suit the required applications. For example, n can be 2, 3, 4, 8, 11, 12, 16 or more. PEG linkers are suitable because they have favourable properties such as water solubility. Other non PEG linkers can also be used in cystein linkage.

By using similar approaches, identical Faz variants can also be made into homo-dimers. Homo-bifunctional linkers with DIBO functional groups can be used to link two molecules of the same Faz variant to make homo-dimers using $Cu^{2+}$ free click chemistry. An example of a linker is given below:

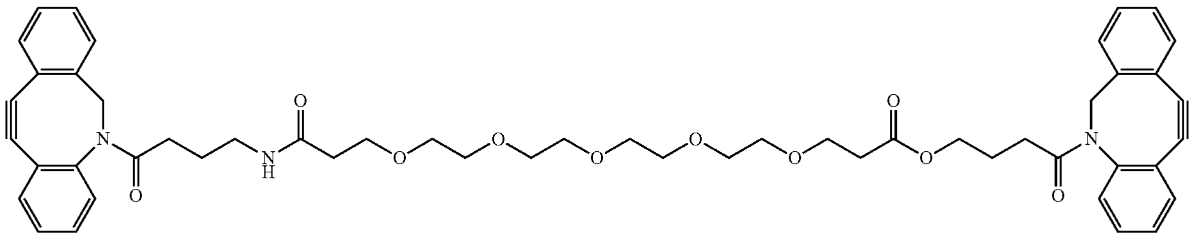 [SMILES: O=C(CCOCCOCCOCCOCCOCCC(=O)OCCCC(=O)N1Cc2ccccc2C#Cc2ccccc21)NCCCC(=O)N1Cc2ccccc2C#Cc2ccccc21]

The length of the PEG linker can vary to include 2, 4, 8, 12, 16 or more PEG units. Such linkers can also be made to incorporate a florescent tag to ease quantifications. Such fluorescence tags can also be incorporated into Maleimide linkers.

Preferred transport control proteins of the invention are shown in the Table 7 below.

TABLE 7

| Preferred transport control proteins of the invention |
|---|
| Hel308Mbu-A700C dimer 2 kDa |
| Hel308Mbu-A700C dimer 3.4 kDa |
| Hel308Mbu-Q442C 2 kDa linker homodimer |

TABLE 7-continued

| Preferred transport control proteins of the invention |
|---|
| Hel308Mbu-Q442C 3.4 kDa linker homodimer |
| Hel308Mbu-A700C 2 kDa linker homodimer |
| Hel308Mbu-A700C-strepII. 2kDa PEG homodimer |
| MspA dimer treated with proteaseK lower band |
| MspA dimer treated with proteaseK upper band |
| MspA dimer treated with proteaseK + heat treatment lower band |
| MspA dimer treated with proteaseK + heat treatment upper band |
| Hel308Mhu-WT 2kDa Dimer |
| Helicase 2k dimer (Hel308Mbu R681A, R687A, A700C – STrEP) |
| Helicase 2k dimer (Hel308Mbu R687A, A700C – STrEP) |
| Hel308Mhu-WT 2kDa Dimer |
| Hel308Tga N674C Dimer 2 kDa |
| Hel308Tga N674C Dimer 2 kDa tests for assay |
| Hel308 Tga-R657A-N674C-STrEP Dimer 2 kDa |

The transport control protein may be a polynucleotide binding domain derived from a helicase. For instance, the transport control protein preferably comprises the sequence shown in SEQ ID NO: 61 or 62 or a variant thereof. A variant of SEQ ID NO: 61 or 62 is a protein that has an amino acid sequence which varies from that of SEQ 1D NO: 61 or 62 and which retains polynucleotide binding activity This can be measured as described above. The variant may include modifications that facilitate binding of the polynucleotide and/or facilitate its activity at high salt concentrations and/or room temperature.

Over the entire length of the amino acid sequence of SEQ ID NO: 61 or 62, a variant will preferably be at least 50% homologous to that sequence based on amino acid identity. More preferably, the variant polypeptide may be at least 55%, at least 60%, at least 65%, at least 70%., at least 75%, at least 80%, at least 85%, at least 90% and more preferably at least 95%, 97% or 99% homologous based on amino acid identity to the amino acid sequence of SEQ ID NO: 61 or 62 over the entire sequence. There may be at least 80%, for example at least 85%, 90% or 95%, amino acid identity over a stretch of 40 or more, for example 50, 60, 70 or 80 or more. contiguous amino acids (C"hard homology") Homology is determined as described above. The variant may differ from the wild-type sequence in any of the ways discussed below with reference to SEQ ID NOs: 2 and 4.

The topoisomerase is preferably a member of any of the Moiety Classification (EC) groups 5.99.1.2 and 5.99.1.3.

The transport control protein may be any of the enzymes discussed above.

The transport control protein may be labelled with a revealing label. The label may be any of those described above.

The transport control protein may be isolated from any protein-producing organism, such as *E. coli, T. thermophilus* or bacteriophage, or made synthetically or by recombinant means. For example, the transport control protein may be synthesized by in vitro translation and transcription as described below. The transport control protein may be produced in large scale following purification as described above.

The SSB is preferably attached to the transport control protein such that the resulting construct has the ability to control the movement of the target polynucleotide. Such a construct is a useful tool for controlling the movement of a polynucleotide during Strand Sequencing. A problem which occurs in sequencing polynucleotides, particularly those of 500 nucleotides or more, is that the molecular motor which is controlling translocation of the polynucleotide may disengage from the polynucleotide. This allows the polynucleotide to be pulled through the pore rapidly and in an uncontrolled manner in the direction of the applied field. The construct is less likely to disengage from the polynucleotide being sequenced. The construct can provide increased read lengths of the polynucleotide as it controls the translocation of the polynucleotide through a nanopore. The ability to translocate an entire polynucleotide through a nanopore under the control of the construct described above allows characteristics of the polynucleotide, such as its sequence. to be estimated with improved accuracy and speed over known methods. This becomes more important as strand lengths increase and molecular motors are required with improved processivity. The construct is particularly effective in controlling die translocation of target polynucleotides of 500 nucleotides or more, for example 1000 nucleotides, 5000, 10000, 20000, 50000, 100000 or more.

The construct has the ability to control the movement of a polynucleotide. The ability of a construct to control the movement of a polynucleotide can be assayed using any method known in the art. For instance, the construct may be contacted with a polynucleotide and the position of the polynucleotide may be determined using standard methods. The ability of a construct to control the movement of a polynucleotide is typically assayed as described in the Examples.

The construct may be isolated, substantially isolated, purified or substantially purified. A construct is isolated or purified if it is completely free of any other components, such as lipids, polynucleotides or pore monomers. A construct is substantially isolated if it is mixed with carriers or diluents which will not interfere with its intended use. For instance, a construct is substantially isolated or substantially purified if it is present in a form that comprises less than 10%, less than 5%, less than 2% or less than 1% of other components, such as lipids, polynucleotides or pore monomers.

In the construct, the transport control protein, such as the helicase, is attached to the SSB. The transport control protein is preferably covalently attached to the SSB. The transport control protein may be attached to the SSB at more than one, such as two or three, points.

The transport control protein can be covalently attached to the SSB using any method known in the art. The transport control protein and SSB may be produced separately and then attached together. The two components may be attached in any configuration. For instance, they may be attached via their terminal (i.e. amino or carboxy terminal) amino acids. Suitable configurations include, but are not limited to, the amino terminus of the SSB being attached to the carboxy terminus of the transport control protein and vice vera Alternatively, the two components may be attached via amino acids within their sequences. For instance, the SSB may be attached to one or more amino acids in a loop region of the transport control protein. In a preferred embodiment, terminal amino acids of the SSB are attached to one or more amino acids in the loop region of a transport control protein. Terminal amino acids and loop regions can be identified using methods known in the art (Edman P., Acts Chemica Scandinavia, (1950), 283-293). For instance, loop regions can be identified using protein modeling. This exploits the fact that protein structures are more conserved than protein sequences amongst homologues. Hence, producing atomic resolution models of proteins is dependent upon the identification of one or more protein structures that are likely to resemble the structure of the query sequence. in order to assess whether a suitable protein structure exists to use as a "template" to build a protein model, a search is performed on the protein data bank (PDB) database. A protein structure is considered a suitable template if it shares a reasonable level of sequence identity with the query sequence. If such a template exists. then the template sequence is "aligned" with the query sequence, i.e. residues in the query sequence are mapped onto the template residues The sequence alignment and template structure are then used to produce a structural model of the query sequence. Hence, the quality of a protein model is dependent upon the quality of the sequence alignment and the template structure.

The two components may be attached via their naturally occurring amino acids, such as cysteines, threonines, serines, aspartates, asparagines, glutamates and glutamines. Naturally occurring amino acids may be modified to facilitate attachment. For instance, the naturally occurring amino acids may be modified by acylation, phosphorylation, glycosylation or farnesylation. Other suitable modifications are known in the art. Modifications to naturally occurring amino acids may be post-translation modifications. The two components may be attached via amino acids that have been introduced into their sequences. Such amino acids are preferably introduced by substitution The introduced amino acid may be cysteine or a non-natural amino acid that facilitates attachment. Suitable non-natural amino acids include, but are not limited to, 4-azido-L-phenylalanine (Faz), and any one of the amino acids numbered 1-71 included in FIG. 1 of Liu C. C. and Schultz P. G., Annu. Rev. Biochem., 2010, 79, 413-444. The introduced amino acids may be modified as discussed above.

In a preferred embodiment, the transport control protein is chemically attached to the SSB, for instance via a linker molecule. Linker molecules are discussed in more detail below. One suitable method of chemical attachment is cysteine linkage. This is discussed in more detail below.

The transport control protein may be transiently attached to the SSB by a hexa-his tag or Ni-NTA. The transport control protein and SSB may also be modified such that they transiently attach to each other.

In another preferred embodiment, the transport control protein is genetically fused to the SSB. A transport control protein is genetically fused to a SSB if the whole construct is expressed from a single polynucleotide sequence. The coding sequences of the transport control protein and SSB may be combined in any way to form a single polynucleotide sequence encoding the construct. Genetic fusion of a pore to a nucleic acid binding protein is discussed in International Application No. PCT/GB09/001679 (published as WO 2010/004265).

The transport control protein and SSB may be genetically fused in any configuration. The transport control protein and SSB may be fused via their terminal amino acids. For instance, the amino terminus of the SSB may be fused to the carboxy terminus of the transport control protein and rice versa. The amino acid sequence of the SSB is preferably added in frame into the amino acid sequence of the transport control protein. In other words, the SSB is preferably inserted within the sequence of the transport control protein. In such embodiments, the transport control protein and SSB are typically attached at two points, i.e. via the amino and carboxy terminal amino acids of the SSB. If the SSB is inserted within the sequence of the transport control protein, it is preferred that the amino and carboxy terminal amino acids of the SSB are in close proximity and are each attached to adjacent amino acids in the sequence of the transport control protein or variant thereof. In a preferred embodiment, the SSB is inserted into a loop region of the transport control protein.

The construct retains the ability of the transport control protein to control the movement of a polynucleotide. This ability of the transport control protein is typically provided by its three dimensional structure that is typically provided by its β-strands and α-helices. The α-helices and β-strands are typically connected by loop regions. In order to avoid affecting the ability of the transport control protein to control the movement of a polynucleotide. the SSB is preferably genetically fused to either end of the transport control protein or inserted into a surface-exposed loop region of the transport control protein. The loop regions of specific transport control proteins can be identified using methods known in the art. For instance, the loop regions can be identified using protein modelling, x-ray diffraction measurement of the protein in a crystalline state (Rupp B (2009). Biomolecular Crystallography: Principles, Practice and Application to Structural Biology. New York: Garland Science.), nuclear magnetic resonance (NMR) spectroscopy of the protein in solution (Mark Rance; Cavanagh, John; Wayne J. Fairbrother; Arthur W. Hunt III; Skelton, NNicholas J. (2007). Protein NMR spectroscopy: principles and practice (2nd ed.). Boston: Academic Press.) or cryo-electon microscopy of the protein in a frozen-hydrated state (van Heel M, Gowen B, Matadeen R, Orlova E V, Finn R, Pape T, Cohen D, Stark H, Schmidt R, Schatz M, Patwardhan A (2000). "Single-particle electron cryo-microscopy: towards atomic resolution" Q Rev Biophys. 33: 307-69. Structural information of proteins determined by above mentioned methods are publicly available from the protein bank (PDB) database.

For Hel308 helicases (SEQ ID NOs: 10, 13, 16 and 19), O-strands can only be found in the two RecA-like engine domains (domains 1 and 2). These domains are responsible for coupling the hydrolysis of the fuel nucleotide (normally ATP) with movement. The important domains for ratcheting along a polynucleotide are domains 3 and 4, but above all domain 4. Interestingly, both of domains 3 and 4 comprise only α-helices. There is an important α-helix in domain 4 called the ratchet helix. As a result, in the Hel308 embodiments of the invention, the SSB is preferably not genetically fused to any of the the α-helixes.

The transport control protein may be attached directly to the SSB. The transport control protein is preferably attached to the SSB using one or more, such as two or three, linkers. The one or more linkers may be designed to constrain the mobility of the SSB. The linkers may be attached to one or more reactive cysteine residues, reactive lysine residues or non-natural amino acids in the transport control protein and/or SSB. The non-natural amino acid may be any of those discussed above. The non-natural amino acid is preferably 4-azido-L-phenylalanine (Faz). Suitable linkers are well-known in the art.

The transport control protein is preferably attached to the SSB using one or more chemical crosslinkers or one or more peptide linkers Suitable chemical crosslinkers are well-known in the art. Suitable chemical crosslinkers include, but are not limited to, those including the following functional groups: maleimide, active esters, succinimide, azide, alkyne (such as dibenzocyclooctynol (DIBO or DBCO), difluoro cycloalkynes and linear alkynes), phosphine (such as those used in traceless and non-traceless Staudinger ligations), haloacetyl (such as iodoacetamide) phosgene type reagents. sulphonyl chloride reagents. isothiocyanates. acyl halides, hydrazines, disulphides, vinyl sulfones, aziridines and photoreactive reagents (such as aryl azides, diaziridines).

Reactions between amino acids and functional groups may be spontaneous, such as cysteine/maleimide, or may require external reagents, such as Cu(I) for linking azide and linear alkynes.

Linkers can comprise any molecule that stretches across the distance required. Linkers can vary in length from one carbon (phosgene-type linkers) to many Angstroms. Examples of linear molecules., include but are not limited to, are polyethyleneglycols (PEGs), polypeptides, polysaccharides, deoxyribonucleic acid (DNA), peptide nucleic acid (PNA), threose nucleic acid (TNA), glycerol nucleic acid (GNA), saturated and unsaturated hydrocarbons, polyamides. These linkers may be inert or reactive, in particular they may be chemically cleavable at a defined position, or may be themselves modified with a fluorophore or ligand. The linker is preferably resistant to dithiothreitol (DTT).

Cleavable linkers can be used as an aid to separation of constructs from non-attached components and can be used to further control the synthesis reaction. For example, a hetero-bifunctional linker may react with the transport control protein, but not the SSB. If the free end of the linker can be used to bind the transport control protein to a surface, the unreacted transport control proteins from the first reaction can be removed from the mixture. Subsequently, the linker can be cleaved to expose a group that reacts with the SSB. In addition, by following this sequence of linkage reactions, conditions may be optimised first for the reaction to the transport control protein, then for the reaction to the SSB after cleavage of the linker. The second reaction would also be much more directed towards the correct site of reaction with the SSB because the linker would be confined to the region to which it is already attached.

Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate. The most preferred crosslinkers are succinimidyl 3-(2-pyridyldithio)propionate (SPDP) and maleimide-PEG(2 kDa)-maleimide (alpha,omega-bis-maleimido poly(ethylene glycol)).

The transport control protein may be covalently attached to the bifunctional crosslinker before the transport control protein/crosslinker complex is covalently attached to the SSB. Alternatively, the SSB may be covalently attached to the bifunctional crosslinker before the bifunctional crosslinker/SSB complex is attached to the transport control protein. The transport control protein and SSB may be covalently attached to the chemical crosslinker at the same time.

The transport control protein may be attached to the SSB using two different linkers that are specific for each other One of the linkers is attached to the transport control protein and the other is attached to the SSB. Once mixed together, the linkers should react to form a construct. The transport control protein may be attached to the SSB using the hybridization linkers described in International Application No. PCT/GB10/000132 (published as WO 2010/086602). In particular, the transport control protein may be attached to the SSB using two or more linkers each comprising a hybridizable region and a group capable of forming a covalent bond. The hybridizable regions in the linkers hybridize and link the transport control protein and the SSB. The linked transport control protein and the SSB are then coupled via the formation of covalent bonds between the groups. Any of the specific linkers disclosed in International Application No. PCT/GB10/000132 (published as WO 2010/086602) may be used in accordance with the invention.

The transport control protein and the SSB may be modified and then attached using a chemical crosslinker that is specific for the two modifications. Any of the crosslinkers discussed above may be used.

Alternatively, the linkers preferably comprise amino acid sequences. Such linkers are peptide linkers. The length, flexibility and hydrophilicity of the peptide linker are typically designed such that it does not to disturb the functions of the transport control protein and SSB. Preferred flexible peptide linkers are stretches of 2 to 20, such as 4, 6, 8, 10 or 16. serine and/or glycine amino acids. More preferred flexible linkers include $(SG)_1$, $(SG)_2$, $(SG)_3$, $(SG)_4$, $(SG)_5$, $(SG)_8$, $(SG)_{10}$, $(SG)_{15}$ or $(SG)_{20}$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline.

The linkers may be labelled. Suitable labels include, but are not limited to, fluorescent molecules (such as Cy3 or AlexaFluor®555), radioisotopes, e.g. $^{125}I$, $^{35}S$, enzymes, antibodies. antigens, polynucleotides and ligands such as biotin. Such labels allow the amount of linker to be quantified. The label could also be a cleavable purification tag, such as biotin, or a specific sequence to show up in an identification method. such as a peptide that is not present in the protein itself, but that is released by trypsin digestion.

A preferred method of attaching the transport control protein to the SSB is via cysteine linkage. This can be mediated by a bi-functional chemical linker or by a polypeptide linker with a terminal presented cysteine residue. Linkage can occur via natural cysteines in the transport control protein and/or SSB. Alternatively, cysteines can be introduced into the transport control protein and/or SSB. If the transport control protein is attached to the SSB via cysteine linkage, the one or more cysteines have preferably been introduced to the transport control protein and/or SSB by substitution.

The length, reactivity, specificity, rigidity and solubility of any bi-functional linker may be designed to ensure that the SSB is positioned correctly in relation to the transport control protein and the function of both the transport control protein and SSB is retained. Suitable linkers include bismaleimide crosslinkers, such as 1,4-bis(maleimido)butane (BMB) or bis(maleimido)hexane. One draw back of bi-functional linkers is the requirement of the transport control protein and SSB to contain no further surface accessible cysteine residues if attachment at specific sites is preferred, as binding of the bi-functional linker to surface accessible cysteine residues may be difficult to control and may affect substrate binding or activity. If the transport control protein and/or SSB does contain several accessible cysteine residues, modification of the transport control protein and/or SSB may be required to remove them while ensuring the modifications do not affect the folding or activity of the transport control protein and SSB. This is discussed in International Application No. PCT/GB10/000133 (published as WO 2010/086603). In a preferred embodiment, a reactive cysteine is presented on a peptide linker that is genetically attached to the SSB. This means that additional modifications will not necessarily be needed to remove other accessible cysteine residues from the SSB. The reactivity of cysteine residues may be enhanced by modification of the adjacent residues, for example on a peptide linker. For instance, the basic groups of flanking arginine, histidine or lysine residues will change the pKa of the cysteines thiol group to that of the more reactive S' group. The reactivity of cysteine residues may be protected by thiol protective groups such as 5,5'-dithiobis-(2-nitrobenzoic acid)(dTNB). These may be reacted with one or more cysteine residues of the SSB or transport control protein, either as a monomer or pan of an oligomer, before a linker is attached. Selective deprotection of surface accessible cysteines may be possible using reducing reagents immobilized on beads (for example immobilized tris(2-carboxyethyl)phosphine, TCEP).

Another preferred method of attaching the transport control protein to the SSB is via 4-azido-L-phenylalanine (Faz) linkage. This can be mediated by a bi-functional chemical linker or by a polypeptide linker with a terminal presented Faz residue. The one or more Faz residues have preferably been introduced to the transport control protein and/or SSB by substitution.

Cross-linkage of transport control proteins or SSB to themselves may be prevented by keeping the concentration of linker in a vast excess of the transport control protein and/or SSB. Alternatively, a “lock and key” arrangement may be used in which two linkers are used. Only one end of each linker may react together to form a longer linker and the other ends of the linker each react with a different part of the construct (i.e. transport control protein or SSB). This is discussed in more detail below.

The site of attachment is selected such that, when the construct is contacted with a polynucleotide, both the transport control protein and the SSB can bind to the polynucleotide and control its movement.

Attachment can be facilitated using the polynucleotide binding activities of the transport control protein and the SSB. For instance, complementary polynucleotides can be used to bring the transport control protein and SSB together as they hybridize. The transport control protein can be bound to one polynucleotide and the SSB can be bound to the complementary polynucleotide. The two polynucleotides can then be allowed to hybridise to each other. This will bring the transport control protein into close contact with the SSB, making the linking reaction more efficient. This is especially helpful for attaching two or more transport control proteins in the correct orientation for controlling movement of a target polynucleotide. An example of complementary polynucleotides that may be used are shown below.

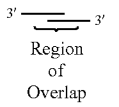

Tags can be added to the construct to make purification of the construct easier. These tags can then be chemically or enzymatically cleaved off, if their removal is necessary. Fluorophores or chromophores can also be included. and these could also be cleavable.

A simple way to purify the construct is to include a different purification tag on each protein (i e. the transport control protein and the SSB), such as a hexa-His-tag and a Strep-Tag®. If the two proteins are different from one another, this method is particularly useful. The use of two tags enables only the species with both tags to be purified easily.

If the two proteins do not have two different tags, other methods may be used. For instance, proteins with free surface cysteines or proteins with linkers attached that have not reacted to form a construct could be removed, for instance using an iodoacetamide resin for maleimide linkers.

Constructs can also be purified from unreacted proteins on the basis of a different DNA processivity property. In particular, a construct can be purified from unreacted proteins on the basis of an increased affinity for a polynucleotide, a reduced likelihood of disengaging from a polynucleotide once bound and/or an increased read length of a polynucleotide as it controls the translocation of the polynucleotide through a nanopore.

The invention provides a construct comprising at least one helicase and an SSB as described above, wherein the helicase is attached to the SSB and the construct has the ability to control the movement or a polynucleotide. The construct may comprise two or more helicases, such as three, four, five or more helicases. The construct may comprise any of the helicases described above. Any of the discussion concerning attaching a transport control protein to an SSB equally applies to this embodiment.

Srand Sequencing

In a preferred embodiment, the method comprises:

(a) contacting the target polynucleotide with a transmembrane pore and a SSB as defined above such that the target polynucleotide moves through the pore and the SSB does not move through the pore; and (b) measuring the current passing through the pore as the polynucleotide moves with respect to the pore wherein the current is indicative of one or more characteristics of the target polynucleotide and thereby characterising the target polynucleotide. The target polynucleotide is preferably contacted with the pore and the SSB on the same side of the membrane.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the an and disclosed in the Example. The method is typically carried out with a voltage applied across the membrane and pore The voltage used is typically from +2 V to −2 V. typically −400 mV to +400 mV. The voltage used is preferably in a range having a lower limit selected from −400 mV, −300 mV, −200 mV, −150 mV, −100 mV. −50 mV, −20 mV and 0 mV and an upper limit independently selected from +10 mV, +20 mV, 4−50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used KCl, NaCl and a mixture of potassium ferrocyanide and potassium ferricyanide are preferred. The salt concentration may be at saturation. The salt concentration may be 3 M or lower and is typically from 0. I to 2.5 M, from 0.3 to 1.9 M, from 0.5 to 1.8 M, from 0.7 to 1.7% M, from 0.9 to 1.6 M or from 1 M to 1.41M. The salt concentration is preferably from 150 mM to 1 M. Hel308, XPD, RecD and TraI helicases surprisingly work under high salt concentrations. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 N or at least 3.0 M. High salt concentrations provide a high signal to noise ratio and allow for currents indicative of the presence of a nucleotide to be identified against the background of normal current fluctuations The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4 5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C. from 16° C. to 90° C., from 17° C. to 85° C., from 18° C. to 80° C., 19° C. to 70° C. or from 20° C. to 60° C. The methods are typically carried out at room temperature. The methods are optionally carried out at a temperature that supports enzyme function, such as about 37° C.

The method may be carried out in the presence of free nucleotides or free nucleotide analogues and/or an enzyme cofactor that facilitates the action of the transport control protein. The method may also be carried out in the absence of free nucleotides or free nucleotide analogues and in the absence of an enzyme cofactor The free nucleotides may be one or more of any of the individual nucleotides discussed above The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP). deoxythymidine triphosphate (dTTP), deoxynridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the transport control protein to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The target polynucleotide may be contacted with the SSB and the pore in any order. It is preferred that, when the target polynucleotide is contacted with the SSB and the pore. the target polynucleotide firstly forms a complex with the SSB. When the voltage is applied across the pore, the target polynucleotide/SSB complex then forms a complex with the pore and controls the movement of the polynucleotide through the pore As discussed above. helicases may work in two modes with respect to the pore. The constructs of the invention comprising such helicases can also work in two mode. First, the method is preferably carried out using the construct such that it moves the target sequence through the pore with the field resulting from the applied voltage. In this mode the 5' end of the DNA is first captured in the pore, and the construct moves the DNA into the pore such that the target sequence is passed through the pore with the field until it finally translocates through to the trans side of the bilayer. Alternatively, the method is preferably carried out such that the construct moves the target sequence through the pore against the field resulting from the applied voltage. In this mode the 3' end of the DNA is first captured in the pore, and the construct moves the DNA through the pore such that the target sequence is pulled out of the pore against the applied field until finally ejected back to the cis side of the bilayer.

Polynucleotide Sequences

Any of the proteins described herein may be expressed using methods known in the art. Polynucleotide sequences may be isolated and replicated using standard methods in the art. Chromosomal DNA may be extracted from a helicase producing organism, such as *Methanococcoides burtonii*, and/or a SSB producing organism, such as *E. coli*. The gene encoding thesequence of interest may be amplified using PCR involving specific primers. The amplified sequences may then be incorporated into a recombinant replicable vector such as a cloning vector. The vector may be used to replicate the polynucleotide in a compatible host cell Thus polynucleotide sequences may be made by introducing a polynucleotide encoding the sequence of interest into a replicable vector, introducing the vector into a compatible host cell. and growing the host cell under conditions which bring about replication of the vector. The vector may be recovered from the host cell. Suitable host cells for cloning of polynucleotides are known in the art and described in more detail below.

The polynucleotide sequence may be cloned into a suitable expression vector. In an expression vector, the polynucleotide sequence is typically operably linked to a control sequence which is capable of providing for the expression of the coding sequence by the host cell. Such expression vectors can be used to express a construct.

The term “operably linked” refers to a juxtaposition wherein the components described are in a relationship permitting them to function in their intended manner. A control sequence “operably linked” to a coding sequence is ligated in such a way that expression of the coding sequence is achieved under conditions compatible with the control sequences. Multiple copies of the same or different polynucleotide may be introduced into the vector The expression vector may then be introduced into a suitable host cell. Thus, a construct can be produced by inserting a polynucleotide sequence encoding a construct into an expression vector, introducing the vector into a compatible bacterial host cell, and growing the host cell under conditions which bring about expression of the polynucleotide sequence.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example an ampicillin resistance gene. Promoters and other expression regulation signals may be selected to be compatible with the host cell for which the expression vector is designed. A T7, trc, lac, ara or $\lambda_L$ promoter is typically used.

The host cell typically expresses the construct at a high level. Host cells transformed with a polynucleotide sequence will be chosen to be compatible with the expression vector used to transform the cell. The host cell is typically bacterial and preferably *E. coil*. Any cell with a λ DE3 lysogen, for example C41 (DE3), BL21 (DE3), JM109 (DE3), B834 (DE3), TUNER, Origami and Origami B, can express a vector comprising the 17 promoter.

Other Methods

The invention also provides a method of forming a sensor for characterising a target polynucleotide. The method comprises forming a complex between a pore and a SSB as described above The complex may be formed by contacting the pore and the SSB in the presence of the target polynucleotide and then applying a potential across the pore. The applied potential may be a chemical potential or a voltage potential as described above.

Alternatively, the complex may be formed by covalently attaching the pore to the SSB. Methods for covalent attachment are known in the art and disclosed, for example, in International Application Nos. PCT/GB09/001679 (published as WO 2010/004265) and PCT/GB10/000133 (published as WO 2010/086603). Methods are also discussed above with reference to attaching the SSB to the transport control protein. The complex is a sensor for characterising the target polynucleotide. The method preferably comprises forming a complex between a pore derived from Msp and a SSB. Any of the embodiments discussed above with reference to the methods of the invention equally apply to this method. The invention also provides a sensor produced using the method of the invention.

Kits

The present invention also provides a kit for characterising a target polynucleotide. The kit comprises (a) a pore and (b) a SSB as described above. Any of the embodiments discussed above with reference to the method of the invention equally apply to the kits.

The kit may further comprise the components or a membrane, such as the phospholipids needed to form an amphiphilic layer, such as a lipid bilayer.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides Apparatus The invention also provides an apparatus for characterising a target polynucleotide. The apparatus comprises a plurality of pores and a plurality of SSBs as described above. The apparatus preferably further comprises instructions for carrying out the method of the invention. The apparatus may be any conventional apparatus for polynucleotide analysis, such as an array or a chip. Any of the embodiments discussed above with reference to the methods of the invention are equally applicable to the apparatus of the invention.

The apparatus is preferably set up to carry out the method of the invention.

The apparatus preferably comprises:

a sensor device that is capable of supporting the plurality of pores and being operable to perform polynucleotide characterisation using the pores and SSBs; and at least one reservoir for holding material for performing the characterisation.

The apparatus preferably comprises:

a sensor device that is capable of supporting the membrane and plurality of pores and being operable to perform polynucleotide characterising using the pores and SSBs as described above;

at least one reservoir for holding material for performing the characterising;

a fluidics system configured to controllably supply material from the at least one reservoir to the sensor device; and one or more containers for receiving respective samples, the fluidics system being configured to supply the samples selectively from the one or more containers to the sensor device. The apparatus may be any of those described in International Application No. PCT/GB08/004127 (published as WO 2009/077734), PCT/GB10/000789 (published as WO 2010/122293), International Application No. PCT/GB10/002206 (not yet published) or International Application No PCT/US99/25679 (published as WO 00/28312).

Methods of Producing Constructs of the Invention

The invention also provides a method of producing a construct of the invention. The method comprises attaching. preferably covalently attaching, an SSB as defined above to at least one helicase. Any of the helicases and SSBs discussed above can be used in the methods The site of and method of attachment are selected as discussed above.

The method preferably further comprises determining whether or not the construct is capable of controlling the movement of a polynucleotide. Assays for doing this are described above if the movement of a polynucleotide can be controlled, the helicase and SSB have been attached correctly and a construct of the invention has been produced. If the movement of a polynucleotide cannot be controlled, a construct of the invention has not been produced. The following Example illustrates the invention.

Example 1—Expression and Purification of EcoSSB-WT (SEO ID NO: 65) and EcoSSB Mutants (SEO ID NO's: 66-69)

All proteins were expressed with an N-terminal hexahistidine tag and TEV protease digestion site in BL21 STAR (DE3) competent cells (Invitrogen). Transformed colonies from LB-agar plates with 100 μg/ml ampicillin were grown in TB media with 100 μg/ml ampicillin and 20 μg/ml chloramphenicol at 37° C. for 7 h until OD600 reached 1 5 for EcoSSB-WT (SEQ ID NO: 65), EcoSSB-CterAla (SEQ ID NO: 66) and EcoSSB-NGGN (SEQ ID NO: 67) and 0.15 for EcoSSB-Q152del (SEQ ID NO 68) and EcoSSB-G117del (SEQ ID NO 69) (slow growth may be due to high toxicity of these mutants). Cultures were moved to 18° C. and allowed to cool for 30 mins before isopropyl β-D-1-thiogalactopyranoside (IPTG) was added to a final concentration of 1 mM and fermentation continued overnight (16-18h). Cells were harvested by centrifugation at 4000 g and pellets were lysed for 2 h at 4° C. in a buffer containing 1× BugBuster (Novagen), 50 mN TrisHCl pH 8.0, 500 mM NaCl, 20 mM imidazole and 5% (w/v) glycerol, protease inhibitors (Calbiochem Protease Inhibitor Cocktail set V) and Benzonase nuclease (Sigma). The lysate was then centrifuged and filtered through 0.22 μm filters before loading onto HisTrapFF crude columns (GE Healthcare) equilibrated in buffer A (50 mM TrisHCl pH 8.0, 500 mM NaCl, 20 mM imidazole, 5% (w/v) glycerol) After loading, the column was washed for 20 column volumes (CV) with buffer A and 20 CV with buffer W (50 mM TrisHCl pH 8 0, 1000 mM NaCl, 40 mM imidazole, 5% (w/v) glycerol, 0.1% (w/v) Tween20). Proteins were eluted in buffer B (50 mM TrisHCl pH 8.0, 500 mM NaCl, 500 mM imidazole, 5% (w/v) glycerol) This and all other chromatography steps were performed on an AktaXpress system.

The eluted proteins from the HisTrapFF column were precipitated using ammonium sulphate by adding stock solution of 300 g/L ammonium sulphate to give a final concentration of 150 g/L. Samples were incubated at 4° C. for 2 h and centrifuged at 17,000 g. Resulting pellets were resupended in buffer containing 50 mM TrisHCl pH 8.0, 500 mM NaCl, 1 mM DTT and 0.5% EDTA. His-tagged TEV protease was added to 1:1 molar ratio and samples were incubated overnight at 4° C. The reaction mix was then loaded onto a second HisTrapFF crude column equilibrated in buffer C (50 mM TrisHCl pH 8.0, 1000 mM NaCl, 20 mM imidazole, 5% (w/v) glycerol) The flowthrough containing the protein of interest with the his-tag removed was collected and the column washed with buffer B to collect uncleaved sample and TEV protease.

For mutants EcoSSB-Q152del (SEQ ID NO. 68) and EcoSSB-G117del (SEQ ID NO: 69) additional purification steps were required to remove EcoSSB-WT (SEQ ID NO: 65) contaminant carried through from *E. coil* expression. The flowthrough from the second HisTrapFF column was diluted tenfold with buffer D (50 mM TrisHCl pH 8.0) and loaded onto a MonoQ HR5/5 column (GE Healthcare). The flowthrough from the monoQ column containing the recombinant protein was then loaded onto a HiTrap Heparin column (GE Healthcare) equilibrated in buffer E (20 mM TrisHCl pH 7.0, 2 mM DTI). A gradient was applied over 20 CV to 100% buffer F (20 mM TrisHCl pH 7.0, 2 mM DTT, 2000 mM NaCl). The proteins eluted in approximately 360 mM NaCl (EcoSSB-Q152del, SEQ ID NO: 68) and 550 mM NaCl (EcoSSB-G117del, SEQ ID NO. 69). For storage, glycerol was added to 20% volume to all samples Example 2—Permanent Blocking or a Nanopore by the C-Terminus or SSB Initial experiments designed to first assess the potential use of SSB as an additive or as a translocation facilitator protein for nanopore DNA sequencing quickly determined that addition of the E. co/i SSB protein (EcoSSB-WT, SEQ ID NO: 65), in complex with ssDNA, to the cis chamber results in rapid blocking of the nanopore under positive potential. This blocking was permanent and could only be cleared on reversal of potential, unlike the transient blocking events observed for the translocation of ssDNA.

The SSB protein front *E. coil* SSB (EcoSSB-WT, SEQ ID NO: 65) is a very well characterised protein due to its essential role in DNA replication, repair and recombination. *E. coli* SSB generally exists in solution as a homotetramer in the absence of DNA. This tetrameric protein is largely a compact globular structure consisting of the N-terminal two thirds from each protein subunit, which constitutes the ssDNA binding domain. The C-terminal third of each subunit comprises a flexible glycine proline rich random peptide coil that also contains a region of highly negatively charged amino acids (Lu and Keck. 2008).

As the C-terminal third of each subunit is not required for ssDNA binding then a deletion mutant of the C-terminal third of the SSB protein was designed (EcoSSB-G117del, SEQ ID NO. 69). In addition, as negatively charged polymers, such as DNA, are known to interact with nanopores then a protein that lacked only the last 15 negatively charged amino acids was also designed (EcoSSB-Q152del. SEQ ID NO. 68). To maintain the full length protein, mutations to charge neutralise the acidic residues in the C-terminus were also designed (EcoSSB-CterAla, SEQ ID NO: 66 and EcoSSB-CterNGCGN, SEQ ID NO: 67).

Alignment of *Escherichia coli* Single Strand DNA Binding Protein (EcoSSB) Mutants (EcoSSB-WT is SEQ ID NO: 65, EcoSSB-CterAla is SEQ ID NO: 66, EcoSSB-CterNGGN is SEQ ID NO: 67, EcoSSB-Q152del is SEQ ID NO: 68, EcoSSB-G117del is SEQ ID NO: 69).

```
EcoSSB-WT        ASAGVNKVILVGNLGQDPEVRYMPNGGAVANITLATSESWRDKATGEMKEQTEWHRVVLF   60
EcoSSB CterAla   ASRGVNKVILVGNLGQDPEVRYMPNGGAVANITLATSESWRDKATGEMKEQTEWHRVVLF   60
EcoSSB-CLerNGGN  ASRGVNKVILVGNLGQDPEVRYMPNGGAVANITLATSESWRDKATGEMKEQTEWHRVVLF   60
EcoSSB-Q152del   ASAGVNKVILVGNLGQDPEVRYMPNGGAVANITLATSESWRDKATGEMKEQTEWHRVVLF   60
EcoSSB-G117del   ASRGVNKVILVGNLGQDPEVRYMPNGGAVANITLATSESWRDNATGEMKEQTEWHRVVLF   60
                 ************************************************************
```

-continued

Alignment of *Escherichia coli* Single Strand DNA Binding Protein (EcoSSB) Mutants (EcoSSB-WT is SEQ ID NO: 65, EcoSSB-CterAla is SEQ ID NO: 66, EcoSSB-CterNGGN is SEQ ID NO: 67, EcoSSB-Q152del is SEQ ID NO: 68, EcoSSB-G117del is SEQ ID NO: 69).

```
EcoSSB-WT        GKLAEVASEYLRKGSQVYIEGQLRTRKWTDQSGQDRYTTEVVVNVGGTMQMLGGRQGGGA    120
EcoSSB-CLerAla   GKLAEVASEYLRKGSQVYIEGQLRTRKWTDQSGQDRYTTEVVVNVGGTMQMLGGRQGGGA    120
EcoSSB-CterNGGN  GKLAEVASEYLRKGSQVYIEGQLRTRKWTDQSGQDRYTTEVVVNVGGTMQMLGGRQGGGA    120
EcoSSB-Q152del   GKLAEVASEYLRKGSQVYIEGQLRTRKWTDQSGQDRYTTEVVVNVGGTMQMLGGRQGGGA    120
EcoSSB-G117del   GKLAEVASEYLRKGSQVYIEGQLRTRKWTDQSGQDRYTTEVVVNVGGTMQMLGGRQG---    117
                 *********************************************************

EcoSSB-WT        PAGGNIGGGQPQGGWGQPQQPQGGNQFSGGAQSRPQQSAPAAPSNEPPMDFDDDIFF       177
EcoSSB-CterAla   PAGGNIGGGQPQGGWGQPQQPQGGNQFSGGAQSRPQQSAPAAPSNEPPMAFAAAIFF       177
EcoSSB-CterNGGN  PAGGNIGGGQPQGGWGQPQQPQGGNQFSGGAQSRPQQSAPAAPSNEPPMNFGGNIFF       177
EcoSSB-Q152del   PAGGNIGGGQPQGGWGQPQQPQGGNQFSGGAQ-------------------------       152
EcoSSB-G117del   ---------------------------------------------------------
```

To determine the improvement or otherwise of the SSB mutants on nanopore blocking, experiments were carried out to assess the blocking occurrences in the presence of ssDNA only (Table 8) and then subsequently in the presence of ssDNA+SSB (Table 9).

Electrical measurements were acquired using 128 well silicon chips (format 75 μm diameter, 20 μm depth and 250 μm pitch) which were silver plated (WO 2009/077734). Chips were initially washed with 20 mL ethanol, then 20 mL $dH_2O$, then 20 mL ethanol prior to CF4 plasma treatment. The chips used were then pre-treated by dip-coating, vacuum-sealed and stored at 4° C. Prior to use, the chips were allowed to warm to room temperature for at least 20 minutes.

Bilayers were formed by passing a series of slugs of 3.6 mg/mL 1,2-diphytanoyl-glycero-3-phosphocholine lipid (DPhPC, Avanti Polar Lipids, AL, USA) dissolved in 400 mM KCl, 25 mM Tris, pH 7.5, at 0.45 μL/s across the chip. Initially a lipid slug (250 μL) was flowed across the chip, followed by a 100 μL slug of air Two further slugs of 155 μL and 150 μL of lipid solution, each separated by a 100 μL slug of air were then passed over the chip. After bilayer formation the chamber was flushed with 3 mL of buffer at a flow rate of 3 μl/s Electrical recording of the bilayer formation was carried out at 10 kHz with an integration capacitance of 1.0 pF.

A solution of the biological nanopore was prepared using αHL-(E111N/K147N)$_7$ (NN) (Stoddart, D. S. et al., (2009), *Proceeding of the National Academy of Science of the Untied States of America* 106, p7702-7707) (1 μM diluted 1/1000) in 400 mM KCl, 25 mM Tris pH 7.5. A holding potential of +160 mV was applied and the solution flowed over the chip. Pores were allowed to enter bilayers until 10% occupancy (12 single pores) was achieved. The sampling rate and integration capacitance were maintained at 10 kHz and 1.0 pF respectively and the potential reduced to zero.

A programme was set which cycled through periods of positive holding potential +160 mV for 10 seconds followed by a negative holding potential of □160 mV for 50 seconds and finally a rest period where no potential was applied for 15 seconds. 70mer polyT (100 nM, SEQ 1D NO. 83) and a control experiment was run for 15 minutes. The solution on the chip was then replaced with 100 nM polyT (SEQ ID NO: 83) which had been pre-incubated with 100 nM of each SSB. Blocking was then quantified by assigning the data into bins according to the proportion of time the pore is open for within the period of positive potential before blocking. It can be seen that on addition of EcoSSB-WT (SEQ ID NO: 65) the pore rapidly blocks on positive potential and remains so until the potential is reversed. In contrast to this however, somewhat surprisingly both of the C-terminal mutant proteins do not show the blocking behaviour of the wild-type enzyme. This suggests that the negative charge of the C-terminus is bringing about an interaction between the flexible C-terminal part of the SSB protein and the nanopore and so giving the permanent blockades observed.

TABLE 8

| ssDNA only | | | | | | | | |
|---|---|---|---|---|---|---|---|---|
| | Proportion of time when the open pore is not blocked by DNA | % | | Proportion of time when the open pore is not blocked by DNA | % | | Proportion of time when the open pore is not blocked by DNA | % |
| EcoSSB-WT | x ≤ 0.25 | 18.60% | EcoSSB-CterAla | x ≤ 0.25 | 10.40% | EcoSSB-Q152del | x ≤ 0.25 | 19.60% |
| | ≤0.25 x ≤0.50 | 9.30% | | ≤0.25 x ≤0.50 | 8.30% | | ≤0.25 x ≤0.50 | 5.90% |
| | ≤0.50 x ≤0.75 | 20.90% | | ≤0.50 x ≤0.75 | 10.40% | | ≤0.50 x ≤0.75 | 9.80% |
| | x ≥ 0.75 | 51.20% | | x ≥ 0.75 | 70.80% | | x ≥ 0.75 | 64.70% |

TABLE 9

| SSB:ssDNA | | | | | | | | |
|---|---|---|---|---|---|---|---|---|
| | Proportion of time when the open pore is not blocked by DNA | % | | Proportion of time when the open pore is not blocked by DNA | % | | Proportion of time when the open pore is not blocked by DNA | % |
| EcoSSB-WT | x ≤ 0.25 | 93.00% | EcoSSB-CterAla | x ≤ 0.25 | 12.50% | EcoSSB-Q152del | x ≤ 0.25 | 1.90% |
| | ≤0.25 x ≤0.50 | 7.00% | | ≤0.25 x ≤0.50 | 10.40% | | ≤0.25 x ≤0.50 | 11.80% |
| | ≤0.50 x ≤0.75 | 0% | | ≤0.50 x ≤0.75 | 25.00% | | ≤0.50 x ≤0.75 | 27.50% |
| | x ≥ 0.75 | 0% | | x ≥ 0.75 | 52.10% | | x ≥ 0.75 | 58.80% |

To confirm that the mutant SSB proteins are still able to interact with and bind to the DNA a small sample of EcoSSB-WT (SEQ ID NO: 65) and mutant SSB complexes (EcoSSB-Q52del, SEQ ID NO: 68) with 70mer polyT (SEQ ID NO: 83) were analysed on a 5% TBE gel, to determine presence of the bandshift typical for a protein DNA interactions (FIG. 1) It can be seen that the EcoSSB-Q152del mutant (SEQ ID NO: 68) is not impaired in its ability to form a complex with the 70mer polyT (SEQ ID NO: 83), when compared to the EcoSSB-WT (SEQ ID NO: 65). The slight shift in position of the protein DNA complex is likely due to the deletion of the C-terminus and also the charge removal.

Figure 2:
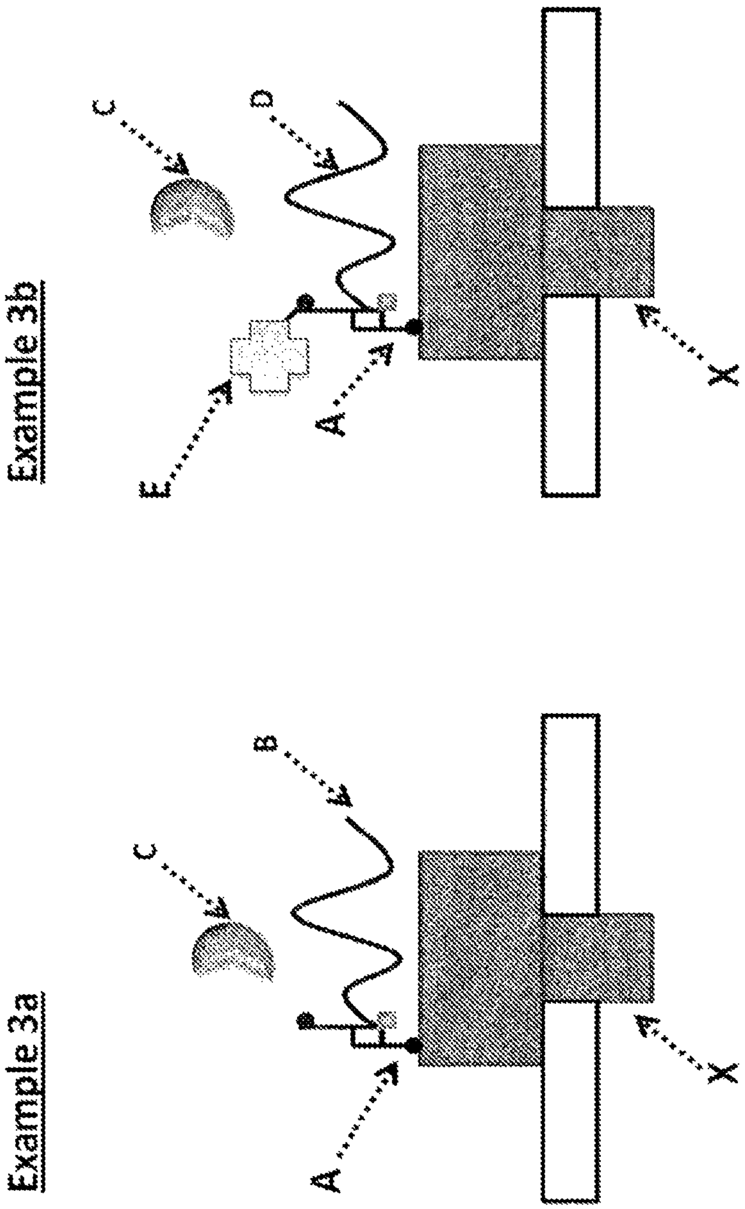
FIG. 2 shows diagrams of the systems used in Example 3a and 3b to investigate pore blocking by a strand of DNA covalently attached to the nanopore. In Example 3a (left-hand side) a nanopore (labelled X) is covalently attached to a short strand of DNA (labelled A) which contains two uracil's labelled with azidohexanoic acid and which has a thiol group at the 5' end of the strand. A can be covalently attached to a sequence (labelled B), which contains alkyne residues, has a thiol at the 5' end and has a Cy3 fluorescent tag at the 3' end. This covalent attachment occurs by click chemisty by reaction of the alkyne residues in B with the azidohexanoic acid labelled uracil residues in A. The Cy3 fluorescent tag at the 3' end of B is indicated by a grey square. An exonuclease I mutant enzyme is added in free solution (labelled C). In Example 3b (right-hand side) a nanopore (labelled X) is covalently attached to a short strand of DNA (labelled A) which also contains two U's labelled with azidohexanoic acid. A can be covalently attached to a sequence (labelled D), which contains alkyne residues, has a thiol at the 5' end and has a Cy3 fluorescent tag at the 3' end of the strand This covalent attachment occurs by click chemisty by reaction of the alkyne residues in D with the azidohexanoic acid labelled uracil residues in A. A PhiE polymerase mutant enzyme (labelled E) is also is covalently attached by reaction with the group at the 5' end of D. The Cy3 fluorescent group at the 3' end of D is indicated by a grey square. The exonuclease T mutant enzyme is added in free solution (labelled C, SEQ ID NO: 80).
Figure 3:
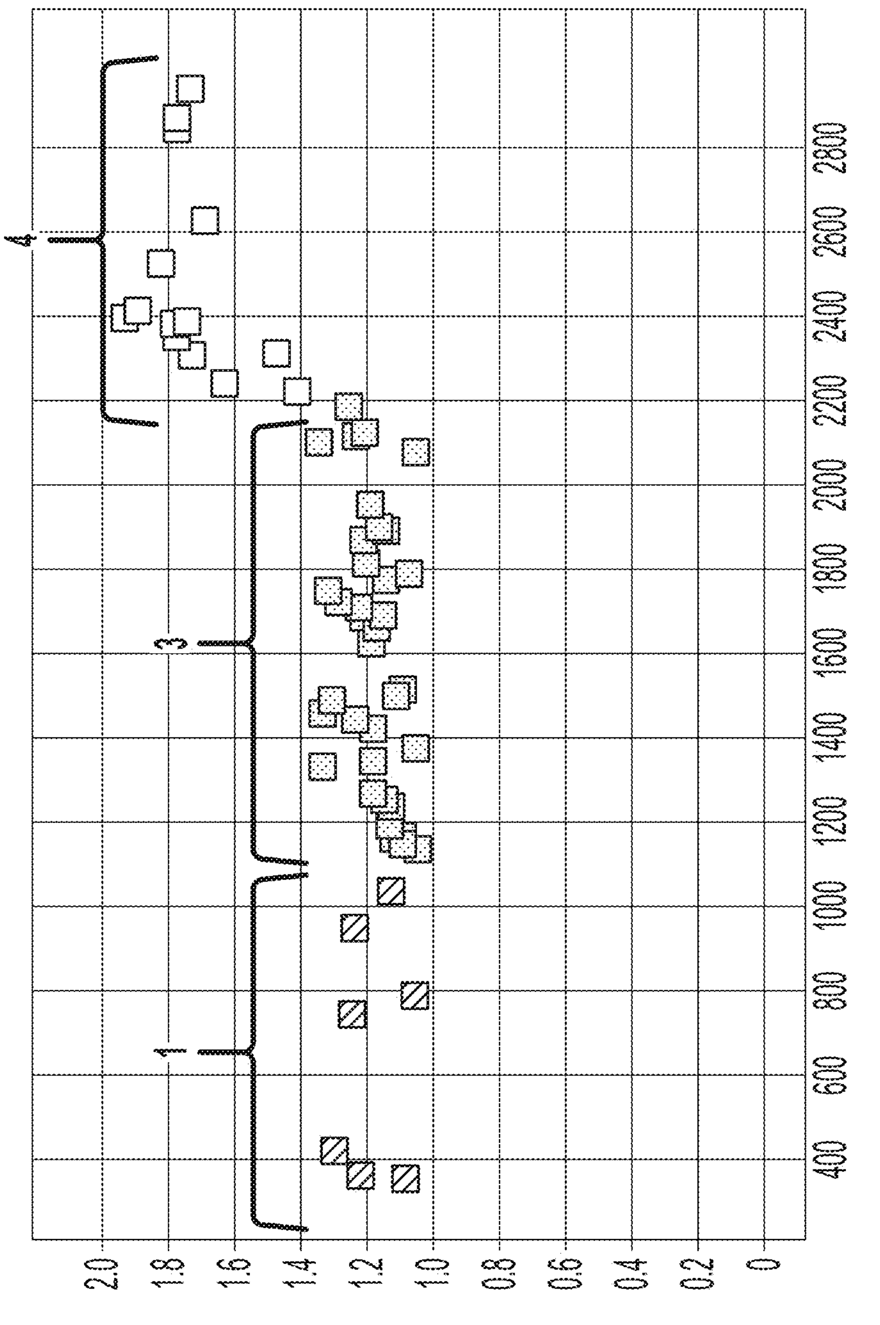
FIG. 3 shows intramolecular blocking of an alpha-hemolysin mutant nanopore (6 subunits of SEQ TD NO. 77 with the mutation N139Q and one subunit of SEQ TD NO: 77 with the mutations N139Q/L135C/E287C, with 5 aspartates, a Flag-tag and H6 tag to aid purification and a DNA strand (SEQ ID NO: 78) reacted by its 5' end thiol group to position 287 of this subunit) by a DNA strand ((comprising SEQ ID NO: 79, which has a thiol at the 5' end and a Cy3 fluorescent tag at the 3' end of the strand) which is covalently attached, via click chemistry, to the DNA (SEQ ID NO: 78 (which has a thiol group at the 5' end of the strand) which is attached to the mutant nanopore) in the absence of SSB (see FIG. 2, Example 3a for diagram). Multiple pores were allowed to insert into multiple bilayers on a chip system until at least 10% occupancy was achieved. The potential was then cycled accordingly; 5 seconds+150 mV, 1 second −150 mV and 4 seconds 0 mV. The axis lables for the plot shown in this figure are y-axis=relative DNA block current level and x-axis time (s). Time periods of 10 mins were recorded for each section, section I is the control period (400 mM KCl, 25 mM Tris, 10 uM EDTA, pH 7.5), section 3 is the period after $Mg^{2+}$ buffer flush (400 mM KCl, 25 mM Tris, 10 mM $MgCl_2$, pH7.5) and section 4 is addition of free exonuclease I mutant enzyme (100 nM, SEQ ID NO. 80) to clear the pore by digestion of the analyte DNA (SEQ ID NO: 79, which has a thiol at the 5' end and a Cy3 fluorescent tag at the 3' end of the strand). It can be seen that during the control period the DNA (comprising SEQ ID NO: 79, which has a thiol at the 5' end and a Cy3 fluorescent tag at the 3' end of the strand) attached to the pore rapidly brings about a DNA block level. No SSB was added in this experiment and flushing of the system with Mg2+ buffer flush continued to show the DNA rapidly blocking the pore. On addition of the free exonuclease 1 mutant enzyme (SEQ ID NO: 80) the DNA strand (comprising SEQ TD NO. 79, which has a thiol at the 5' end and a Cy3 fluorescent tag at the 3' end of the strand) is digested and so the relative block level is increased, as the open pore level is now observed instead of the DNA blocking level.
Figure 4:
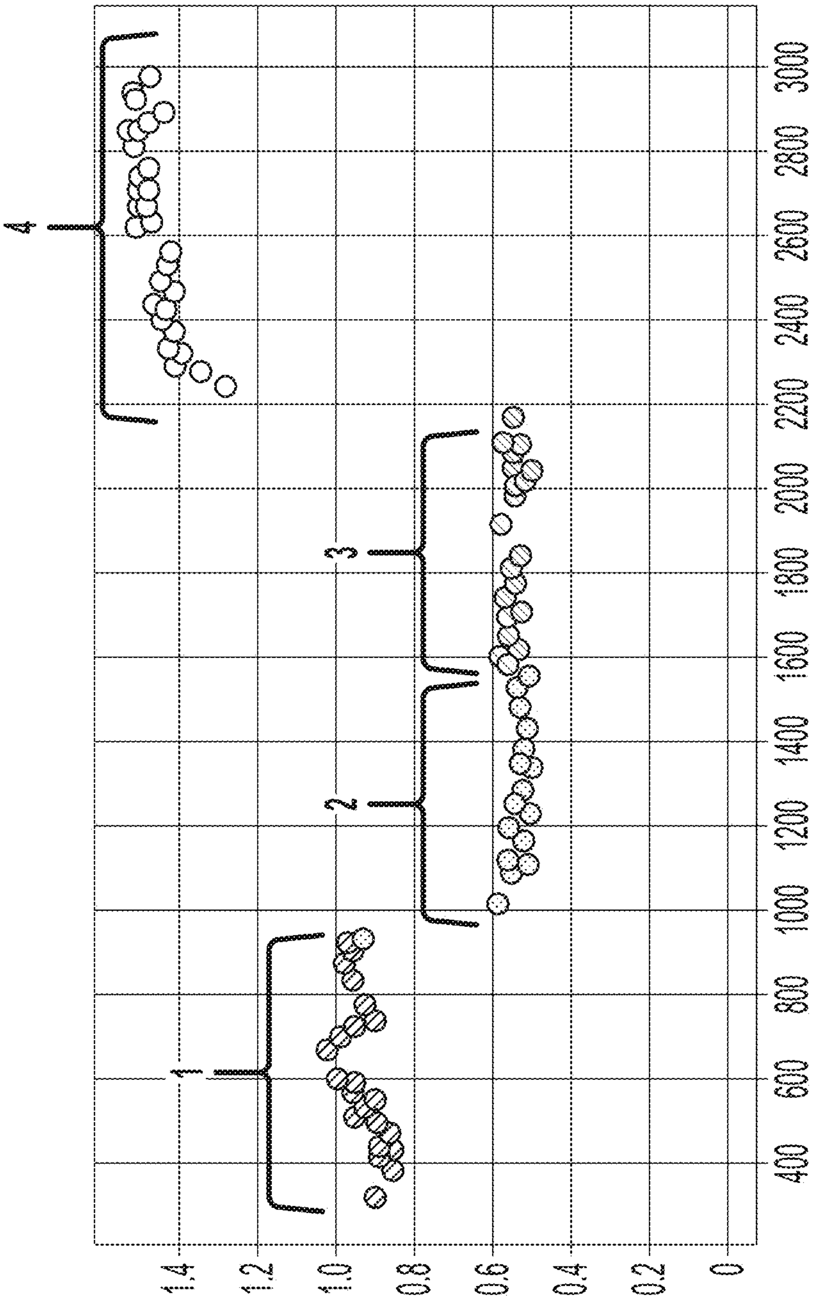
FIG. 4 shows the effect on intramolecular blocking of an alpha-hemolysin mutant nanopore (6 subunits of SEQ ID NO: 77 with the mutation N139Q and one subunit of SEQ ID NO: 77 with the mutations N I39Q/L135C/E287C, with 5 aspartates, a Flag-tag and H6 tag to aid purification and a DNA strand (SEQ ID NO: 78) reacted by its 5' end thiol to position 287 of this subunit) by a DNA strand ((comprising SEQ ID NO: 7), which has a thiol at the 5' end and a Cy3 fluorescent tag at the 3' end of the strand) which is covalently attached, via click chemistry, to the DNA (SEQ ID NO: 78, which also has a thiol group at the 5' end of the strand) which is attached to the mutant nanopore) upon the addition of EcoSSB-WT (SEQ UD NO-65) (see FIG. 2, Example 3a for diagram). Multiple pores were allowed to insert into multiple bilayers on a chip system until at least 10% occupancy was achieved. The potential was then cycled accordingly; 5 seconds+150 mV, 1 second −150 mV and 4 seconds 0 mV. The axis lables for the plot shown in this figure are y-axis=relative DNA block current level and x-axis=time (s). Time periods of 10 mins were recorded for each section; section 1 is the control period (400 mM KCl, 25 mM Tris, 10 uM EDTA, pH 7.5), section 2 is the SSB period (10 nM, SEQ ID NO. 65), section 3 is the period after $Mg^{2+}$ buffer flush (400 mM KCL, 25 mM Tris, 10 mM $MgCl_2$, pH 7.5) and section 4 is addition of free exonuclease I mutant enzyme (100 nM, SEQ ID NO: 80) to clear the pore by digestion of the analyte DNA (comprising SEQ ID NO: 79, which has a thiol at the 5' end and a Cy3 fluorescent tag at the 3' end of the strand). It can be seen that during the control period the DNA (comprising SEQ ID NO: 79, which has a thiol at the 5' end and a Cy3 fluorescent tag at the 3' end of the strand) attached to the pore rapidly brings about a DNA block level. On addition of EcoSSB-WT (SEQ ID NO. 65) the nanopore blocks to a greater current deflection to that observed for the DNA blocking level. This is due to the interaction of the negatively charged C-terminus of the EcoSSB-WT (SEQ ID NO: 65) with the nanopore instead of the DNA. The interaction between EcoSSB-WT (SEQ ID NO: 65) is quite stable as the buffer flush (section 3) does not remove the bound protein. On addition of the free exonuclease T mutant enzyme (SEQ ID NO: 80) the DNA strand (comprising SEQ ID NO: 79, which has a thiol at the 5' end and a Cy3 fluorescent tag at the 3' end of the strand) is digested and so the relative block level is increased, as the open pore level is now observed as the DNA has been removed and the SSB is no longer in close association with the nanopore.
Figure 5:
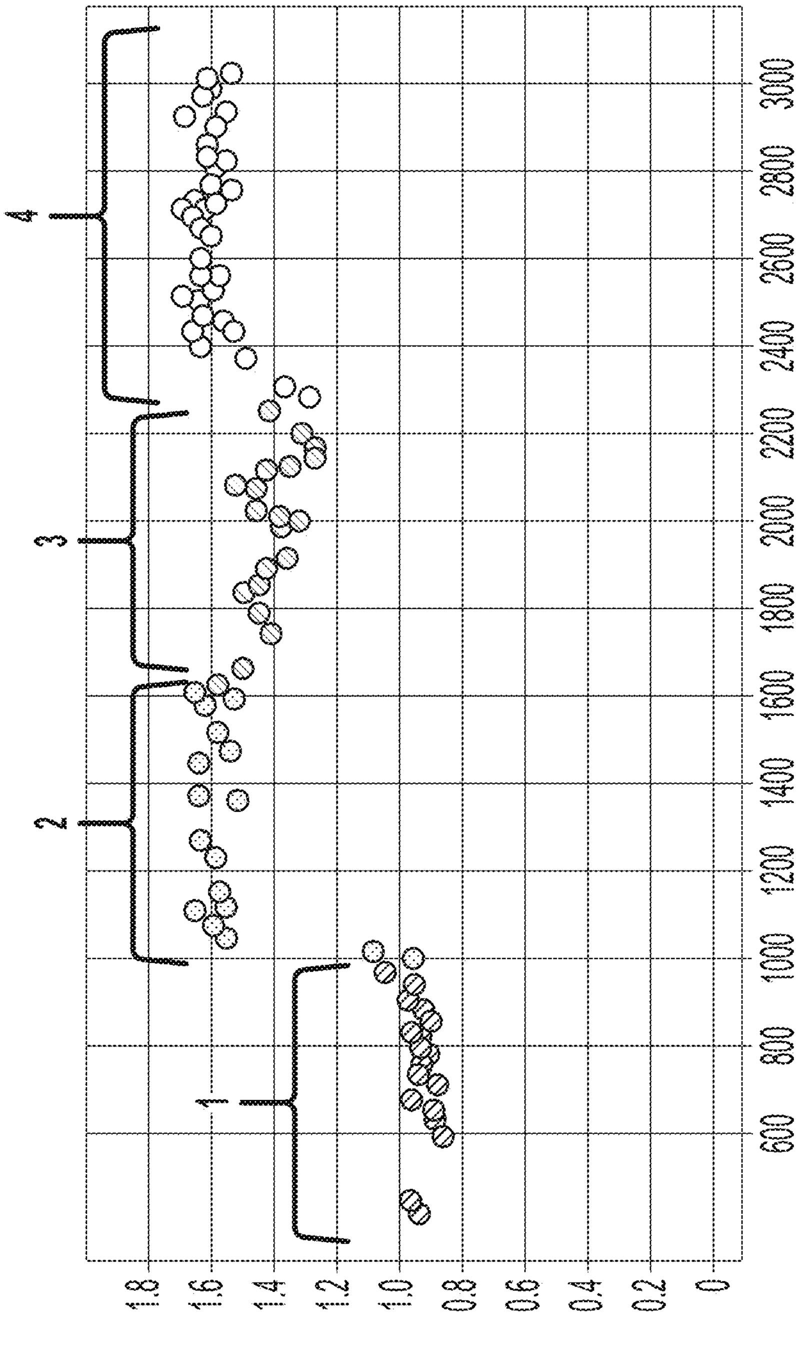
FIG. 5 shows the effect on intramolecular blocking of an alpha-hemolysin mutant nanopore (6 subunits of SEQ ID NO: 77 with the mutation N139Q and one subunit of SEQ ID NO: 77 with the mutations N139Q/L135C/E287C. with 5 aspartates, a Flag-tag and H6 tag to aid purification and a DNA strand (SEQ ID NO. 78) reacted by its 5' end thiol to position 287 of this subunit) by a DNA strand ((comprising SEQ ID NO: 79, which has a thiol at the 5' end and a Cy3 fluorescent tag at the 3' end of the strand) which is covalently attached, via click chemistry, to the DNA (SEQ ID NO: 78, which also has a thiol group at the 5' end of the strand) which is attached to the mutant nanopore) upon the addition of EcoSSB-Q152del (SEQ ID NO. 68)(see FIG. 2, Example 3a for diagram). Multiple pores were allowed to insert into multiple bilayers on a chip system until at least 10% occupancy was achieved. The potential was then cycled accordingly; 5 seconds +150 mV, 1 second −150 mV and 4 seconds 0 mV. The axis lables for the plot shown in this figure are y-axis=relative DNA block current level and x-axis=time (s). Time periods of 10 mins were recorded for each section: section 1 is the control period (400 mM KCl, 25 mM Tris, 10 uM EDTA. pH 7.5), section 2 is the SSB period (10 nM, SEQ ID NO: 68), section 3 is the period after $Mg^{2+}$ buffer flush (400 mM KCl, 25 mM Tris, 10 mM $MgCl_2$, pH 7.5) and section 4 is addition of free exonuclease 1 mutant enzyme (100 nM, SEQ ID NO: 80) to clear the pore by digestion of the analyte DNA (comprising SEQ ID NO: 79, which has a thiol at the 5' end and a Cy3 fluorescent tag at the 3' end of the strand). It can be seen that during the control period the DNA attached to the pore (comprising SEQ ID NO: 79, which has a thiol at the 5' end and a Cy3 fluorescent tag at the 3' end of the strand) rapidly brings about a DNA block level. On addition of EcoSSB-Q152del (SEQ ID NO: 68) the DNA block level is abolished similar to that observed for addition of free exonuclease 1 mutant enzyme (SEQ ID NO. 80). This is because the protein sequesters the DNA (comprising SEQ ID NO: 79, which has a thiol group at the 5' end and a Cy3 fluorescent tag at the 3' end of the strand) such that it cannot interact with the pore and block it. The EcoSSB-Q152del (SEQ ID NO: 68) was not observed to block the pore as the WT-EcosSSB (SEQ ID NO: 65) did. The interaction between EcoSSB-Q152del (SEQ ID NO. 68) is quite stable as the buffer flush (section 3) does not remove the bound protein. On addition of the free exonuclease I mutant enzyme (SEQ ID NO: 80) the DNA strand (comprising SEQ ID NO: 79, which has a thiol at the 5' end and a Cy3 fluorescent tag at the 3' end of the strand) is digested, the open pore level is observed as the DNA has been removed.

Example 3—Abolition of ssDNA Blocking by a Pore:DNA Complex Using SSBs that Lack a Negatively Charged C-Terminus When using a nanopore as a possible sequencing platform. having control over the DNA can often be an important consideration. An example, of this can be seen in exopore sequencing where not only can the cleaved bases interact with the nanopore, as desired, but also the DNA strand itself. Interaction of the strand itself may abolish the sequencing read either through disruption of the flow of bases to the detector or by stripping the DNA analyte from the enzyme. To assay for the ability of SSB to abolish DNA nanopore interactions, an extreme case scenario was used. A DNA strand (SEQ ID NO: 78, which has a thiol group at the 5' end of the strand) was covalently attached to a single subunit of haemolysin (SEQ ID NO: 77 with the mutations N139Q/L135C/E287C and with 5 aspartates, a Flag-tag and H6 tag to aid purification) and another strand of DNA ((comprising SEQ ID NO: 79 for Example 3a or comprising SEQ ID NO: 81 for Example 3b, both of which contain a thiol at the 5' end and a Cy3 fluorescent tag at the 3' end of the strand), which contains in its sequence alkyne residues (shown as n in SEQ ID NO's: 79 and 81. both of which contain a thiol at the 5' end and a Cy3 fluorescent tag at the 3' end of the strand) which can react with the azidohexanoic acid residues in SEQ ID NO. 78 (which also has a thiol group at the 5' end of the strand) via click chemistry, so as to give rapid pore blocking by the DNA strand (comprising SEQ ID NO: 79 or 81 both of which contain a thiol at the 5' end and a Cy3 fluorescent tag at the 3' end of the strand) on applied positive potential (see FIG. 2 for the system investigate for Examples 3a and 3b). Blocking is extremely rapid due to the intramolecular concentration given by cross reacting the analyte to the protein (FIGS. 3-5).

Sequences Used:

```
                                        SEQ ID NO: 79
Thiol-GCnACGGAGACn--Cy3(where n is an alkyne)

                                        SEQ ID NO: 81
Thiol-GCnACGGAGACn--Cy3(where n is an alkyne)
```

Example 3a

Chip experiments were set-up as described in Example 2. A solution of the mutant α-haemolysin nanopore (6 subunits of SEQ ID NO: 77 with the mutation N139Q and one subunit of SEQ ID NO: 77 with the mutations N139Q/L35C/E287C, with 5 aspartates, a Flag-tag and H6 tag to aid purification and a DNA strand (SEQ ID NO: 78) reacted by its 5' end thiol to position 287 of this subunit, which is also attached to a second piece of DNA (comprising SEQ ID NO: 79 (which has a thiol at the 5' end and a Cy3 fluorescent tag at the 3' end of the strand)) via click chemistry) was flowed over the chip. Multiple pores were allowed to insert into multiple bilayers until at least 10% occupancy was achieved. The sampling rate was changed to 1 kHz and the potential was cycled accordingly; 5 secs+150 mV. 1 secs □150 mV, and 4 secs 0 mV. Time periods of 10 mins were recorded for each section; Section I is the control period (400 mM KCl, 25 mM Tris, 10 μM EDTA, pH 7.5), section 2 is the SSB period (10 nM, if appropriate), section 3 is the period after $Mg^{2+}$ buffer flush (400 mM KCl, 25 mM Tris, 10 mM MgC2, pH 7.5) and section 4 is the addition of free exonuclease 1 mutant enzyme (100 nM, SEQ ID NO: 80) to clear the pore by digestion of the analyte DNA (comprising SEQ ID NO: 79, which has a thiol at the S' end and a Cy3 fluorescent tag at the 3' end of the strand) Data from multiple pores was collated and plotted according to block level observed. In all cases, time is given along the X-axis and the relative DNA block current level is given along the Y-axis (so I is current level observed when DNA is blocking the nanopore).

It can be seen in FIG. 3 that during the control period (section 1) the DNA (comprising SEQ ID NO. 79. which has a thiol at the 5' end and a Cy3 fluorescent tag at the 3' end of the strand) attached to the pore rapidly brings about a DNA block level. On addition of the free exonuclease 1 mutant enzyme (SEQ ID NO: 80, FIG. 3, section 4) the DNA strand (comprising SEQ ID NO 79, which has a thiol at the 5' end and a Cy3 fluorescent tag at the 3' end of the strand) is digested and so the relative block level is increased, as the open pore level is now observed instead of the DNA blocking level. On addition of EcoSSB-WT (SEQ ID NO: 65, FIG. 4, section 2) the nanopore blocks to a greater current deflection to that observed for just the DNA block level (SEQ ID NO: 79 which has a thiol at the 5' end and a Cy3 fluorescent tag at the 3' end of the strand). so is less than 1. This is due to the interaction of the negatively charged C-terminus of the EcoSSB-WT (SEQ ID NO: 65) with the nanopore instead of the DNA (SEQ ID NO: 79 which has a thiol at the 5' end and a Cy3 fluorescent tag at the 3' end of the strand) Again the pore clears on digestion of the DNA strand by exonuclease I mutant enzyme (SEQ ID NO: 80, FIG. 4, section 4), as not only is the strand removed but also the EcoSSB-WT protein is no longer in close association with the nanopore, therefore, the C-terminus of EcoSSB-WT is not observed to block the pore. On addition of the Eco-SSB-Q 152del (SEQ ID NO: 68, FIG. 5, section 2), however, the DNA block level is abolished, similar to that observed for addition of free exonuclease I mutant enzyme (SEQ ID NO: 80). This is because EcoSSB-Q152del (SEQ ID NO: 68) sequesters the DNA such that it cannot interact with the pore and block it, and also the protein itself does no block the pore as was observed for EcoSSB-WT (SEQ ID NO: 65).

In all cases, as the EcoSSB interaction with ssDNA is quite a stable interaction, the buffer flush does not remove the bound protein (for either EcoSSB-WT or EcoSSB-Q152del). The protein can be removed by flush with $Mg^{2+}$ and 100 nM PolyT70mer in solution to out-compete the SSB for the DNA strand on the pore and so re-observe the DNA block levels.

Example 3b

Figure 6:
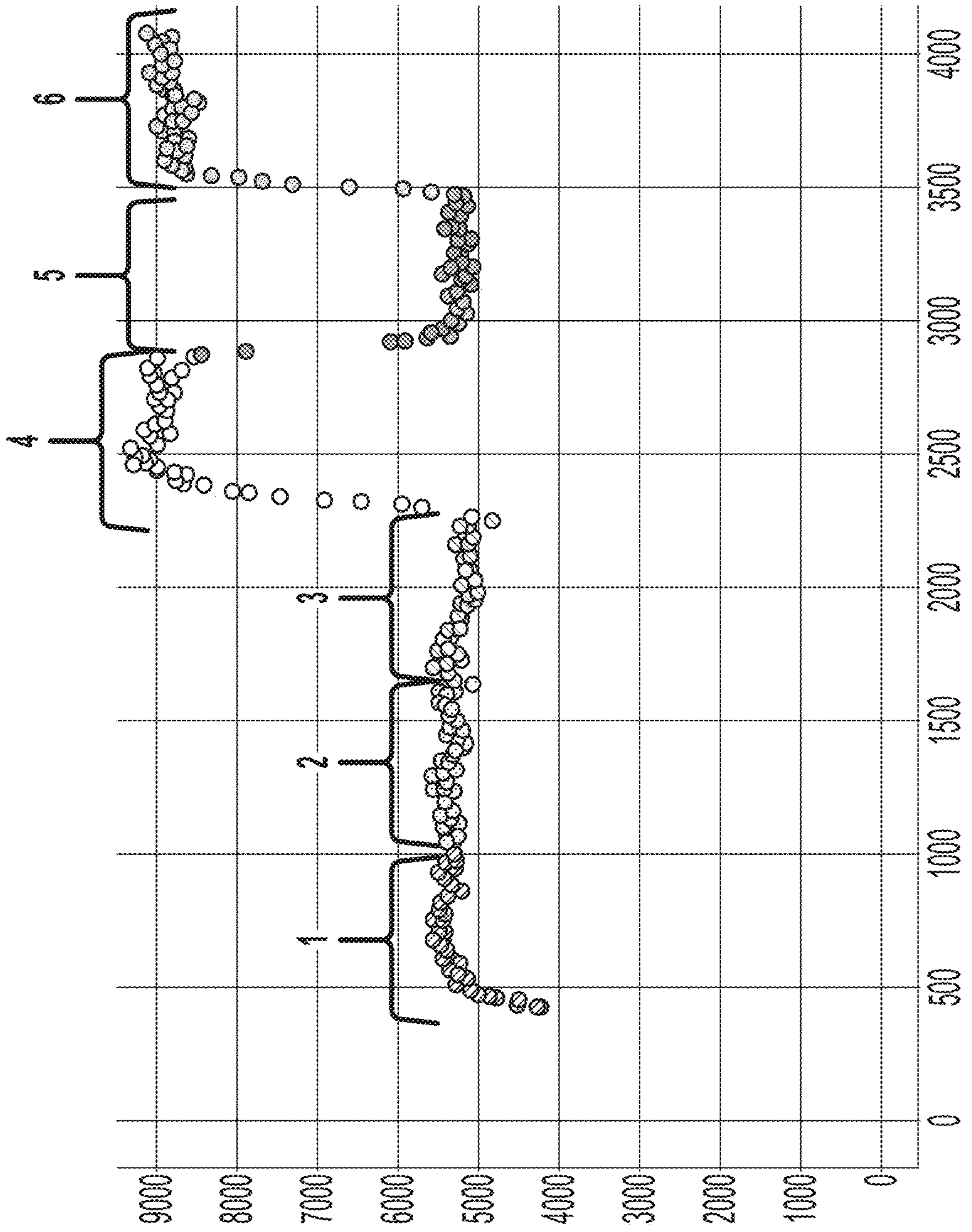
FIG. 6 shows the effect on intramolecular blocking of an alpha-hemolysin mutant nanopore (6 subunits of SEQ ID NO. 77 with the mutation N1390 and one subunit of SEQ ID NO. 77 with the mutations N139Q/L135C/E287C and with 5 aspartates, a Flag-tag and H6 tag to aid purification and a DNA stand (SEQ ID NO: 78) reacted by its 5' end thiol to position 287 of this subunit), by a DNA strand ((comprising SEQ ID NO: 81 which has a thiol at the 5' end and a Cy3 fluorescent tag at the 3' end of the strand) which is covalently attached, via click chemistry, to the DNA (SEQ ID NO. 78, which also has a thiol group at the 5' end of the strand) which is attached to the mutant nanopore) and SEQ ID NO. 81 (which has a thiol at the 5' end and a Cy3 fluorescent tag at the 3' end of the strand) is also covalently attached by a thiol group at its 5' end (SEQ ID NO. 81) to the mutant PhiE polymerase enzyme (SEQ ID NO: 82) at position 373), upon the addition of a WT-SSB that naturally lacks an acidic C-terminus (p5 protein from Phi29 virus, SEQ ID NO: 64) (see FIG. 2 Example 3b for diagram). Multiple nanopores were allowed to insert into multiple bilayers on a chip system until at least 10% occupancy was achieved. The potential was then cycled accordingly; 5 seconds+150 mV, 1 second −150 mV and 4 seconds 0 mV. The axis lables for the plot shown in this figure are y-axis =relative DNA block current level and x-axis=time (s). Time periods of 10 mins were recorded for each section; section I is the control period (400 mM KCl, 25 mM Tris, 10 uM EDTA. pH 7.5), section 2 is the 100 nM Phi29 p5 SSB (SEQ ID NO: 64) period, section 3 is the 1 μM Phi29 p5 SSB (SEQ ID NO: 64) period, section 4 is the 10 μM phi29 p5 SSB (SEQ ID NO: 64) period, section 5 is the period after EDTA buffer flush (400 mM KCl, 25 mM Tris, 10 uM EDTA, pH 7.5) and section 6 is addition of the free exonuclease I mutant enzyme ((100 nM, SEQ ID NO: 80) in 400 mM KCl, 25 mM Tris, 10 mM $MgCl_2$, pH7.5) to clear the pore by digestion of the analyte DNA (comprising SEQ ID NO: 81, which has a thiol at the 5' end and a Cy3 fluorescent tag at the 3' end of the strand). It can be seen that during the control period the DNA attached to the pore (comprising SEQ ID NO: 81, which has a thiol at the 5' end and a Cy3 fluorescent tag at the 3' end of the strand) rapidly brings about a DNA block level. This blocking continues until addition of Phi29 p5 SSB (SEQ ID NO: 64) reaches 10 μM (section 4), three orders of magnitude more than was required for the EcoSSB-Q152del (SEQ ID NO: 68, FIG. 5). Phi29 p5 SSB (SEQ ID NO: 64) has very dynamic binding to the DNA (comprising SEQ ID NO: 81, which has a thiol at the 5' end and a Cy3 fluorescent tag at the end of the strand) as a buffer flush (section 5) removed the bound protein On addition of the free exonuclease I mutant enzyme (SEQ ID NO: 80) the DNA strand is digested and so the relative block level is increased, as the open pore level is now observed as the DNA has been removed. This level is similar to that seen when the SSB bound the DNA strand, except that with the SSB the strand is merely physically constrained from entering the pore and not digested.
Figure 7:
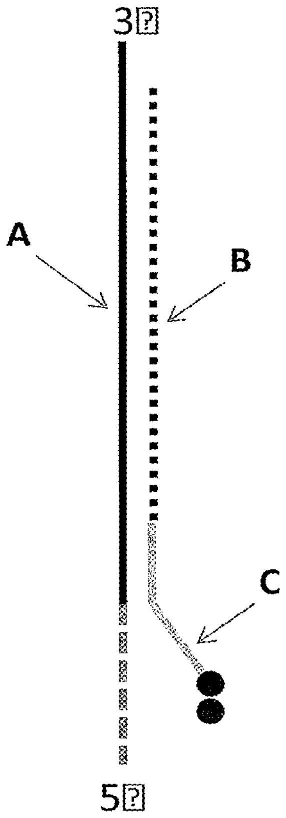
FIG. 7 shows the DNA substrate design used in Example 4. The DNA substrate is made up of SEQ ID NO: 70 (labelled A) which is the PhiX 5 kB sense strand which has a 50 spacer unit at the 5' end, SEQ ID NO. 71 (lablled B) which is the PhiX 5 kB anti-sense strand and SEQ ID NO: 72 (labelled C) which has at the 3' end of the sequence, six iSp18 spacers attached to two thymine residues and a Y cholesterol TEG (indicated by the two black circles).

Not all single strand DNA binding proteins have a negatively charged C-terminus. However, commercially available SSBs such as EcoSSB-WT (SEQ ID NO: 65) and T4 gp32 (SEQ ID NO. 55) all contain a negatively charged C-termini. We identified a suitable SSB from the Phi29 virus (p5) (SEQ ID NO: 64) that based on the primary structure appears to lack a C-terminal negatively charged tail, which is common to most bacterial SSBs (Gascon, Lazaro, er al. 2000). To assess the blocking of a nanopore by this protein, as well as its ability to shield this DNA from the nanopore, a similar experiment to Example 3a was carried out (FIG. 6).

Chip experiments were set-up as described in Example 2. A solution of the mutant a-haemolysin nanopore (6 subunits of SEQ ID NO: 77 with the mutation N139Q and one subunit of SEQ ID NO: 77 with the mutations N139Q/L135C/E287C and with 5 aspartates, a Flag-tag and H6 tag to aid purification and a DNA strand (SEQ ID NO: 78) reacted by its 5' end thiol to position 287 of this subunit. which is also attached to a second DNA strand (comprising SEQ ID NO: 81 (which has a thiol at the 5' end and a Cy3 fluorescent tag at the 3' end of the strand), which is itself covalently attached by a thiol group at its S' to the mutant PhiE polymerase enzyme (SEQ ID NO: 82) at position 373) via click chemistry) was flowed over the chip. Multiple pores were allowed to insert into multiple bilayers until at least 10% occupancy was achieved. The sampling rate was changed to 1 kHz and the potential was cycled accordingly; 5 sems +150 mV, 1 secs □150 mV, and 4 secs 0 mV. Time periods of 10 mins were recorded for each section before titration of Phi29 p5; section 1 is the control period (400 mM KCl, 25 mM Tris, 10 uM EDTA, pH 7.5). Section 2 is the 100 nM Phi29 p5 SSB (SEQ ID NO: 64) period, Section 3 is the 1 uM Phi29 p5 SSB (SEQ ID NO: 64) period. section 4 is 10 uM Phi29 p5 SSB (SEQ ID NO: 64) period, section 5 is the period after EDT A buffer flush (400 mM KCl, 25 mM Tris, 10 uM EDTA, pH 7.5) and section 6 is addition of the free exonuclease I mutant enzyme (000 nM, SEQ ID NO: 80) to clear the pore by digestion of the analyte (comprising SEQ ID NO: 81, which has a thiol at the 5' end and a Cy3 fluorescent tag at the 3' end of the strand).

It can be seen that during the control period (FIG. 6, section 1) the DNA attached (comprising SEQ ID NO: 81, which has a thiol at the 5' end and a Cy3 fluorescent tag at the 3' end of the strand) to the pore rapidly brings about a DNA block level. This blocking continues until addition of Phi29 p5 SSB (SEQ ID NO: 64) reaches 10 uM (FIG. 6, section 4), three orders of magnitude more than was required for the EcoSSB-Q152del (FIG. 5). At 10 uM concentration of Phi29 p5 SSB (SEQ ID NO. 64) the binding protein is shielding the DNA strand (comprising SEQ ID NO 81, which has a thiol at the 5' end and a Cy3 fluorescent tag at the 3' end of the strand) from the pore A flush of buffer is enough to remove the Phi29 p5 SSB (SEQ ID NO: 64. FIG. 6, section 5) as presumably this protein has very dynamic binding and so the protein is easily washed away. On addition of free exonuclease I mutant enzyme (SEQ ID NO: 80, FIG. 6, section 6) the DNA strand (comprising SEQ ID NO: 81, which has a thiol at the 5' end and a Cy3 fluorescent tag at the 3' end of the strand) is digested and so the relative block level is increased, as the open pore level is now observed instead of the DNA blocking level This is similar to that seen when the Phi29 p5 SSB (SEQ ID NO: 64) bound the DNA strand (comprising SEQ ID NO: 81, which has a thiol at the 5' end and a Cy3 fluorescent tag at the 3' end of die strand) except that with the Phi29 p5 SSB (SEQ ID NO: 64) the strand is merely physically constrained from entering the pore and not digested.

Example 4—Additive Effect of a Modified SSB for Strand Sequencing

Common failures of existing sequencing chemistries such as pyrosequencing can come from the fact that as templates become larger, then secondary structure within the DNA molecule affects enzyme performance. SSB's were, therefore, investigated to see if they could prevent the formation of secondary structure in strand sequencing experiments.

Electrical measurements were acquired from single MspA nanopores (ONT Ref-MspA(B2C), SEQ ID NO: 2 with mutations G75S/G77S/L88N/Q126R) inserted in 1,2-diphytanoyl-glycero-3-phosphocholine lipid (Avanti Polar Lipids) bilayers. Bilayers were formed across ~100 um diameter apertures in 20 um thick PTFE films (in custom Delrin chambers) via the Montal-Mueller technique, separating two 1 mL buffered solutions. All experiments were carried out in the stated buffered solution. Single-channel currents were measured on Axopatch 200B amplifiers (Molecular Devices) equipped with 1440A digitizers. Platinum electrodes are connected to the buffered solutions so that the cis compartment (to which both nanopore and enzyme/DNA are added) is connected to the ground of the Axopatch headstage, and the trans compartment is connected to the active electrode of the headstage.

After achieving a single pore in the bilayer (buffer solution=400 mM NaCl, 100 mM HEPES pH 8 0, 10 mM potassium ferrocyanide, 10 mM potassium ferricyanide, MspA nanopore-*E. coli* MS(B1-G75S-G77S-L88N-Q126R)8 MspA (SEQ ID NO: 2 with the mutations G75S/G77S/L88N/Q126R), ATP 41 mM) and $MgCl_2$ (1 mM) were added to the cis compartment of the electrophysiology chamber. A control experiment was run at +140 mV. The 5 kB phiX DNA (SEQ ID NO's: 70 (which has 50 spacer units at the 5' end of the sequence), 56 and 57 (which at the 3' end of the sequence has six iSp18 spacers attached to two thymine residues and a 3' cholesterol TEG), 0.5 nM) was then added to the cis compartment of the electrophysiology chamber and a further experiment run to check for DNA translocation events. The helicase Hel308Tga (SEQ ID NO: 16, 1 μM) was then added to the cis compartment and a further control experiment was run Finally, SSB (either EcoSSB-WT (SEQ ID NO: 65) or EcoSSB-Q152del (SEQ ID NO: 68) at 1 μM). Experiments were carried out at a constant potential of +140 mV.

Figure 8:
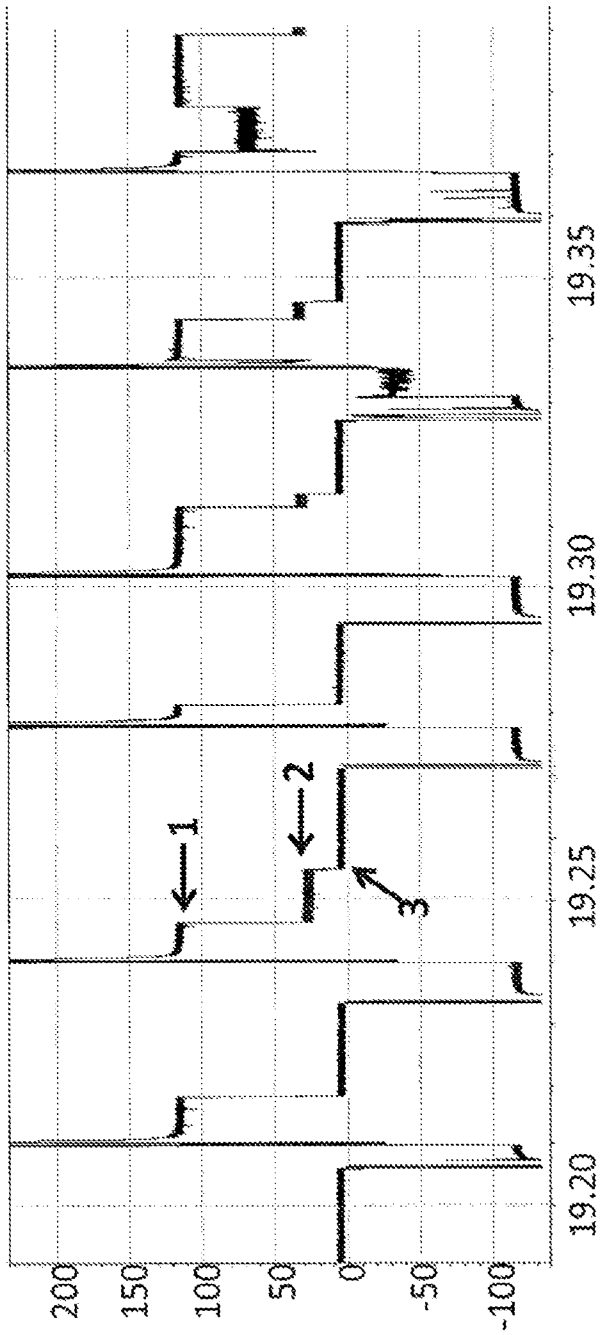
FIG. 8 shows a current trace (y-axis label=current (pA) and x-axis label=time (min)) observed when helicase-controlled 5 kB DNA (SEQ ID NOs 70 (has 50 spacer unit at the 5' end of the sequence), 71 and 72 (which at the 3' end of the sequence has six iSp18 spacers attached to two thymine residues and a 3' cholesterol TEG)) movement was investigated in the presence of EcoSSB-WT (SEQ ID NO: 65). Level 1 corresponds to the open pore level. Level 2 corresponds to the DNA block level. Level 3 corresponds to when EcoSSB-WT (SEQ ID NO: 65) has blocked the nanopore. Addition of EcoSSB-WT (SEQ ID NO: 65) caused the pore to block to a steady level preventing the observation of helicase controlled DNA movement.
Figure 9:
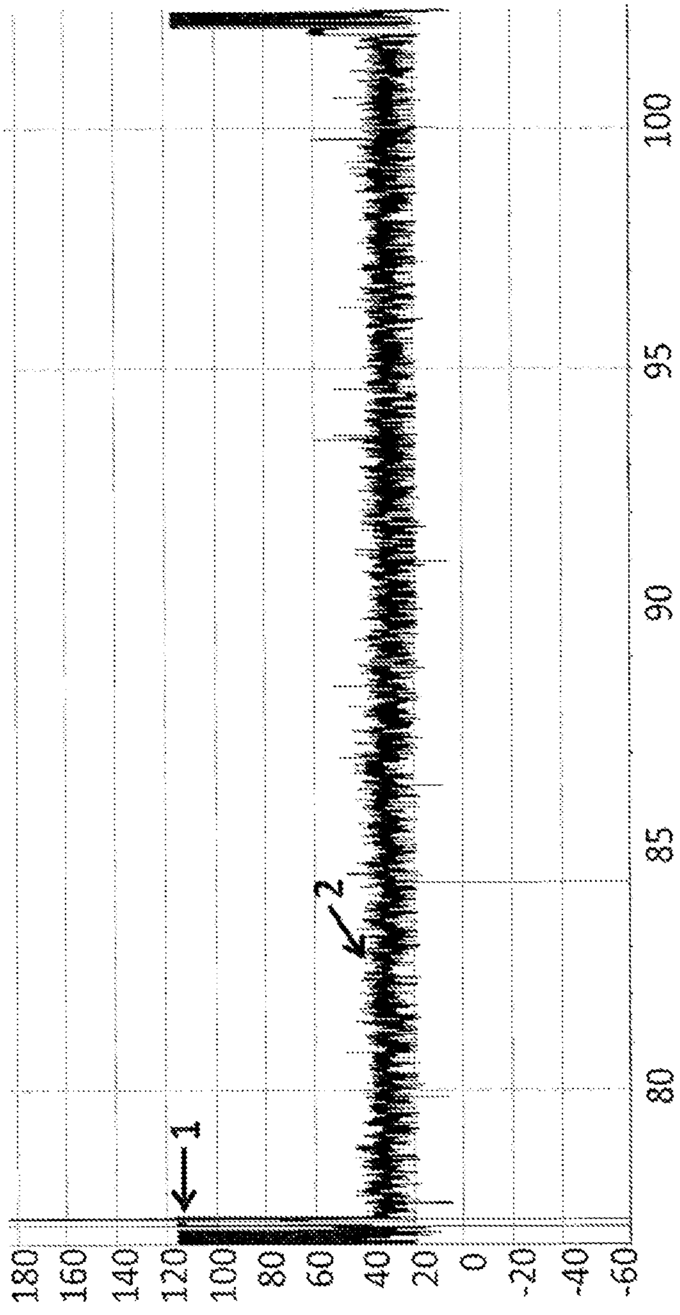
FIG. 9 shows a current trace (y-axis label:=current (pA) and x-axis label M time (min)) observed when helicase-controlled 5 kB DNA (SEQ ID NOs 70 (has a 50 spacer unit at the 5' end of the sequence), 71 and 72 (which at the 3' end of the sequence has six iSp18 spacers attached to two thymine residues and a 3' cholesterol TEG)) movement was investigated in the presence of EcoSSB-Q152del (SEQ ID NO: 68). Level 1 corresponds to the open pore level. Level 2 corresponds to the DNA block level Addition of EcoSSB-Q152del (SEQ ID NO. 68) facilitated the observation of helicase controlled DNA movement along the entire length of a 5 kB strand of DNA. This data indicates that EcoSSB-Q 152del (SEQ ID NO: 68) could be a suitable additive for nanopore DNA sequencing.

Previous attempts using a Hel308 enzyme homologue, from *T. gammatolerans*, to process a 5 kb dsDNA template (SEQ ID NO's 70 (which has 50 spacer units at the 5' end of the sequence), 56 and 57 (which at the 3' end of the sequence has six iSp18 spacers attached to two thymine residues and a 3' cholesterol TEG)), with an abasic leader for capture by the nanopore, proved difficult to obtain. Addition of EcoSSB-WT (SEQ ID NO: 65) again appeared to cause the pore to block to a steady level (See FIG. 8, level 3). However, on addition of EcoSS-Q152del (SEQ ID NO: 68) helicase controlled DNA movement was observed that seemed to process the strand all the way to the end (FIG. 9 shows one 5 kB DNA helicase controlled DNA movement).

The fact that the EcoSSB-Q 152del (SEQ ID NO: 68) seemingly allows the enzyme to process 5kb of continuous data again indicates that an SSB protein lacking a C-terminal negative charge could be a suitable additive for nanopore DNA sequencing.

Example 5

This Example compares the DNA binding ability of various transport control proteins, such as a helicase, a helicase dimer, a helicase attached to a nucleic acid binding domain or a helicase attached to an enzyme, and constructs, comprising a transport control protein attached to an SSB, using a fluorescence based assay.

Figure 10:
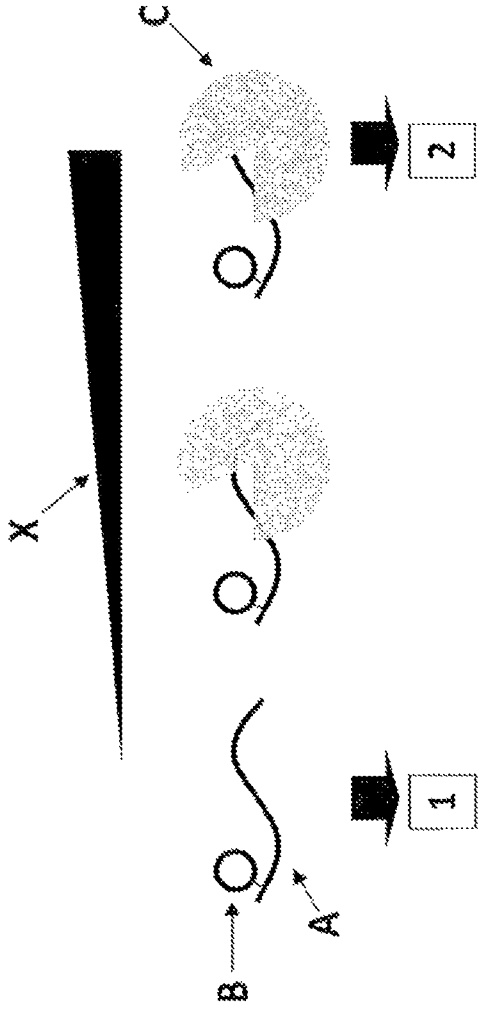
FIG. 10 shows a fluorescence assay for testing the DNA binding ability of various transport control proteins, such as a helicase or helicase dimer, and constructs, comprising a transport control protein attached to an SSB. A custom fluorescent substrate was used to assay the ability of various transport control proteins and constructs to bind to single-stranded DNA. The 88 nt single-stranded DNA substrate (1 nM final, SEQ ID NO: 73, labelled A) has a carboxyfluorescein (FAM) base at its 5' end (circle labelled B). As the transport control protein or construct (labelled C) binds to the oligonucleotide in buffered solution (400 mM NaCl, 10 mM Hepes, pH 8 0, 1 mM $MgCl_2$), the fluorescence anisotropy (a property relating to the rate of free rotation of the olignucleotide in solution) increases The lower the amount of transport control protein or construct needed to affect an increase in anisotropy, the tighter the binding affinity between the DNA and the transport control protein or construct. Situation I with no transport control protein or construct bound has a faster rotation and low anisotropy, whereas, situation 2 with the transport control protein or construct bound has slower rotation and high anisotropy. The black bar labelled X corresponds to increasing transport control protein or construct concentration (the thicker the bar the higher the transport control protein or construct concentration).

A custom fluorescent substrate was used to assay the ability of various transport control proteins and constructs to bind to single-stranded DNA. The 88 nt single-stranded DNA substrate (1 nM final, SEQ ID NO: 73) has a carboxyfluorescein (FAM) base at its 5' end As the transport control protein or construct binds to the oligonucleotide in a buffered solution (400 mM NaCl, 10 mM Hepes, pH8 0, 1 mM $MgCl_2$), the fluorescence anisotropy (a property relating to the rate of free rotation or the oligonucleotide in solution) increases The lower the amount of transport control protein or construct needed to affect an increase in anisotropy, the tighter the binding affinity between the DNA and transport control protein or construct (FIG. 10).

The transport control proteins that were tested include:

1) Hel308 Mbu monomer (SEQ ID NO: 10);
2) Hel308 Mbu A70AC 2 kDa dimer (where each monomer unit comprises SEQ 1D NO: 10 with the mutation A700C, with one monomer unit being linked to the other via position 700 of each monomer unit using a 2 kDa PEG linker).
3) Hel308 Mbu-GTGSGA-(HhH)2 (where a helicase monomer unit (SEQ ID NO: 10) is attached by the linker sequence GTGSGA to a (HhH)2 domain (SEQ ID NO: 74));
4) Hel308 Mbu-GTGSGA-(HhH)2-(HhH)2 (where a helicase monomer unit (SEQ ID NO: 10) is attached by the linker sequence GTGSGA to a (HhH)2-4HhH)2 domain (SEQ ID NO-1S 75)); and
5) Hel308 Mbu-GTGSGA-UL42HV1-I320Del (where a helicase monomer unit (SEQ ID NO: 10) is attached by the linker sequence GTGSGA to UL42HV1-I320Del (SEQ ID NO: 76))

The constructs that were tested in the assay include:

a) Hel308 Mbu-GTGSGA-gp32RB69CD (where a helicase monomer unit (SEQ ID NO: 10) is attached by the linker sequence GTGSGA to the SSB gp32RB69CD (SEQ ID NO: 59)).
b) Hel308 Mbu-GTGSGA-gp2.5T7-R211Del (where a helicase monomer unit (SEQ ID NO: 10) is attached by the linker sequence GTOSGA to the SSB gp2.5T7-R211 Del (SEQ ID NO: 60)); and
c) gp32-RB69CD-GTGSGT-Hel308 Mbu (where the SSB gp32-RB69CD (SEQ ID NO: 59) is attached by the linker sequence GTGSGT to the helicase monomer unit (SEQ ID NO-10)).

Figure 11:
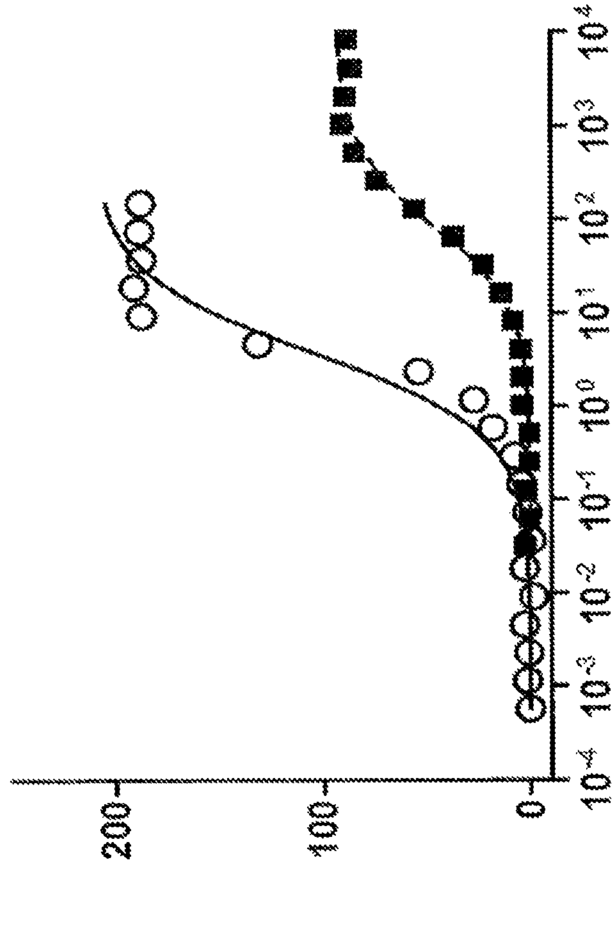
FIG. 11 shows the change in anisotropy of the DNA oligonucleotide (SEQ ID NO: 73, which has a carboxyfluorescein base at its 5' end) with increasing amounts of various transport control proteins (y-axis label=Anisotropy (blank subtracted), x-axis label=Protein Concentration (nM)) The data with black square points correspond to the Hel308 Mbu monomer (SEQ ID NO 10) The data with the empty circles correspond to the Hel308 Mbu A700C 2 kDa dimer (where each monomer unit comprises SEQ ID NO: 10 with the mutation A700C, with one monomer unit being linked to the other via position 700 of each monomer unit using a 2 kDa PEG linker). A lower concentration of the Hel308 Mbu A700C 2 kDa dimer is required to affect an increase in anisotropy, therefore, the dimer has a higher binding affinity for the DNA than the monomer.

FIG. 11 shows the change in anisotropy of the DNA oligonucleotide (SEQ ID NO: 73, which has a carboxyfluorescein base at its 5' end) with increasing amounts of Hel308 Mbu A700C 2 kDa dimer (empty circles) in comparison with the Hel308 Mbu monomer (black squares).

Figure 12:
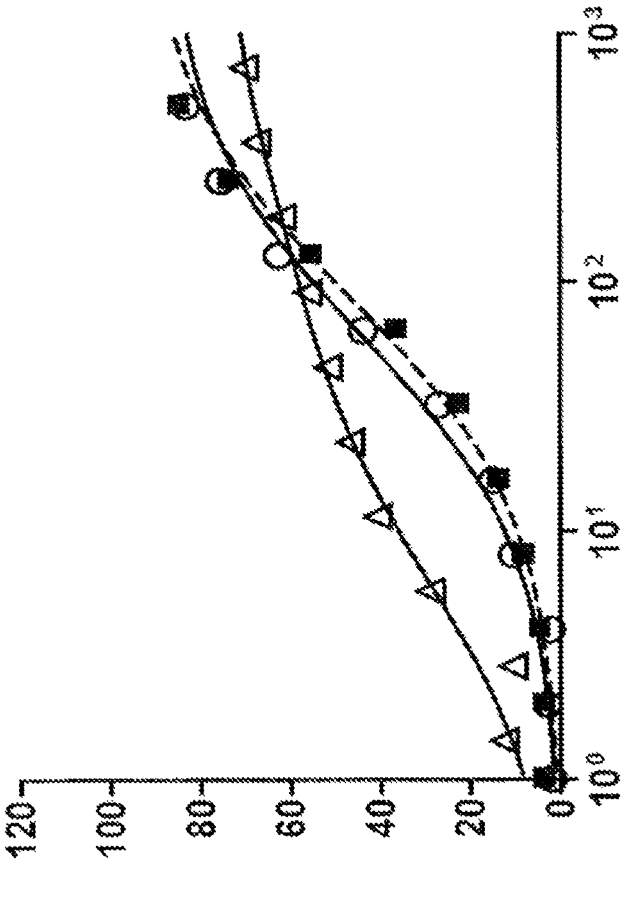
FIG. 12 shows the change in anisotropy of the DNA oligonucleotide (SEQ ID NO: 73, which has a carboxyfluorescein base at its 5' end) with increasing amounts of transport control proteins (y-axis label=Anisotropy (blank subtracted), x-axis label=Protein Concentration (nM)). The data with black square points correspond to the Hel308 Mbu monomer (SEQ ID NO: 10). The data with the empty circles correspond to Hel308 Mbu-GTGSGA-(HhH)2 (where a helicase monomer unit (SEQ ID NO: 10) is attached by the linker sequence GTGSGA to a (HhH)2 domain (SEQ ID NO: 74)) and the data with the empty triangles correspond to Hel308 Mbu-GTGSGA-(HhH)2-(HhH)2 (where a helicase monomer unit (SEQ ID NO: 10) is attached by the linker sequence GTGSGA to a (HhH)2-(HhH)2 domain (SEQ ID NO: 75)). The Hel308 Mbu helicases with additional helix-hairpin-helix binding domains attached show an increase in anisotropy at a lower concentration than the Hel308 Mbu monomer (SEQ ID NO. 10). This indicates that the helicases with additional (HhH)2 binding domains attached (Hel308 Mbu-GTGSGA-(HhH)2 and Hel308 Mbu-GTGSGA-(HhH)2-(HhH)2) have a stronger binding affinity for DNA than Hel308 Mbu monomer. The Hel308 Mbu-GTGSGA-(HhH)2-(HhH)2, which has four HhH domains, was observed to bind DNA more tightly than Hel308 Mbu-GTGSGA-(HhH)2 which only has two HhH domains

FIG. 12 shows the change in anisotropy of the DNA oligonucleotide (SEQ ID NO: 73, which has a carboxyfluorescein base at its 5' end) with increasing amounts of Hel308 Mbu-GTGSGA-(HhH)2 (empty circles) and Hel308 Mbu-GTGSGA-(HhH)2-(HhH)2 (empty triangles) in comparison with the Hel308 Mbu monomer (black squares).

Figure 13:
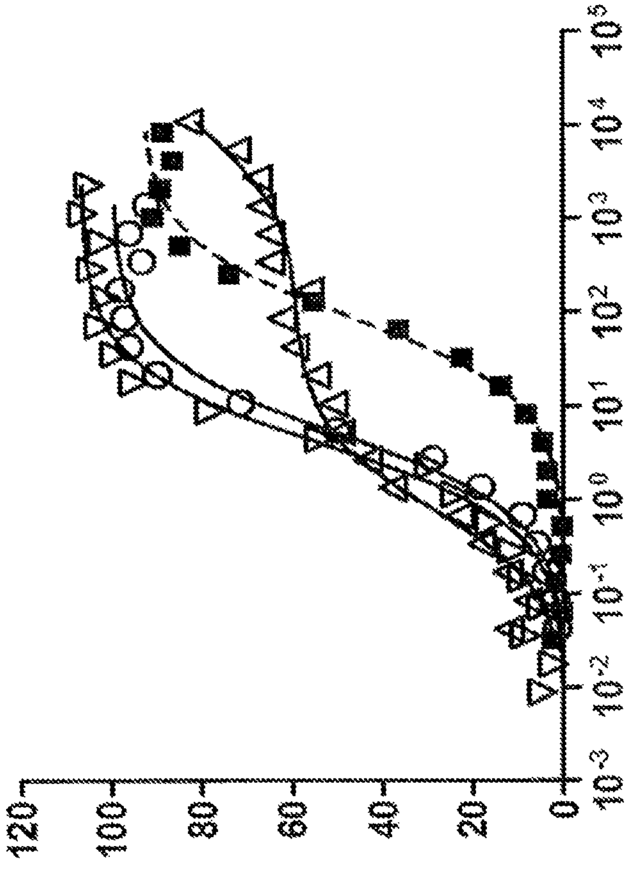
FIG. 13 shows the change in anisotropy of the DNA oligonucleotide (SEQ ID NO: 73, which has a carboxyfluorescein base at its 5' end) with increasing amounts of various transport control proteins or constructs (y-axis label=Anisotropy (blank subtracted), x-axis label=Protein Concentration (nM)) The data with black square points corresponds to the Hel308 Mbu monomer (SEQ ID NO: 10). The data with the empty circles correspond to Hel308 Mbu-GTGSGA-UL 42HV1-I320Del (where a helicase monomer unit (SEQ ID NO: 10) is attached by the linker sequence GTGSGA to UL42HVI-I320Del (SEQ ID NO: 76)), the data with the empty triangles pointing up correspond to Hel308 Mbu-GTGSGA-gp32RB69CD (where a helicase monomer unit (SEQ ID NO: 10) is attached by the linker sequence GTGSGA to gp32RB69CD (SEQ ID NO: 59)) and the data with empty triangles pointing down correspond to Hel308 Mbu-GTGSGA-gp2.5T7-R211 Del (where a helicase monomer unit (SEQ ID NO: 10) is attached by the linker sequence GTGSGA to gp2.5T7-R211Del (SEQ ID NO: 60)). All of the constructs (Hel308 Mbu-GTGSGA-UL42HV1-I320Del, Hel308 Nbu-GTGSGA-gp32RB69C) and Hel308 Mbu-GTGSGA-gp2.5T7-R211Del) show an increase in anisotropy at a lower concentration than the monomer Hel308 Mbu. This indicates that the constructs have a stronger binding affinity for DNA than the transport control protein—Hel308 Mbu monomer.

FIG. 13 shows the change in anisotropy of the DNA oligonucleotide (SEQ ID NO: 73, which has a carboxyfluorescein base at its 5' end) with increasing amounts of Hel308 Mbu-GTGSGA-UL42HV1-I320Del (empty circles), Hel308 Mbu-GTGSGA-gp32RB69CD (empty triangles pointing up) and Hel308 Mbu-GTGSGA-gp2.5T7-R211Del (empty triangles pointing down) in comparison with the Hel308 Mbu monomer (black squares).

Figure 14:
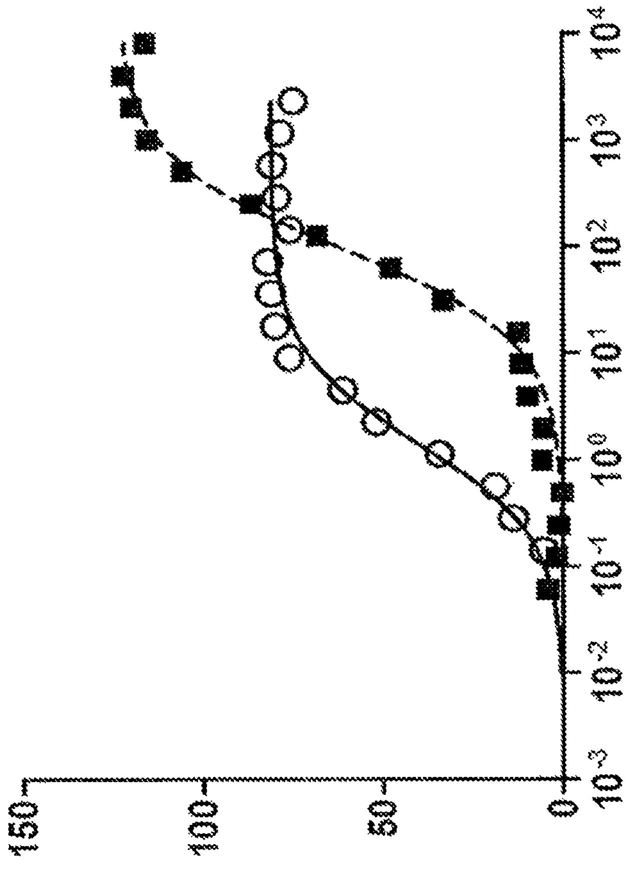
FIG. 14 shows the change in anisotropy of the DNA oligonucleotide (SEQ ID NO: 73, which has a carboxyfluorescein base at its 5' end) with increasing amounts of a transport control protein or a construct (y-axis label=Anisotropy (blank subtracted). x-axis label=Protein Concentration (nM)). The data with black square points correspond to the Hel308 Mbu monomer (SEQ ID NO: 10). The data with the empty circles correspond to (gp32-RB69CD)-Hel308 Mbu (where the gp32-RB69CD (SEQ ID NO: 59) is attached by the linker sequence GTGSGT to the helicase monomer unit (SEQ ID NO: 10)). The construct (gp32-RB69CD)-Hel308 Mbu shows an increase in anisotropy at a lower concentration than the monomer Hel308 Mbu, indicating tighter binding to the DNA was observed with the construct in comparison to the transport control protein—Hel308 Mbu monomer.

FIG. 14 shows the change in anisotropy of the DNA oligonucleotide (SEQ ID NO: 73, which has a carboxyfluorescein base at its S' end) with increasing amounts of (gp32-RB69CD)-Hel308 Mbu (empty circles) in comparison to the Hel308 Mbu monomer black squares).

All of the transport control proteins and constructs that were investigated showed an increase in anisotropy at a lower concentration than the transport control protein, Hel308 Mbu monomer (SEQ ID NO: 10).

Figure 15:
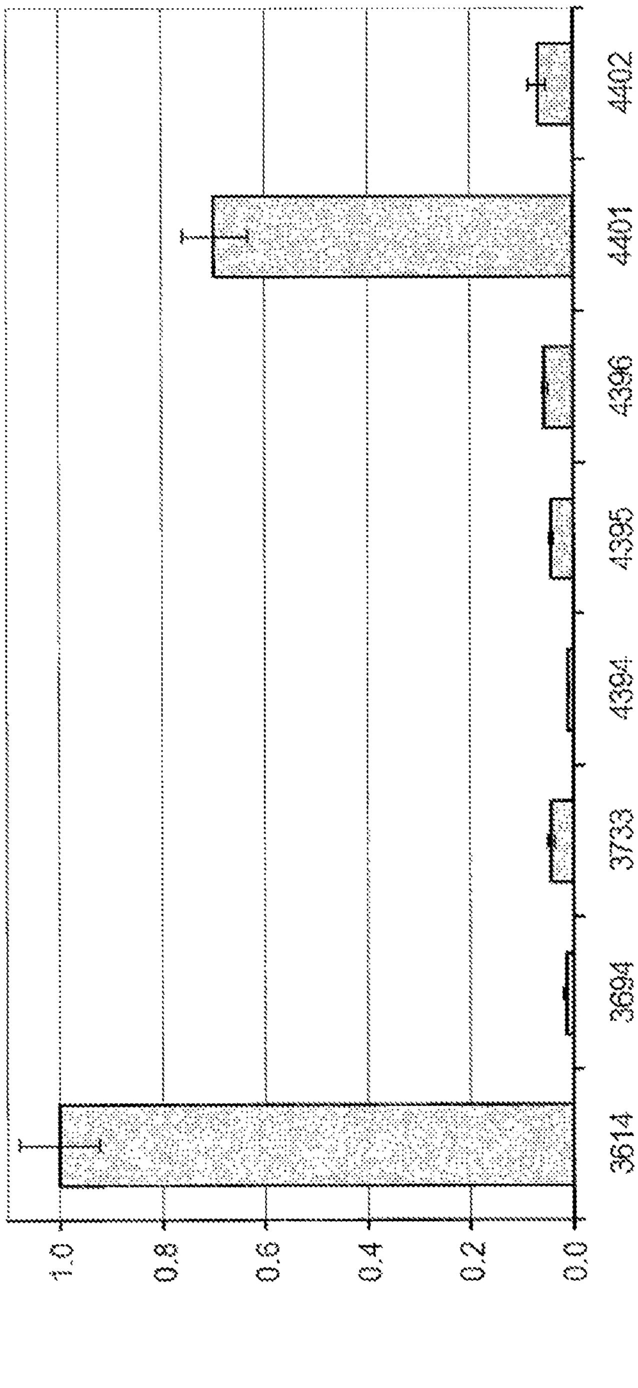
FIG. 15 shows relative equilibrium dissociation constants ($K_d$) (with respect to the Hel308 Mbu monomer) for various transport control proteins and constructs, obtained through fitting two phase dissociation binding curves through the data shown in FIGS. 11-14 using Graphpad Prism software (y-axis label=Relative $K_d$, x-axis label=Ref. Number). The reference numbers correspond to the following Hel308 (Mbu) constructs—3614=Hel308 (Mbu), 3694=(gp32-RB69CD)-Hel308 Mbu, 3733=Hel308 (Mbu)-A700C 2 kDa PEG dimer, 4401=Hel308 (Mbu)-GTGSGA-(HhH)2, 4402=Hel308 (Mbu)-GTGSGA-(HhH)2-(HhH)2, 4394=Hel308 (Mbu)-GTGSGA-gp32RB69CD, 4395=Hel308 (Mbu)-GTGSGA-gp2.5T7-R112Ded and 4396=Hel308 (Mbu)-GTGSGA-UL42HV1-1320) el. All of the transport control proteins and constructs (Hel308 Mbu A700C 2 kDa dimer, Hel308 Mbu-GTGSGA-(HhH)2, Hel308 Mbu-GTOSGA-(HhH)2-(HhH)2, Hel308 Mbu-GTGSGA-UL42HV1-I320Del, Hel308 Mbu-GTGSGA-gp32RB69CD. Hel308 Mbu-GTGSGA-gp2.5T7-R211Del and (gp32-RB69CD)-Hel308 Mbu) show a lower equilibrium dissociation constant than the transport control protein-Hel308 Mbu monomer.

FIG. 15 shows the relative equilibrium dissociation constants (KA) (with respect to Hel308 Mbu monomer SEQ ID NO: 10 whose data corresponds to column number 3614 in FIG. 15) for various transport control proteins and constructs obtained through fitting two phase dissociation binding curves through the data shown in FIGS. 11-14, using Graphpad Prism software. All of the other transport control proteins and constructs that were tested show a lower equilibrium dissociation constant than the Hel308 Mbu monomer alone. Therefore, the other transport control proteins and constructs tested all showed stronger binding to DNA than the Hel308 Mbu monomer.

The invention claimed is:

1. A method of characterising a target polynucleotide, comprising:

a) contacting the target polynucleotide with a transmembrane pore and a single-stranded binding protein (SSB), wherein the SSB comprises one or more amino acid insertions in its C-terminal region relative to a wild-type SSB that decreases the net negative charge of the C-terminal region relative to the wild-type SSB and the decrease in the net negative charge of the C-terminal region reduces blockage of the pore relative to the wild-type SSB, wherein the one or more amino acid insertions are one or more insertions of positively charged amino acids which neutralize one or more negatively charged amino acids;

b) moving the polynucleotide through the pore, wherein the SSB does not move through the pore; and c) taking one or more measurements as the polynucleotide moves with respect to the pore wherein the measurements are indicative of one or more characteristics of the target polynucleotide and thereby characterising the target polynucleotide.

2. A method according to claim 1, wherein the C-terminal region comprises about the last 10 to about the last 60 amino acids of the C-terminal end.

3. A method according to claim 1, wherein the one or more positively charged amino acids are histidine (H), lysine (K) and/or arginine (R).

4. A method according to claim 1, wherein:

the SSB is (a) derived from the SSB of *E. coli*, the SSB of *Mycobacterium tuberculosis*, the SSB of *Deinococcus radiodurans*, the SSB of *Thermus* thermophiles, the SSB from *Sulfolobus solfataricus*, the human replication protein A 32 kDa subunit (RPA32) fragment, the CDCl3 SSB from *Saccharomyces cerevisiae*, the Primosomal replication protein N (PriB) from *E. coli*, the PriB from *Arabidopsis thaliana*, the hypothetical protein At4g28440, the SSB from T4, the SSB from RB69, the SSB from T7 or a variant thereof; or (b) derived from the sequence shown in SEQ ID NO: 65 or a variant thereof.

5. A method according to claim 1, wherein the one or more characteristics are selected from: (i) the length of the target polynucleotide, (ii) the identity of the target polynucleotide, (iii) the sequence of the target polynucleotide, (iv) the secondary structure of the target polynucleotide, and/or (v) whether or not the target polynucleotide is modified or whether or not the target polynucleotide is modified by methylation, by oxidation, by damage, with one or more proteins or with one or more labels, tags or spacers.

6. A method according to claim 1, wherein step (a) further comprises contacting the polynucleotide with a transport control protein such that the transport control protein controls the movement of the target polynucleotide through the pore and wherein the transport control protein does not move through the pore.

7. A method according to claim 6, wherein the transport control protein is derived from an exonuclease, polymerase, helicase, or topoisomerase.

8. A method according to claim 7, wherein the SSB is attached to the transport control protein and the resulting construct has the ability to control the movement of the target polynucleotide.

9. A method according to claim 1, wherein at least a portion of the polynucleotide is single stranded.

10. A method according to claim 1, wherein the target polynucleotide is contacted with the pore and the SSB on the same side of the membrane.

11. A method according to claim 1, wherein the pore is a transmembrane protein pore, wherein the protein is selected from hemolysin, leukocidin, *Mycobacterium smegmatis* porin A (MspA), MspB, MspC, MspD, outer membrane phospholipase A, *Neisseria* autotransporter lipoprotein (NalP) and WZA.

12. A method according to claim 1, wherein the barrel or channel of the pore has a diameter of less than 7 nm at its narrowest point.

13. The method of claim 4, wherein (b) further comprises:

i) substitution of one or more of amino acids 170, 172, 173 and 174 in SEQ ID NO: 65 with a positively charged, uncharged, non-polar or aromatic amino acid;

ii) substitution of one or more of amino acids 168, 169, 171, 175, 176 and 177 in SEQ ID NO: 65 with a positively charged amino acid; or iii) the sequence set forth in SEQ ID NO: 66 or 67.

* * * * *